(12) United States Patent
Pell et al.

(10) Patent No.: US 11,253,283 B2
(45) Date of Patent: Feb. 22, 2022

(54) METHODS AND DEVICES FOR SOFT TISSUE DISSECTION

(71) Applicant: Physcient, Inc., Durham, NC (US)

(72) Inventors: Charles Anthony Pell, Durham, NC (US); Hugh Charles Crenshaw, Durham, NC (US); Ryan Moody, Durham, NC (US); Eric Torr Espenhahn, Cary, NC (US)

(*) Notice: Subject to any disclaimer, the term of this patent is extended or adjusted under 35 U.S.C. 154(b) by 92 days.

(21) Appl. No.: 16/230,175

(22) Filed: Dec. 21, 2018

(65) Prior Publication Data
US 2019/0117252 A1 Apr. 25, 2019

Related U.S. Application Data

(63) Continuation of application No. 15/457,169, filed on Mar. 13, 2017, now Pat. No. 10,639,056, which is a
(Continued)

(51) Int. Cl.
*A61B 17/32* (2006.01)
*A61B 17/00* (2006.01)

(52) U.S. Cl.
CPC ............ *A61B 17/320016* (2013.01); *A61B 2017/00858* (2013.01); *A61B 2017/320004* (2013.01);
(Continued)

(58) Field of Classification Search
CPC .......... A61B 17/148; A61B 17/320016; A61B 17/32002; A61B 17/320068;
(Continued)

(56) References Cited

U.S. PATENT DOCUMENTS

| 900,300 A | 10/1908 | Nicolas |
| 1,192,451 A | 7/1916 | Pfefferkorn |
| (Continued) | | |

FOREIGN PATENT DOCUMENTS

| CN | 101352363 A | 1/2009 |
| CN | 101686839 A | 3/2010 |
| (Continued) | | |

OTHER PUBLICATIONS

Notice of Rejection for Japanese Patent Application No. 2016-563016, dated Feb. 12, 2019, 11 pages.
(Continued)

*Primary Examiner* — Tuan V Nguyen
(74) *Attorney, Agent, or Firm* — Withrow & Terranova, PLLC

(57) ABSTRACT

A differential dissecting instrument for differentially dissecting complex tissue is disclosed. The differential dissecting instrument comprises a handle and an elongate member having a first end and a second end, wherein the first end is connected to the handle. The differential dissecting instrument comprises a differential dissecting member configured to be rotatably attached to the second end and further comprises at least one tissue engaging surface. The differential dissecting instrument comprises a mechanism configured to mechanically rotate the differential dissecting member around an axis of rotation, thereby causing the at least one tissue engaging surface to move in at least one direction against the complex tissue. The at least one tissue engaging surface is configured to selectively engage the complex tissue such that the at least one tissue engaging surface disrupts at least one soft tissue in the complex tissue, but does not disrupt firm tissue in the complex tissue.

31 Claims, 77 Drawing Sheets

Related U.S. Application Data continuation of application No. 14/065,191, filed on Oct. 28, 2013, now Pat. No. 9,592,069, which is a continuation-in-part of application No. 13/872,766, filed on Apr. 29, 2013, now Pat. No. 9,538,995.

(60) Provisional application No. 61/783,834, filed on Mar. 14, 2013, provisional application No. 61/744,936, filed on Oct. 6, 2012, provisional application No. 61/687,587, filed on Apr. 28, 2012.

(52) U.S. Cl.
CPC .............. *A61B 2017/32006* (2013.01); *A61B 2017/320028* (2013.01); *A61B 2017/320044* (2013.01); *A61B 2017/320064* (2013.01)

(58) Field of Classification Search
CPC ......... A61B 2017/32006; A61B 2017/320028; A61B 2017/320044; A22B 5/16; A22B 5/163; A22B 5/168
See application file for complete search history.

(56) References Cited

U.S. PATENT DOCUMENTS

| | | | |
|---|---|---|---|
| 1,506,510 A | 8/1924 | Thuau | |
| 1,945,247 A | 1/1934 | Wezel | |
| 2,547,134 A | 4/1951 | McLean | |
| 2,766,524 A | 10/1956 | Dagneau | |
| 2,972,350 A | 2/1961 | Deker | |
| 3,263,681 A | 8/1966 | Nechtow et al. | |
| 3,435,522 A | 4/1969 | Wezel et al. | |
| 3,554,197 A | 1/1971 | Dobble | |
| 3,618,611 A | 11/1971 | Urban | |
| 3,978,862 A | 9/1976 | Morrison | |
| 4,106,181 A | 8/1978 | Mattchen | |
| 4,432,117 A | 2/1984 | Iskiw | |
| 4,477,256 A | 10/1984 | Hirsch | |
| 4,490,885 A | 1/1985 | Iskiw et al. | |
| 4,572,187 A | 2/1986 | Schetrumpf | |
| 4,608,982 A | 9/1986 | Pollard | |
| 4,749,376 A | 6/1988 | Kensey et al. | |
| 4,768,504 A | 9/1988 | Ender | |
| 4,844,088 A | 7/1989 | Kambin | |
| 4,990,134 A | 2/1991 | Auth | |
| 5,201,752 A | 4/1993 | Brown et al. | |
| 5,205,816 A | 4/1993 | Dodson et al. | |
| 5,405,348 A | 4/1995 | Anspach, Jr. et al. | |
| 5,441,445 A | 8/1995 | Karubian et al. | |
| 5,445,561 A | 8/1995 | Elmer | |
| 5,456,011 A | 10/1995 | Inkster | |
| 5,522,788 A | 6/1996 | Kuzmak | |
| 5,527,331 A | 6/1996 | Kresch et al. | |
| 5,591,186 A | 1/1997 | Wurster et al. | |
| 5,658,307 A | 8/1997 | Exconde | |
| 5,707,383 A | 1/1998 | Bays et al. | |
| 5,725,479 A | 3/1998 | Knight et al. | |
| 5,779,713 A | 7/1998 | Turjanski et al. | |
| 5,817,121 A | 10/1998 | Christoudias | |
| 5,871,497 A | 2/1999 | Young | |
| 5,919,203 A | 7/1999 | Husted et al. | |
| 5,925,055 A | 7/1999 | Adrian et al. | |
| 6,001,120 A | 12/1999 | Levin | |
| 6,080,102 A | 6/2000 | Konou et al. | |
| 6,391,040 B1 | 5/2002 | Christoudias | |
| 6,423,078 B1 | 7/2002 | Bays et al. | |
| 6,869,439 B2 | 3/2005 | White et al. | |
| 7,018,328 B2 | 3/2006 | Mager et al. | |
| 7,367,981 B2 | 5/2008 | Bernaz | |
| 7,422,592 B2 | 9/2008 | Morley et al. | |
| D581,053 S | 11/2008 | Gesler, III | |
| 7,540,875 B2 | 6/2009 | Jessen | |
| 7,686,823 B2 | 3/2010 | Pingleton et al. | |
| 7,842,058 B2 | 11/2010 | Simpson et al. | |
| 8,048,100 B2 | 11/2011 | Kadykowski et al. | |
| 8,052,662 B2 | 11/2011 | Zelickson et al. | |
| 8,157,832 B2 | 4/2012 | Refai | |
| 8,372,096 B2 | 2/2013 | Kadykowski et al. | |
| 8,460,331 B2 | 6/2013 | Chin | |
| 8,636,759 B2 | 1/2014 | Pingleton et al. | |
| 9,538,995 B2 | 1/2017 | Crenshaw et al. | |
| 9,592,069 B2 | 5/2017 | Moody et al. | |
| 2002/0062062 A1 | 5/2002 | Belson et al. | |
| 2003/0009166 A1 | 1/2003 | Moutafis et al. | |
| 2003/0144680 A1 | 7/2003 | Kellogg et al. | |
| 2005/0107816 A1 | 5/2005 | Pingleton et al. | |
| 2005/0209610 A1 | 9/2005 | Carrison | |
| 2006/0009796 A1 | 1/2006 | Carusillo et al. | |
| 2007/0167966 A1 | 7/2007 | Simpson et al. | |
| 2008/0045993 A1* | 2/2008 | Mathis ........... A61B 17/320068 606/190 |
| 2008/0119860 A1 | 5/2008 | McCarthy | |
| 2008/0306335 A1 | 12/2008 | Lau et al. | |
| 2009/0261690 A1 | 10/2009 | Mashimo et al. | |
| 2009/0312783 A1 | 12/2009 | Whayne et al. | |
| 2010/0010525 A1 | 1/2010 | Lockard et al. | |
| 2010/0016853 A1 | 1/2010 | Burbank | |
| 2010/0114138 A1 | 5/2010 | Graham | |
| 2010/0222801 A1 | 9/2010 | Pingleton et al. | |
| 2010/0241130 A1 | 9/2010 | Deli et al. | |
| 2010/0256662 A1 | 10/2010 | Racenet et al. | |
| 2010/0312186 A1 | 12/2010 | Suchdev et al. | |
| 2011/0034918 A1 | 2/2011 | Reschke | |
| 2012/0071909 A1 | 3/2012 | Fischvogt et al. | |
| 2012/0101489 A1 | 4/2012 | Bloom et al. | |
| 2012/0109172 A1 | 5/2012 | Schmitz et al. | |
| 2012/0191121 A1 | 7/2012 | Chen et al. | |
| 2012/0209141 A1 | 8/2012 | Peliks | |
| 2013/0310869 A1 | 11/2013 | Crenshaw et al. | |
| 2013/0331833 A1 | 12/2013 | Bloom | |
| 2014/0058394 A1 | 2/2014 | Siegal et al. | |
| 2014/0114339 A1 | 4/2014 | Pingleton et al. | |
| 2014/0364890 A1 | 12/2014 | Moody et al. | |
| 2017/0035449 A1 | 2/2017 | Pell et al. | |
| 2017/0042562 A1 | 2/2017 | Moody et al. | |
| 2017/0281302 A1 | 10/2017 | Pell et al. | |

FOREIGN PATENT DOCUMENTS

| | | |
|---|---|---|
| CN | 103648415 A | 3/2014 |
| DE | 202009006907 U1 | 8/2009 |
| EP | 1882538 A2 | 1/2008 |
| EP | 2777523 A1 | 9/2014 |
| GB | 1457544 A | 12/1976 |
| JP | 2010051439 A | 3/2010 |
| JP | 2012035088 A | 2/2012 |
| WO | 0149194 A2 | 7/2001 |
| WO | 2001049194 A2 | 7/2001 |
| WO | 2006017066 A2 | 2/2006 |
| WO | 2007100914 A2 | 9/2007 |
| WO | 2008022257 A2 | 2/2008 |
| WO | 2008127887 A1 | 10/2008 |
| WO | 2013033566 A1 | 3/2013 |
| WO | 2009134346 A2 | 11/2019 |

OTHER PUBLICATIONS

First Office Action for Mexican Patent Application No. MX/a/2014/013035, dated Feb. 11, 2019, 4 pages.
Examination Report for Indian Patent Application No. 201617014492, dated Jun. 15, 2020, 7 pages.
Decision to Grant for Japanese Patent Application No. 2018-079250, dated May 19, 2020, 5 pages.
Non-Final Office Action for U.S. Appl. No. 15/457,169, dated Apr. 26, 2019, 26 pages.
Notice of Allowance for U.S. Appl. No. 15/304,720, dated Jun. 5, 2019, 9 pages.
Office Action for Canadian Patent Application No. 2,871,827, dated May 3, 2019, 3 pages.
Notice of Allowance for U.S. Appl. No. 15/457,169, dated Dec. 30, 2019, 10 pages.

(56) References Cited

OTHER PUBLICATIONS

Notice of Allowance for U.S. Appl. No. 15/304,679, dated Oct. 29, 2019, 8 pages.
Office Action for Canadian Patent Application No. 2,871,827, dated Oct. 11, 2019, 4 pages.
Notice of Preliminary Rejection for Korean Patent Application No. 10-2014-7033376, dated Oct. 29, 2019, 7 pages.
Final Office Action for U.S. Appl. No. 15/457,169, dated Sep. 20, 2019, 7 pages.
Notice of Acceptance for Australian Patent Application No. 2014342631, dated Jul. 15, 2019, 3 pages.
Notice of Rejection for Japanese Patent Application No. 2018-079250, dated Jul. 30, 2019, 11 pages.
Examination Report for Indian Patent Application No. 201617039251, dated Dec. 11, 2020, 7 pages.
U.S. Appl. No. 13/872,766, filed Apr. 29, 2013, now U.S. Pat. No. 9,538,995.
U.S. Appl. No. 14/065,191, filed Oct. 28, 2013, now U.S. Pat. No. 9,592,069.
U.S. Appl. No. 15/457,169, filed Mar. 13, 2017.
U.S. Appl. No. 15/304,679, filed Oct. 17, 2016.
U.S. Appl. No. 15/304,720, filed Oct. 17, 2016.
First Office Action for Chinese Patent Application No. 201810330380.3, dated Aug. 4, 2020, 25 pages.
Examination Report for Indian Patent Application No. 9469/DELNP/2014, dated Oct. 15, 2020, 7 pages.
Notice of Rejection for Japanese Patent Application No. 2019-153470, dated Oct. 20, 2020, 12 pages.
First Examination Report for New Zealand Patent Application No. 719240, dated Jul. 7, 2020, 5 pages.
First Examination Report for New Zealand Patent Application No. 758574, dated Jul. 7, 2020, 6 pages.
Extended European Search Report for European Patent Application No. 19177704.4, dated Nov. 14, 2019, 8 pages.
Preliminary Office Action for Brazilian Patent Application No. 112014027081-3, dated Dec. 16, 2019, 5 pages.
Extended European Search Report for European Patent Application No. 19200561.9, dated Feb. 5, 2020, 12 pages.
Decision to Grant for Korean Patent Application No. 10-2014-7033376, dated Mar. 26, 2020, 4 pages.
Examination Report for Australian Patent Application No. 2019253899, dated Apr. 27, 2020, 3 pages.
Cox, III, et al., "Decreased Splatter in Dermabrasion," Archives of Facial Plastic Surgery, vol. 2, Jan.-Mar. 2000, pp. 23-26.
Non-Final Office Action for U.S. Appl. No. 13/872,766, dated Jun. 17, 2016, 34 pages.
Non-Final Office Action for U.S. Appl. No. 14/065,191, dated May 31, 2016, 23 pages.
First Office Action for Chinese Patent Application No. 201380034142.3, dated Jun. 2, 2016, 8 pages.
Extended European Search Report for European Patent Application No. 13780834.1, dated Aug. 21, 2015, 5 pages.
Examination Report for European Patent Application No. 13780834.1, dated Jul. 21, 2016, 3 pages.
First Examination Report for New Zealand Patent Application No. 701634, dated Jan. 14, 2016, 3 pages.
Further Examination Report for New Zealand Patent Application No. 701634, dated Apr. 26, 2016, 2 pages.
Further Examination Report Postponed Acceptance for New Zealand Patent Application No. 701634, dated Jul. 27, 2016, 1 page.
International Search Report and Written Opinion for International Patent Application No. PCT/US2013/038673 dated Sep. 27, 2013, 23 pages.
International Preliminary Report on Patentability for International Patent Application No. PCT/US2013/038673, dated Nov. 6, 2014, 16 pages.
International Search Report and Written Opinion for International Patent Application No. PCT/US2014/062382, dated Feb. 3, 2015, 12 pages.
International Preliminary Report on Patentability for International Patent Application No. PCT/US2014/062382, dated May 12, 2016, 9 pages.
Invitation to Pay Additional Fees and Partial International Search for International Patent Application No. PCT/US2015/026466, dated Jun. 18, 2015, 7 pages.
International Search Report and Written Opinion for International Patent Application No. PCT/US2015/026466, dated Sep. 15, 2015, 14 pages.
International Preliminary Report on Patentability for International Patent Application No. PCT/US2015/026466, dated Oct. 27, 2016, 9 pages.
International Search Report and Written Opinion for International Patent Application No. PCT/US2015/027156, dated Aug. 3, 2015, 11 pages.
International Preliminary Report on Patentability for International Patent Application No. PCT/US2015/027156, dated Nov. 3, 2016, 9 pages.
Notice of Allowance and Examiner-Initiated Interview Summary for U.S. Appl. No. 13/872,766, dated Nov. 4, 2016, 11 pages.
Notice of Allowance and Examiner-Initiated Interview Summary for U.S. Appl. No. 14/065,191, dated Jan. 10, 2017, 11 pages.
Second Office Action and Search Report for Chinese Patent Application No. 201380034142.3, dated Feb. 15, 2017, 21 pages.
Notice of Rejection for Japanese Patent Application No. 2015-509216, dated Feb. 28, 2017, 18 pages.
Supplementary Examination Report for Singapore Patent Application No. 11201406985P, dated Jan. 19, 2017, 2 pages.
Non-Final Office Action for U.S. Appl. No. 15/304,679, dated Feb. 4, 2019, 11 pages.
Non-Final Office Action for U.S. Appl. No. 15/304,720, dated Dec. 10, 2018, 13 pages.
Examination Report No. 1 for Australian Patent Application No. 2013251330, dated Jun. 22, 2017, 5 pages.
Examination Report No. 2 for Australian Patent Application No. 2013251330, dated Jun. 4, 2018, 2 pages.
Notice of Acceptance for Australian Patent Application No. 2013251330, dated Jul. 2, 2018, 3 pages.
Examination Report No. 1 for Australian Patent Application No. 2014342631, dated Jul. 27, 2018, 3 pages.
Third Office Action for Chinese Patent Application No. 201380034142.3, dated Sep. 5, 2017, 4 pages.
First Office Action for Chinese Patent Application No. 201480071443.8, dated Nov. 29, 2017, 27 pages.
Second Office Action for Chinese Patent Application No. 201480071443.8, dated Oct. 12, 2018, 12 pages.
Extended European Search Report for European Patent Application No. 14857187.0, dated Jun. 12, 2017, 8 pages.
Examination Report for European Patent Application No. 14857187.0, dated Jan. 31, 2019, 6 pages.
Extended European Search Report for European Patent Application No. 15780427.9, dated Nov. 14, 2017, 7 pages.
Extended European Search Report for European Patent Application No. 17180994.0, dated Dec. 6, 2017, 8 pages.
Examiner's Decision of Rejection for Japanese Patent Application No. 2015-509216, dated Dec. 19, 2017, 8 pages.
Notice of Rejection for Japanese Patent Application No. 2016-526849, dated Jul. 31, 2018, 12 pages.
Final Notice of Rejection for Japanese Patent Application No. 2016-526849, dated Jan. 22, 2019, 9 pages.
First Examination Report for New Zealand Patent Application No. 725053, dated May 3, 2017, 5 pages.
Further Examination Report for New Zealand Patent Application No. 725053, dated Jan. 8, 2018, 2 pages.
Notice of Eligibility for Grant and Supplementary Examination Report for Singapore Patent Application No. 11201603273P, dated Sep. 4, 2017, 3 pages.
Notice of Rejection for Japanese Patent Application No. 2019-236041, dated Mar. 30, 2021, 10 pages.
Notice of Preliminary Rejection for Korean Patent Application No. 10-2016-7013851, dated Mar. 26, 2021, 11 pages.
Second Office Action for Chinese Patent Application No. 201810330380.3, dated May 24, 2021, 18 pages.

(56) References Cited

OTHER PUBLICATIONS

First Office Action for Mexican Patent Application No. MX/a/2016/005573, dated Jun. 21, 2021, 7 pages.

* cited by examiner

FIG. 3D-1
Side View
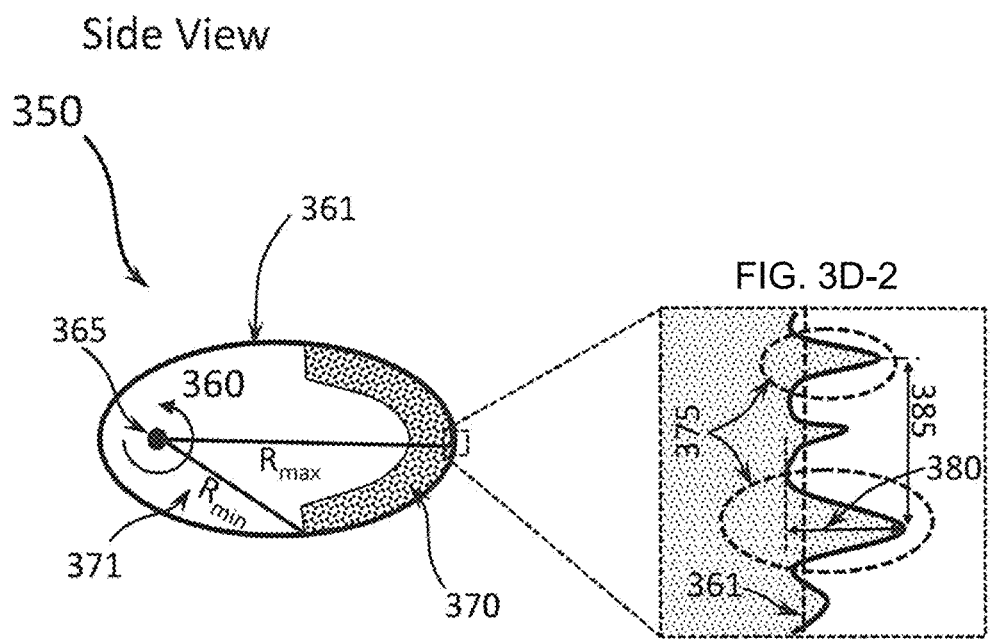
FIG. 3D-2
FIG. 3D-3
Front View
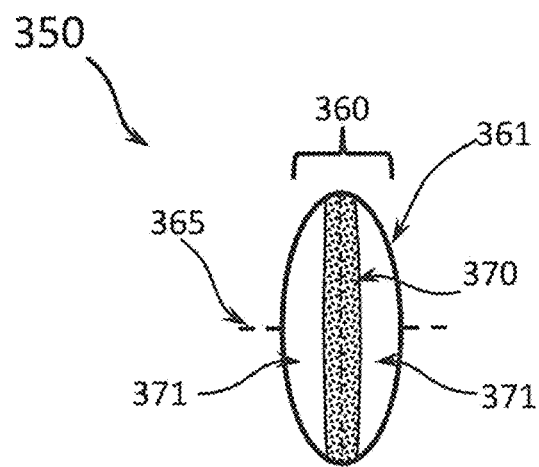

DDM Type I

DDM Type II

DDM Type III

DDM Type IV

Front View

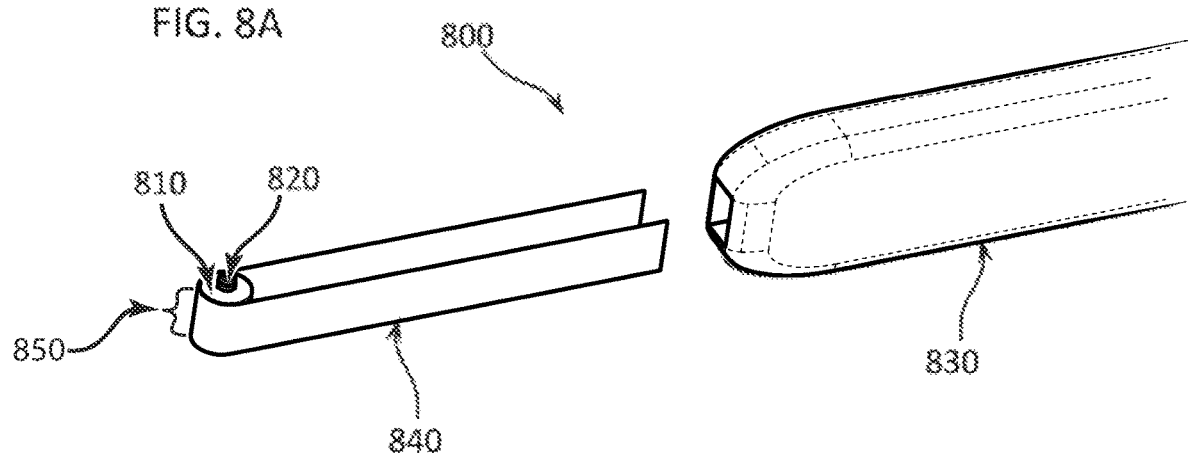
FIG. 8A
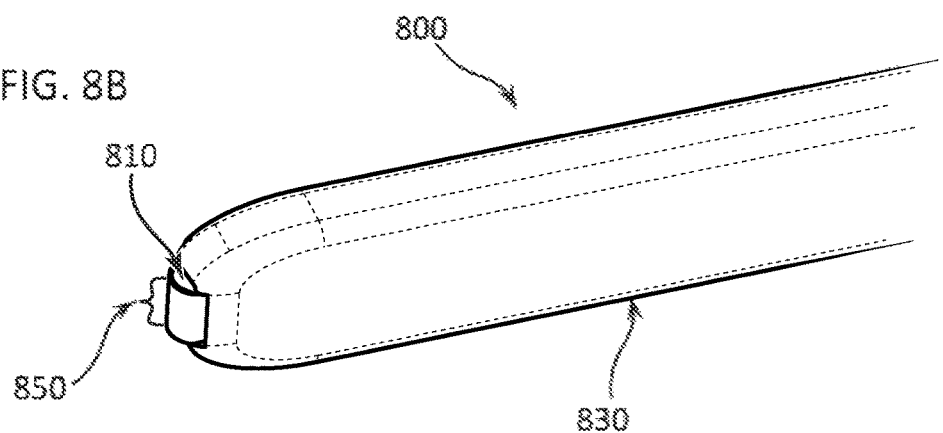
FIG. 8B
FIG. 8C
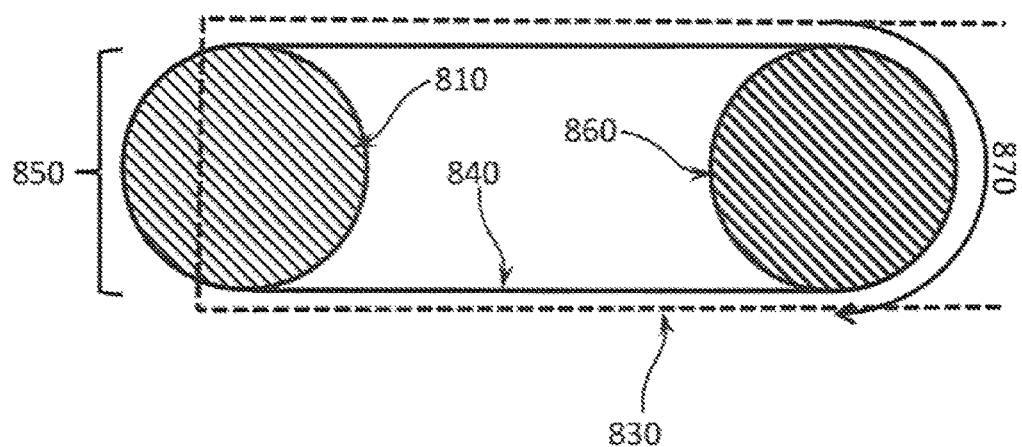

FIG. 14-1  
Position 1
FIG. 14-2  
Position 2
FIG. 14-3  
Position 3
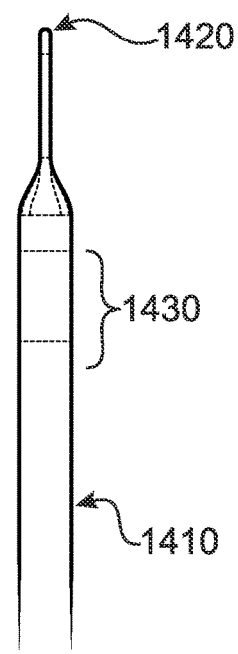
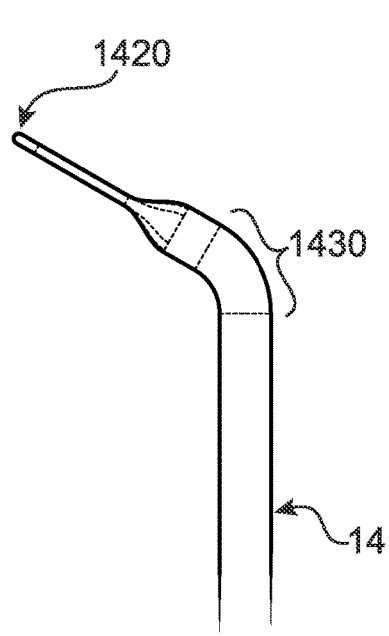
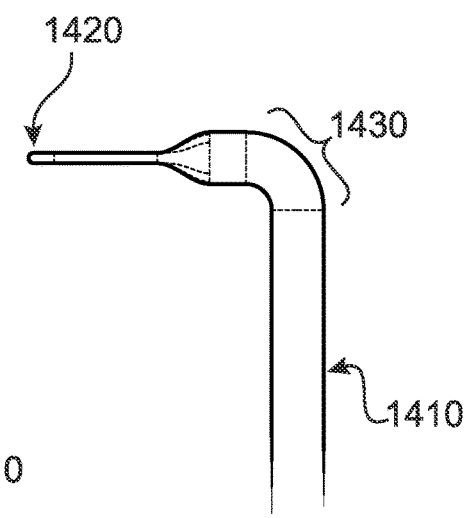

$1 \text{ mm} \leq R_A \leq 100 \text{ mm}$
$0.5 \text{ mm} \leq R_S \leq 10 \text{ mm}$
$0.05 \text{ mm} \leq R_E \leq 10 \text{ mm}$ FIG. 15C
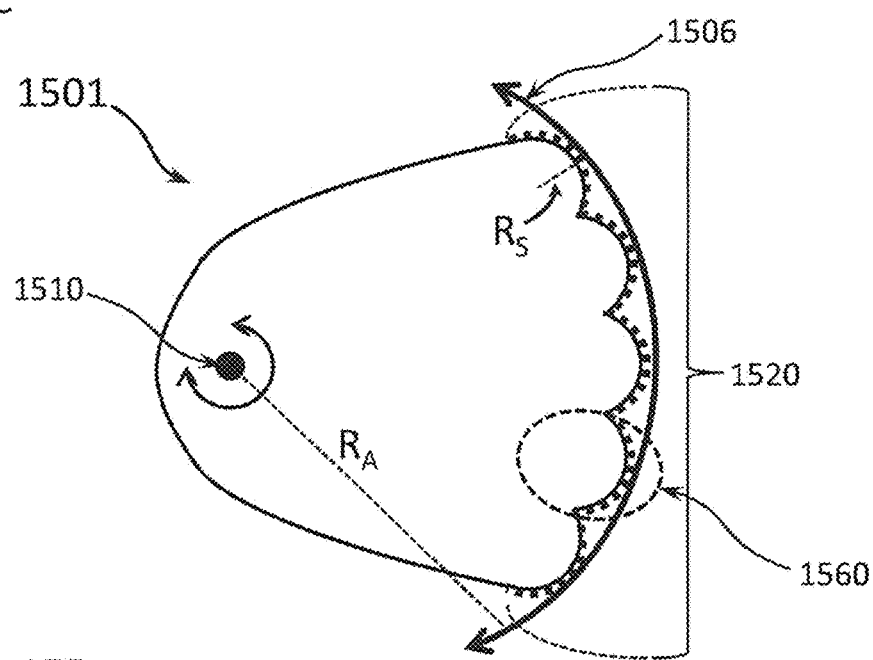
FIG. 15D
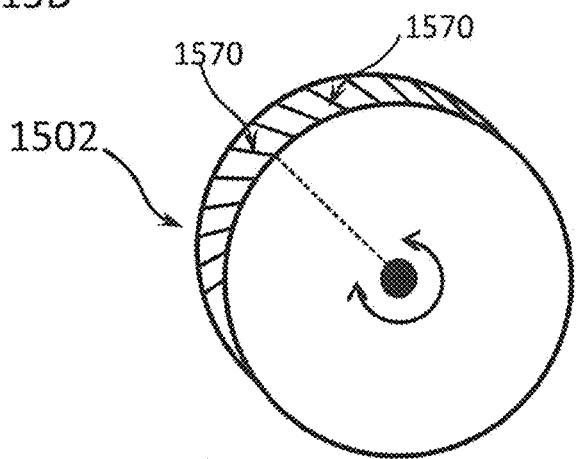
FIG. 15E-1    FIG. 15E-2    FIG. 15E-3
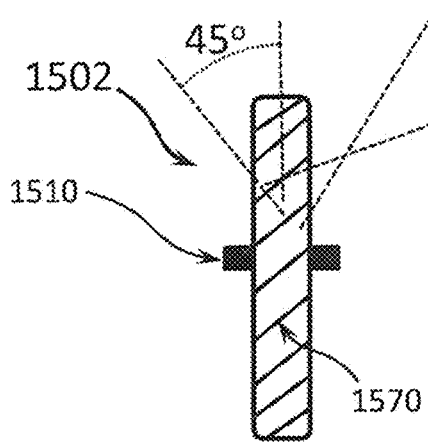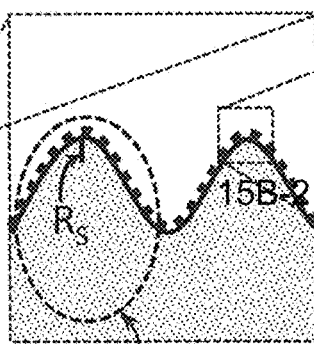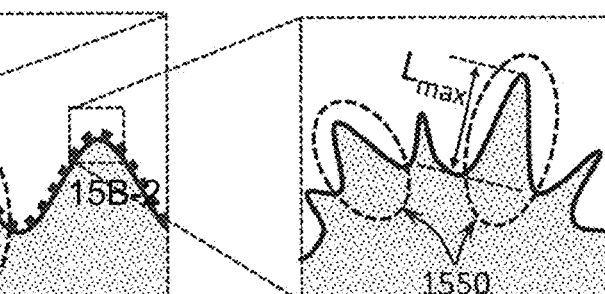

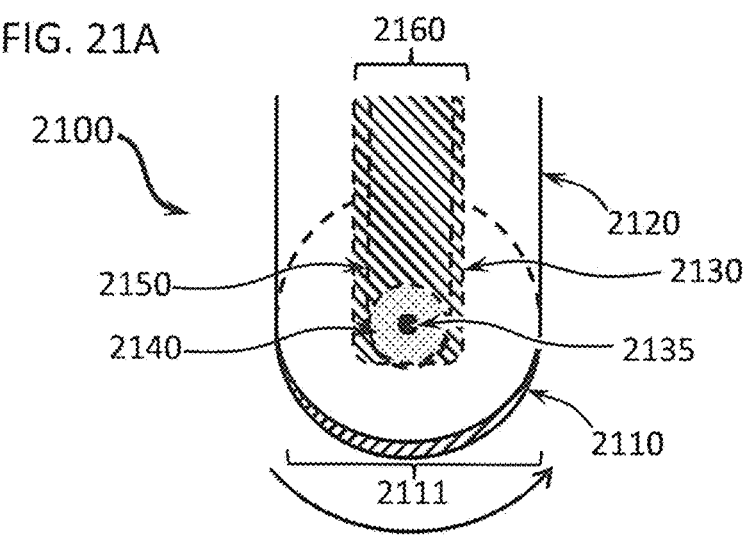
FIG. 21A
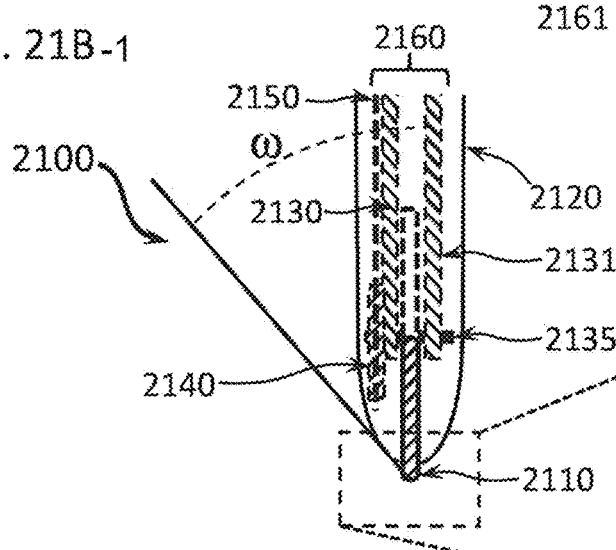
FIG. 21B-1
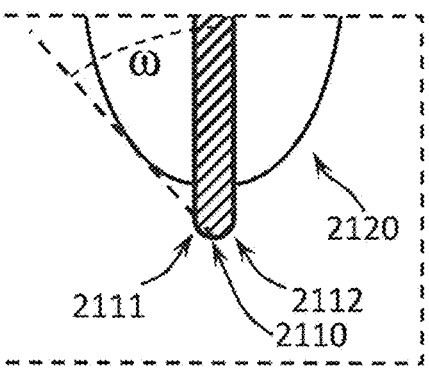
FIG. 21B-2
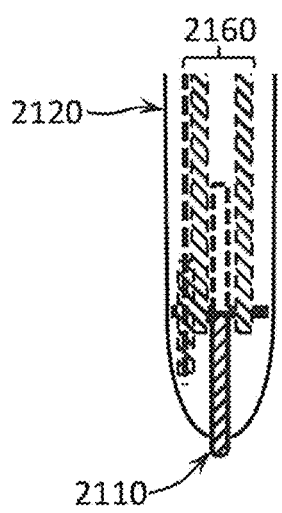
FIG. 21C-1 Position 1
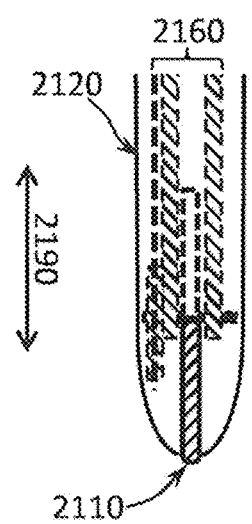
FIG. 21C-2 Position 2
FIG. 21C-3 Position 3
FIG. 21C-4 Position 4

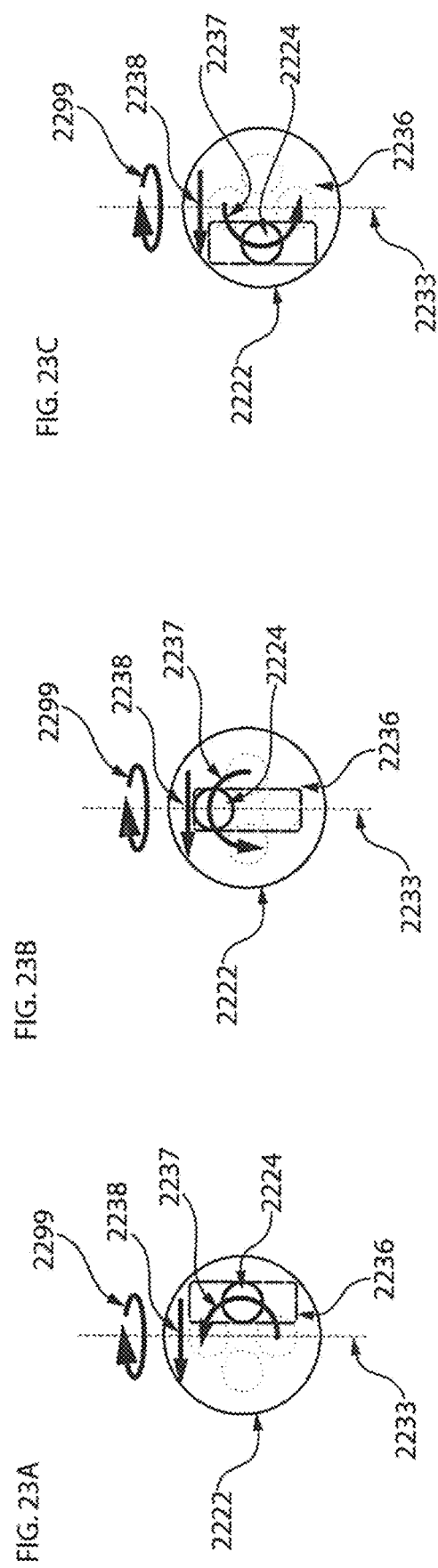

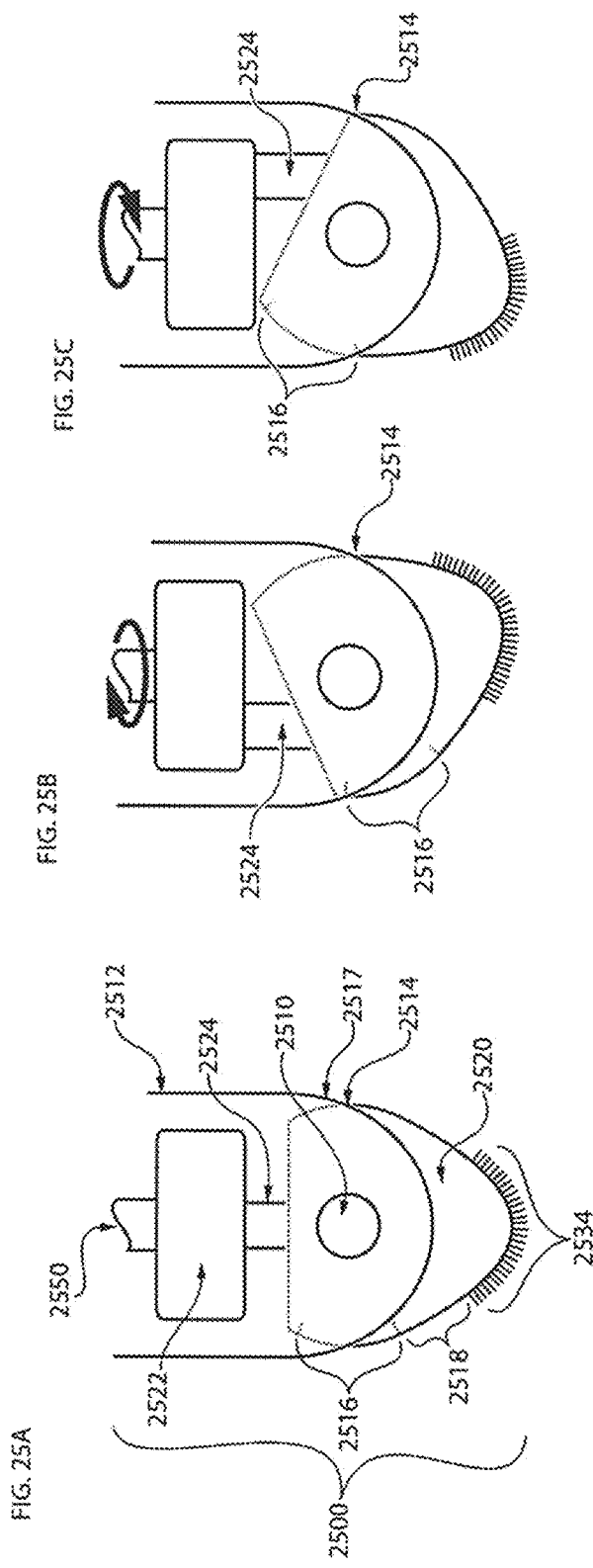

Side View

Top View

Side View

Top View

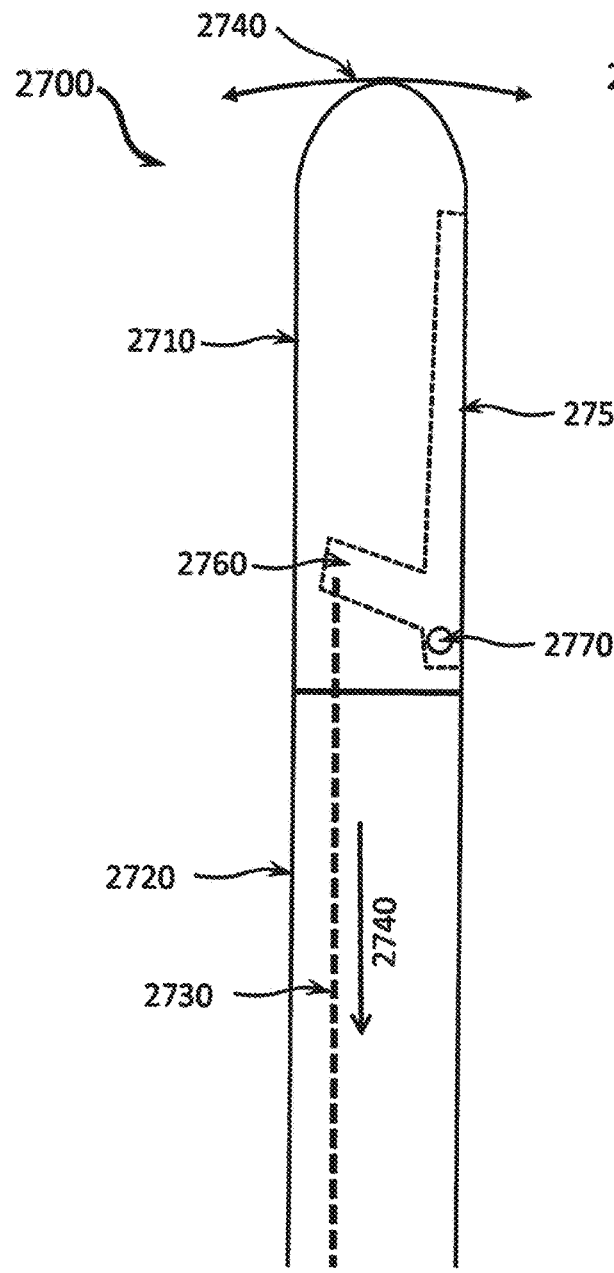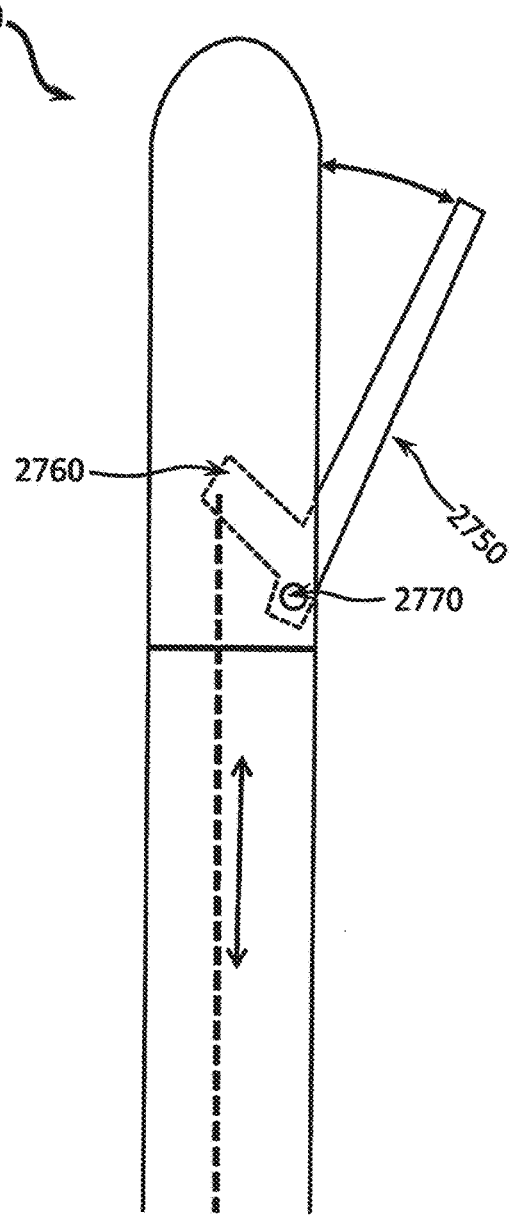

FIG 29A
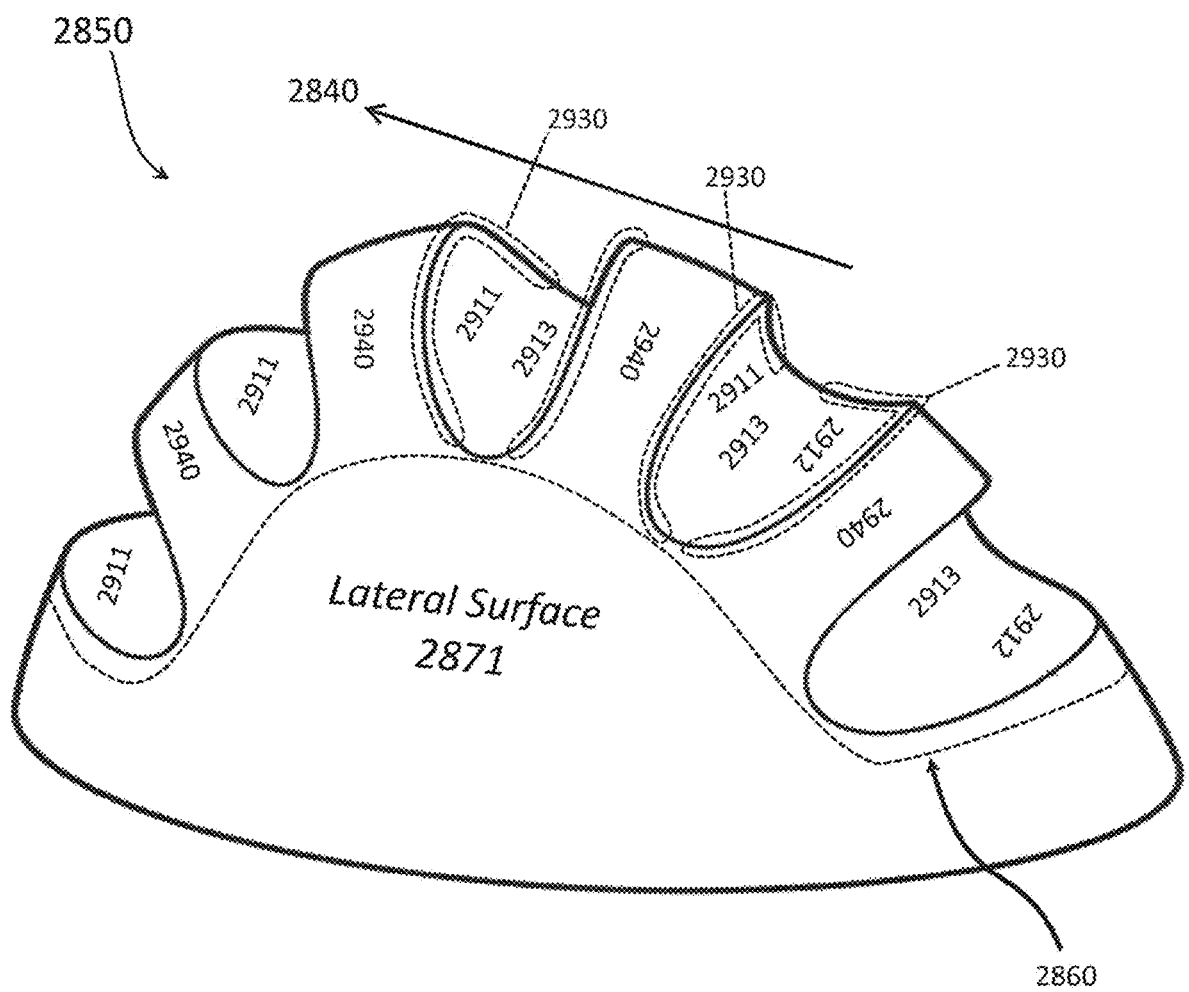
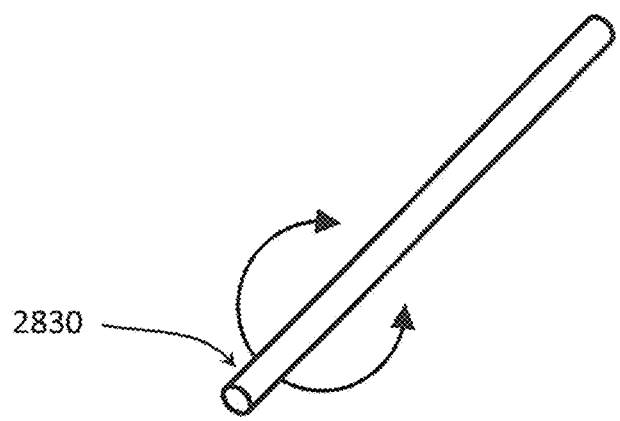

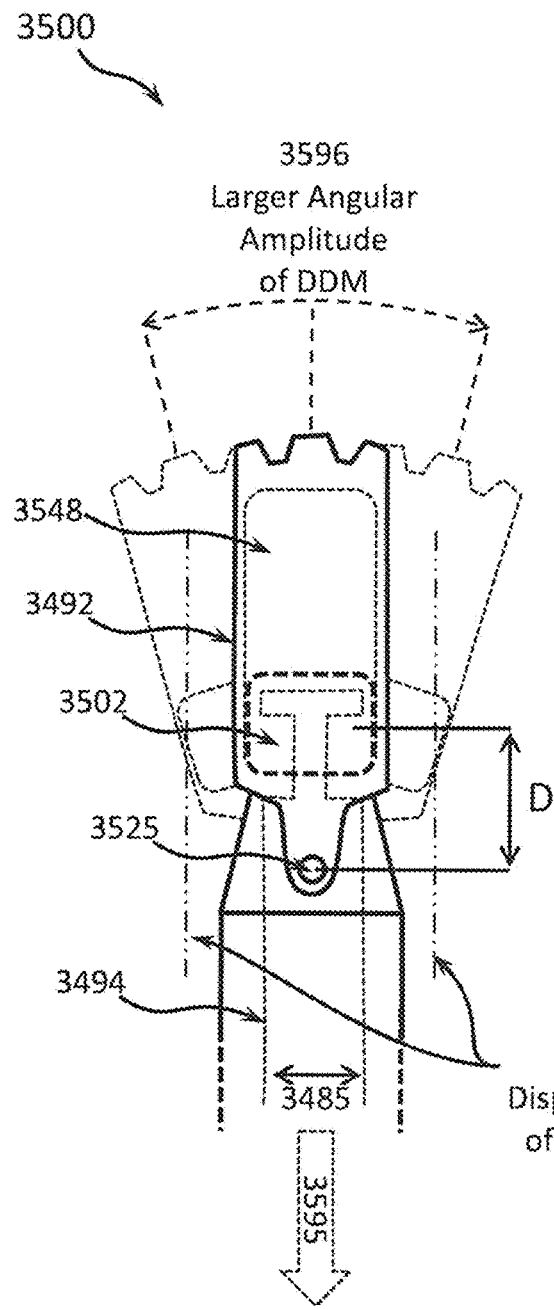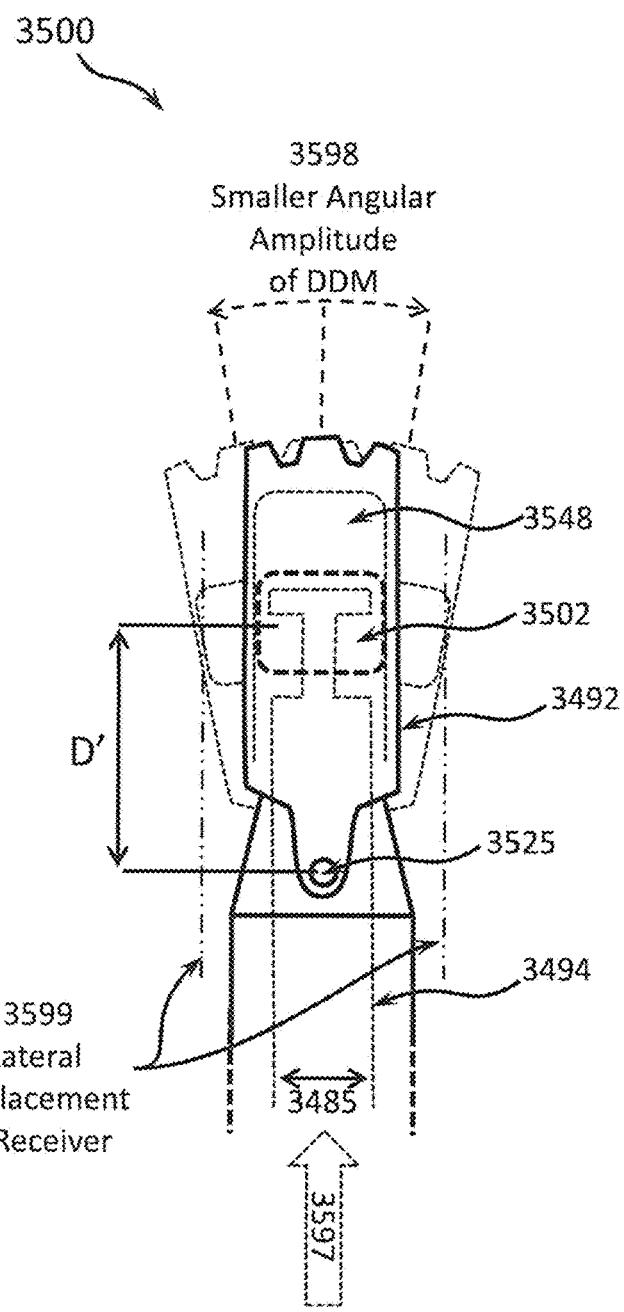

FIG. 36A-1
FIG. 36A-2
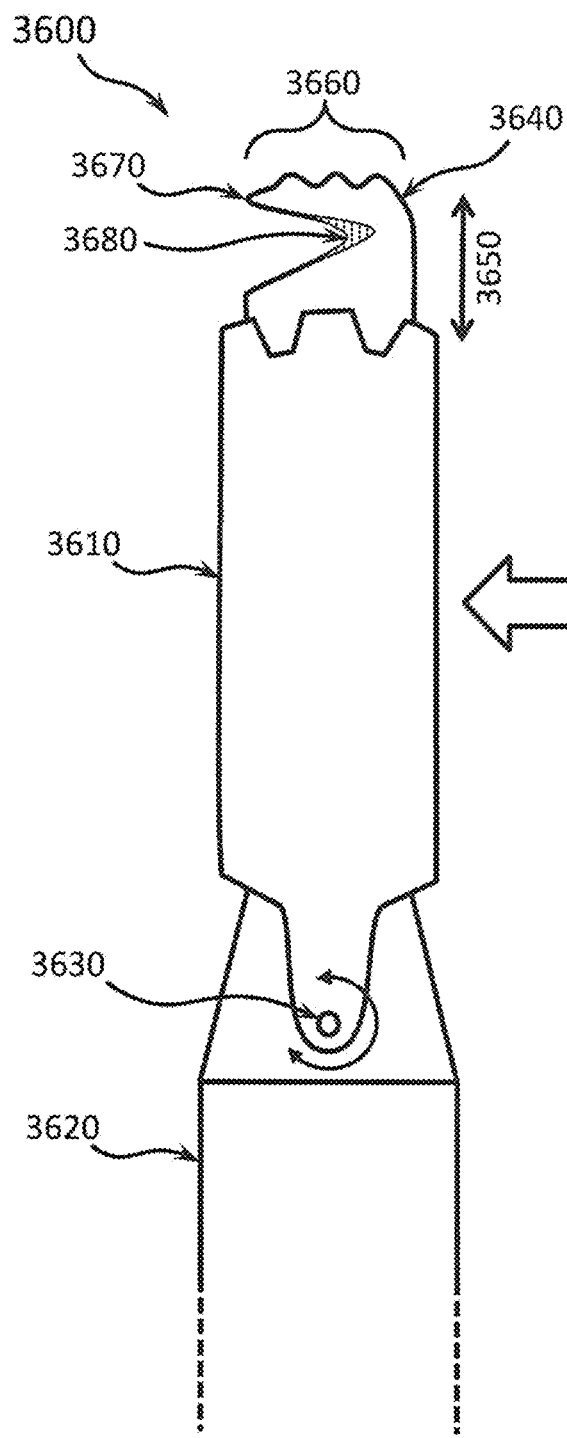
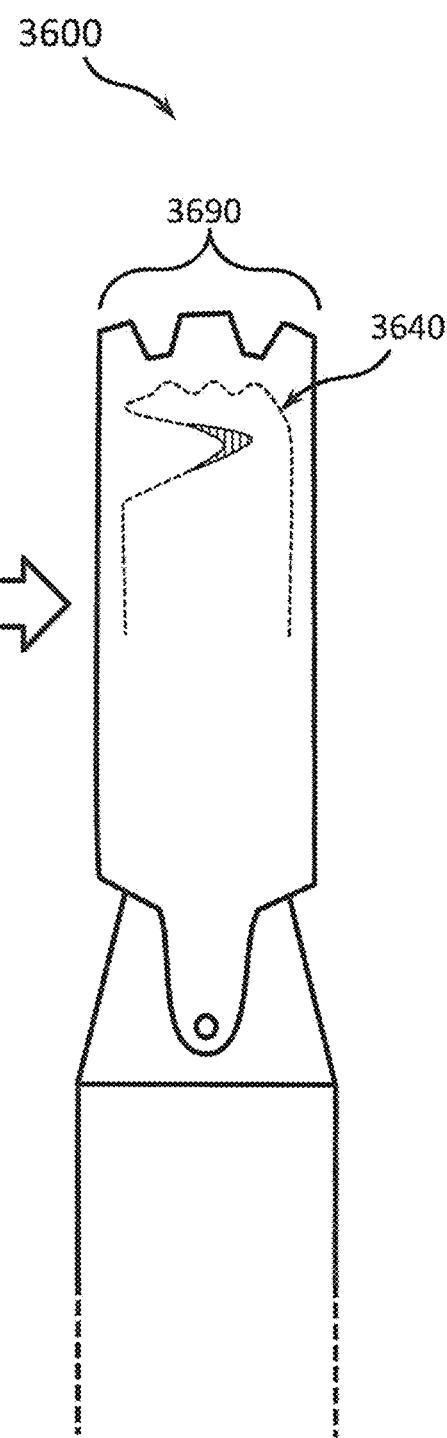

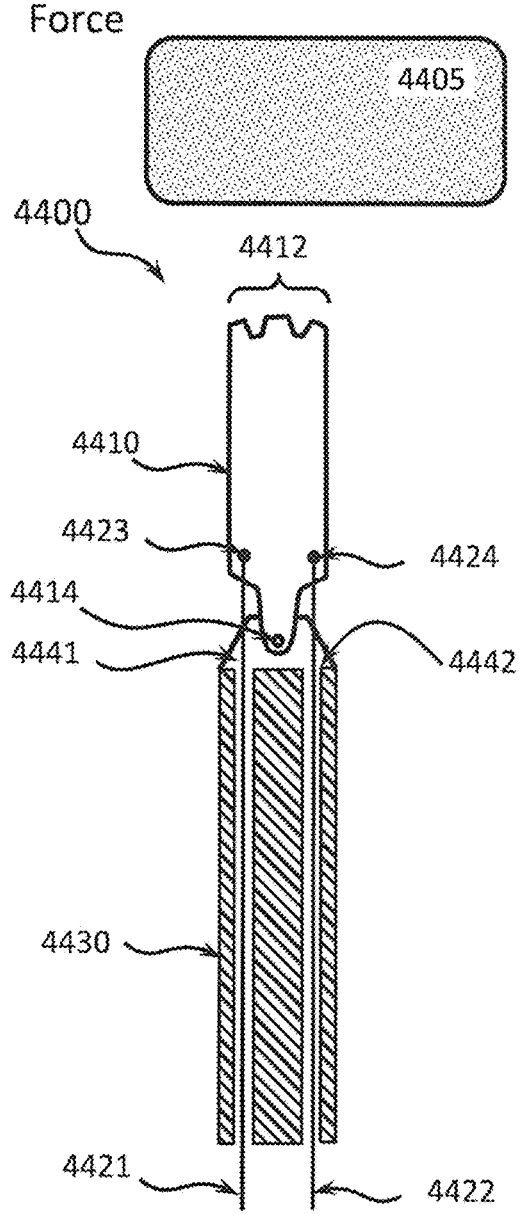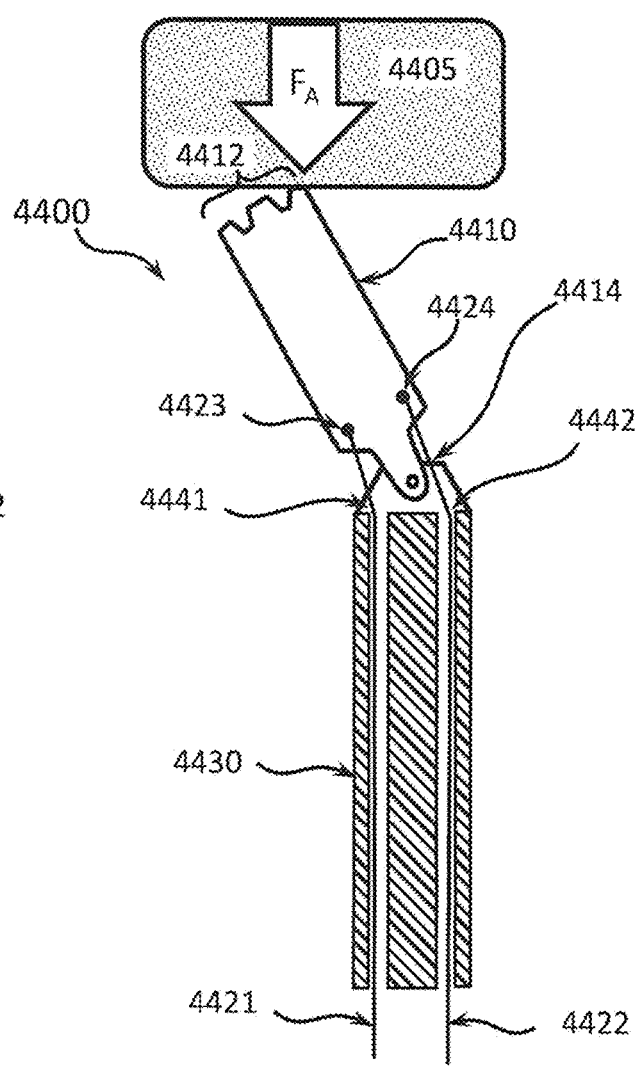
FIG. 44A-1
No External Force
FIG. 44A-2
External Force

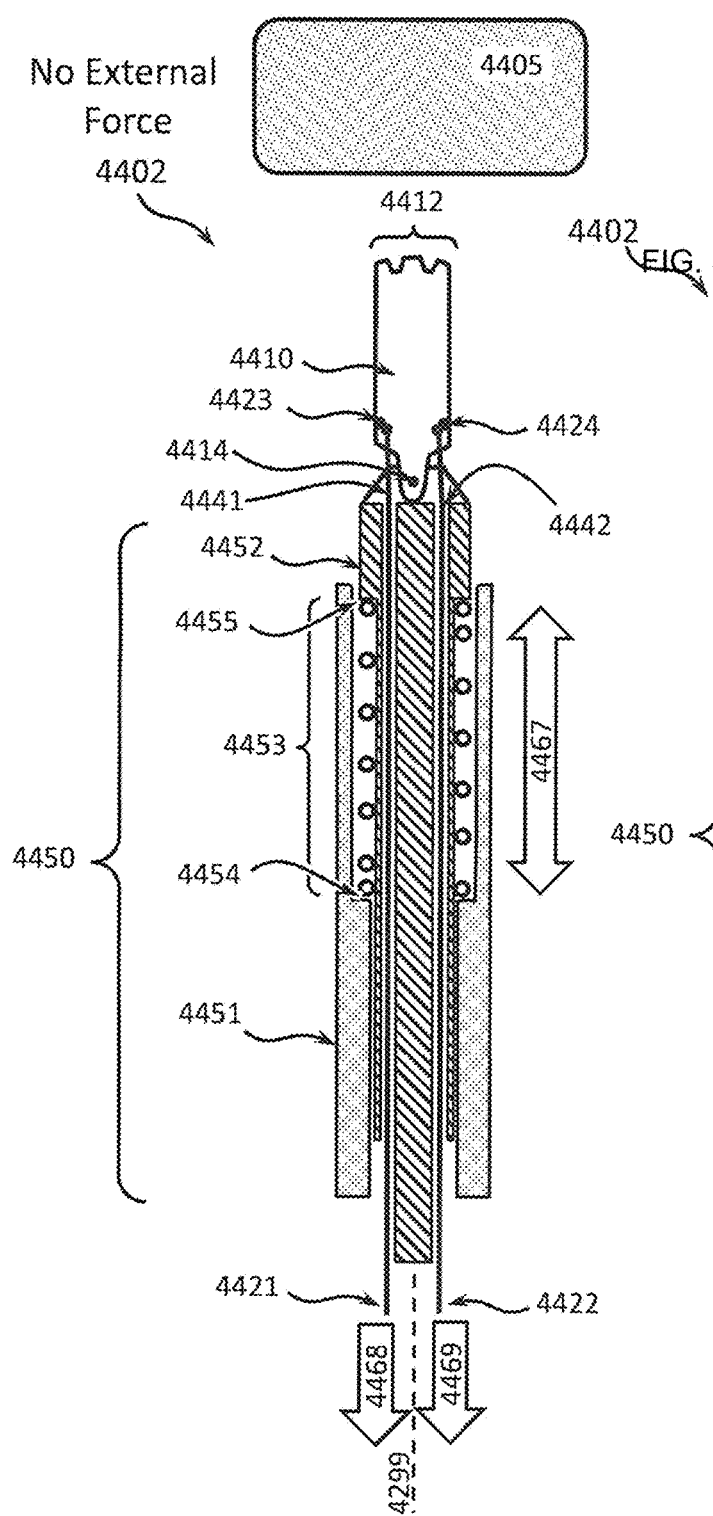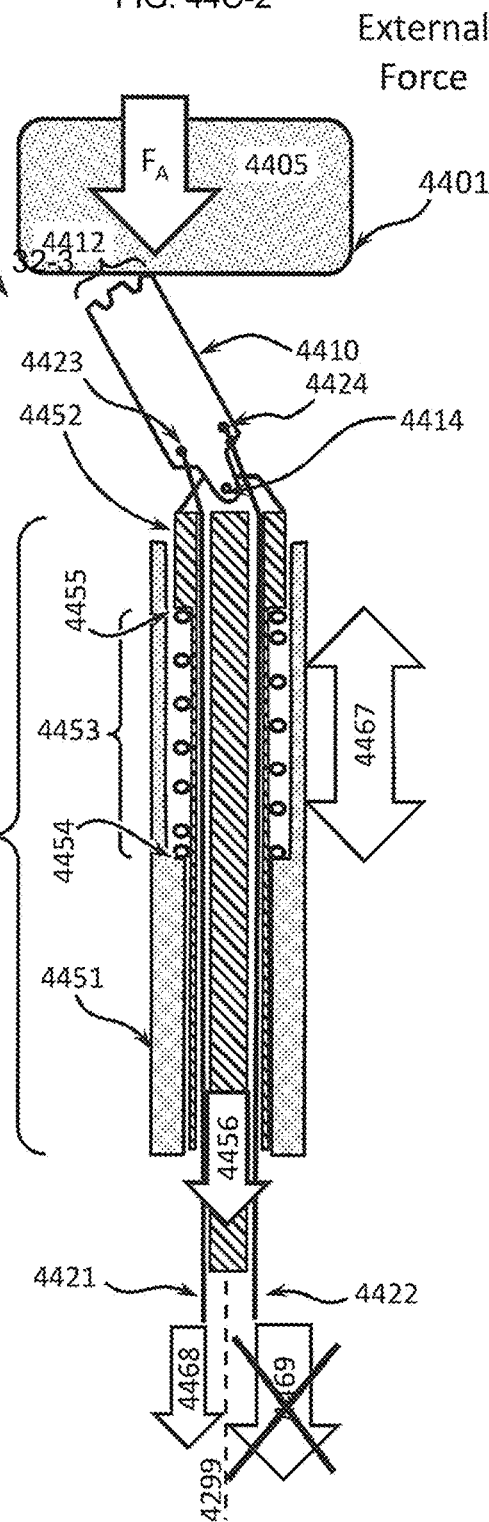

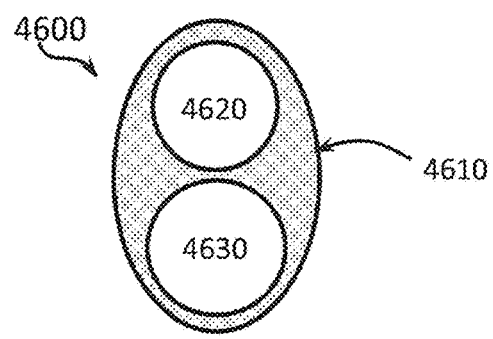
FIG. 46A-1 Front View
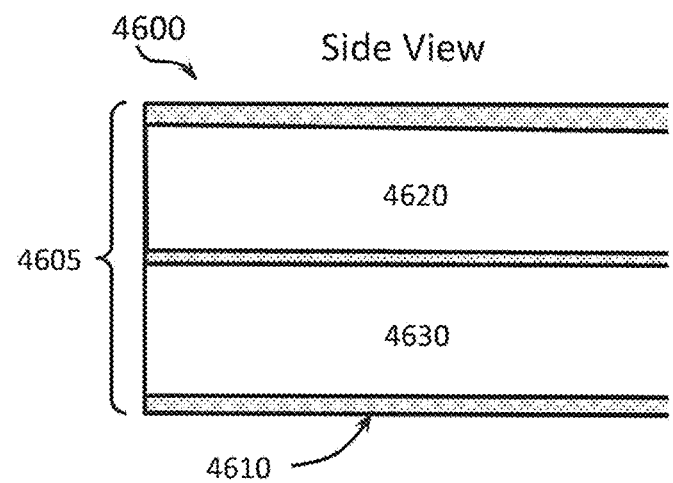
FIG. 46A-2 Side View
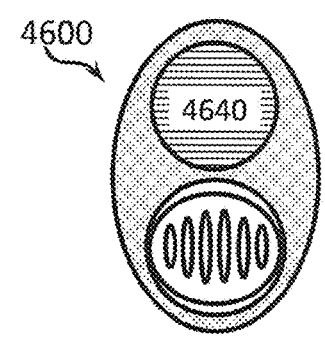
FIG. 46B-1 Front View
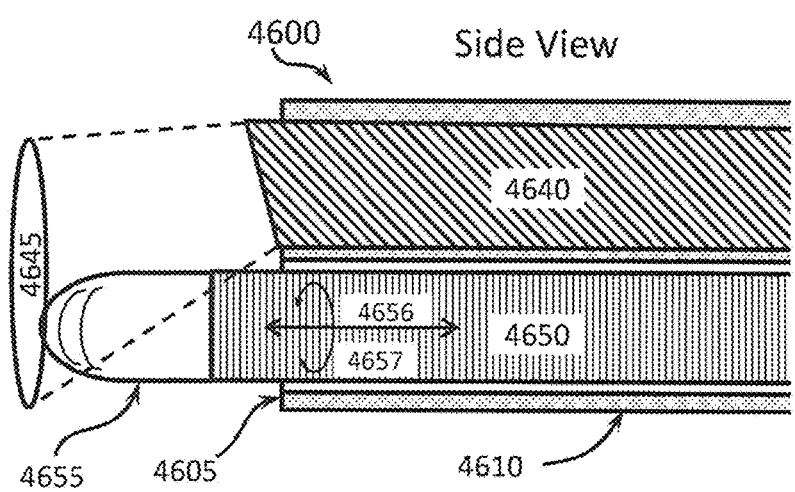
FIG. 46B-2 Side View
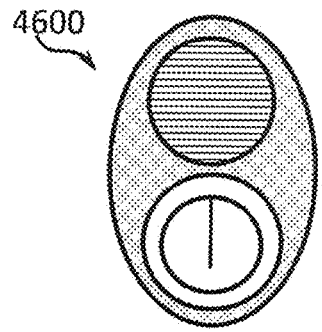
FIG. 46C-1 Front View
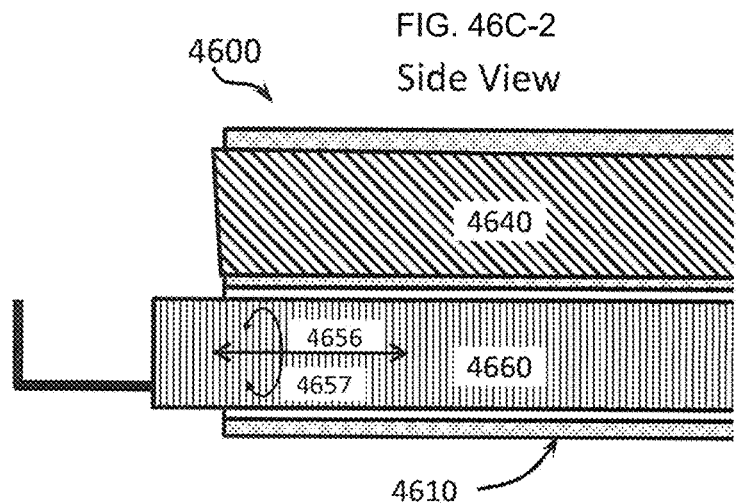
FIG. 46C-2 Side View Front View Side View Front View Side View

METHODS AND DEVICES FOR SOFT TISSUE DISSECTION

PRIORITY APPLICATIONS

The present application is a continuation of, and claims priority to, U.S. patent application Ser. No. 15/457,169, entitled "Methods and Devices for Soft Tissue Dissection," filed Mar. 13, 2017, which is a continuation of, and claims priority to, U.S. patent application Ser. No. 14/065,191, entitled "Methods and Devices for Soft Tissue Dissection," filed Oct. 28, 2013, now issued as U.S. Pat. No. 9,592,069, which is a continuation-in-part application of, and claims priority to, U.S. patent application Ser. No. 13/872,766, entitled "Methods and Devices for Soft Tissue Dissection," filed Apr. 29, 2013, now issued as U.S. Pat. No. 9,538,995, which claims priority to: U.S. Provisional Patent Application No. 61/687,587, entitled "Instrument for Soft Tissue Dissection," filed on Apr. 28, 2012; U.S. Provisional Patent Application No. 61/744,936, entitled "Instrument for Soft Tissue Dissection," filed on Oct. 6, 2012; and U.S. Provisional Patent Application No. 61/783,834, entitled "Instruments, Devices, and Related Methods for Soft Tissue Dissection," filed on Mar. 14, 2013, all of which are incorporated herein by reference in their entireties.

BACKGROUND

Field of the Disclosure

The field of the disclosure relates to methods or devices used to dissect tissue during surgery or other medical procedures.

Technical Background

Surgeons frequently are required to sever or separate tissues during a surgical procedure. Two techniques are commonly used: (1) "sharp dissection" in which the surgeon uses a cutting instrument to slice a tissue, cutting with either scissors, a scalpel, electrosurgery, or other slicing instrument and (2) blunt dissection.

The advantage of sharp dissection is that the cutting instrument easily cuts through any tissue. The cut itself is indiscriminate, slicing through any and all tissues to which the instrument is applied. This is also the disadvantage of sharp dissection, especially when trying to isolate a first tissue without damaging it, when the first tissue is embedded in and obscured by a second tissue or, more commonly, in many tissues. Accidental cutting of a blood vessel, a nerve, or of the bowel, for example, is not an uncommon occurrence for even the most experienced surgeons and can lead to serious, even life-threatening, intra-operative complications and can have prolonged consequences for the patient.

Isolation of a first tissue that is embedded in other tissues is thus frequently performed by blunt dissection. In blunt dissection, a blunt instrument is used to force through a tissue, to force apart two tissues, or to otherwise separate tissues by tearing rather than cutting. Almost all surgeries require blunt dissection of tissues to expose target structures, such as blood vessels to be ligated or nerve bundles to be avoided. Examples in thoracic surgery include isolation of blood vessels during hilar dissection for lobectomy and exposure of lymph nodes.

Blunt dissection includes a range of maneuvers, including various ways to tear soft tissues, such as the insertion of blunt probes or instruments, inverted action (i.e., spreading) of forceps, and pulling of tissues with forceps or by rubbing with a "swab dissector" (e.g. surgical gauze held in a forceps). When needed, sharp dissection is used judiciously to cut tissues that resist tearing during blunt dissection.

The general goal is to tear or otherwise disrupt tissue, such as membranes and mesenteries, away from the target structure without tearing or disrupting either the target structure or critical structures such as nearby vessels or nerves. The surgeon capitalizes on the different mechanical behaviors of tissues, such as the different stiffness of adjacent tissues or the existence of planes of softer tissue between firmer tissues. Frequently, the goal is to isolate a target tissue that is mechanically firm, being composed of more tightly packed fibrous components, and is embedded in a tissue that is mechanically soft, being composed of more loosely packed fibrous components (for example, loose networks of collagen, reticulin, and elastin). More tightly packed fibrous tissues include tissues composed of tightly packed collagen and other fibrous connective tissues, usually having highly organized anisotropic distributions of fibrous components, often with hierarchical composition. Examples include blood vessels, nerve sheaths, muscles, fascia, bladders, and tendons. More loosely packed fibrous tissues have a much lower number of fibers per unit volume or are composed of less well organized materials such as fat and mesenteries. Fibrous components include fibers, fibrils, filaments, and other filamentous components. When a tissue is referred to as "fibrous", the reference is typically to extracellular filamentous components, such as collagen and elastin—proteins that polymerize into linear structures of varying and diverse complexity to form the extracellular matrix. As mentioned in the previous paragraph, the density, orientation, and organization of fibrous components greatly determine the tissue's mechanical behavior. Sometimes, tissues are referred to as "tough, fibrous tissues" indicating that the fibrous or filamentous components are densely packed and comprise a significant fraction of the bulk of the tissue. However, all tissues are fibrous, to one extent or another, with fibers and other filamentous extracellular components being present in virtually every tissue.

What is important to the present discussion is that softer tissues tear more easily than firmer tissues, so blunt dissection attempts to proceed by exerting sufficient force to tear softer tissue but not firmer tissue.

Blunt dissection can be difficult and is often time-consuming. Judging the force to tear a soft tissue, but not a closely apposed firm tissue is not easy. Thus, blood vessels can be torn. Nerves can be stretched or torn. In response, surgeons attempt judicious sharp dissection, but blood vessels and nerves can be cut, especially a smaller side branch. This all leads to long, tedious dissections and increased risk of complications, like bleeding, air leaks from the lungs, and nerve damage.

Surgeons frequently use forceps for blunt dissection. FIGS. 1A and 1B show a typical forceps 10 of the prior art. FIG. 1A shows the forceps 10 in the closed position for clamping a tissue 34 between the opposing first clamp element 30 and second clamp element 31. FIG. 1B shows the forceps 10 in the open position, forcing tissue 34 apart. A first finger engager 20 and an opposing second finger engager 21 are used to actuate the mechanism. First finger engager 20 drives first clamp element 30, and second finger engager 21 drives second clamp element 31. A pivot 40 attaches the first clamp element 30 and the second clamp element 31, permitting a scissor-like action to force the first clamp element 30 and the second clamp element 31 together or apart, thereby clamping tissue 34 between the two clamp surfaces 35 and 36 or rending tissue 34 by the spreading of the first clamp element 30 and the second clamp element 31. Frequently, a ratcheting clasp 50 is used to lock the first clamp element 30 and the second clamp element 31 together.

Laparoscopic and thoracoscopic (collectively referred here as "endoscopic") instruments use a similar action. FIG. 2 shows an example of an endoscopic forceps 110 of the prior art. A first finger engager 120 and an opposing second finger engager 121 are used to actuate the mechanism. First finger engager 120 is rigidly mounted to the instrument body 150. Second finger engager 121 drives opposing clamp elements 130 and 131. A pivot 140 attaches the two clamp elements 130 and 131, such that actuation of second finger engager 121 forces clamp elements 130 and 131 together, thereby clamping a tissue between two clamp surfaces 135 and 136. As in FIG. 1, endoscopic forceps 110 can be used to force a tissue apart. Clamp elements 130 and 131 are closed, inserted into a tissue, and then opened to tear the tissue.

For either instrument, forceps 10 or endoscopic forceps 110, a surgeon performs blunt dissection by closing the forceps, pushing the closed forceps into a tissue and then, optionally, opening the forceps inside the tissue, using the force applied by opening of the jaws of the forceps to tear the tissue apart. A surgeon thus proceeds to dissect a tissue by a combination of pushing into the tissue and opening the jaws of the forceps.

Blunt dissection is commonly used for wet and slick tissues, and the smooth, passive surfaces of most surgical instruments slide easily along the tissue, impairing the instrument's ability to gain purchase and separate the tissue. Furthermore, the surgeon has only limited control, being able only to jab, move sideways, or separate. An improved instrument for blunt dissection that could differentially separate soft tissues while not disrupting firm tissues would greatly facilitate many surgeries.

SUMMARY OF THE DETAILED DESCRIPTION

Embodiments disclosed include methods and devices for blunt dissection, which differentially disrupt a patient's soft tissues while not disrupting that patient's firm tissues. In one embodiment, a differential dissecting instrument for differentially dissecting complex tissue is disclosed. The differential dissecting instrument comprises a handle, a central longitudinal axis, and an elongate member having a proximal end and a distal end. The differential dissecting instrument also comprises a differential dissecting member configured to be rotatably attached to the distal end, the differential dissecting member comprising at least one tissue engaging surface, a first torque-point, the first torque-point disposed to a first side of the axis of rotation of the differential dissecting member, and a mechanism, configured to mechanically rotate the differential dissecting member around the axis of rotation thereby causing the at least one tissue engaging surface to move in at least one direction against the complex tissue. The mechanism comprises at least one force-transmitting member possessing a distal end and a proximal end, the distal end being attached to the first torque-point member. The proximal end of the at least one force-transmitting member is attached to a motive source configured to oscillate the differential dissecting member. Further, the at least one tissue engaging surface is configured to selectively engage the complex tissue such that when the differential dissecting member is pressed by the surgeon into the patient's complex tissue, the at least one tissue engaging surface moves across the complex tissue and the at least one tissue engaging surface disrupts at least one soft tissue in the complex tissue, but does not disrupt firm tissue in the complex tissue.

BRIEF DESCRIPTION OF THE FIGURES

FIG. 1A shows forceps used to grasp tissue;

FIG. 1B shows exemplary forceps used in blunt dissection to divide tissue;

FIG. 3A through 3F-2 show an exemplary differential dissecting instrument. FIGS. 3A through 3C show a differential dissecting instrument having a rotating differential dissecting member within a shroud. FIG. 3D-1 through 3D-3 show front and side views of a differential dissecting member; FIG. 3D-1 is a side view of a differential dissecting member, while FIG. 3D-2 depicts a close-up of the surface of the differential dissecting member, and FIG. 3D-3 shows a front view of that same differential dissecting member. FIG. 3E-1 through FIG. 3E-4 show four different types of differential dissecting members, differential dissecting member type I, type II, type III, and type IV, respectively. FIG. 3F-1 and FIG. 3F-2 show a differential dissecting member in front and side view, respectively, including a tissue to be dissected;

FIGS. 4D through 4F illustrate how a differential dissecting member engages and disrupts tissues having dispersed fibrous components but is unable to engage, and thus disrupt, fibrous components;

FIGS. 5A through 5C-2 show the tissue engaging end of different exemplary differential dissecting instruments comprising a dissecting wheel mounted in a shroud. FIGS. 5A through 5B show an instrument with one configuration of a dissecting wheel and FIG. 5C-1 and FIG. 5C-2 show another instrument with a different configuration of a dissecting wheel; FIG. 5C-1 depict the dissecting wheel in exploded view away from the instrument, while FIG. 5C-2 shows the dissecting wheel in place;

FIGS. 8A through 8C show an exemplary differential dissecting instrument that uses a flexible belt as a differential dissecting member;

FIG. 14-1 through FIG. 14-3 show how the elongate member of an exemplary differential dissecting instrument can be articulated with a bendable region to facilitate placement of the differential dissecting member; FIG. 14-1 depicts the elongate member of the differential dissecting instrument in Position 1, straight, FIG. 14-2 shows the elongate member of the differential dissecting instrument bent at 45 degrees, and FIG. 14-3 illustrates the elongate member of the differential dissecting instrument bent at 90 degrees;

FIGS. 15A through 15E-3 show different exemplary differential dissecting members illustrating several important dimensions and features of differential dissecting members; FIG. 15A shows a top view of an exemplary differential dissecting member that rotates about a rotational joint; further, FIG. 15B-1 through 15B-3 depict a differential dissecting member as in FIG. 15A; FIG. 15B-1 shows the differential dissecting member in side view cross-section, FIG. 15B-2 depicts a close-up view of the tip of the differential dissecting member shown in FIG. 15B-1, and FIG. 15B-3 shows a close-up view of the surface of the differential dissecting member shown in FIG. 15B-2; FIG. 15C illustrates another embodiment of a differential dissecting member having a scalloped tissue engaging surface; FIG. 15D shows an oblique view of the differential dissecting member depicted in FIG. 15C; FIG. 15E-1 illustrates an end-on view of the differential dissecting member depicted in FIG. 15C, FIG. 15E-2 depicts a close-up view of the tissue-engaging surface of the differential dissecting member shown in FIG. 15E-1, and FIG. 15E-3 details a very close-up view of the surface features of the differential dissecting member shown in FIG. 15E-1 and FIG. 15E-2;

FIG. 16-1 through FIG. 16-3 show one exemplary means for changing the level of aggressiveness of a differential dissecting member; FIG. 16-1 shows a differential dissecting member with some pointed, but still-not-sharp features, FIG. 16-2 shows a differential dissecting member with more rounded features than shown in FIG. 16-1, and FIG. 16-3 shows a differential dissecting member with even more blunt features than those differential dissecting members shown in FIG. 16-1 or FIG. 16-2;

FIG. 17A, FIGS. 17B-1, and 17B-2 show how features, such as scalloping, of the tissue engaging surface result in the tissue engaging surface having varying angles of attack as it moves over a tissue; FIG. 17A depicts a differential dissecting member with a lobate form, FIG. 17B-1 shows that same differential dissecting member impinging on a tissue, and FIG. 17B-2 is a close-up view of the lobes of the lobate differential dissecting member detailing the angles of attack of the tissue engaging surface with respect to the tissue;

FIG. 19D illustrates how this strain can align fibrous components inside the tissue, thereby facilitating their disruption by the tissue engaging surface;

FIGS. 21A through 21C-4 show how relative movement of the shroud and the differential dissecting member of a differential dissecting instrument vary the wedge angle and thus can produce more or less strain in a tissue; FIG. 21A shows a side view of a differential dissecting member that has a thin dissecting wheel and is wrapped in a shroud; FIG. 21B-1 and FIG. 21B-2 further illustrate a front view of the shrouded differential dissecting member in FIG. 21A and a close-up view of same, respectively; FIG. 21C-1 through FIG. 21C-4 show four different positions of a shroud covering the differential dissecting member of the differential dissecting instrument;

FIGS. 23A through 23C further illustrate the scotch yoke mechanism shown in FIG. 22;

FIGS. 25A through 25D further illustrate the scotch yoke mechanism shown in FIG. 22, including how more of the differential dissecting member can be shrouded to reduce trauma to a patient's tissues. FIGS. 25A through 25C show a profile view of an embodiment of a largely shrouded differential dissecting member assembly comprising a differential dissecting member that reciprocates about a shrouded pivot shaft, wherein FIG. 25A shows the differential dissecting member in a first position, FIG. 25B shows the differential dissecting member rotated in a first direction about the shrouded pivot shaft, and FIG. 25C shows the differential dissecting member rotated in a second direction about the shrouded pivot shaft. FIG. 25D depicts an oblique view of the largely shrouded differential dissecting member assembly of FIGS. 25A-25C;

FIG. 26A-1, FIG. 26A-2, FIGS. 26B-1, and 26B-2 show how an exemplary differential dissecting member can be fitted with retractable blade to permit a differential dissecting instrument to also perform sharp dissection of tissues; FIG. 26A-1 and FIG. 26B-1 show side views while FIG. 26A-2 and FIG. 26B-2 show top views; FIG. 26A-1 and FIG. 26A-2 show the differential dissecting member with a retractable scalpel withdrawn, while FIG. 26B-1 and FIG. 26B-2 show the same differential dissecting member with the retractable scalpel extended;

FIGS. 27A and 27B show how an exemplary differential dissecting member can be fitted with a clasping member to permit a differential dissecting instrument to act as forceps;

FIGS. 29A through 29E-2 show magnified views of the tissue engaging surface and lateral surfaces of the differential dissecting member in FIG. 28 with the tissue engaging surface being comprised of an alternating series of valleys and projections; FIG. 29C-2 depicts a close-up of the corner of a projection shown in FIG. 29C-1; FIG. 29E-1 and FIG. 29E-2 show two alternative versions of arrangements of valleys and projections forming the surface of a differential dissecting member;

FIGS. 35A through 35C-2 show an enlarged view of the differential dissecting member of the differential dissecting instrument in FIG. 34, including how this mechanism can also be used to vary the amplitude of oscillation of the differential dissecting member; FIG. 35A shows an exploded view of an exemplary Differential Dissecting Instrument; FIG. 35B depicts the details of assembly of an exemplary differential dissecting member; FIG. 35C-1 and FIG. 35C-2 depict how the angular amplitude of a differential dissecting member can be controlled via the longitudinal position of the cam receiver body;

FIGS. 36A-1, 36A-2, 36B-1, 36B-2, 36B-3, and 36B-4 show an exemplary retractable blade that is a retractable hook having a more aggressive tissue engaging surface plus a hook with a sharpened elbow permitting selective slicing of tissue for sharp dissection; FIG. 36A-1 depicts the hook extended from the differential dissecting member, FIG. 36A-2 shows it retracted into the differential dissecting member; FIGS. 36B-1 and 36B-2 show the hook extended, and FIGS. 36B-3 and 36B-4 show the hook retracted; FIG. 36B-1 and FIG. 36B-3 depict the differential dissecting member in static position, while FIG. 36B-2 and FIG. 36B-4 show the differential dissecting member actively oscillating;

FIGS. 37-1, 37-2, 37-3, and 37-4 illustrate how the retractable hook shown in FIGS. 36A and 36B can be used to quickly and safely divide a membranous structure, like the peritoneum; FIG. 37-1 shows the hook extended from the tip of a static differential dissecting member while the differential dissecting instrument is suspended by the surgeon above a patient's tissue, FIG. 37-2 depicts the hook extended from the oscillating differential dissecting member and so oscillating against the surface of the tissue, FIG. 37-3 shows the static differential dissecting member with extended hook engaging the edge of a tissue capsule, and FIG. 37-4 depicts the differential dissecting member oscillating with extended hook, so cutting the tissue capsule layer;

FIGS. 40-1 and 40-2 show an exemplary laparoscopic version of a differential dissecting instrument having electromechanical actuators distal to an articulation[[;]], and in the straight and bent positions, respectively;

FIGS. 44A-1 through 44C-2 show different embodiments of mechanisms that protect a both a differential dissecting instrument and a tissue being dissected from excessive loading;

FIGS. 46A-1, 46A-2, 46B-1, 46B-2, 46C-1, and 46C-2 show an instrument for tunneling with a differential dissecting instrument coupled with an endoscope; and FIGS. 47A-1 through 47D show another instrument for tunneling with a differential dissecting instrument coupled with an endoscope and including accessory components to enhance dissection and to improve the field of view for the endoscope. FIGS. 47A-1 and 47A-2 show front and side views, respectively, of a distal end of a dissecting system according to one embodiment that includes an inflatable annular balloon. FIGS. 47B-1 and 47B-2 show front and side views, respectively, of the dissecting system of FIGS. 47A-1 and 47A-2, with the balloon inflated. FIG. 47D shows a side view of an exemplary dissecting system with an attached insufflation system.

DETAILED DESCRIPTION

Figure 1A:
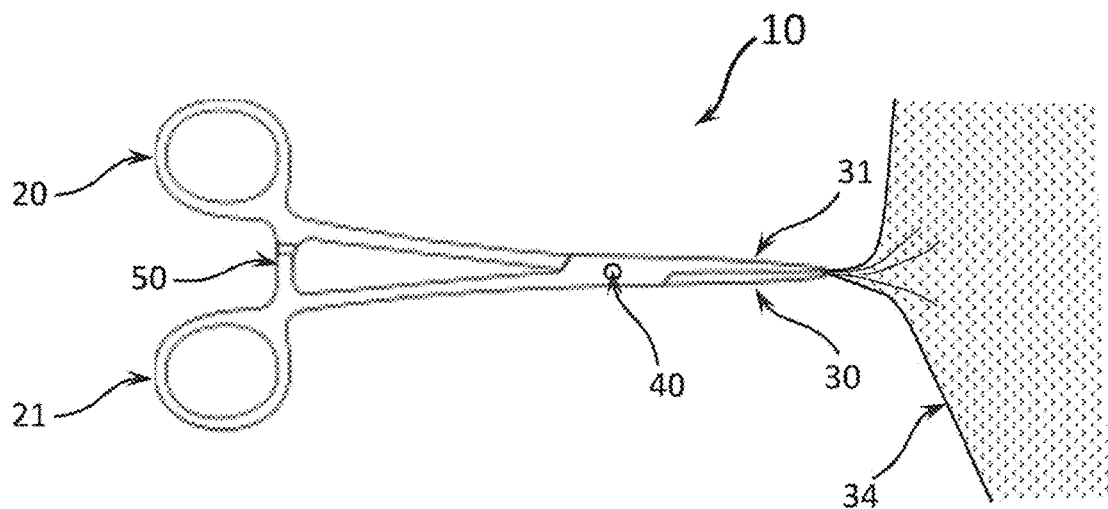
FIGS. 1A and 1B show examples of the prior art.
Figure 1B:
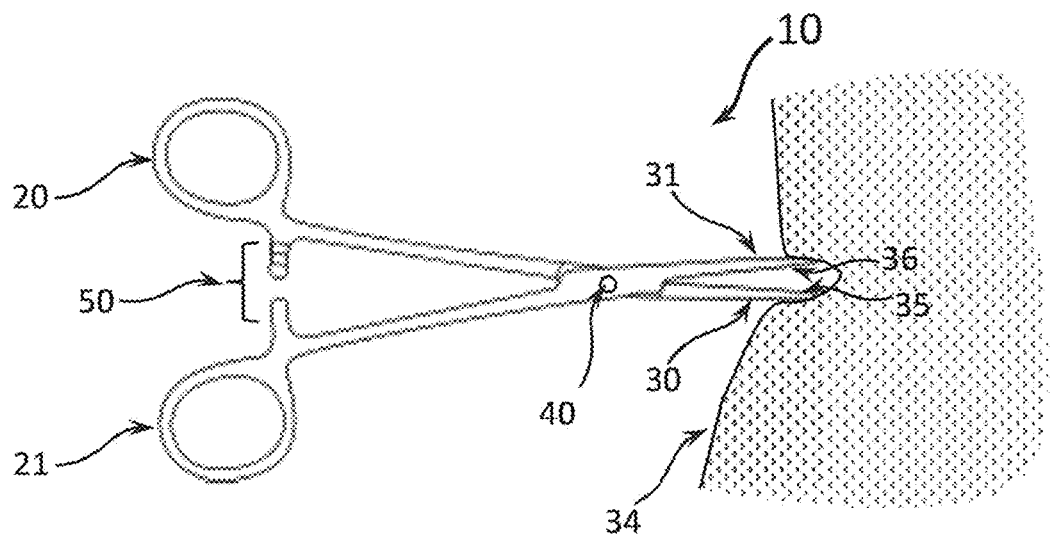

Embodiments disclosed include methods and devices for blunt dissection, which differentially disrupt a patient's soft tissues while not disrupting that patient's firm tissues. In one embodiment, a differential dissecting instrument for differentially dissecting complex tissue is disclosed. The differential dissecting instrument comprises a handle, a central longitudinal axis, and an elongate member having a proximal end and a distal end. The differential dissecting instrument also comprises a differential dissecting member configured to be rotatably attached to the distal end, the differential dissecting member comprising at least one tissue engaging surface, a first torque-point, the first torque-point disposed to a first side of the axis of rotation of the differential dissecting member, and a mechanism, configured to mechanically rotate the differential dissecting member around the axis of rotation thereby causing the at least one tissue engaging surface to move in at least one direction against the complex tissue. The mechanism comprises at least one force-transmitting member possessing a distal end and a proximal end, the distal end being attached to the first torque-point member. The proximal end of the at least one force-transmitting member is attached to a motive source configured to oscillate the differential dissecting member. Further, the at least one tissue engaging surface is configured to selectively engage the complex tissue such that when the differential dissecting member is pressed by the surgeon into the patient's complex tissue, the at least one tissue engaging surface moves across the complex tissue and the at least one tissue engaging surface disrupts at least one soft tissue in the complex tissue, but does not disrupt firm tissue in the complex tissue.

Specifically, "Differential Dissecting Instruments" are disclosed. The term "differential" is used because a Differential Dissecting Instrument can disrupt Soft Tissue while avoiding disruption of Firm Tissue. The effector end of a Differential Dissecting Instrument can be pressed against a tissue comprised of both Firm Tissue and Soft Tissue, and the Soft Tissue is disrupted far more readily than the Firm Tissue. Thus, when a Differential Dissecting Instrument is pressed into a Complex Tissue, the Differential Dissecting Instrument disrupts Soft Tissue, thereby exposing Firm Tissues. This differential action is automatic—a function of the device's design. Far less attention is required of an operator than traditional methods for blunt dissection, and risk of accidental damage to tissues is greatly reduced.

For the purposes of this application, "Soft Tissue" is defined as the various softer tissues separated, torn, removed, or otherwise typically disrupted during blunt dissection. "Target Tissue" is defined as the tissue to be isolated and its integrity preserved during blunt dissection, such as a blood vessel, gall bladder, urethra, or nerve bundle. "Firm Tissue" is defined as tissue that is mechanically stronger, usually including one or more layers of tightly packed collagen or other extracellular fibrous matrices. Examples of Firm Tissues include the walls of blood vessels, the sheaths of nerve fibers, fascia, tendons, ligaments, bladders, pericardium, and many others. A "Complex Tissue" is a tissue composed of both Soft Tissue and Firm Tissue and can contain a Target Tissue.

Figure 3A:
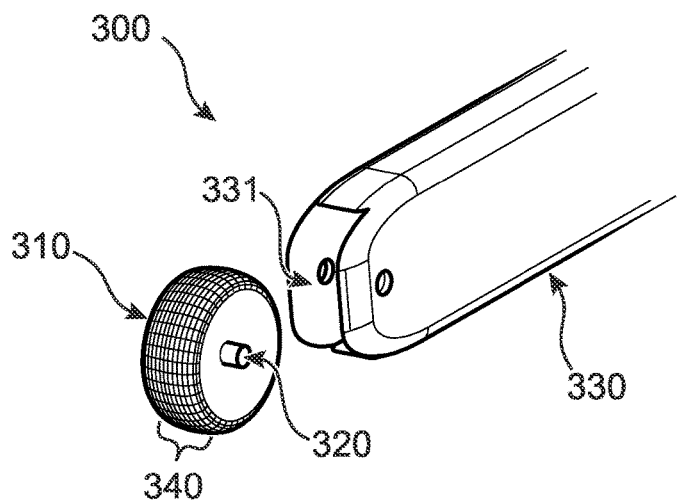
Figure 3B:
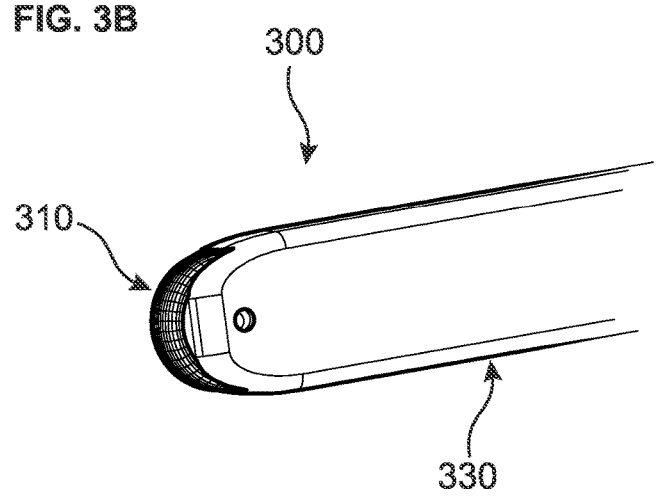
Figure 3C:
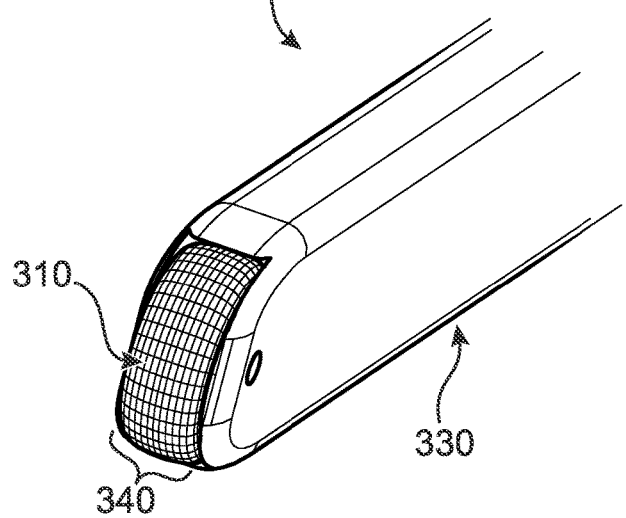

FIGS. 3A, 3B, and 3C show the effector end of a Differential Dissecting Instrument 300 that can differentially disrupt Soft Tissue while not disrupting Firm Tissues. In this embodiment, a dissecting member comprises a dissecting wheel 310 that rotates around shaft 320 that is held inside cavity 331 inside shroud 330. FIG. 3A shows the separate parts. FIGS. 3B and 3C show two different views of the assembly. The dissecting wheel 310 is turned by any of several mechanisms, such as a motor or a manually driven drive with appropriate means of transmission. Dissecting wheel 310 has tissue engaging surface 340 that can grab and disrupt Soft Tissue but not Firm Tissue. Examples of tissue engaging surface 340 and dissecting wheel 310 include a diamond grinding wheel or an abrasive stone or a surface otherwise covered by small obtrusions or projections (further defined below) from the surface. Shroud 330 obscures portions of dissecting wheel 310 such that only one portion of dissecting wheel 310 is exposed. In use, dissecting wheel 310 rotates at a speed ranging from approximately sixty (60) to approximately twenty-five thousand (25,000) rpm or from approximately sixty (60) to approximately one hundred thousand (100,000) rpm, with speed being operator selectable. Additionally, the direction of rotation of dissecting wheel 310 can be reversed by the operator. Alternately, dissecting wheel 310 can oscillate (reciprocal oscillation) with a frequency ranging from about sixty 60 to approximately twenty thousand (20,000) cycles per minute in one embodiment. In another embodiment, the dissecting wheel 310 can oscillate (reciprocal oscillation) with a frequency ranging from about 2,000 to 1,000,000 cycles per minute.

Dissecting wheel 310 is one example of a "Differential Dissecting Member" (hereinafter "DDM") that can differentially disrupt Soft Tissue but not Firm Tissue. FIG. 3D shows side, front, and oblique views of one embodiment of a DDM 350 that has been separated from the rest of the Differential Dissecting Instrument 300 for clarity. DDM 350 is comprised of a body 360 having an axis of rotation 365 about which body 360 rotates. Rotation can be oscillatory (i.e. back-and-forth) or continuous. Body 360 has an outer surface 361 with a tissue engaging surface 370 distributed over at least a portion of the outer surface 361 of body 360. Non-tissue engaging surface 371 is the portion of outer surface 361 not covered by tissue engaging surface 370. In this embodiment, no portion of outer surface 361 that contacts a tissue, and especially tissue engaging surface 370, should have features that are sufficiently sharp to slice tissue, so there should be no knife edges (like a scalpel or scissors), no sharply pointed teeth (like a saw), no sharp corners, and no sharp-edged fluting (like a drill bit or an arthroscopic shaver), where sharp means possessing a radius of curvature less than 25 μm. Typical maximum dimensions of a DDM are between approximately three (3) and approximately twenty (20) millimeters (mm). Alternatively, a small version for microsurgery can measure between approximately two (2) and approximately five (5) mm.

The tissue engaging surface 370 is further comprised of a plurality of projections 375 (shown in expanded detail view of FIGS. 3D-1 through 3D-3) from the outer surface 361 of body 360, each projection 375 having a projection length 380 measured from trough to peak in a direction substantially perpendicular to that local region of outer surface 361 of body 360. Different projections 375 on tissue engaging surface 370 can all have the same projection length 380, or they can have different projection lengths 380. Projections 375 preferably have a projection length 380 less than approximately one (1) mm. Alternatively, for some embodiments the projection length can be greater than approximately one (1) mm but less than approximately five (5) mm. Collectively, all projections 375 on a tissue engaging surface 370 have an average projection length ($P_{avg}$). Projections 375 are separated by gaps 385, preferably spanning a distance of approximately 0.1 mm to approximately ten (10) mm.

Figure 2:
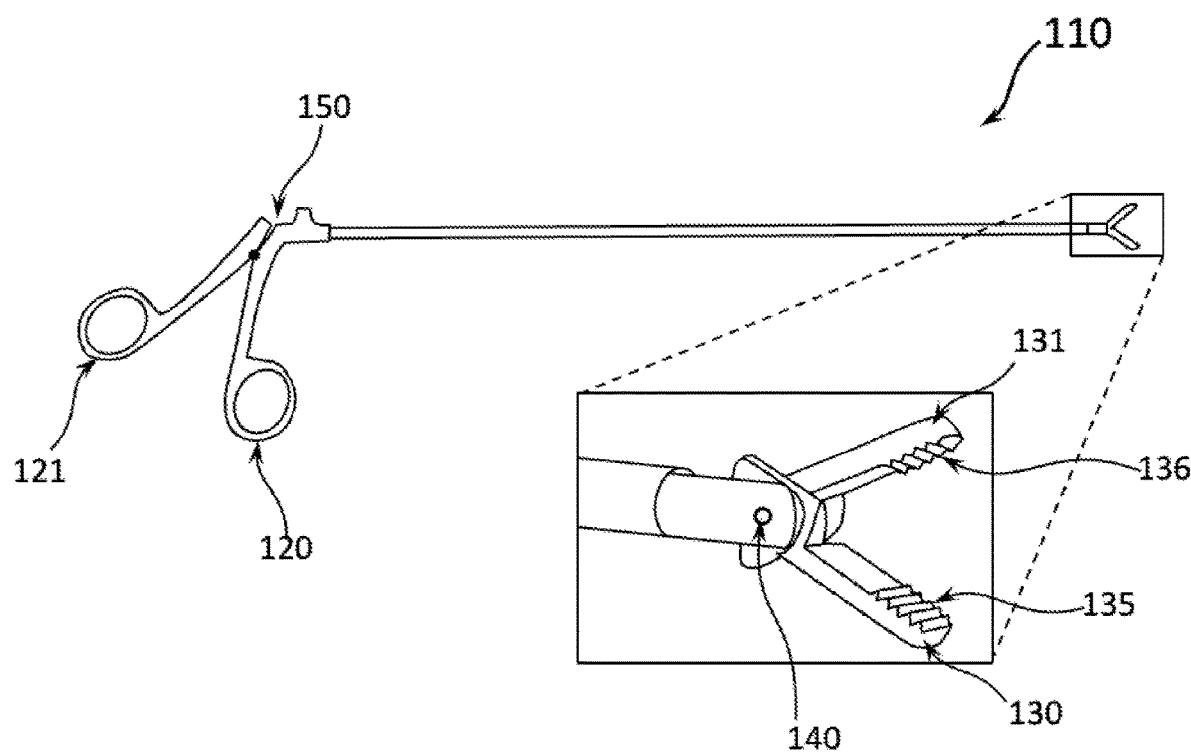
FIG. 2 shows laparoscopic forceps of the prior art.
Figures 1, 3E:
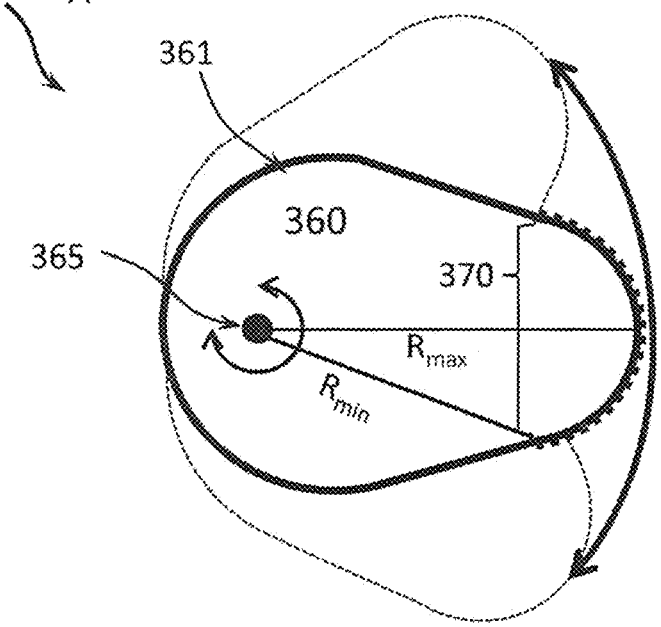
Figures 2, 3E:
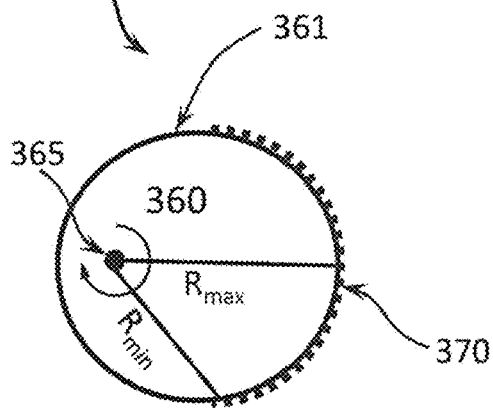
Figures 3, 3E:
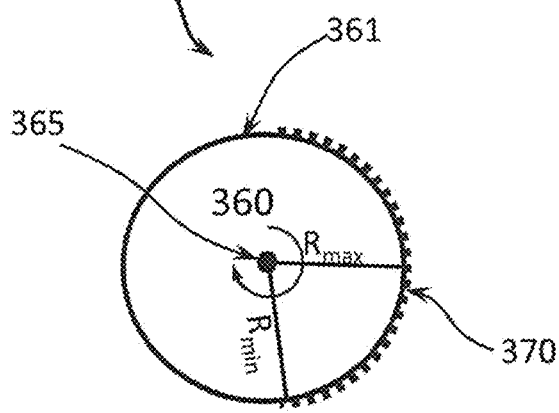

Referring now to FIGS. 3D-1 through 3D-3, FIG. 3D-1 through 3D-3 show front and side views of a differential dissecting member. FIG. 3D-1 is a side view of a differential dissecting member, while FIG. 3D-2 depicts a close-up of the surface of the differential dissecting member, and FIG. 3D-3 shows a front view of that same differential dissecting member. Body 360 of FIGS. 3D-1 through 3D-3 can optionally be shaped such that tissue engaging surface 370 is located at varying distances from the axis of rotation 365. Thus, a placement radius R can be measured in a plane perpendicular to the axis of rotation 365 from the axis of rotation 365 to any point on tissue engaging surface 370. There will thus be a minimum placement radius $R_{min}$ having the shortest length and a maximum placement radius $R_{max}$ having the longest length, and as shown in FIGS. 3D-1 through 3D-3 and 3E-1 through 3E-4, $R_{min}$ is greater than zero whenever the tissue engaging surface 370 does not completely cover the surface 361 of the DDM 350. Thus, if body 360 is shaped such that tissue engaging surface 370 is located at varying distances from the axis of rotation 365, then ($R_{max}$–Rmin) will be greater than zero. In some embodiments of a DDM, this relationship ($R_{max}$–$R_{min}$) is greater than approximately one (1) mm. In other embodiments this relationship ($R_{max}$–$R_{min}$) is greater than $P_{avg}$. Alternatively, as shown in the examples in FIG. 3D-1 through 3D-3 and FIG. 3E-1 through 3E-4, $R_{min}$ is typically at least 5% shorter than $R_{max}$. Typical sizes for a DDM are $R_{min}$>approximately one (1) mm and $R_{max}$<approximately fifty (50) mm; however, smaller versions for microscopic dissections can have smaller dimensions of $R_{min}$>approximately 0.5 mm and $R_{max}$<approximately five (5) mm.

Referring now to FIGS. 3E-1 through 3E-4, four different embodiments of a DDM are shown in side view, with the axis of rotation 365 being perpendicular to the plane of the page. The cross-sectional profile of a DDM in a plane perpendicular to the axis of rotation 365 is important, as will be discussed in subsequent paragraphs. Below are four scenarios for a cross-sectional profile of a DDM.

DDM Type I: The cross-sectional profile can be any shape, except circular or a wedge of a circle. The axis of rotation 365 is located at any point within the cross-section as shown in FIG. 3D-1 through 3D-3 that yields the result that $P_{avg}<(R_{max}-R_{min})$. As shown in FIG. 3D-1 through 3D-3, a DDM Type I can include regular cross-sectional profiles and irregular cross-sectional profiles, including various asymmetries, wavy/undulating/scalloped borders, cut-outs, involute borders, etc. In this example, the DDM Type I reciprocally oscillates between two end positions (dotted outlines). Alternatively, motion can be rotational.

DDM Type II: The cross-sectional profile is circular or the wedge of a circle. The axis of rotation 365 is located at any point within the cross-section such that it yields the result that $P_{avg}<(R_{max}-R_{min})$ (i.e. the axis of rotation 365 is not close to the center of the circle).

DDM Type III: The cross-sectional shape is circular or the wedge of a circle. The axis of rotation 365 is located at any point within the cross-section sufficiently close to the center of the circle such that it yields the result that $P_{avg}\sim(R_{max}-R_{min})$ (i.e. the axis of rotation 365 is approximately at the center of the circle).

DDM Type IV: The cross-sectional shape has a regularly repeating feature on the perimeter, such as scalloping, that yields the result that $P_{avg}<(R_{max}-R_{min})$ no matter where the axis of rotation 365 is located, including at the centroid of the cross-sectional shape. A Type I DDM and a Type IV DDM are closely related in that the axis of rotation 365 can be anywhere within the cross-sectional shape and still yield the result that $P_{avg}<(R_{max}-R_{min})$.

The scallops, undulations, or any regularly repeating feature of a DDM do not include perforations or holes in the tissue engaging surface 370 for which the walls of the perforations do not significantly contact tissue. For example, the aspirating passages disclosed in U.S. Pat. No. 6,423,078 comprise holes in the abrasive surface, which act as the tissue engaging surface, of an abrading member. These holes do not comprise the features disclosed for DDMs because the holes act only as fluidic ports in the tissue engaging surface, and the walls of the aspirating passages are not brought to bear on tissue. Nevertheless, DDMs disclosed herein can include aspirating passages such as these.

DDMs of Type I through IV can also include any variety of shape out of the plane of the page. As stated earlier, "The cross-sectional profile of a DDM in a plane perpendicular to the axis of rotation 365 is important". Thus, dissecting wheel 310 in FIG. 3A through FIG. 3C is an example of a DDM Type III.

Figures 3, 3E, 4:
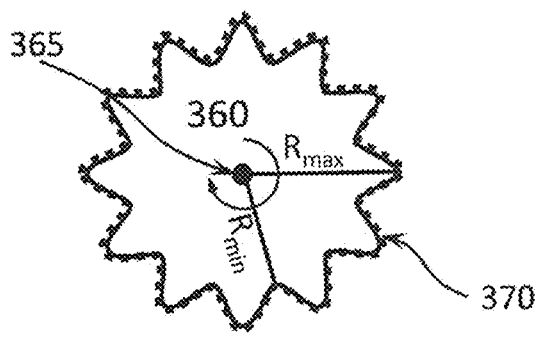
Figures 1, 3F:
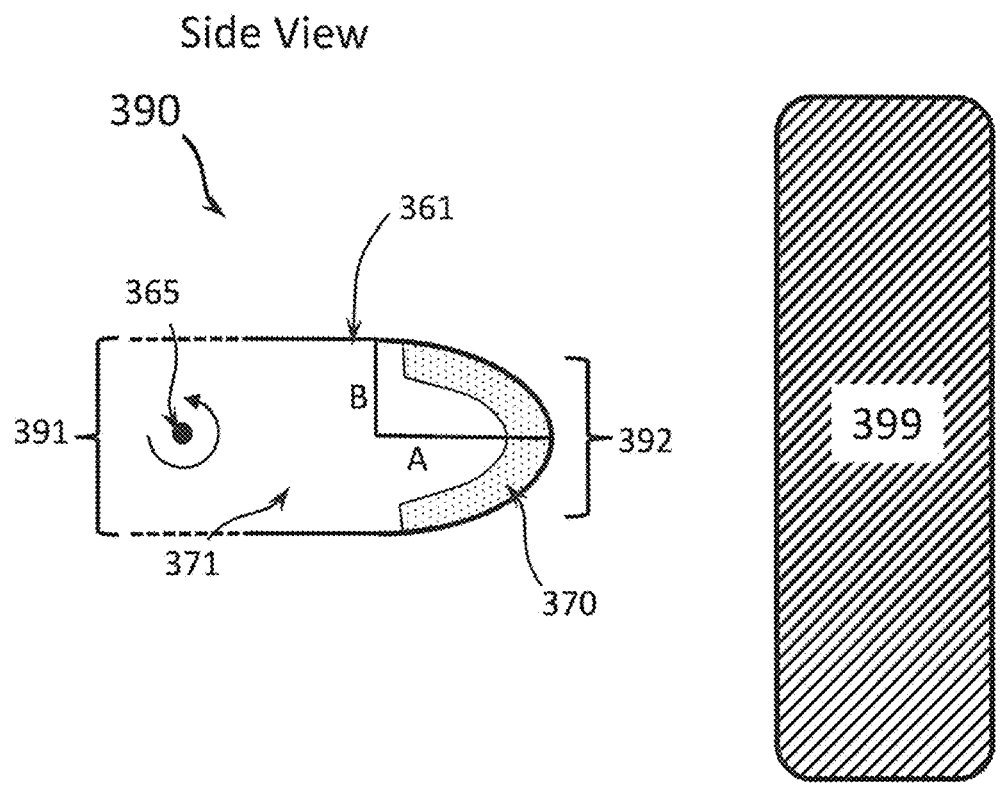
Figures 2, 3F:
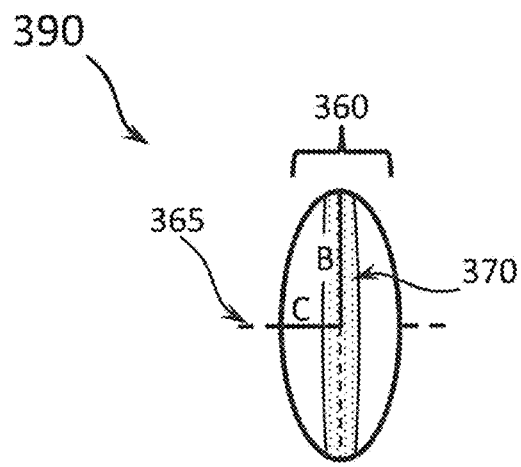

FIGS. 3F-1 and 3F-2 illustrates a DDM 390 that is similar to the DDM 350 shown in FIGS. 3D-1 through 3D-3. DDM 390 has a first end and a second end 392 wherein the first end 391 is directed away from the Complex Tissue 399 and is rotatably engaged with a mechanism (not shown) such that DDM 390 is rotated about an axis of rotation 365 by the mechanism. The mechanism can include motorized and manual drives. The second end 392 is directed toward the Complex Tissue 399 and comprises a semi-ellipsoid shape defined by three orthogonal semi-axes: the major semi-axis A, the first minor semi-axis B, and the second minor semi-axis C, wherein major semi-axis A lies in the direction of a line connecting the first end 391 and the second end 392; minor semi-axis C is parallel to the axis of rotation 365 (i.e. A is perpendicular to the axis of rotation 365); and minor semi-axis B is perpendicular to both major semi-axis A and minor semi-axis C. The semi-ellipsoid can have a range of shapes (e.g., there may be different relationships between the lengths of the three semi-axes, including A=B=C, A≠B≠C, A>B and A>C). In one embodiment, A>B>C has been found to be very effective for a DDM.

Figure 4A:
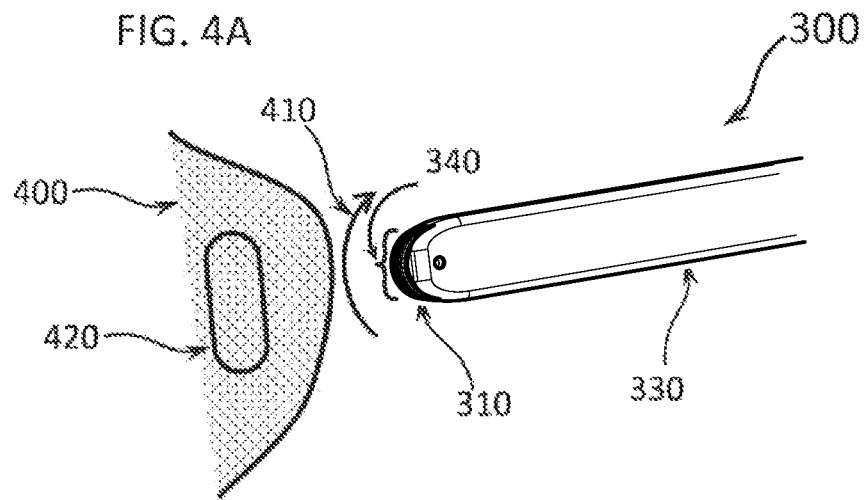
FIGS. 4A through 4F show how an exemplary differential dissecting instrument disrupts soft tissue, but not firm tissue, in a complex tissue, exposing the firm tissue.
Figure 4B:
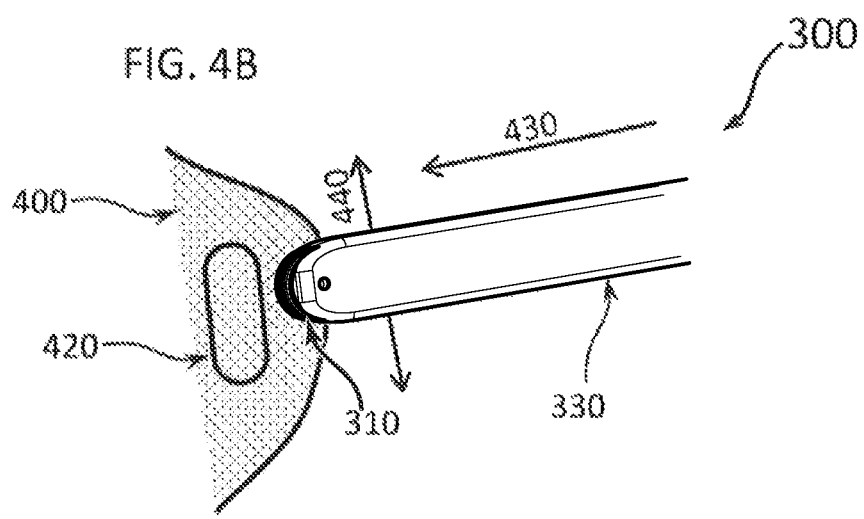
Figure 4C:
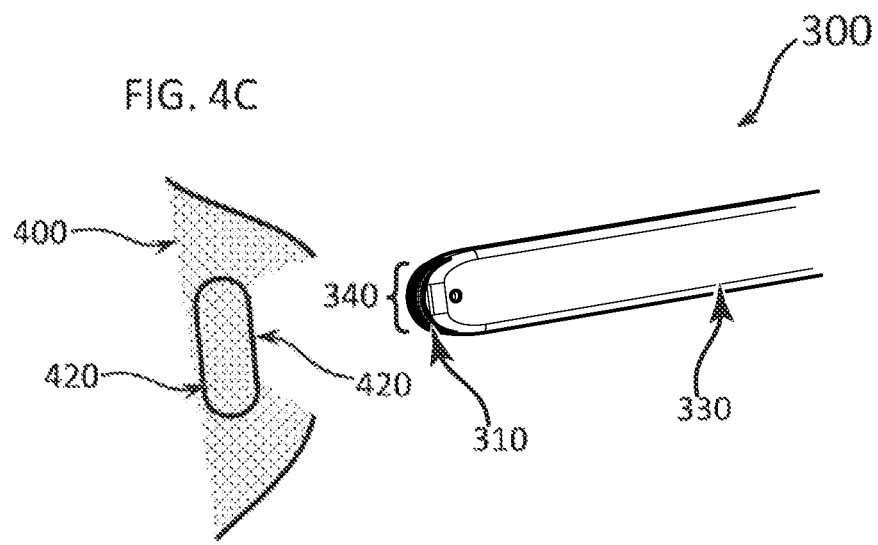

FIGS. 4A through 4C show how the effector end of Differential Dissecting Instrument 300 can be used for dissection of a Complex Tissue, comprised of both Soft Tissue and Firm Tissue, wherein the DDM is a dissecting wheel 310. In FIG. 4A, an operator initiates rotation of dissecting wheel 310, as indicated by arrow 410, before or upon contact with a Soft Tissue 400. In FIG. 4B, the operator then presses the exposed tissue engaging surface 340 of dissecting wheel 310 into the volume of the Soft Tissue 400 for blunt dissection to reach the Target Tissue 420 within. The arrows 430 and 440 in FIG. 4B show two possible operator-executed motions of the Differential Dissecting Instrument 300. Only the portion of tissue engaging surface 340 of dissecting wheel 310 exposed outside of shroud 330 contacts the Soft Tissue 400 and thereby disrupts that portion of Soft Tissue 400 in contact with tissue engaging surface 340. Because the exposed, moving portion of tissue engaging surface 340 can disrupt tissue without further action by the surgeon (e.g. without the surgeon's forcefully scrubbing a Differential Dissecting Instrument 300 against Soft Tissue 400), tissue can be disrupted simply by application of the rotating dissecting surface 340 of dissecting wheel 310 to any part of Soft Tissue 400; however, when dissecting wheel 310 contacts the Firm Tissue of Target Tissue 420, it does not disrupt the Target Tissue 420. Note that pushing dissecting wheel 310 into Soft Tissue 400 as indicated by the arrowhead on arrow 430 is a "plunge"—the dissecting wheel 310 can be pushed blindly into Soft Tissue 400 because it will not disrupt Firm Tissue and will, therefore, not disrupt Target Tissue 420. Other motions of Differential Dissecting Instrument 300 can be used to dissect Soft Tissue 400, including motion orthogonal to arrows 430 and 440, curvaceous motions, and other 3D motions. Once Target Tissue 420 has been exposed, Differential Dissecting Instrument 300 can be withdrawn, exposing the Target Tissue 420, as shown in FIG. 4C.

Figure 4D:
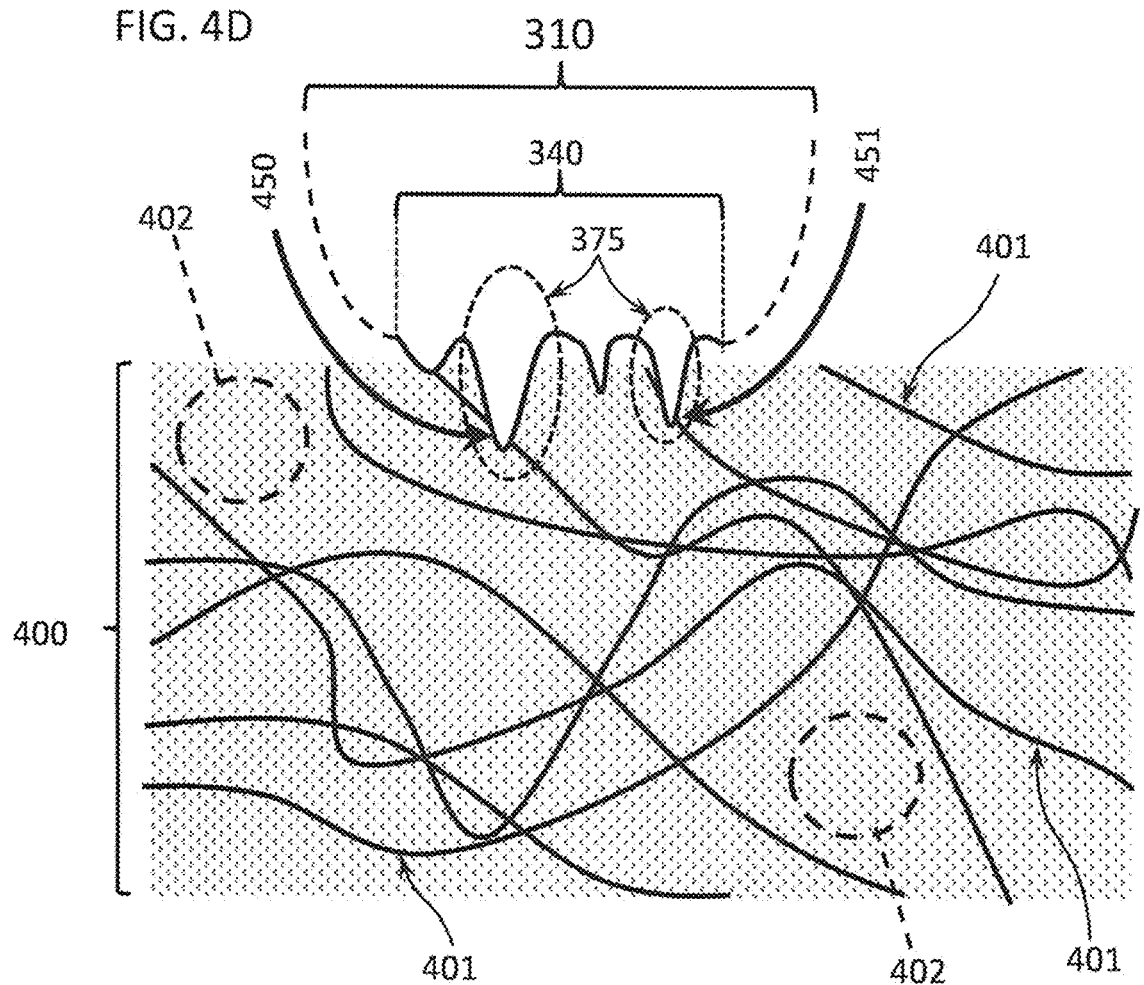
Figure 4E:
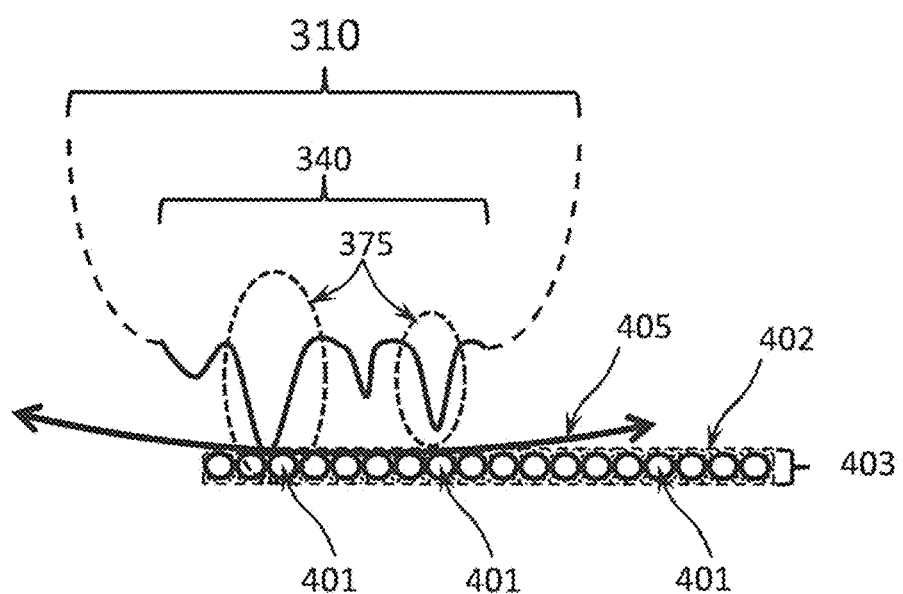
Figure 4F:
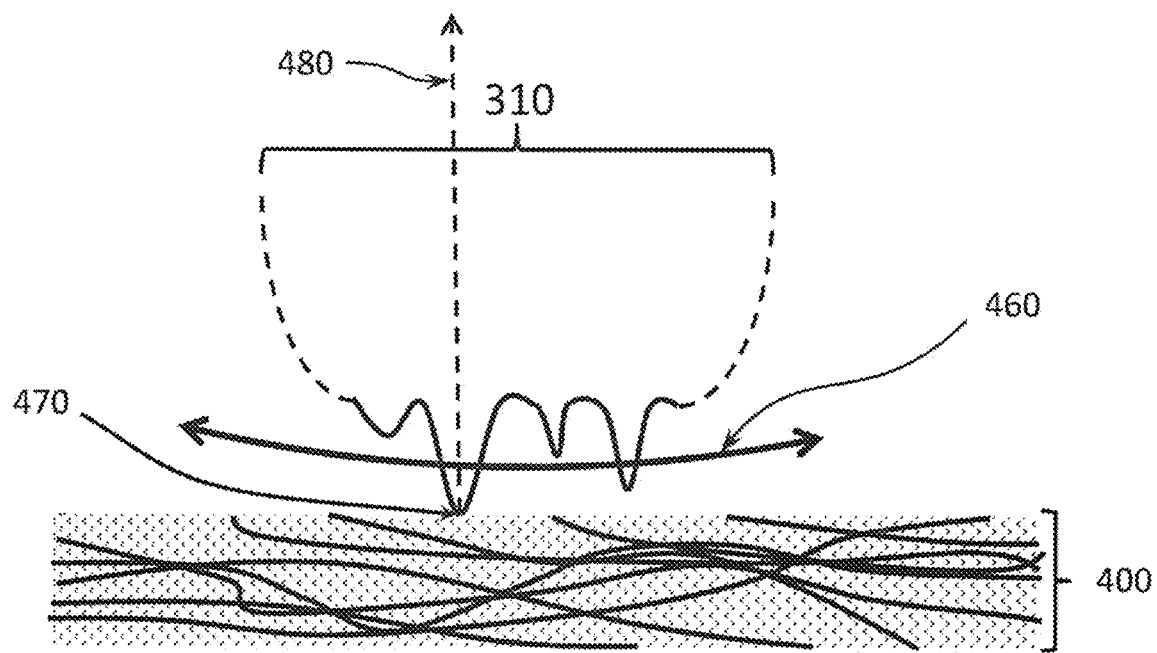

FIG. 4D through FIG. 4F show how one embodiment of a DDM disrupts Soft Tissue but won't disrupt Firm Tissue. FIG. 4D depicts a sectional view of a DDM as dissecting wheel 310 with tissue engaging surface 340 having projections 375. Dissecting wheel 310 moves in and out of the plane of the page, with shaft 320 (not shown) substantially parallel to the plane of the page. The projections 375 thus move through the plane of the page. FIG. 4D further shows a volume of Soft Tissue 400 that remains substantially in place as dissecting wheel 310, tissue engaging surface 340, and projections 375 travel through the plane of the page. Given the motion of the projections 375 relative to the roughly stationary Soft Tissue 400, dissecting wheel 310 disrupts Soft Tissue 400. In detail, the Soft Tissue 400 is comprised of both fibrous components 401 and gel-like material 402. (Soft Tissues are frequently composed of extracellular material with fibrous components 401, e.g.

collagen fibers and small bundles of fibers, and with thin sheet components, e.g. thinner membranes, dispersed in water-swollen gel-like materials.) Projections 375 are capable of sweeping through gel-like material 402 such that they encounter and then snag individual fibrous components 401 (e.g. at points 450 and 451); fibrous components 401 are then torn by the relative motion of projections 375 on the dissecting wheel 310 through the plane of the page and Soft Tissue 400. As dissecting wheel 310 is pushed deeper into tissue 400, projections 375 will snag deeper and deeper fibrous components, also tearing them. Thus, Soft Tissues 400 with dispersed components can be dissected with a DDM.

FIG. 4E shows, in contrast to FIG. 4D, how a tightly packed fibrous tissue can resist dissection by a dissecting wheel 310. Firm Tissues 403 are frequently comprised of fibrous components 401 that are tightly packed either into parallel, crossed, or other organized arrays (e.g. fascia and blood vessel walls), or into tightly packed 2D and 3D meshes, and a gel-like material 402 covers the arrays of fibrous components 401. In FIG. 4E, a Firm Tissue 403 is composed of a gel-like material 402 (stippled region) thinly coating a layer of tightly packed fibrous components 401, the filaments of which are depicted with their long axes perpendicular to the plane of the page, thus the cross-section of the fibrous components 401 is depicted as circular. In this image the dissecting wheel 310 reciprocally oscillates left-right on the page, as indicated by arrow 405, sweeping projections 375 over the surface of Firm Tissue 403. Due to the tight packing of fibrous components 401 in this Firm Tissue 403, projections 375 are unable to separately engage and snag fibrous components 401, and are thus unable to apply sufficient stress to tear fibrous components 401. Furthermore, gel-like material 402 serves as a lubricant, causing projections 375 to tend to slip off of the tightly packed fibrous components 401 of Firm Tissue 403. Finally, any compliance of the surface of Firm Tissue 403 exposed to dissecting wheel 310 will prevent developing tension in the Firm Tissue 403 or fibrous components 401, resulting in the Firm Tissue 403 deflecting away from any pressure exerted by dissecting wheel 310. Firm Tissues 403 thus resist disruption by DDMs by a combination of tight packing of fibrous and sheet components 401, lubrication of these components by gel-like materials 402, and compliance of the Firm Tissue 403.

Motion of a DDM, as stated above, can be either rotational or oscillatory. The velocity of a point on a DDM past a specific region of tissue strongly influences the ability of a DDM to disrupt that tissue. FIG. 4F depicts a dissecting wheel 310 that sweeps left-right within the plane of the page (as shown by double headed arrow 460) over a Soft Tissue 400 with a point of contact 470. The translational velocity of point of contact 470 is determined by the rotational velocity of the DDM and the distance 480 separating point of contact 470 from the center of rotation (not shown). For rotational motion, the translational velocity equals $2\pi D\omega$, where D is the distance 480 and $\omega$ is the rotational frequency in rotations per second. For oscillatory motion, the translational velocity equals $D\Psi 2X$, where D is the distance 480, $\Psi$ is the oscillatory frequency in cycles per second, and X is the angle swept in radians. For a differential dissector, distance 480 ranges from about one (1) mm to about forty (40) mm; rotational velocity ranges from approximately two (2) rotations per second to approximately three hundred fifty (350) rotations per second; oscillatory frequency ranges from about two (2) hertz (Hz) to about three hundred fifty (350) Hz; and angle swept ranges from 2° to 270°. Thus, the translational velocity of point of contact 470 on a differential dissector can range from about one (1) mm per second to about sixty thousand (60,000) mm per second. In one embodiment, a distance 480 of approximately fifteen (15) mm and an oscillatory motion with frequency of approximately one hundred (100) Hz sweeping through about forty-five degrees (45°), yielding about twenty-four hundred (2400) mm per second, is very effective for a number of Soft Tissues. Note that this means that the velocities of operator-executed motions (as shown in FIG. 4) are always smaller than the velocity of a point of contact on a DDM during dissection because surgeons are careful during dissections, moving their instruments only slowly (usually much less than one hundred (100) mm per second). Additionally, motion of the DDM is described throughout this document as arising from a rotational motion (continuous rotation or reciprocal, i.e., back-and-forth, oscillation). However, any motion of a DDM, including rectilinear motion, relative to a tissue such that the tissue engaging surface of the DDM appropriately engages the tissue, as described above, can be used.

A DDM can be forced against a blood vessel wall, the pleura, the pericardium, the esophagus, the gall bladder, and almost any other organ or tissue comprised of or covered by a tightly packed fibrous tissue, and the DDM will not significantly disrupt such a Firm Tissue under light hand pressure. Conversely, a DDM can be forced against a mesentery or other Soft Tissue, and the Soft Tissue will rapidly disrupt under light hand pressure. Differential dissectors fitted with any one of a variety of DDMs as disclosed herein have been found by the inventors to rapidly dissect between the planes of lobes in the lung, to dissect an interior mammary artery away from the inner wall of the chest, to separate the blood vessels and bronchiole in the hilum of a lung lobe, to dissect the esophagus from surrounding tissues, to penetrate through bulk muscle between, rather than through, the fiber bundles, to dissect fascia and tendons away from muscle fibers, to clean dissected fascia, to expose branched vascular and lymphatic structures, to dissect pockets into tissues and to separate tissue planes in many different tissues. The utility of a differential dissector is broad and, thus, has many potential uses. Importantly, due to the composition of skin and of surgical gloves, the skin or surgical gloves are not cut or otherwise disrupted by a DDM, even when significant pressure is applied. The inventors have shown that an oscillating DDM of the type disclosed herein can be held against a cheek of the face without any harm. Thus, a differential dissector is inherently safe to use, which simplifies use during surgery, especially when the surgeon's fingers must be near the point of dissection.

DDMs are preferably formed from a rigid material, such as a metal or a rigid polymer (e.g., Shore A equal to or greater than 70), rather than from softer polymers and elastomers (e.g. Shore A less than 70). Use of a rigid material keeps the projections from the tissue engaging surface from deflecting away from the tissue, as might occur if a softer material was used. DDMs or their component portions can be machined from bulk material, constructed via stereolithography, molded by any of the means well known in the art (e.g. injection molding), or by any such method known in the art.

The projections of a tissue engaging surface of a DDM can be fabricated by any of several means. Projections can be formed by coating the tissue engaging surface with grit similar to sandpaper using grit coarser than 1000 but finer than 10 on the Coated Abrasive Manufacturers Institute standard. Grit can include particles composed of diamond, carborundum, metal, glass, sand or other materials known in the art. Projections can be formed into the surface of the material composing a DDM by sanding, sandblasting, machining, chemical treatment, electrical discharge machining, or other methods known in the art. Projections can be molded directly into the surface of a DDM. Projections can be formed onto the surface by stereolithography. Projections can be irregularly shaped, like particles of grit, or they can be regularly shaped having defined faceted, curved, or sloped surfaces. The projections may be elongate, and the long axis of these projections may have an angle with respect to the tissue engaging surface. Projections possess a cross-sectional shape when viewing the tissue engaging surface from above, and this shape may be round, faceted, or complex. The cross-sectional shapes of projections may be oriented with respect to the direction of travel of the DDM.

Keeping the tissue wet helps differential dissection. A well-wetted Firm Tissue is better lubricated, greatly reducing disruption by a DDM. Conversely, a well-wetted Soft Tissue remains water-swollen and soft, separating the spacing of individual fibers, facilitating their being engaged and torn by the projections from the tissue engaging surface of a DDM. Wetting of the tissue can be accomplished by any of several means, including simply irrigating the tissue with physiological saline during dissection. Irrigation can be performed with procedures already used in surgery, such as an irrigation line, or by one of the devices disclosed below. Additionally, wetting of the tissue, and thus also the tissue engaging surface of the DDM, reduces clogging of the tissue engaging surface with disrupted tissue.

Figure 5A:
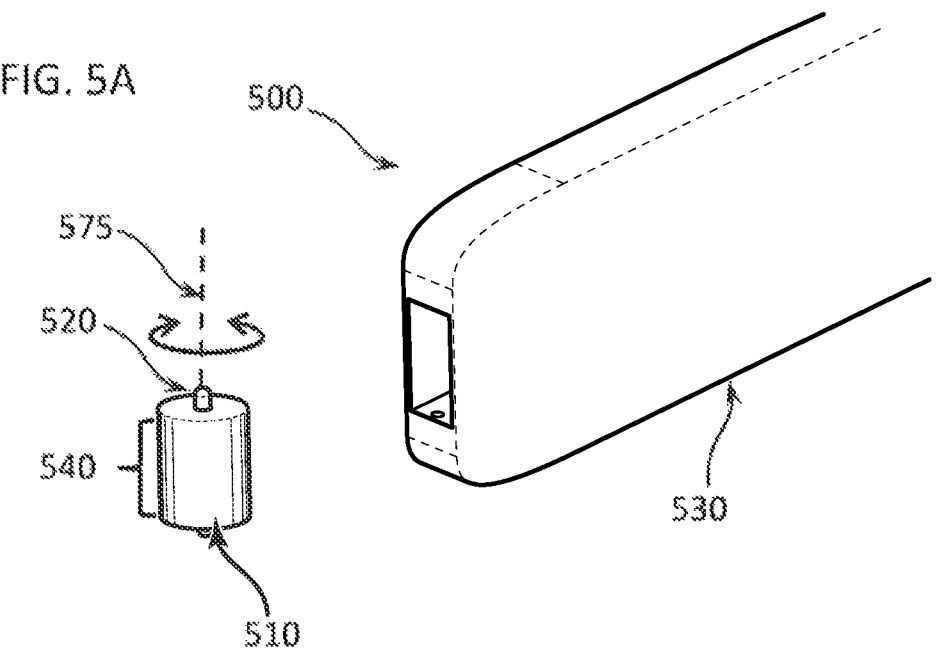
Figure 5B:
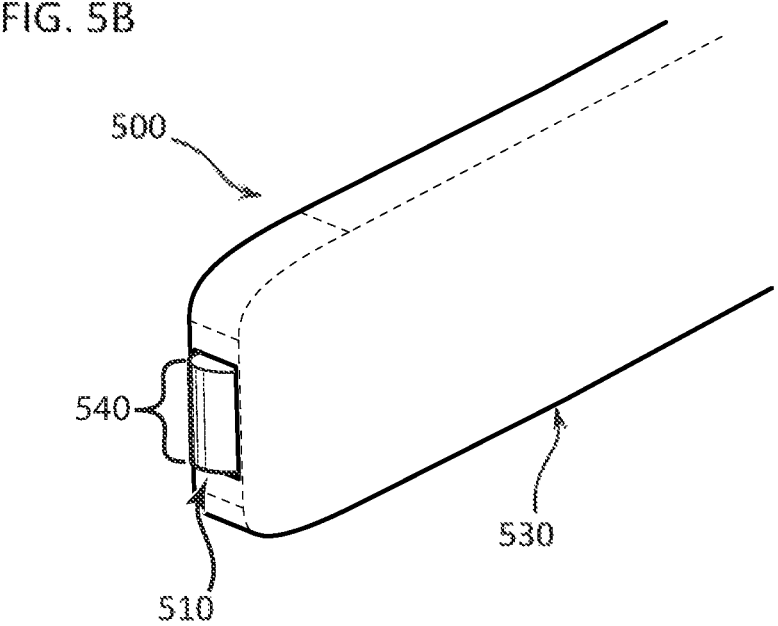

FIG. 5A and FIG. 5B show another embodiment of the effector end of a Differential Dissecting Instrument 500 which has a DDM Type III configured as a circular cylinder 510. FIG. 5A shows circular cylinder 510, with shaft 520 separate from the shroud 530. The tissue engaging surface 540 covers the side of circular cylinder 510. The two-headed arrow indicates rotation about the axis of rotation 575. FIG. 5B shows both parts configured for use with only a limited portion of tissue engaging surface 540 exposed.

Figures 1, 5C:
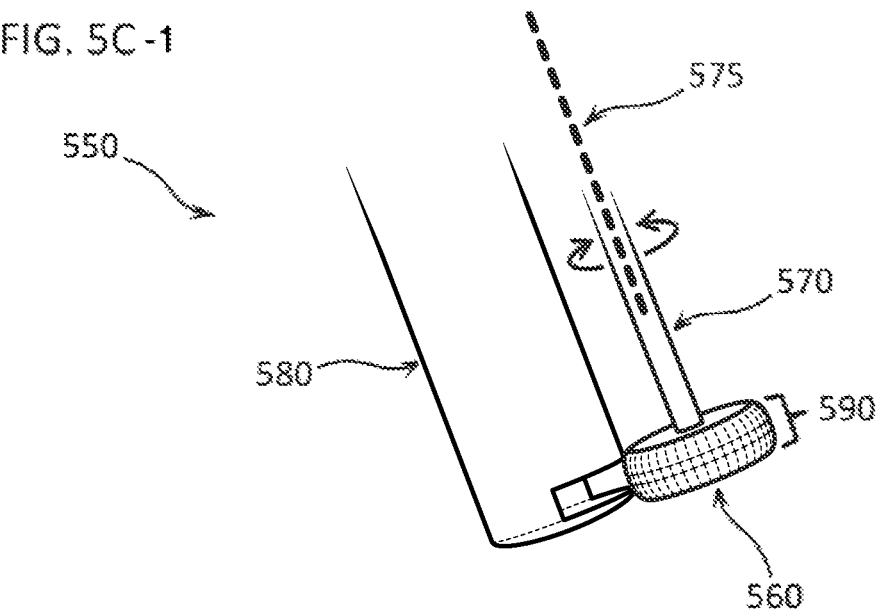
Figures 2, 5C:
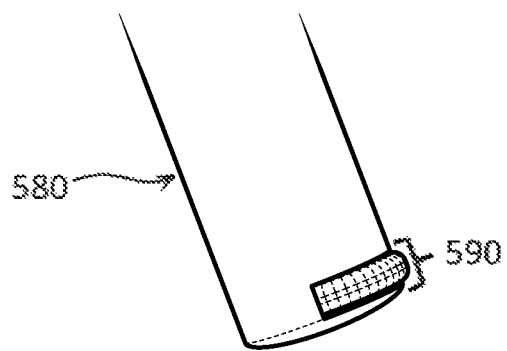

FIGS. 5C-1 and 5C-2 show another embodiment of the effector end of a Differential Dissecting Instrument with a different configuration for the shroud and DDM, here another DDM Type III. FIGS. 5C-1 and 5C-2 show a Differential Dissecting Instrument 550 with a dissecting wheel 560, with shaft 570 separate from the shroud 580. Tissue engaging surface 590 covers the periphery of dissecting wheel 560. The two-headed arrow indicates the axis of rotation 575. FIG. 5C-2 shows both parts configured for use with only a limited portion of tissue engaging surface 590 exposed. This configuration is problematic because shroud 580 makes it difficult to position the tissue engaging surface 590 against a tissue, and shroud 580 blocks the operator's view.

Figure 6A:
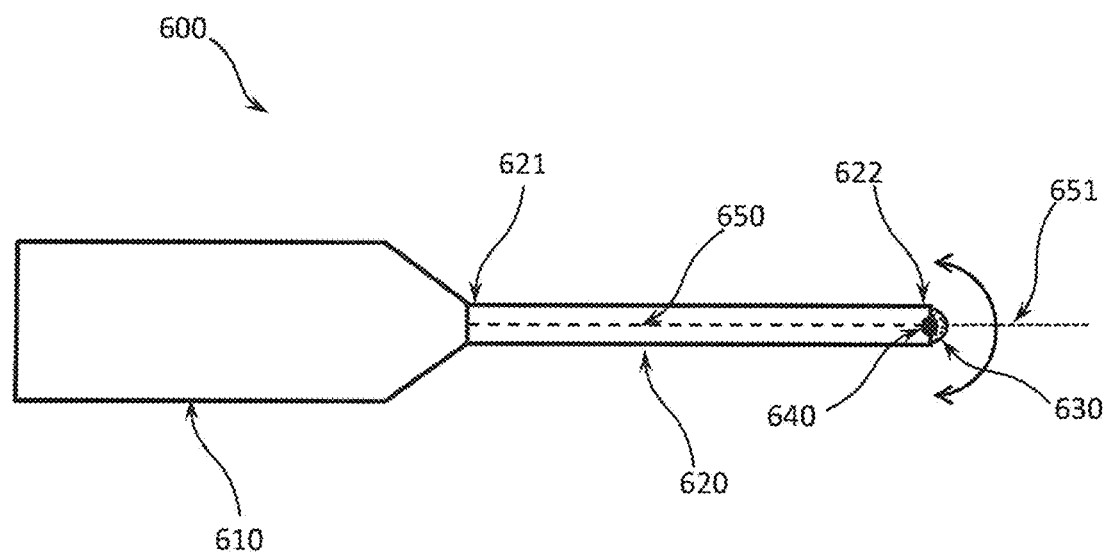
FIGS. 6A through 6D show different configurations of an exemplary differential dissecting member in a differential dissecting instrument showing how the axis of rotation of the differential dissecting member can have many different orientations with respect to the differential dissecting instrument, including differential dissecting instruments having flexible or articulating elongate members.

FIG. 6A shows one embodiment of a Differential Dissecting Instrument 600 that includes a handle 610 for an operator. Handle 610 connects to elongate member 620 comprising a first end 621 connected to handle 610 and a second end 622 connected to a DDM 630. Elongate member 620 can be shorter, allowing better manual control of the DDM 630 on an instrument for open surgery, or it can be longer, allowing Differential Dissecting Instrument 600 to be a laparoscopic instrument. The drive mechanisms for rotating DDM 630, such as a rotating drive shaft for a Scotch yoke or a crank/slider, are readily adapted to any elongate member 620, long or short, or to any device capable of driving DDM 630. DDM 630 is a Type III DDM rotatably mounted to elongate member 620 at second end 622 such that DDM 630 reciprocally oscillates about its axis of rotation 640, as indicated by the double-headed arrow (Axis of rotation 640 is perpendicular to the plane of the page in FIG. 6A). First end 621 and second end 622 define a centerline 650 of elongate member 620. The tangent 651 of centerline 650, as centerline 650 approaches second point 622, and axis of rotation 640 thus define a presentation angle 670 (not shown—perpendicular to page). In this example, the presentation angle 670 is 90° (i.e., axis of rotation 640 is aligned perpendicular to tangent 651). Rather than a handle 610, first end 621 of elongate member 620 can attach to the arm of a robot for robotic surgery. A DDM can easily be adapted to any other device capable of moving or rotating the DDM.

Figure 6B:
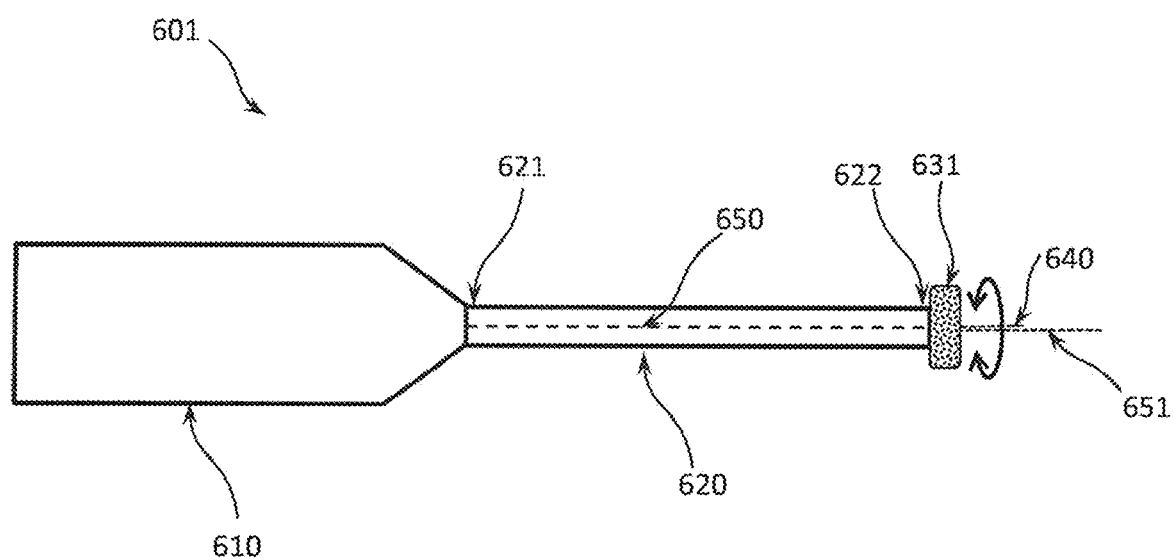

FIG. 6B shows another embodiment of a similar Differential Dissecting Instrument 601 but with the axis of rotation parallel to the centerline. Handle 610 connects to elongate member 620 comprising a first end 621 connected to the handle 610 and a second end 622 connected to a Type III DDM 631. DDM 631 is rotatably mounted to elongate member 620 at second end 622 such that DDM 631 reciprocally oscillates about its axis of rotation 640. The axis of rotation 640 is parallel to the plane of the page in FIG. 6B. First end 621 and second end 622 define a centerline 650 of elongate member 620 with tangent 651 as centerline 650 approaches second end 622. Axis of rotation 640 is thus aligned parallel to tangent 651 (i.e., the presentation angle 670 is 0°). (Again, presentation angle 670 is not presented in FIG. 6B because presentation angle is 0°.) Differential Dissecting Instrument 601 is thus similar to Differential Dissecting Instrument 550 in FIG. 5C and thus has similar limitations, including that it is difficult to position the tissue engaging surface of DDM 631 against a tissue without blocking the operator's view.

Figure 6C:
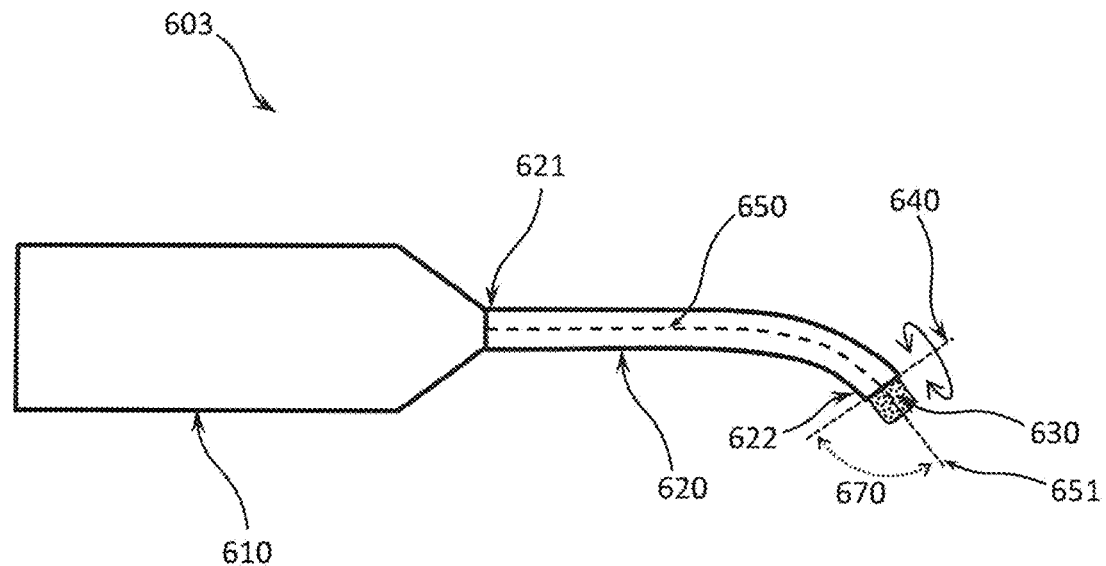

FIG. 6C shows another embodiment of a Differential Dissecting Instrument 603 having a curved elongate member 620 with curved centerline 650 and tangent 651 to centerline 650 as centerline 650 approaches second point 622. The axis of rotation 640 is perpendicular to tangent 651 forming presentation angle 670, which is 90° in this example. Elongate member 620 may similarly be bent, jointed, articulated, or otherwise made of a plurality of parts. In all cases, the presentation angle 670 is formed by the axis of rotation of a DDM and the tangent of the centerline as it approaches second point 622.

Figure 6D:
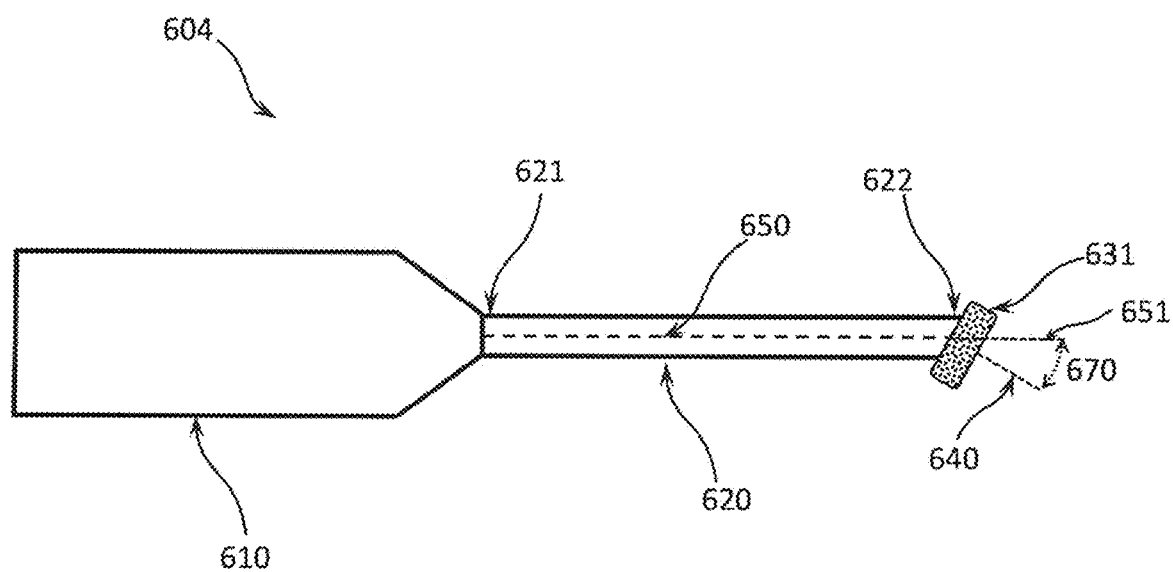

FIG. 6D shows another embodiment of a Differential Dissecting Instrument 604 similar to Differential Dissecting Instrument 602 in FIG. 6B. Handle 610 connects to elongate member 620 comprising a first end 621 connected to the handle 610 and a second end 622 connected to a Type III DDM 631. DDM 631 is rotatably mounted to elongate member 620 at second end 622 such that DDM 631 reciprocally oscillates about its axis of rotation 640. The axis of rotation 640 is parallel to the plane of the page in FIG. 6D. First end 621 and second end 622 define a centerline 650 of elongate member 620 with tangent 651 as centerline 650 approaches second point 622. Axis of rotation 640 is thus aligned at a non-zero angle to tangent 651 (i.e., the presentation angle 670 is between 0° and 90°). In preferred embodiments, presentation angle 670 does not equal 0°, for the reasons described for Differential Dissecting Instrument 603 in FIG. 5C and FIG. 6B.

Figure 7A:
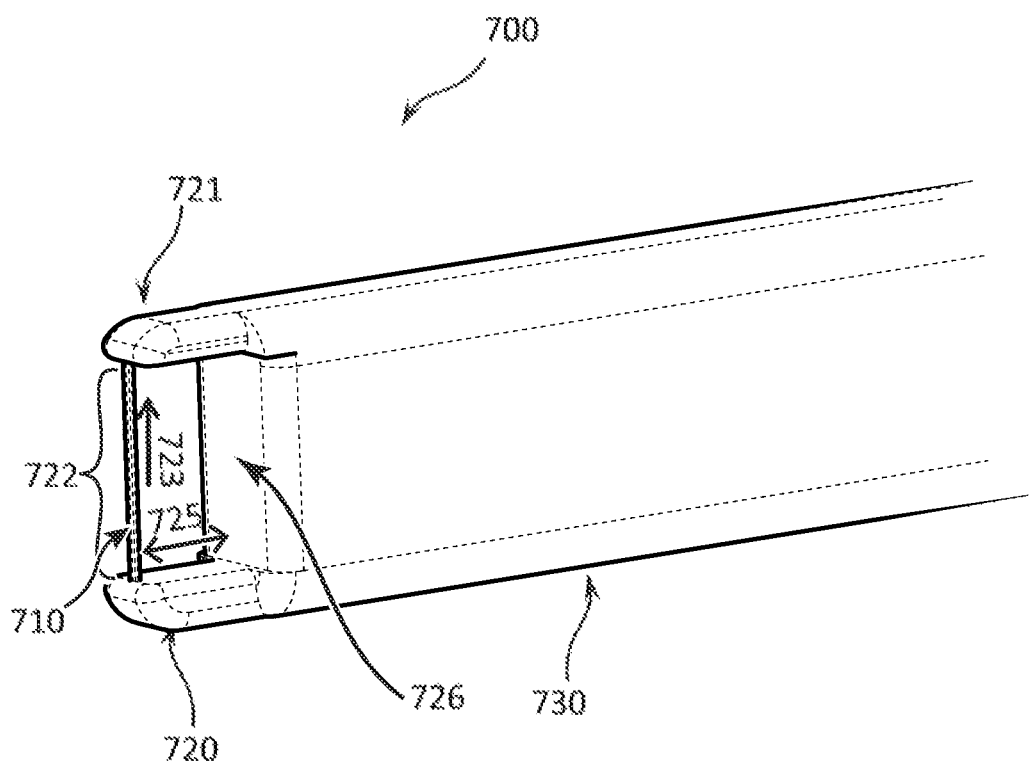
FIGS. 7A and 7B show an exemplary differential dissecting instrument that uses a dissecting wire instead of a dissecting wheel or other differential dissecting member.
Figure 7B:
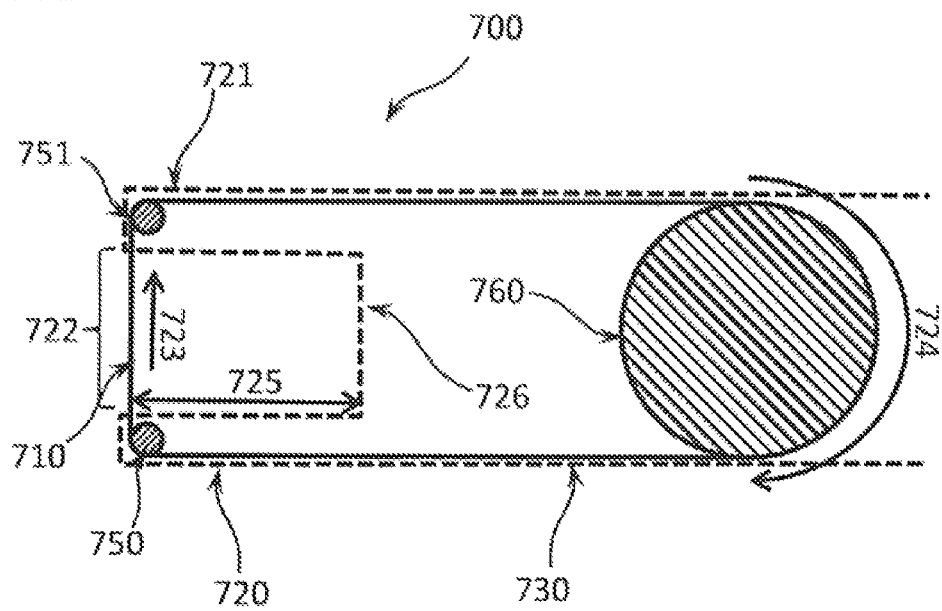

FIG. 7A and FIG. 7B show another embodiment of the effector end of a Differential Dissecting Instrument 700 that uses a dissecting wire 710 as the DDM. FIG. 7A shows the assembled device. Dissecting wire 710 stands out a distance 725 from the backing surface 726 of a shroud 730, the dissecting wire 710 emitting from a first post 720, spanning gap 722, and entering a second post 721 on the end of shroud 730. Dissecting wire 710 is a continuous loop of wire driven such that the exposed section of dissecting wire 710 travels in the direction indicated by arrow 723 across gap 722 in FIG. 7A.

FIG. 7B shows a schematic side view of this embodiment of a Differential Dissecting Instrument 700 that depicts the loop of dissecting wire 710 and drive mechanism. Dissecting wire 710 is a continuous loop that passes over a first idler bearing 750 housed in first post 720 and then emits from first post 720. Dissecting wire 710 travels across gap 722, moving in the direction of arrow 723, and enters second post 721 where it passes over second idler bearing 751. The loop of dissecting wire 710 travels further back in shroud 730 where it passes over a drive wheel 760 which is turned by, for example, a motor in the direction of curved arrow 724. Thus, rotation of drive wheel 760 drives dissecting wire 710. Note that dissecting wire 710 can be a flexible linear element with any cross-sectional shape, so instead of being a wire of circular cross-sectional shape, dissecting wire 710 could be a flexible flat belt with the outward-facing side possessing a tissue engaging surface. Similarly, dissecting wire 710 can be a flexible cord having greater diameter than a wire would permit turning over idler bearings 750 and 751; the flexible cord having a tissue engaging surface. Further, the distance 725 between the dissecting wire 710 and the backing surface 726 can be arbitrarily large or small, for example the distance 725 can be large enough to create a substantial area encircled by the dissecting wire 710, the backing surface 726 and the first post 720 and the second post 721, thus able to surround a Target Tissue to be removed. In contrast, distance 725 can be zero, where the dissecting wire 710 runs along the surface of the shroud 730, or even in a slight accommodating groove that supports the dissecting wire 710 from behind. Such an accommodating groove can have a semicircular cross-sectional shape thus exposing just a portion of the cross-sectional shape of the dissecting wire 710 to the tissue to be dissected. Further, the shape of the backing surface 726 can be flat, or it can be curved, subtly or pronounced, and the curved surface can possess convex areas, concave areas, or a combination.

FIG. 8A-8C show the effector end of a Differential Dissecting Instrument 800 that uses a flexible belt as the DDM. FIG. 8A shows the separate parts. Flexible belt 840 has an outer tissue engaging surface 850. Flexible belt 840 travels over idler wheel 810, which rotates around shaft 820, all of which are housed in shroud 830.

FIG. 8B shows the assembled effector end of Differential Dissecting Instrument 800 with only a limited portion of tissue engaging surface 850 of flexible belt 840 exposed.

FIG. 8C shows a top view of a schematic of one example of how a flexible belt, such as flexible belt 840, can be driven. Idler wheel 810 and drive wheel 860 are mounted inside shroud 830. Flexible belt 840 wraps around idler wheel 810 and drive wheel 860. Drive wheel 860 is powered to rotate such that flexible belt 840 is driven in the direction indicated by curved arrow 870. The tissue engaging surface 850 exposed outside the shroud 830 is then used to disrupt tissue. The drive wheel 860 can be driven by any of several mechanisms, such as a motor, hand crank, etc. The drive wheel 860 and the idler wheel 810 need not be right circular cylinders, nor must their rotational axes be parallel.

The extent of exposure of tissue engaging surfaces outside of the shrouding can be greater or less than those shown in the prior examples. In fact, varying the exposure changes several aspects of the behavior of the Differential Dissecting Instruments.

Figure 9A:
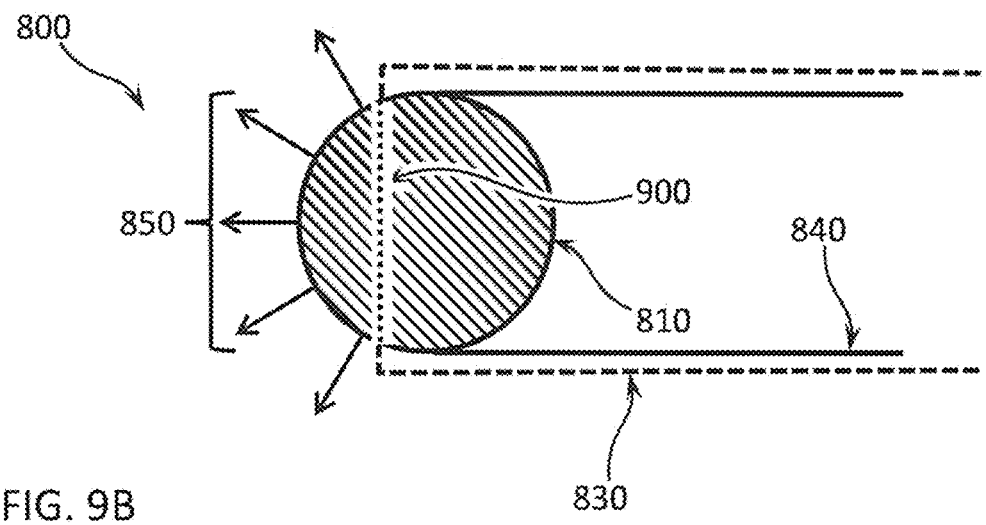
FIGS. 9A through 9C show how a varying the exposure of the tissue engaging surface of a differential dissecting member changes the behavior of a differential dissecting instrument, especially the range of angles of exposure of the tissue engaging surface.
Figure 9B:
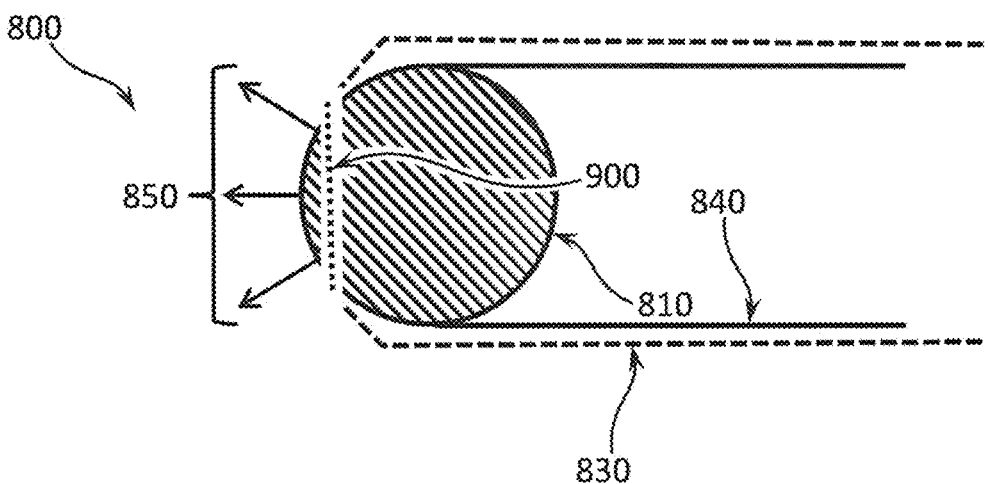
Figure 9C:
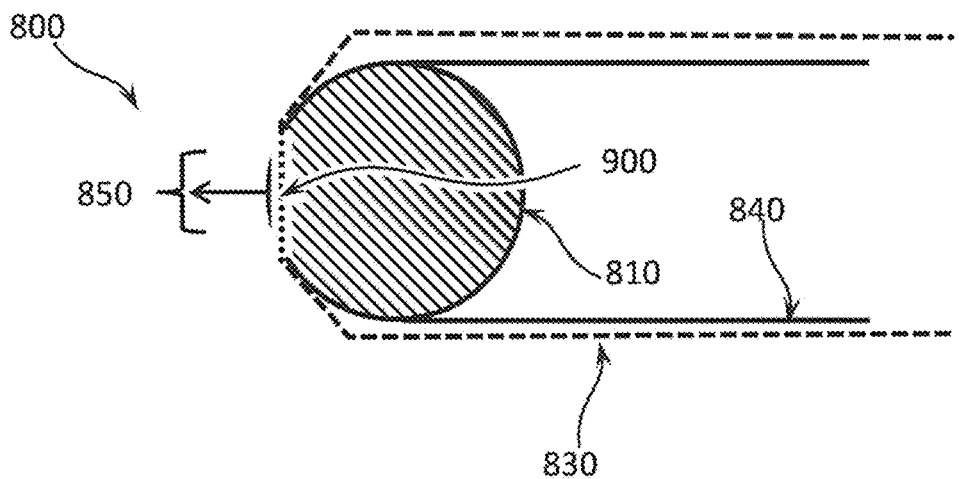

First, a larger exposure, increases the exposed area of the tissue engaging surface, which increases the amount of tissue disrupted per unit time and increases the surface area of tissue removed. Thus, decreasing the exposure allows more precise removal of tissue, but it reduces the total amount of material removed. Second, increasing the exposure changes the angle of exposed tissue engaging surface. Consider FIGS. 9A through 9C, which show top view schematics of the effector end of Differential Dissecting Instrument 800 with successively restricted exposure of tissue engaging surface 850 as controlled by the aperture 900 in the shroud. Aperture 900 is largest in FIG. 9A and smallest in FIG. 9C. As the exposure is restricted, the range of angles of the arrows normal to tissue engaging surface 850 decreases. In FIG. 9A, the tissue engaging surface 850 disrupts both forward and on the sides. In FIG. 9C, the tissue engaging surface 850 disrupts only forward. Thus, when the tissue engaging surface 850 is applied to a tissue, different directions of contact are applied, depending on the angle of the exposed tissue engaging surface.

Second, this increasing angle of exposure of the tissue engaging surface 850 also changes both the angles at which the contacted surface of a tissue is strained and the torque on the instrument. Consider FIGS. 10A-10C which show the friction on a tissue 400 created by application of a tissue engaging surface 1010.

Figure 10A:
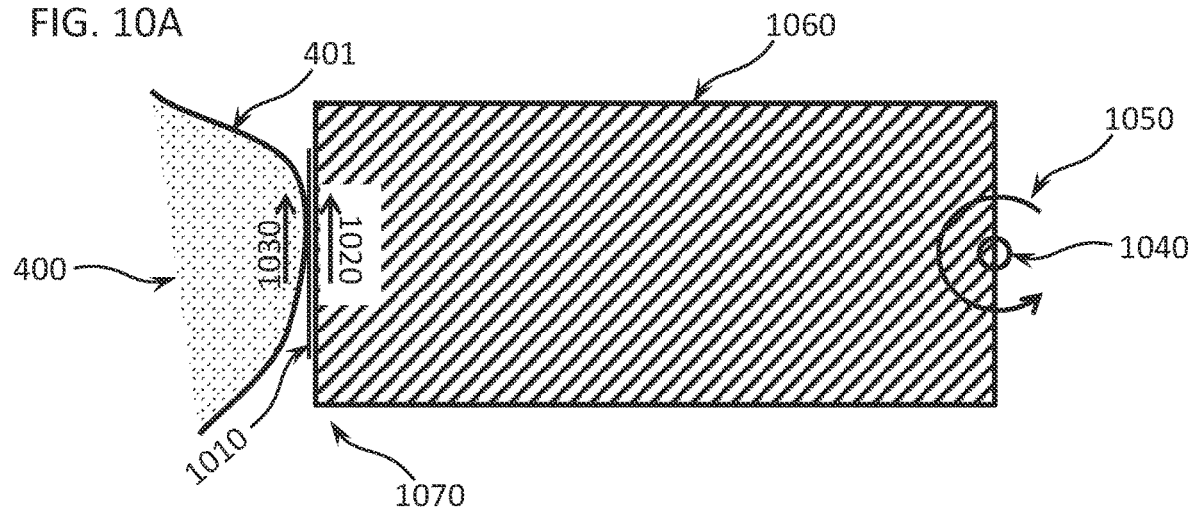
FIGS. 10A through 10C show how a varying the exposure of the tissue engaging surface of a differential dissecting member changes the directions of the friction forces on a tissue and thus the angles of strain on that tissue.

In FIG. 10A, tissue engaging surface 1010 is moving in the direction of arrow 1020. This produces a friction force in the direction of arrow 1030. The larger the area of contact, the larger the friction force. The friction force both pulls the tissue 400 sideways (in the direction of arrow 1030), shearing the tissue 400, and forces the tissue engaging surface 1010 in the direction opposite arrow 1020. If tissue engaging surface 1010 is mounted on an instrument 1060 at a distance from the point 1040 held by an operator, then the friction force places a torque 1050 about point 1040. This torque can cause the end 1070 opposite point 1040 of instrument 1060 to be pulled away from the desired point of application, making control of dissection more difficult. Thus, limiting the extent of exposure of a tissue engaging surface reduces the friction force and improves control by reducing torque on the handle.

Figure 10B:
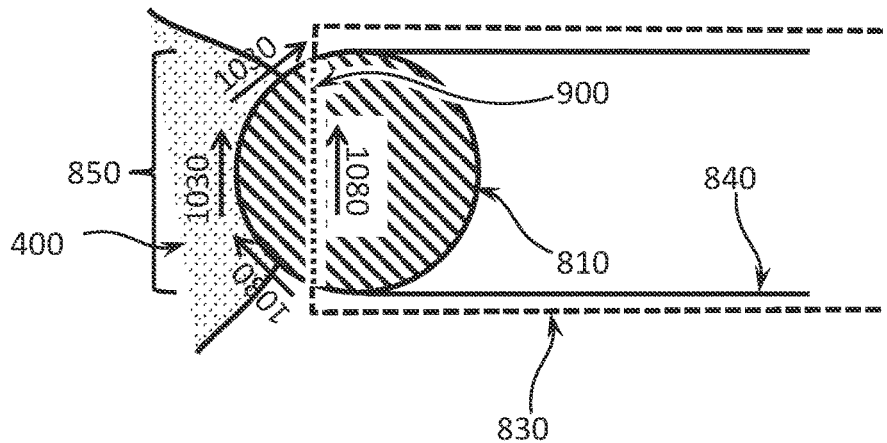
Figure 10C:
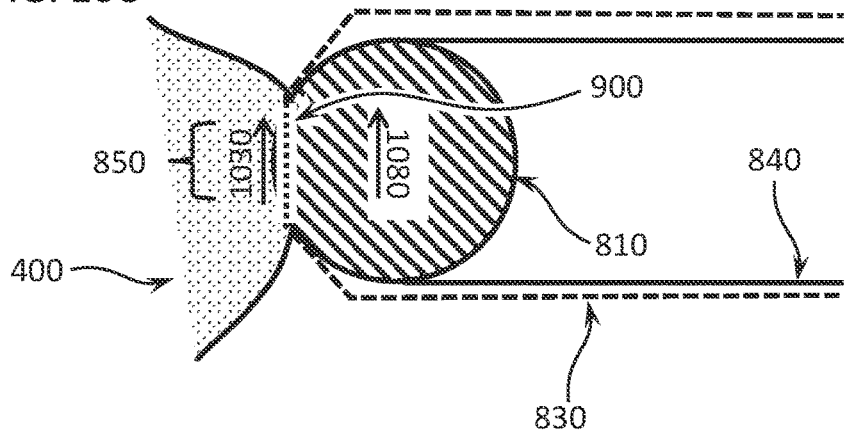

FIG. 10B shows how a circular tissue engaging surface 850 produces friction forces normal to the tissue engaging surface 850 and thus, in different directions depending on the range of contact of the tissue 400 on the circular tissue engaging surface 850. The resulting multidirectional shearing forces on the tissue 400 produce more complex strain patterns in the tissue 400. As in FIG. 10A, the friction force still produces a net upward force 1080 on the tip of shroud 830; however, it does not produce a net left/right (into and out of the tissue 400) force on the tip of shroud 830. FIG. 10C shows that reducing the exposure of tissue engaging surface 850 by narrowing aperture 900 makes the friction force on the tissue more 1-dimensional, simplifying strain patterns in the tissue.

Despite this discussion of friction against a tissue, as discussed above with respect to wetted tissues, a DDM as described herein has the unusual quality of being effective when it has low friction with respect to a Complex Tissue. The non-tissue engaging surface and the tissue engaging surface are effective even when the entire DDM is fully bathed with a lubricant, such as a surgical lubricant or a hydrogel lubricant.

In surgery, it is preferable to minimize unintended transport of tissues to other parts of the body. Disrupted pieces of tissue can adhere to the tissue engaging surfaces of the Differential Dissecting Instruments disclosed here. Unintended transport can be minimized in two ways. First, narrowing and controlling the shape of the aperture 900 as shown in FIG. 10B and FIG. 10C means that fragments of disrupted tissue adhering to the tissue engaging surface 850 will only be transported a short distance before being deposited on or entering the shroud. Similarly, if they attach to but are then thrown tangentially away from the tissue engaging surface 850 by inertia, then narrowing the aperture 900 will reduce the surface area available for adhesion, the time available for adhesion and the distance that material can be accelerated. Second, the tissue engaging surface 850 can be made resistant to tissue adhesion. Surface treatment of a tissue engaging surface 850 can be achieved by any of several techniques known in the art, such as chemical treatment, vapor deposition, sputtering, and others. For example, fluorinating the tissue engaging surface 850 by any of several known methods (e.g. dip coating, chemical deposition, chemical cross-linking such as with silanes, etc.), can make the tissue engaging surface 850 resist tissue adhesion by both hydrophilic materials and carbon-based hydrophobic tissue components. In one embodiment, diamond/carbide coated tissue engaging surfaces may be used, which we have discovered to be much less likely to have tissue adhere to these surfaces.

Transport of materials can also be reduced by the use of an oscillating (reciprocating) motion of the DDM, rather than a continuous unidirectional or continuous rotational motion. Oscillation prevents transport over distances exceeding the distance of oscillation, which can be over only a few degrees of rotation (e.g. 5 degrees to 90 degrees). Any of a number of mechanisms can be used to drive reciprocating oscillating motion with a rotating motor, such as a Scotch yoke or crank/slider.

Tissue adherence is also a problem for decreasing the effectiveness of the tissue engaging surface 850. Clogging of the tissue engaging surface 850 creates a thick coat of material over the tissue engaging surface 850, making it much less effective at ablating Soft Tissue. As above, making the surface resistant to adhesion by tissues decreases this problem. Fluorinated tissue engaging surfaces and diamond/carbide tissue engaging surfaces don't clog as readily, especially when disrupting fatty tissues.

Figure 11A:
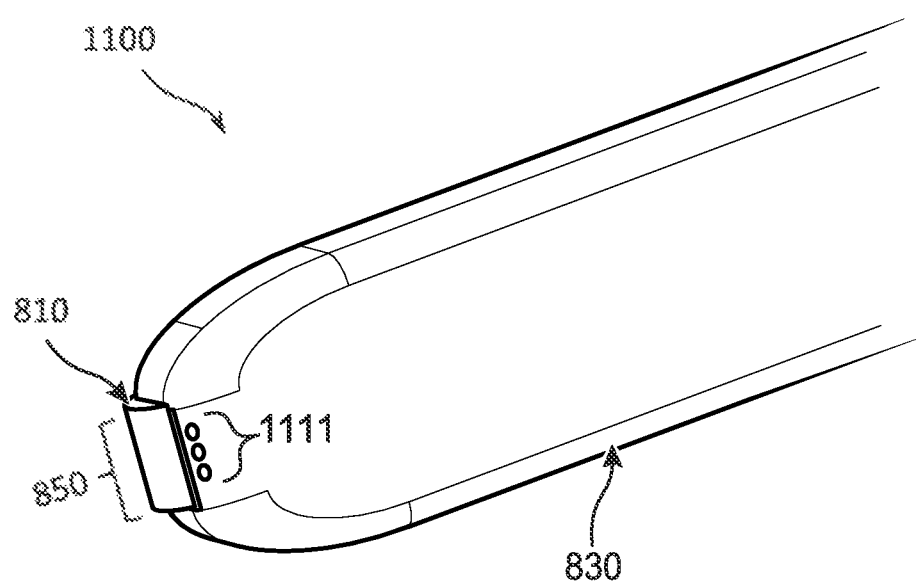
FIGS. 11A and 11B show an exemplary differential dissecting instrument with water outlets that emit beside the differential dissecting member.
Figure 11B:
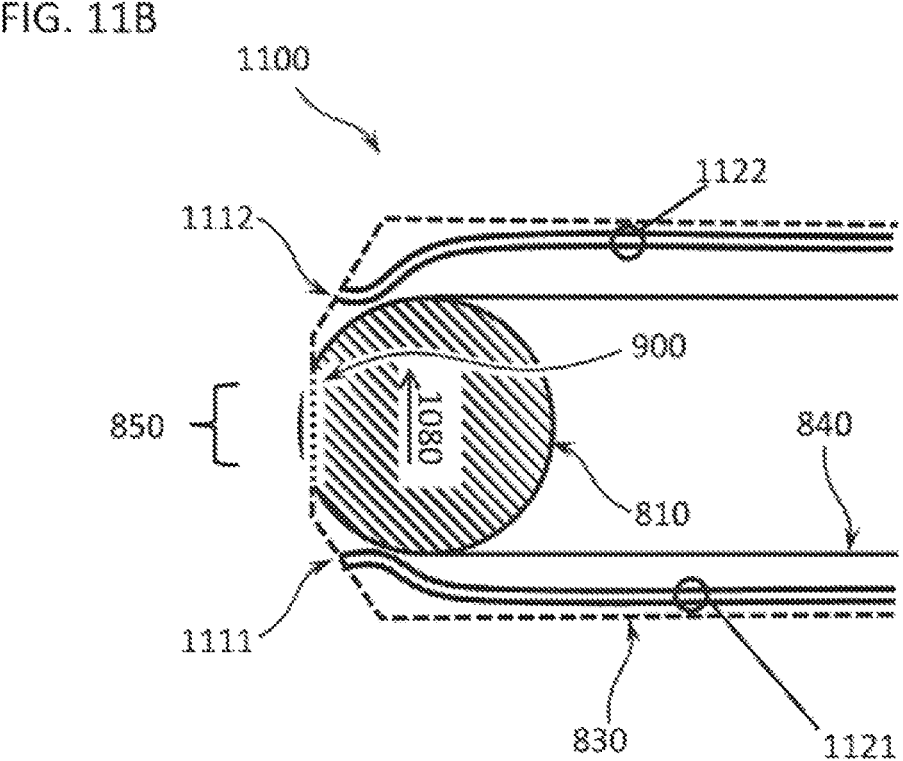

Clogging is also reduced if the tissue is wet and further if the tissue engaging surface 850 is flushed with water, as discussed earlier. FIG. 11A and FIG. 11B show a Differential Dissecting Instrument 1100 in which a first array of 3 water outlets 1111 emits beside tissue engaging surface 850 from shroud 830. A second array of 3 water outlets 1112 emits on the opposite side of tissue engaging surface 850. Other arrangements of water outlets are possible. FIG. 11A shows a solid model in oblique view. FIG. 11B shows the top view for a schematic of Differential Dissecting Instrument 1100 in which water tube 1121 carries water, or other fluid such as physiological saline, inside and to one side of shroud 830 to water outlets 1111, and a second water tube 1122 carries fluid inside and to the other side of shroud 830 to water outlets 1112. Water outlets 1111 and 1112 emit from opposite sides of aperture 900, providing fluid to both sides of tissue engaging surface 850. The liquid emitting from water outlets can, optionally, carry physiologically active materials, either dissolved or suspended in the liquid. Physiologically active materials can include various pharmaceutical compounds (antibiotics, anti-inflammatories, etc.) and active biomolecules (e.g. cytokines, collagenases, etc.)

Figure 12:
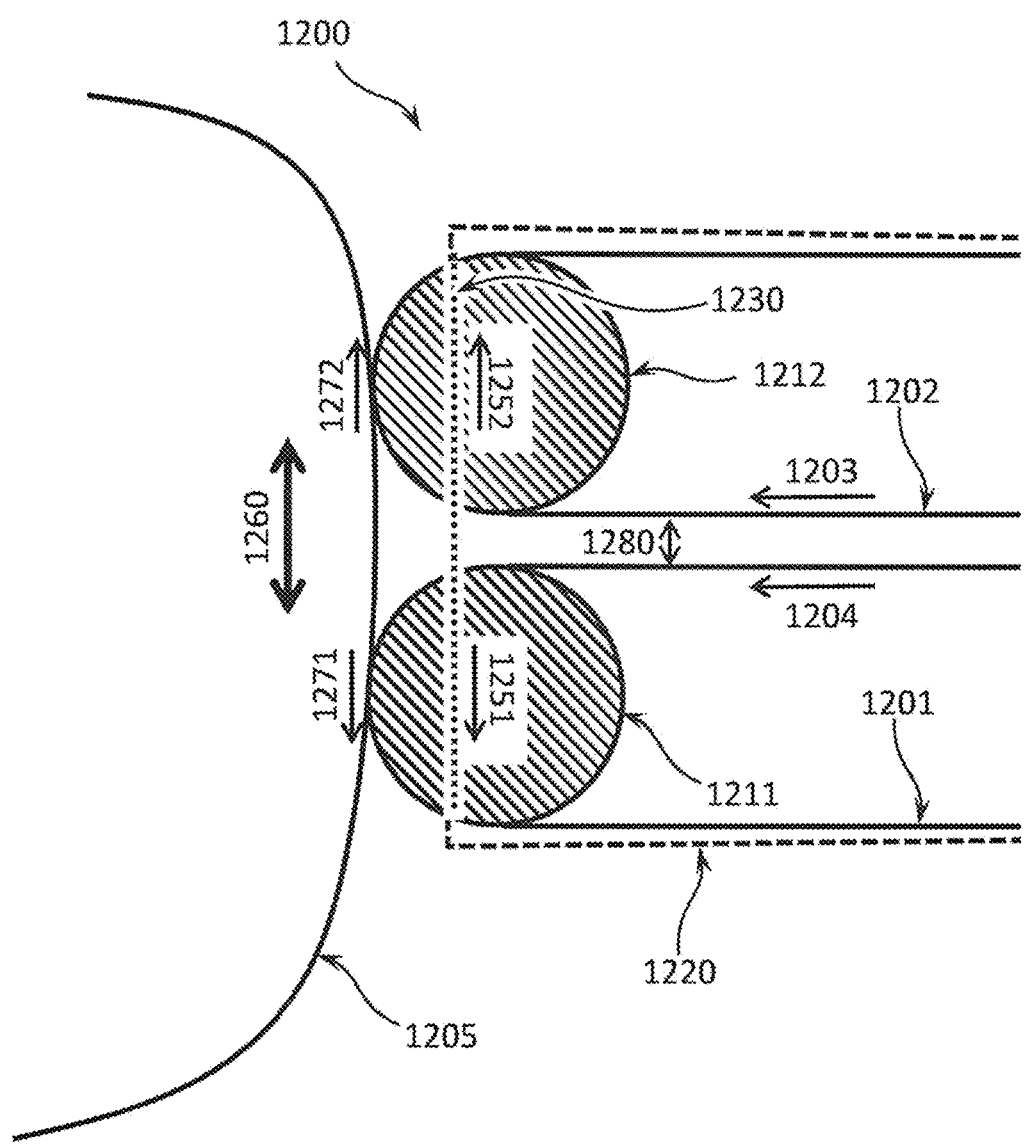
FIG. 12 shows an exemplary differential dissecting instrument having two opposing flexible belts that generate opposing frictional forces and thus reducing torque on the differential dissecting instrument.

Appropriate arrangement of tissue engaging surfaces 850 creates friction forces on tissues that can be used to advantage during blunt dissection. FIG. 12 shows a Differential Dissecting Instrument 1200 having two, opposing flexible belts 1201 and 1202 exposed in aperture 1230. Each belt is configured as in FIG. 10B with flexible belt 1201 running over idle 1211 and flexible belt 1202 running over idle 1212, but the flexible belts 1201 and 1202 circulate in opposite sense with respect to each other. Thus, the flexible belt 1201 and the flexible belt 1202 run side by side in the same direction as shown by arrows 1203 and 1204 but in opposite directions when exposed to the tissue 1205, as shown by arrows 1271 and 1272. Thus, the flexible belt 1201 creates a net force 1251 downward and the flexible belt 1202 creates a net force 1252 upward on shroud 1220, whereby these forces 1251 and 1252 cancel, leaving little or no net force on the shroud 1220. This eliminates any torqueing of Differential Dissecting Instrument 1200 (as described in FIG. 10A), making it easier for an operator to control. Additionally, the opposing directions of motion 1271 and 1272 of flexible belts 1201 and 1202 create opposing frictional forces on tissue 1205 during dissection, thereby pulling the tissue 1205 apart in the region identified by double headed arrow 1260. This pulling action can facilitate blunt dissection by tearing the tissue in the region of double headed arrow 1260. Note that the gap 1280 between flexible belts 1201 and 1202 inside shroud 1220 can be varied and can be reduced to zero such that flexible belts 1201 and 1202 are in contact. Contact between flexible belts 1201 and 1202 can help a drive mechanism match the rates of travel of flexible belts 1201 and 1202. In fact, friction between flexible belts 1201 and 1202 can allow one belt, for example 1201, to drive the other belt, in this example 1202. Thus a motor, for example, can actively drive flexible belt 1201, and flexible belt 1202 is then driven by flexible belt 1201. This can simplify the drive mechanism for two belts.

Figure 13:
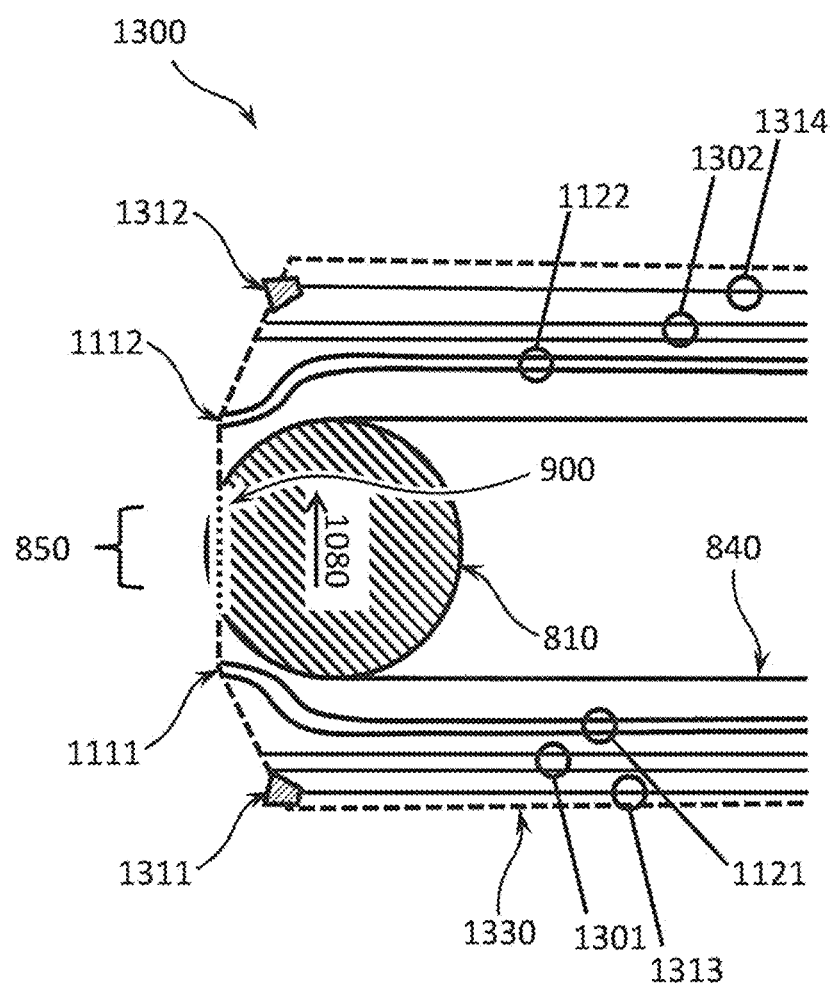
FIG. 13 shows an exemplary differential dissecting instrument can have multiple components placed into the shroud, including suction lines, water tubes, and light emitting diodes.

FIG. 13 shows how the shroud 1330 of a Differential Dissecting Instrument 1300 can house other items, permitting greater functionality. Dissecting wheel 810 is exposed at aperture 900. Suction lines 1301 and 1302 can connect to the front of the shroud 1330 near tissue engaging surface 850, helping to remove any debris from disruption or excess fluid, such as fluid from water tubes 1121 and 1122 which emit through water outlets 1111 and 1112. Light emitting diodes (LEDs) can be placed on shroud 1330 to better illuminate an area for blunt dissection; for example, LEDs 1311 and 1312 are supplied with power by cables 1313 and 1314, respectively, and light from LEDs 1311 and 1312 directly illuminates the tissue in the region of disruption.

FIGS. 14-1 through 14-3 show how the elongate member 1410 of a Differential Dissecting Instrument 1400 can be articulated with a bendable region 1430 such that a user can achieve variable bending of the elongate member 1410 to facilitate placement of the DDM 1420. FIG. 14-1 depicts the elongate member of the differential dissecting instrument in Position 1, straight, FIG. 14-2 shows the elongate member of the differential dissecting instrument bent at 45 degrees, and FIG. 14-3 illustrates the elongate member of the differential dissecting instrument bent at 90 degrees. In Position 1 (FIG. 14-1), the elongate member 1410 is straight. In Position 2 (FIG. 14-2) and then in Position 3 (FIG. 14-3), elongate member 1410 is successively bent at bendable region 1430 such that the DDM 1420 moves from forward-facing in Position 1 to side-facing in Position 3. Bendable region 1430 can be an articulated joint or any other mechanism to permit bending.

Figure 15A:
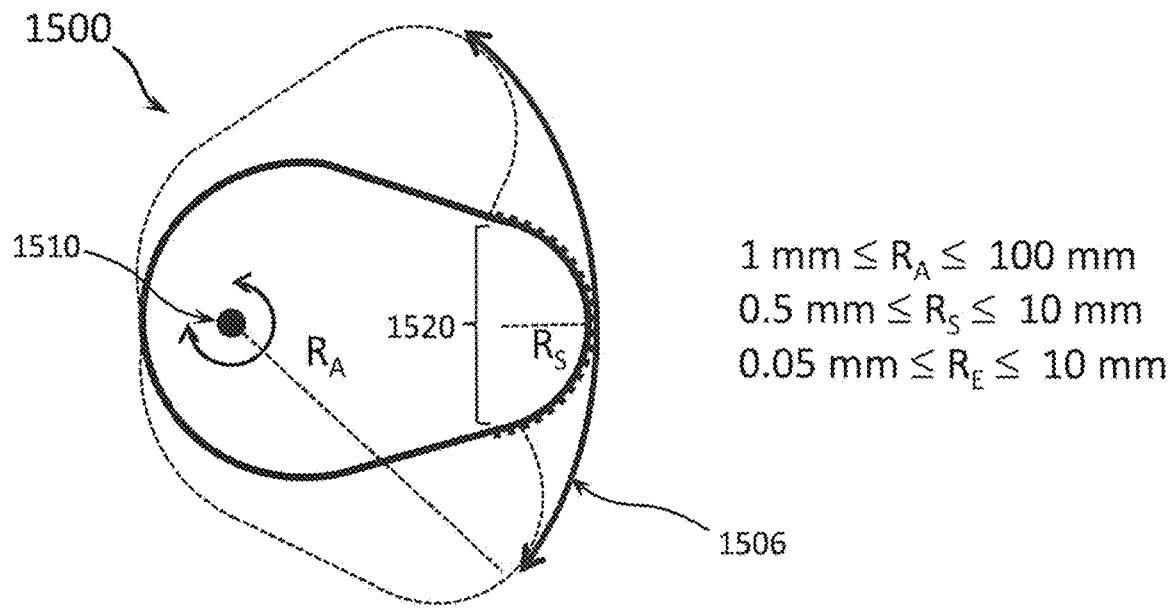

FIGS. 15A-15E show different DDMs, illustrating several important dimensions and features of DDMs. FIG. 15A shows a top view of an exemplary differential dissecting member that rotates about a rotational joint. FIG. 15A shows a top view of a DDM 1500 that rotates about a rotational joint 1510. Actuation of DDM 1500 causes it to reciprocally oscillate up and down, as shown by the double headed arrow 1506 such that tissue engaging surface 1520 (pebbled section) swings through an arc with radius $R_A$. Oscillation of DDM 1500 can swing through a range of ±90 degrees. The tissue engaging surface has a minimum radius $R_S$ in the plane of rotation (the plane perpendicular to the plane of rotation–the plane of the page here).

Figures 1, 2, 3, 15B:
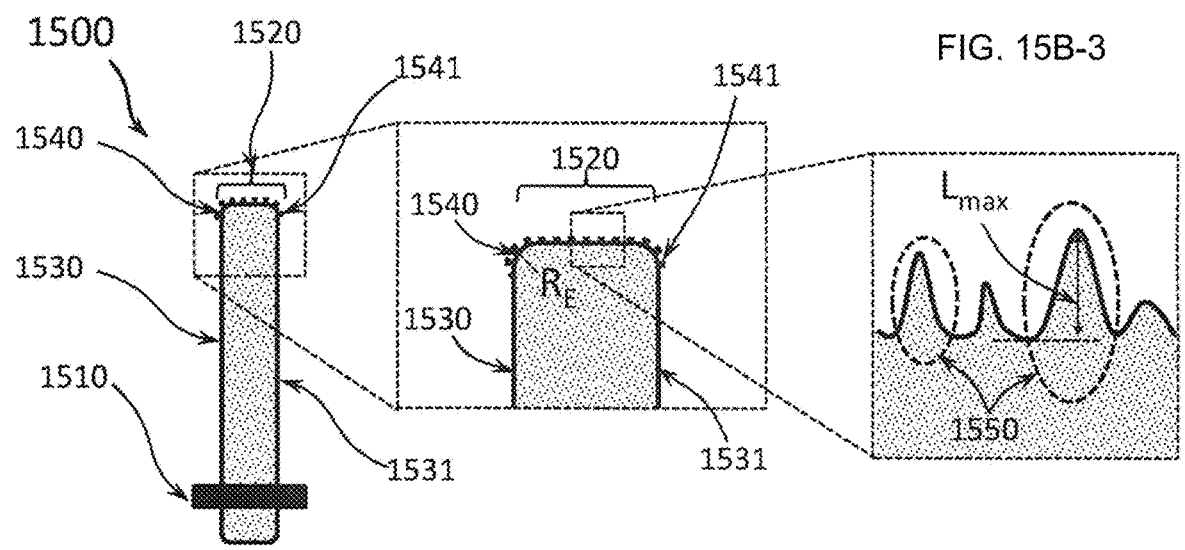

FIG. 15B shows a side view in cross-section with two successively enlarged views. (DDM 1500 thus oscillates in and out of the page in this view.) FIG. 15B-1 through 15B-3 depict a differential dissecting member as in FIG. 15A; FIG. 15B-1 shows the differential dissecting member in side view cross-section, FIG. 15B-2 depicts a close-up view of the tip of the differential dissecting member shown in FIG. 15B-1, and FIG. 15B-3 shows a close-up view of the surface of the differential dissecting member shown in FIG. 15B-2. First side 1530 and tissue engaging surface 1520 join at first margin 1540, having a radius of curvature $R_E$, and second side 1531 and tissue engaging surface 1520 join at second margin 1541, having radius of curvature $R_E$, where the radii of curvature of first margin 1540 and second margin 1541 can be different, but should be large enough such that the first margin 1540 and the second margin 1541 are not sharp. Tissue engaging surface 1520 is then created by projections 1550 with a maximum length $L_{max}$, defined as the maximum length of a feature from the innermost trough to the outermost peak.

FIG. 15C illustrates a different DDM 1501 having a scalloped tissue engaging surface formed by surface features 1560. Here, the surface feature 1560 is a convex lobe, but a surface feature 1560 can be any regular or repeating feature on the tissue engaging surface 1520 having a minimum radius of curvature $R_S$. Furthermore, surface features can have a profile that is not in the plane of rotation, as shown in FIG. 15D and FIG. 15E. FIG. 15D shows an oblique view and FIG. 15E shows an end-on view. FIG. 15E-1 illustrates an end-on view of the differential dissecting member depicted in FIG. 15C, FIG. 15E-2 depicts a close-up view of the tissue-engaging surface of the differential dissecting member shown in FIG. 15E-1, and FIG. 15E-3 details a very close-up view of the surface features of the differential dissecting member shown in FIG. 15E-1 and FIG. 15E-2. The inserts in FIG. 15E show successively magnified sections of the DDM 1502 taken along the 45° angle. DDM 1502 has surface features 1570 with a profile in a plane at 45° to the plane of rotation. As with DDM 1501 in FIG. 15C, the tissue engaging surface 1520 of DDM 1502 has projections 1550 with a maximum length $L_{max}$. In one embodiment, $R_A$ can be between approximately one (1) mm and approximately one hundred (100) mm. In one embodiment, $R_S$ can be between approximately 0.1 mm and approximately ten (10) mm. In one embodiment, $R_E$ can be between approximately 0.05 mm and approximately ten (10) mm, such that no slicing edge is presented to a tissue. Alternatively, for some embodiments of a DDM, Rs and Re can be as small as about 0.025 mm.

DDMs can have tissue engaging surfaces that are scalloped, or notched, or have undulating profiles such that the angle of attack of the tissue engaging surface with respect to the surface of the tissue varies as the tissue engaging surface passes over a given point in the tissue. In fact, the angle of attack varies for any DDM for which $P_{avg} < (R_{max} - R_{min})$, e.g. for a DDM Type I, Type II, or Type IV. A varying angle of attack makes the dissecting action more aggressive, in which a more aggressive DDM is better able to disrupt a firmer tissue and a less aggressive DDM is less able to disrupt that same tissue.

Figures 1, 16:
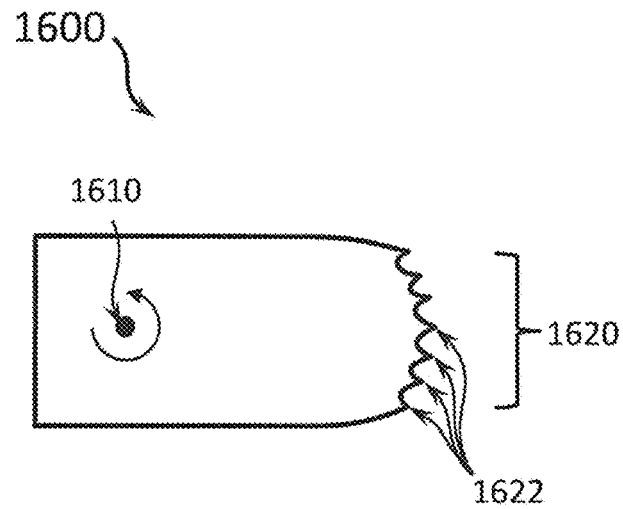
Figures 2, 16:
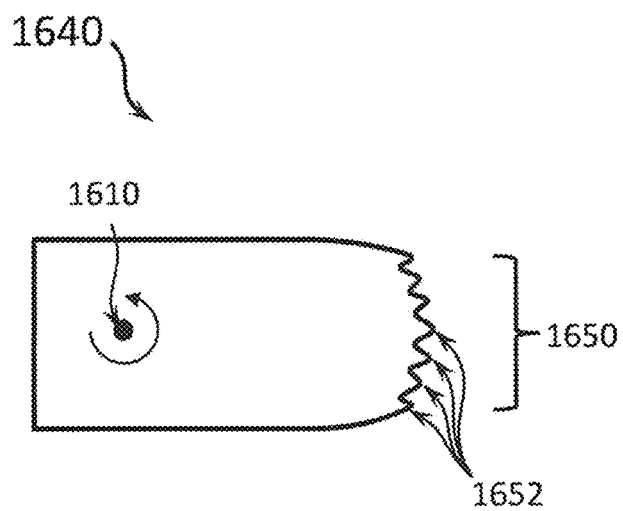
Figures 3, 16:
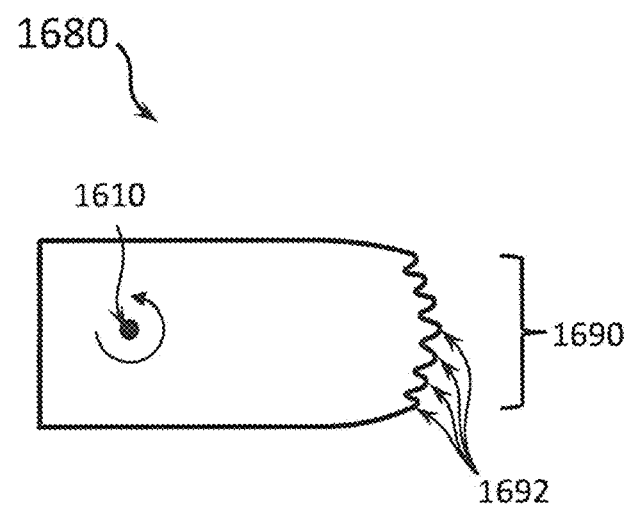

FIGS. 16-1 through 16-3 show an alternate means by which DDMs can be made with different levels of aggressiveness, i.e. the aggressiveness of a DDM can be designed. DDM 1600 rotates about an axis of rotation 1610 and has a tissue engaging surface 1620 bearing projections 1622. These projections (FIG. 16-1) have more pointed tips (but still not sharp enough to slice). DDM 1640 has a tissue engaging surface 1650 bearing projections having more rounded tips 1652 (FIG. 16-2). DDM 1680 has a tissue engaging surface 1690 bearing projections with even more rounded tips 1692 (FIG. 16-3). DDM 1600 is more aggressive than DDM 1640 which is more aggressive than DDM 1680.

Figure 17A:
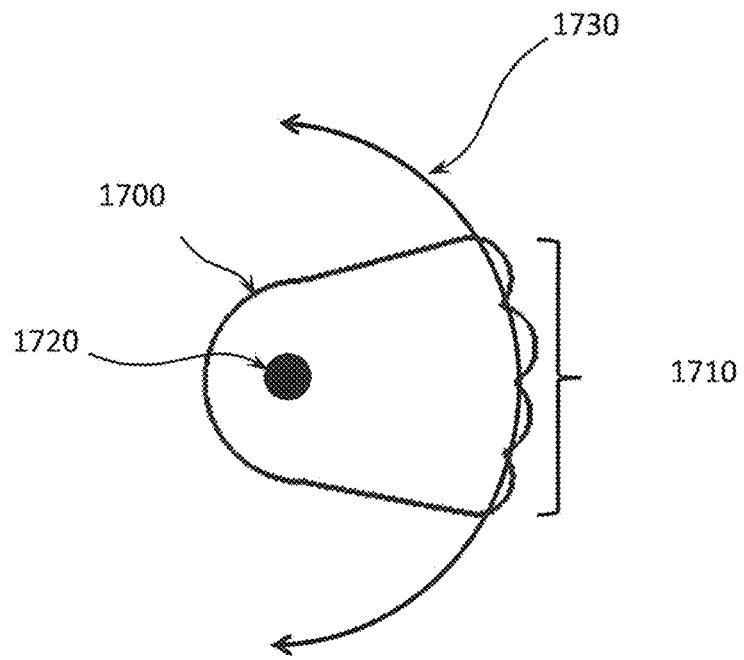

FIG. 17A shows one embodiment of a DDM 1700 having a scalloped tissue engaging surface 1710 and a center of rotation 1720. DDM 1700 is thus an example of a DDM Type IV. Oscillation of DDM 1700 back and forth as shown by double headed arrow 1730 causes tissue engaging surface 1710 to move over a tissue such that the edges of the scallop bring the tissue engaging surface 1710 to bear at different angles of attack as each scallop passes over the tissue.

Figures 1, 17B:
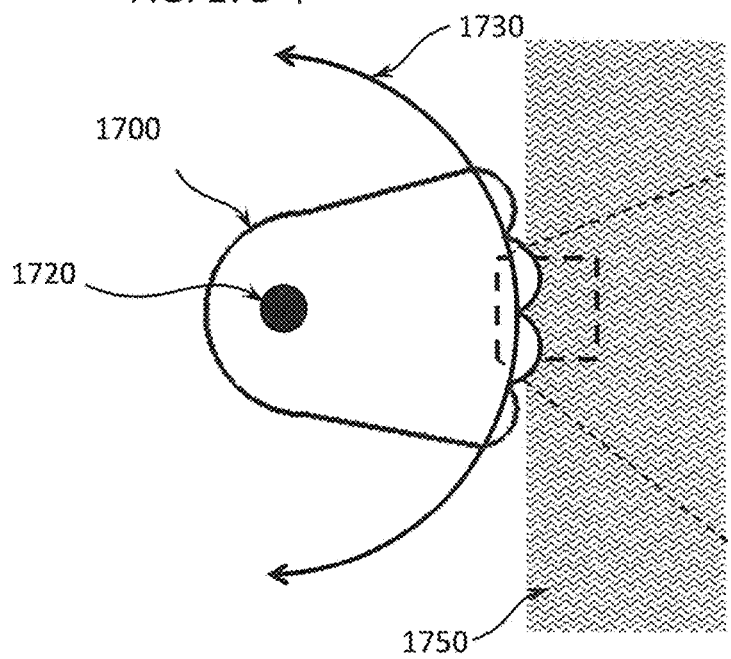
Figures 2, 17B:
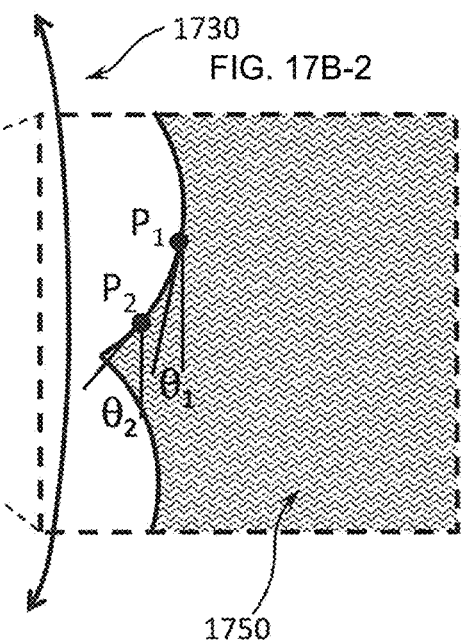
Figure 18:
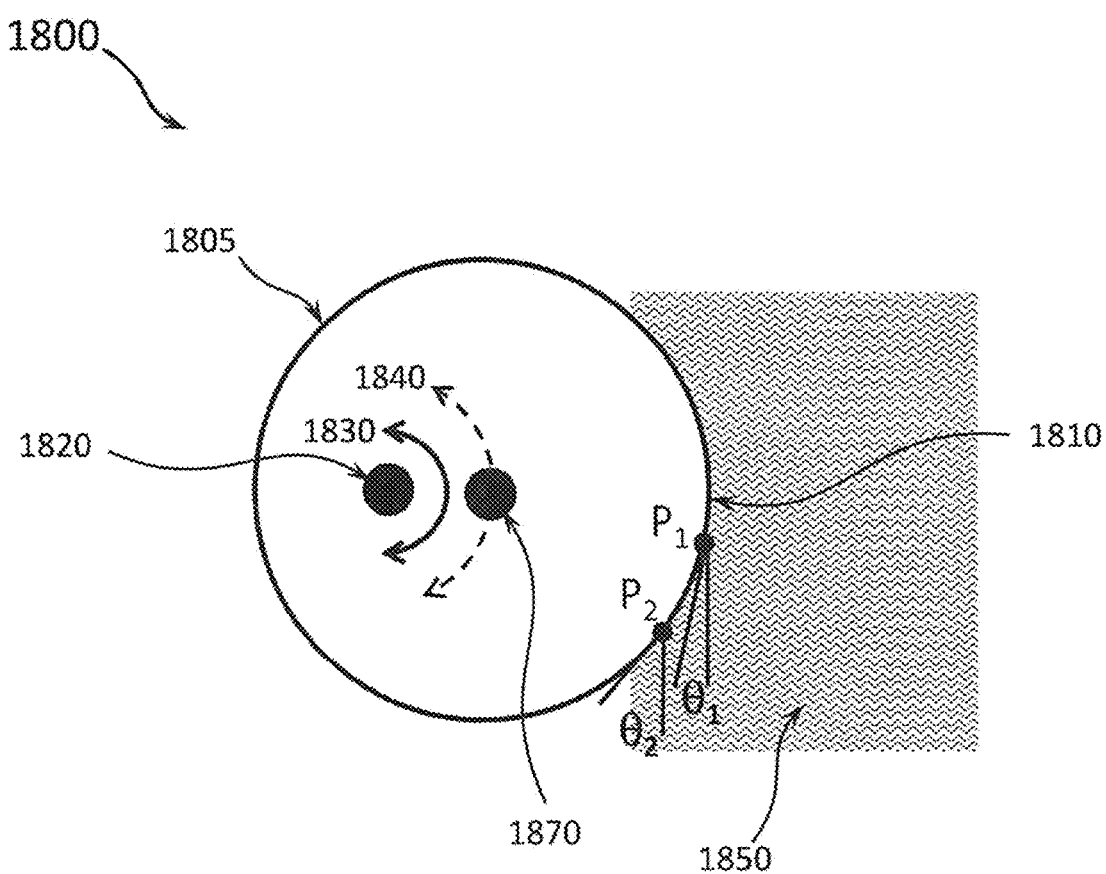
FIG. 18 shows how relative placements of the center of rotation and the center of gravity of an oscillating differential dissecting member can cause a differential dissecting instrument to vibrate.

FIGS. 17B-1 and 17B-2 illustrate the action of DDM 1700 against a tissue 1750. FIG. 17B-1 shows that same differential dissecting member impinging on a tissue, and FIG. 17B-2 is a close-up view of the lobes of the lobate differential dissecting member detailing the angles of attack of the tissue engaging surface with respect to the tissue. The angle of attack (the angle θ between the direction of motion and the tangent to the tissue engaging surface 1710 at a point of contact) is shown at two points $P_1$ and $P_2$ on the tissue engaging surface 1710. $θ_1$ is smaller than $θ_2$. Similar action can be achieved with a DDM 1800, as shown in FIG. 18, by using a circular tissue engaging component 1805 with tissue engaging surface 1810 and a center of rotation 1820 that is not the center of circular tissue engaging component 1805 (e.g., a DDM Type II). Oscillation of tissue engaging component 1805 back and forth as shown by double headed arrow 1830 causes tissue engaging surface 1810 to move over a tissue such that the tissue engaging surface 1810 moves such that the angle of attack varies at each point on the tissue engaging surface 1810 on the perimeter of the circular tissue engaging component 1805.

FIG. 18 illustrates another important point, especially for accelerating motions of a DDM against a tissue 1850, and accelerations occur whenever a DDM is loaded or unloaded and whenever an oscillating DDM decelerates after sweeping one direction and accelerates to sweep in the opposite direction. DDM 1800 is mounted with its center of gravity 1870 displaced from the center of rotation 1820. The solid double-headed arrow 1830 shows the rotation about the center of rotation 1820, and the dashed double-headed arrow 1840 shows the motion of center of gravity 1870. The force of accelerating the mass of DDM 1800 and the distance between the center of gravity 1870 and the center of rotation 1820 create a moment about the center of rotation 1820 which causes a differential dissector to vibrate. This moment will cause the handle of a differential dissector, to which the DDM 1800 is attached, to shake. DDMs composed of denser materials will make the shaking more extreme. It can, thus, be advantageous to make DDMs from less dense materials, like rigid polymers rather than metals, to decrease shaking of the handle. Conversely, one might arrange a countering moment through appropriate distribution of mass within a DDM to place the center of gravity at the axis of rotation.

Figure 19A:
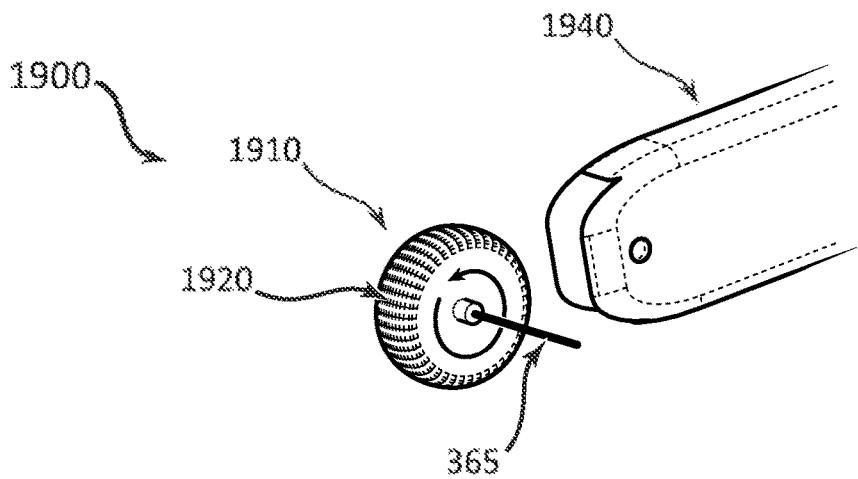
FIGS. 19A through 19D show how an exemplary differential dissecting member, or a shroud surrounding it, strain a tissue in the direction perpendicular to the direction of motion of the tissue engaging surface.
Figure 19B:
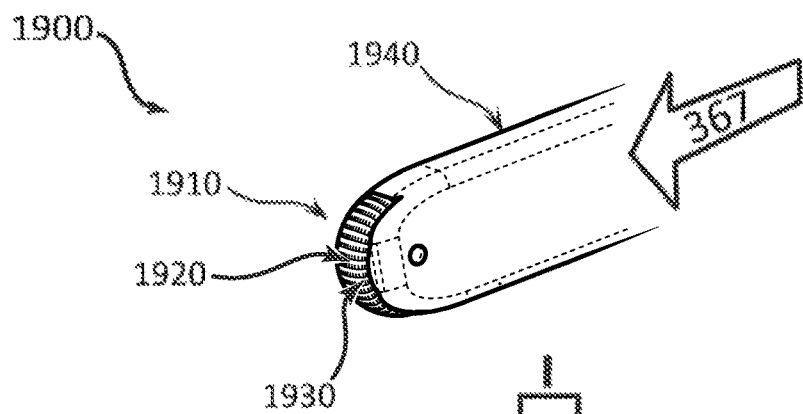
Figure 19C:
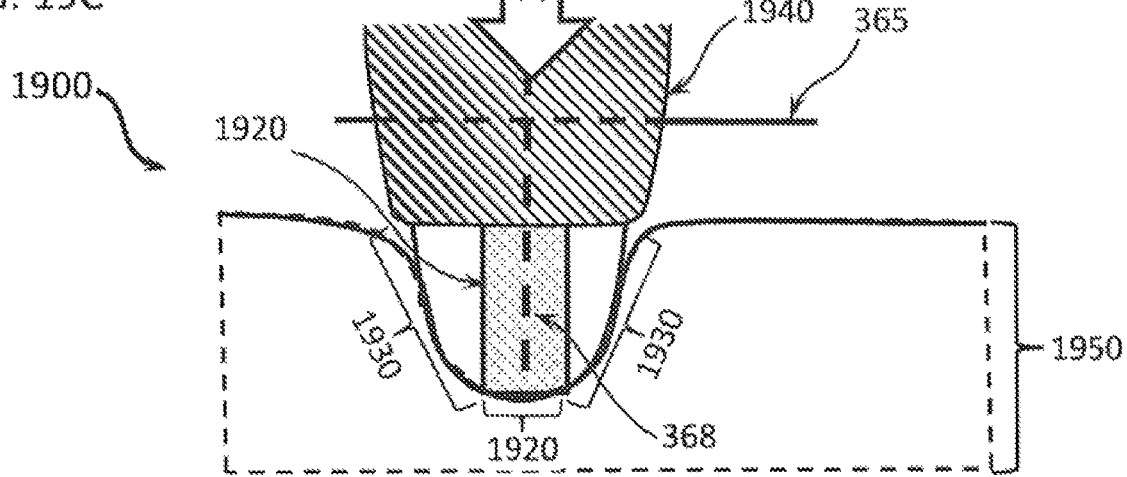

The entirety of the surface of a DDM can be tissue engaging. Alternatively, selected portions of the surface can be tissue engaging. This can be advantageous to restrict dissection effects to one region of the surface of the DDM, the forward-looking surface, for example. FIG. 19A through FIG. 19D show a Differential Dissecting Instrument 1900 that has a DDM that is a dissecting wheel 1910 that is similar to that shown in FIG. 3A through FIG. 3C; however, the tissue engaging surface is restricted to a thin tissue engaging strip 1920 around the outer perimeter of dissecting wheel 1910 which rotates around axis of rotation 365. The remainder comprises the non-tissue engaging surface 1930, disposed laterally to either side of tissue engaging strip 1920, of the exposed surface of the dissecting wheel 1910 and has a much smoother surface, optionally being glass smooth, free of projections, or otherwise unable to engage fibers in the tissues. FIG. 19B illustrates how a dissecting wheel 1910 fits into shroud 1940 and is pressed by an operator in the direction 367. As FIG. 19C illustrates, non-tissue engaging surface 1930, which is smoother than tissue engaging strip 1920, reduces disruption of tissue 1950 after it has been separated by tissue engaging strip 1920. Shroud 1940 further protects tissue 1950 from disruption by dissecting wheel 1910 as the dissector penetrates further into tissue 1950 in the direction of pressing 367.

Figure 19D:
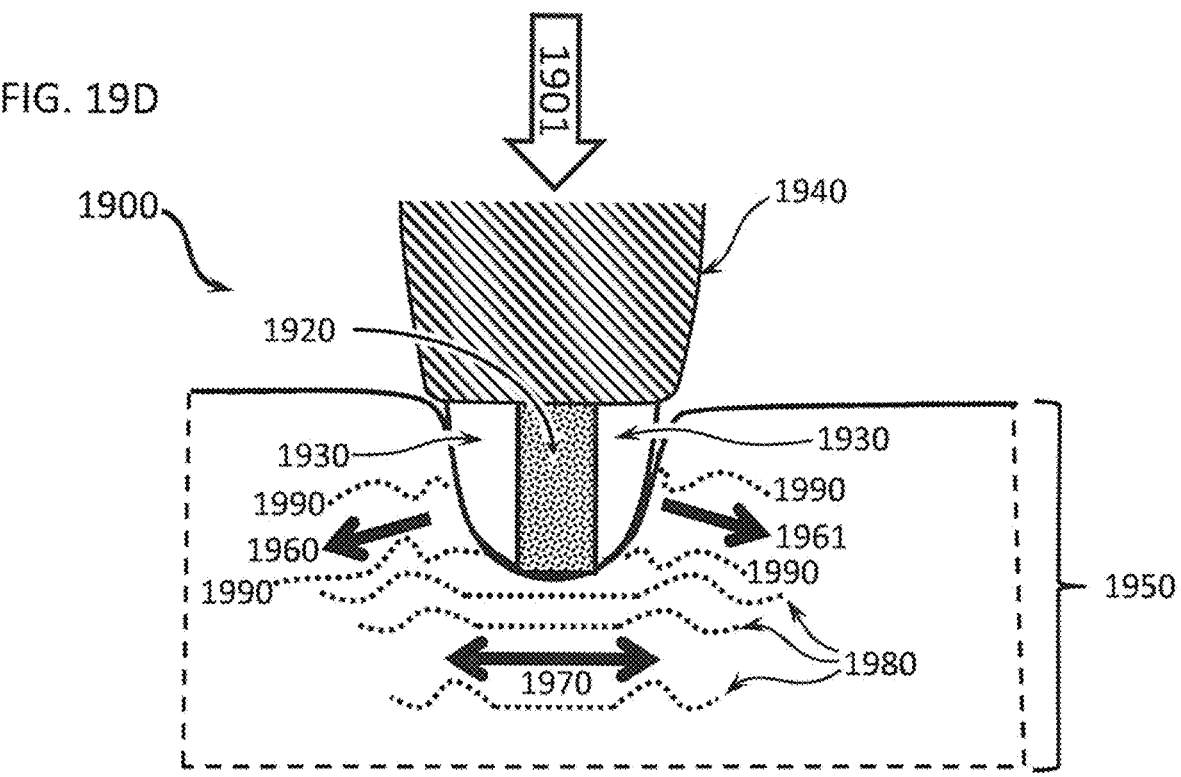

FIG. 19D illustrates an additional, important action of non-tissue engaging surface 1930 and of shroud 1940. When there is a component of motion 1901 in the direction of pressing 367 (not shown here) of Differential Dissecting Instrument 1900 into tissue 1950, these wider portions (non-tissue engaging surface 1930 and of shroud 1940) of Differential Dissecting Instrument 1900 force apart, or wedge, recently separated portions of tissue 1950, aligning and straining the fibrous components 1980 of tissue 1950, putting them in tension and aligning them perpendicular to the motion of tissue engaging strip 1920. This strain in fibrous components 1980 facilitates the ability of the projections of the tissue engaging materials in tissue engaging strip 1920 to grab and tear individual fibers.

As tissue engaging strip 1920 moves past tissue 1950, moving in a direction perpendicular to (and so through) the plane of the page, the projections on tissue engaging strip 1920 therein disrupt tissue 1950, including tearing individual fibrous components 1980 of tissue 1950 (e.g. collagen or elastin fibers). Such fibrous components 1980 frequently have irregular alignments (i.e., irregular orientations) in Soft Tissues. However, as tissue 1950 is disrupted, Differential Dissecting Instrument 1900 pushes into tissue 1950 in the direction of component of motion 1901 such that as remaining tissue engaging surface 1930 and shroud 1940 push into the separated tissue 1950, they push tissue 1950, including severed fibrous components 1990, aside in the direction of arrows 1960 and 1961, aligning previously irregularly oriented fibers and straining material at the point of contact of tissue engaging strip 1920. This local region of strain aligns and strains (and so pre-stresses) unsevered fibrous components 1980 in a direction perpendicular to the direction of motion of tissue engaging strip 1920, as shown by double-ended arrow 1970, facilitating their being grabbed and increasing the likelihood of their being severed by projections from tissue engaging strip 1920. Non-tissue engaging surface 1930 and of shroud 1940 will act as a wedge if they are angled with respect to one another, as shown in FIG. 19C and FIG. 19D or even if they have a width that is wider than the tissue engaging surface 1910. In one embodiment, a semi-ellipsoid shape, as described in FIG. 3F, in which the second minor semi-axis C is a significant fraction of the first minor semi-axis B (e.g., in one embodiment, where 0.2B<C<0.8B), is an effective shape for wedging.

Alignment of fibers, as described in the preceding paragraph, can greatly alter how a DDM performs. Alignment can be achieved by the surgeon straining a tissue in the appropriate directions with their hands or with a separate instrument. Alignment can be achieved by the DDM, as described in the preceding paragraph, by a smooth portion on a tissue engaging wheel, such as non-tissue engaging surface 1930 in FIG. 19C through FIG. 19D, by a smooth shroud, such as shroud 1940 in FIG. 19A through FIG. 19D, or by a separate mechanism on a DDM.

Figure 20:
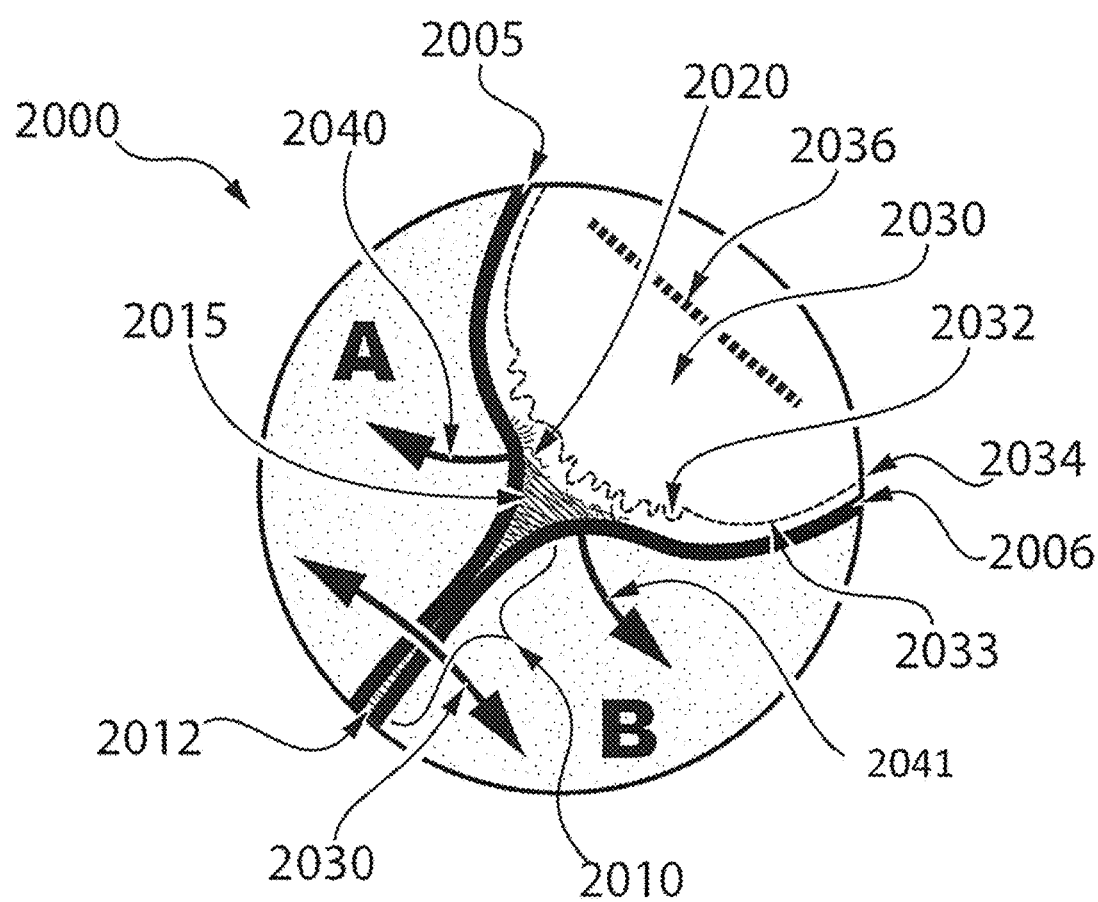
FIG. 20 further illustrates how an exemplary differential dissecting member disrupts tissue, including how the differential dissecting member strains the tissue and disrupts fibrous components, such as interstitial fibers.

FIG. 20 shows details of one version of disruption of tissue segments in a human patient. The region of interest 2000 of the patient is depicted within a circular window, showing a section view through two apposed volumes, namely a tissue segment A apposed to a tissue segment B; the apposition occurs in a region 2010 bridged by both interstitial fibers 2012 and taut interstitial fibers 2015 and further associated with broken interstitial fibers 2020. Also depicted in the circular window is a DDM 2030 possessing a tissue engaging surface 2034 that further possesses projections 2032 and a smooth non-tissue engaging surface 2033. In this view, the DDM 2030 reciprocates about an axis 2036, so that the motion of the fiber-engaging projections 2032 is in and out of the plane of the page (i.e., reciprocally toward and away from the viewer).

Each of the tissue segment A and tissue segment B further has a tissue segment surface 2005 and a tissue segment surface 2006, respectively, composed of relatively tightly packed fibers aligned parallel to tissue segment surface 2005 and tissue segment surface 2006, forming a membranous covering over tissue segment A and tissue segment B (e.g., tissue segments A and B comprise Firm Tissues). Tissue segment A's surface 2005 and tissue segment B's surface 2006 are also three-dimensionally curvaceous. While these tissue segment surfaces 2005 and 2006 may not be in contact with one another at every point, tissue surface 2005 and tissue segment surface 2006 do meet in a region 2010 where tissue segment surface 2005 and tissue segment surface 2006 are apposed in a locally, roughly parallel manner, and are frequently substantially in contact with one another.

In that region 2010, the tissue segment surface 2005 and the tissue segment surface 2006 are secured to one another by a population of relatively loose interstitial fibers 2012 that run substantially perpendicularly to the two apposed tissue segment surfaces 2005 and 2006. This sparse population of interstitial fibers 2012 may or may not also be derived from (or be members of) the populations of fibers comprising the more tightly packed woven surfaces that form the tissue segment surfaces 2005 and 2006. For example, a given fiber comprising part of a tissue segment surface 2005 may run along that surface for some distance before turning away and continuing across the region 2010, thereby becoming a member of the population of interstitial fibers 2012, and further, may continue across the region 2010 to tissue segment surface 2006, where it can turn and interweave therein, thereby becoming a member of the population of fibers comprising tissue segment surface 2006. Thus, the definition of interstitial fibers 2012 includes any fibers crossing, bridging, traversing or otherwise connecting (or intimately associated with) the region 2010 where tissue segment surface 2005 and tissue segment surface 2006 are in apposition. The interstitial fibers 2012 may be the same type of fibers as those comprising the tissue segment surface 2005 and tissue segment surface 2006 of tissue segment A and tissue segment B in one embodiment. In another embodiment, the interstitial fibers 2012 may be a distinct type, and the interstitial fibers 2012 may be strongly or weakly bound, directly or indirectly, to the tissue segment surface 2005 and the tissue segment surface 2006.

In each case, all fibers involved are mechanically capable of transmitting force (via tension) either along the surface of each individual tissue segment, or interstitially, between the two tissue segments, or both. For example, the state of tension of the interstitial fibers 2010 and the fibers comprising the tissue segment surface 2005 and the tissue segment surface 2006 depends on the forces that act upon tissue segment A and tissue segment B, for example when smooth non-tissue engaging surface 2033 wedges into and forces apart these tissue segments in the directions 2040 and 2041. For example, the fibers 2010 resist tensile strains that arise from the motion of tissue segment surface 2005 in the direction 2040 and the motion of tissue segment surface 2006 in the direction 2041 relative to one another, and further, this resistance varies according to the mechanical properties of the fibers. For example, if the unstrained interstitial fibers 2012 are aligned perpendicularly to the two apposed tissue segment surfaces 2005 and 2006, then the distance between tissue segment A and tissue segment B may be increased (as shown by arrow 2030) until the interstitial fibers 2010 first become straightened like the taut interstitial fibers 2015, and then finally the fibers may fail, as is shown by the broken interstitial fibers 2020. The most common fiber type in humans is collagen, which possesses a breaking strain of about 5% beyond unstressed normal length. If tissue segment A and tissue segment B are moved apart as shown by arrow 2030, the collagen fibers (here, unstrained interstitial fibers 2012) will first become taut (as are taut fibers 2015). If the two tissue segments A and B are moved even further apart, collagen fibers will stretch about 5%. Crucially, at this point, if tissue segment A is moved further than 5% beyond taut from tissue segment B, either the taut interstitial fibers 2015 will break, or, if the taut fibers 2012 do not break, the tissue segments themselves may rupture, with deleterious consequences for the patient.

Since surgeons very often must separate, dissever, or otherwise move tissue segments with respect to one another to gain access to various areas inside patients, surgeons are constantly straining fiber populations equivalent to interstitial fibers 2010 throughout patients' bodies. Current practice requires either slicing interstitial fibers to free one tissue segment from another, or tearing interstitial fibers wholesale by applying blunt force with forceps (by opening the jaws, forcing the tissue segments apart, and so tearing the interstitial fibers). Common complications are either slicing into the tissue segments while attempting to cut only the interstitial fibers via sharp dissection or tearing off smaller or larger portions of the tissue segments while attempting blunt dissection of the interstitial fibers. Either approach first strains to tautness the interstitial fibers 2010, then stretches them, and then tears them. The consequences (for example, air leaks and bleeding of segments of the lung) of the aforementioned intimate connection of the interstitial fibers 2010 with the tissue segment surfaces 2005 and 2006 now becomes clear: one must segregate the forces required to cause the interstitial fibers to fail without also subjecting the integrated tissue segments themselves to the same forces.

The embodiments of the Differential Dissecting Instruments disclosed herein are specifically designed to segregate forces on fiber populations by generating an initial separating motion of apposed tissue segments A and B via impingement of the smooth surfaces 2033, thus exposing and tensioning (pre-stressing) individual interstitial fibers 2010, making these fibers much more likely to break, exploiting the opportunity provided by these now taut interstitial fibers 2015, and further allowing those to be discreetly encountered, engaged and converted into broken interstitial fibers 2020 by the local impingement of projections 2032 of the tissue engaging surface 2034 of the Differential Dissecting Member 2030. In this way, a DDM having a smooth-sided non-tissue engaging surface and/or shroud can greatly increase both the speed and effectiveness of dissection of tissues while limiting the extent of that dissection effect to just those fibers within Soft Tissues that connect adjacent regions of Firm Tissues and still preserving those Firm Tissues.

FIG. 21A through FIG. 21C illustrate another Differential Dissecting Instrument 2100 that uses a very thin dissecting wheel 2110 as the DDM. Dissecting wheel 2110 is nearly entirely wrapped in a shroud 2120 to achieve a very thin tissue engaging surface 2009 with shroud 2120 acting to protect, separate and pre-stress the tissue to be dissected, as shown in FIG. 19D.

FIG. 21A shows a side view, and FIG. 21B shows a front view. FIG. 21A shows a side view of a differential dissecting member that has a thin dissecting wheel and is wrapped in a shroud; FIG. 21B-1 and FIG. 21B-2 further illustrate a front view of the shrouded differential dissecting member in FIG. 21A and a close-up view of same, respectively. Dissecting wheel 2110 is mounted on two posts, first post 2130 and second post 2131 (seen in side view of FIG. 21B-1) via rotational axle 2135. Rotational axle 2135 is free to rotate within first post 2130 and second post 2131, but is firmly affixed to dissecting wheel 2110. Sprocket 2140 is also firmly affixed to axle 2135. Sprocket 2140 is turned by drive belt 2150. Thus, a drive mechanism 2160 is created by first post 2130 and second post 2131, axle 2135, sprocket 2140, and drive belt 2150 to turn dissecting wheel 2110 inside shroud 2120 in the direction of arrow 2161. Alternate drive mechanisms can be used, and motion can either be rotational or oscillatory. The first margin 2111 and second margin 2112 of dissecting wheel 2110 preferably are not sharp, as shown in the enlarged portion of FIG. 21B-2. (First and second margins 2111 and 2112 are like first and second margins 1540 and 1541 in FIGS. 15B-1 through 15B-3.) Sharp margins can disrupt more aggressively than a rounded margin; nevertheless, a sharper margin can be used if more aggressive disruption or even disrupting is desired. Furthermore, one margin can be sharper than the other if a differential disruption or disrupting is desired. For example, first margin 2111 can be square or even sharp, while second margin 2112 can be rounded to achieve more aggressive disruption or disrupting on the side of first margin 2111.

Shroud 2120 nearly encloses dissecting wheel 2110, leaving only a fine portion of dissecting wheel 2110 exposed as the tissue engaging surface 2111, and forming a wedge angle $\omega$ that determines the strain on tissue at the point of disruption of dissecting wheel 2110. Larger wedge angles $\omega$ strain tissue more as DDM 2100 is pushed into a tissue. FIGS. 21C-1 through 21C-4 depict DDM 2100 with shroud 2120 in four different positions. Shroud 2120 can be moved independently of drive mechanism 2160 and dissecting wheel 2110, shroud 2120 being able to move in the direction of double headed arrow 2190. Thus, in Position 1 (FIG.

21C-1) only a thin portion of dissecting wheel 2110 is exposed. In Position 2 (FIG. 21C-2), shroud 2120 has been moved in the direction of arrow 2191, leaving a thinner portion of dissecting wheel 2110 exposed and also creating a larger wedge angle ω. In Position 3 (FIG. 21C-3), shroud 2120 has been moved in the direction of arrow 2192 such that shroud 2120 completely encloses dissecting wheel 2110. Thus, dissecting wheel 2110 can no longer disrupt tissue. In this position, the dissecting wheel 2110 effectively acts as a smooth, flat, blunt probe. In Position 4 (FIG. 21C-4), shroud 2120 has moved in the direction of arrow 2193, increasing the exposure seen in Position 1 or Position 2 of dissecting wheel 2110 and decreasing wedge angle ω.

Figure 22:
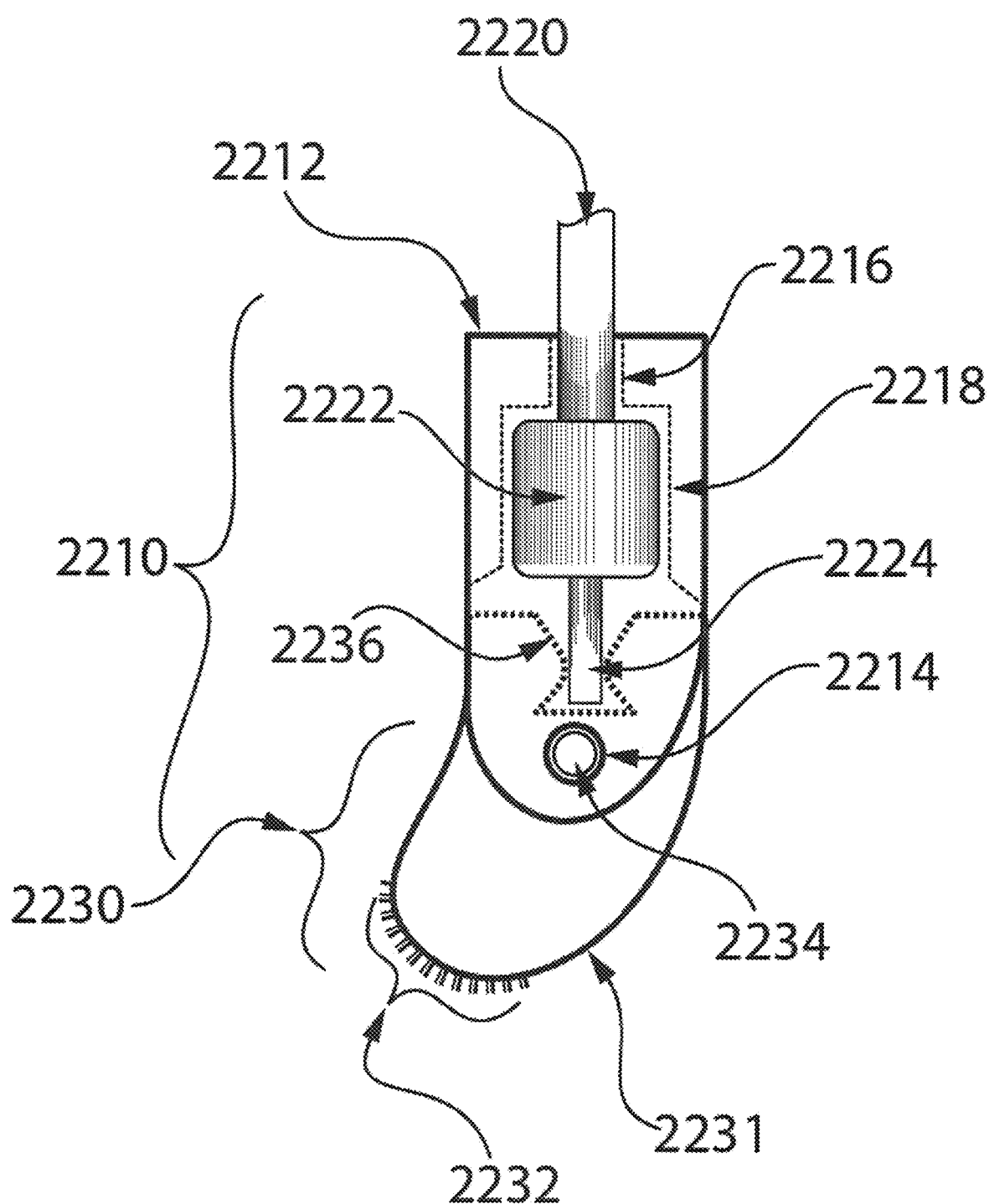
FIG. 22 shows one example of an exemplary reciprocating mechanism for a differential dissecting member that uses a scotch yoke mechanism to convert rotation of a shaft to reciprocal oscillation of a differential dissecting member.

FIG. 22 shows the distal end of a differential dissector 2210, including one embodiment of a reciprocating mechanism, here a scotch yoke. The distal end of differential dissector 2210 includes a housing 2212, which further contains a pivot bearing 2214, a motor shaft bearing 2216, and a shaft drum bearing 2218. FIG. 22 also shows a motor shaft 2220, a shaft drum 2222 coaxial with and affixed to the motor shaft 2220, and a driver pin 2224 which may be parallel but not coaxial to motor shaft 2220, and is itself affixed to the shaft drum 2222. Further, there is a Differential Dissecting Member, DDM 2230, which is associated with the differential dissector housing 2212, and further comprises an outer surface 2231 defining the body of the DDM 2230, a tissue engaging surface 2232 forming at least a portion of the outer surface 2231, a DDM pivot shaft 2234 that fits into the pivot bearing 2214, and further comprises a hollow DDM pin follower 2236 that effectively captures the driver pin 2224. The internal three-dimensional shape of the hollow DDM pin follower 2236 is here shown as a prism, so that in the view shown in FIG. 22 the cross-sectional shape resembles an hourglass, while perpendicular to that view, the cross-sectional shape is rectilinear.

FIG. 23A, FIG. 23B, and FIG. 23C show a sectional view of a portion of the DDM 2230 of FIG. 22 through the narrowest portion of the waist of the hourglass-shaped hollow DDM pin follower 2236 and perpendicular to the rotational axis of the shaft drum 2222. The shape of the DDM pin follower 2236 is in this view rectangular; further, in this view showing the dimensions through the waist of 2236 the height of the rectangle is equal or larger than a diameter described by the outer diameter of the driver pin 2224 along its circular path 2237. The width of the rectangle in this view corresponds to the outer diameter of the driver pin 2224. The DDM 2230 containing the hollow DDM pin follower 2236 rotates about the axis 2233 of the shaft 2234. Thus, the position of the hollow DDM pin follower 2236 and so the rotational position of the DDM 2230 is determined by the rotational position of the driver pin 2224.

In operation, referring to FIG. 22, along with FIGS. 23A-23C, the motor (not shown) turns the motor shaft 2220, which turns the drum 2222 about its axis of rotation, which causes the driver pin 2224 to travel about a circular path 2237, the plane of which is here perpendicular to the rotational axis of the drum 2222. As in a scotch yoke, the rectangularly hollow DDM pin follower 2236 converts the circular path 2237 of the driver pin 2224 into linear travel 2238 of the hollow DDM pin follower 2236; given that the pin follower 2236 is located some distance away from the axis 2233, the DDM 2230 is leveraged about the axis 2233, so converting the rotational path 2237 into linear travel 2238 and so reciprocating motion of the DDM 2230 rotating about the DDM pivot shaft 2234 held by the pivot bearing 2214. The pattern of the reciprocal motion of the DDM 2230 can be controlled by varying the shape of the hollow DDM pin follower 2236, the driver pin 2224, the 3D angle of the axis 2233 about which the shaft 2234 rotates, the distance from the driver pin 2224 to the axis 2233, and also by varying the rotational speed of the motor.

Figure 24B:
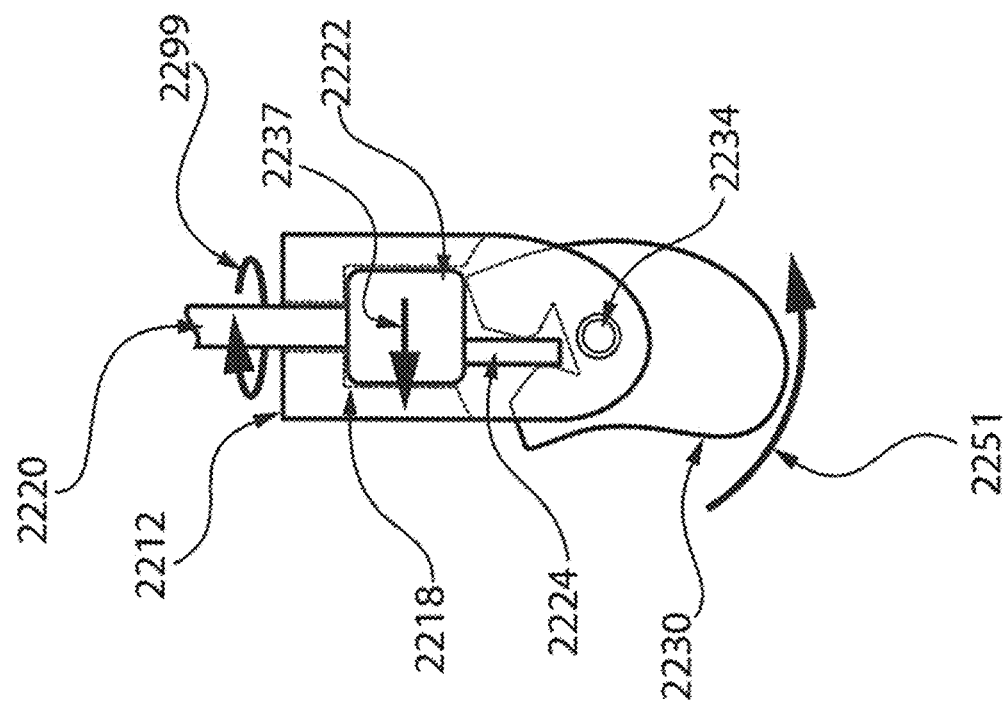
FIGS. 24A and 24B further illustrate the scotch yoke mechanism shown in FIG. 22.
Figure 24A:
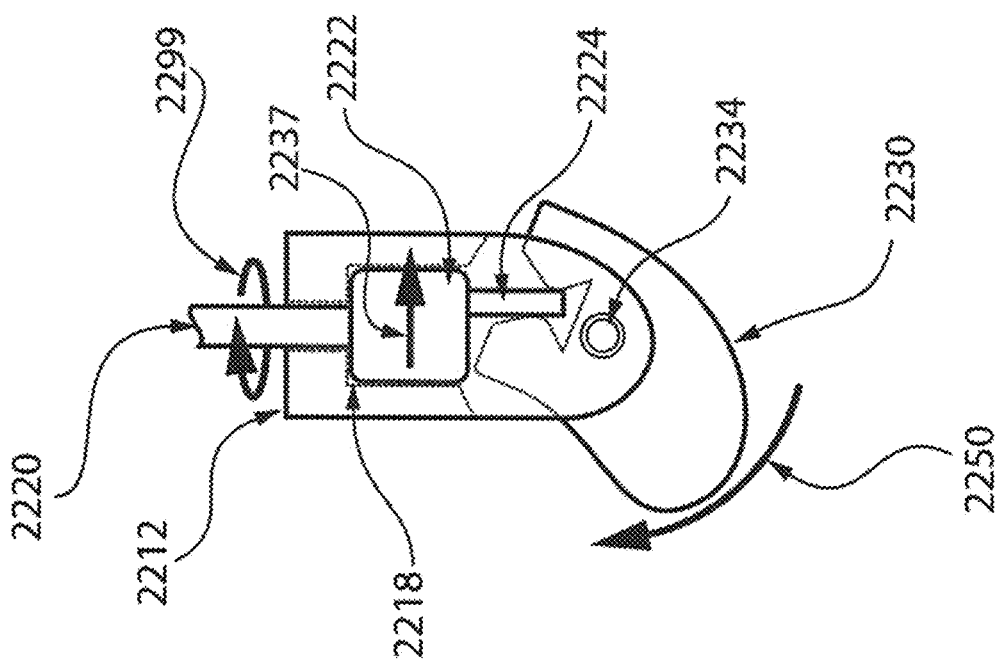

The DDM 2230 of FIG. 22 may have reciprocating motion 2250 and 2251, as shown in side view in FIG. 24A and FIG. 24B. The oscillation sequence shown depicts the extreme positions of the DDM 2230 as the driver pin 2224 travels about circular path 2237 when provided with rotational motion 2299 from the motor (not shown). The action of the tissue engaging surface 2232 of the DDM 2230 on the surface of the tissues to be dissected is best shown in an edge-on view in FIG. 20.

A surgeon operating inside a patient desires to create the least trauma possible to tissues which are not the focus of the procedure, or are simply in the way of the Target Tissue. To this end, FIGS. 25A through 25C depict the profile view of an embodiment of a largely shrouded DDM assembly 2500, further comprising a shrouded pivot shaft 2510 that projects perpendicularly to the page (i.e., at the viewer), an internal motor shaft 2550, an internal driver drum 2522, a driver pin 2524, a DDI housing 2512, a DDM 2520 that reciprocates about the shrouded pivot shaft 2510 (and so within the plane of the page), a tissue engaging DDM surface 2534, a smooth DDM surface 2518, a substantially circular DDM region 2516, a shroud margin 2517, and a shroud-DDM gap 2514. Considered as a whole, with all exterior surfaces of the DDM assembly 2500 included as one, a shrouded DDM assembly 2500 presents a nearly continuous smooth surface to a patient's tissues. In this regard, other than the limited extent of the tissue engaging DDM surface 2534, the entire Differential Dissecting Instrument fitted with the DDM assembly 2500 acts like nothing more than a polished probe.

Once activated, the DDM 2520 reciprocates within and relative to the housing 2512. At the edge of the housing 2512 closest to the DDM 2520 is the shroud margin 2517. Between the shroud margin 2517 and the DDM 2520 is found the shroud-DDM gap 2514. In one embodiment, a Differential Dissecting Instrument fitted with a DDM assembly 2500 includes provisions for preserving the outwardly smooth character of the Differential Dissecting Instrument. The shroud-DDM gap 2514 thus presents a challenge, in that any relative motion of the DDM 2520 with respect to the housing 2512 could enlarge the shroud-DDM gap 2514, presenting sharp edges to the tissues. Alternatively, a portion of the DDM 2520 could impact the housing 2512. Also, in one embodiment, the shroud-DDM gap 2514 is kept as small as possible at all times. To facilitate this, the DDM 2520 has a circular DDM region 2516, defined in this perspective as a portion of the mass of the DDM 2520 having the cross-section of a circle with its center coincident with the axis of the shrouded pivot shaft 2510. This circular DDM region 2516 defines and occupies that portion of the outer surface of the DDM 2520 that passes the shroud margin 2517 during reciprocating motion of the DDM 2520, and at a distance that defines the shroud-DDM gap 2514. Because the circular DDM region 2516 preserves over the angle of rotation the same radius of DDM 2520, this preserves the shroud-DDM gap 2514 at a constant value (i.e., shroud-DDM gap 2514 does not change despite motion of the DDM 2520). Thus, the Differential Dissecting Instrument that is fitted with this DDM assembly presents to the tissues a continuously smooth surface everywhere through time.

Figure 25D:
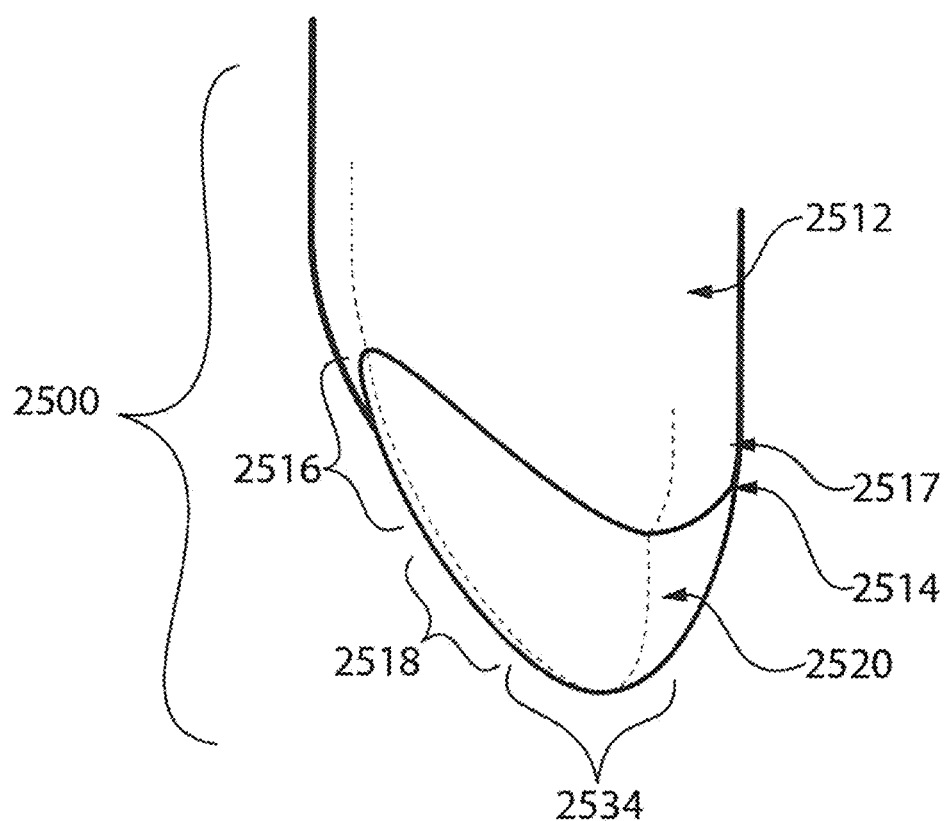

FIG. 25D depicts an oblique view of the largely shrouded DDM assembly 2500, showing a housing 2512, a DDM 2520 that reciprocates about the shrouded pivot shaft 2510 (see FIGS. 25A through 25C), a tissue engaging DDM surface 2534, a smooth DDM surface 2518, a substantially circular DDM region 2516, a shroud margin 2517, and a shroud-DDM gap 2514.

Sharp dissection is frequently performed alternately with blunt dissection when exposing a Target Tissue. This occurs whenever a membrane or a large fibrous component, which resists blunt dissection, is encountered and must be severed for the surgeon to penetrate further into a tissue. Current practice requires that a surgeon either use a suboptimal instrument for blunt dissection (e.g., an inactive electrosurgery scalpel) or to swap instruments while exposing a Target Tissue. Use of a suboptimal instrument decreases the ease of blunt dissection and increases potential risk to a Target Tissue. Swapping consumes time and is distracting, especially for many minimally invasive procedures in which the instrument must pass through a narrow orifice in the body wall and then be gently guided to the site, such as during laparoscopy and thoracoscopy. A Differential Dissecting Instrument can be equipped with a sharp dissecting component that can be selectively activated by a surgeon, eliminating the need for instrument swapping while still providing the surgeon with an optimal instrument.

Figures 1, 26A:
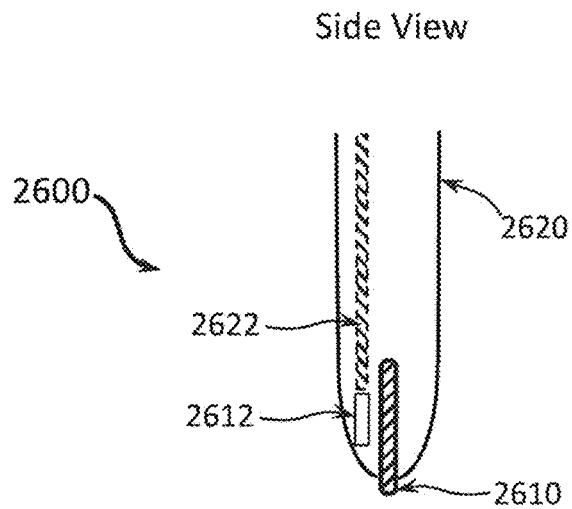
Figures 2, 26A:
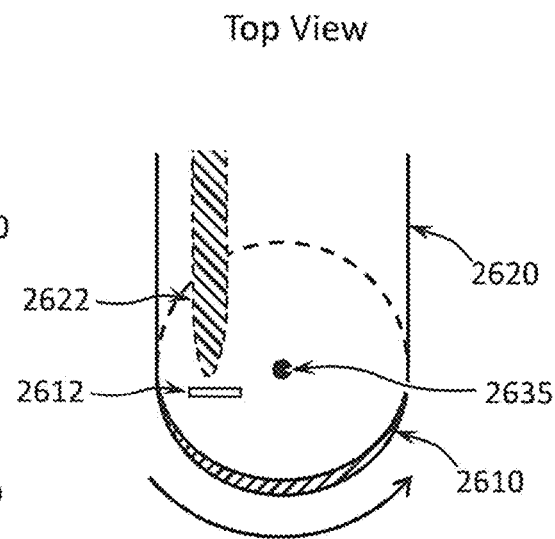
Figures 1, 26B:
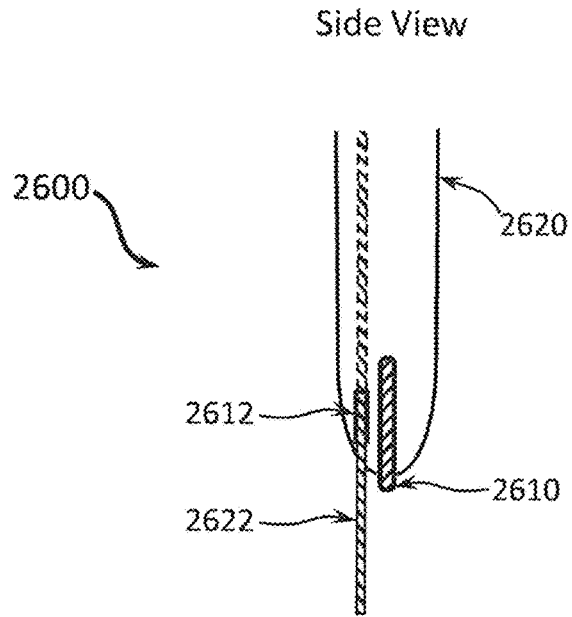
Figures 2, 26B:
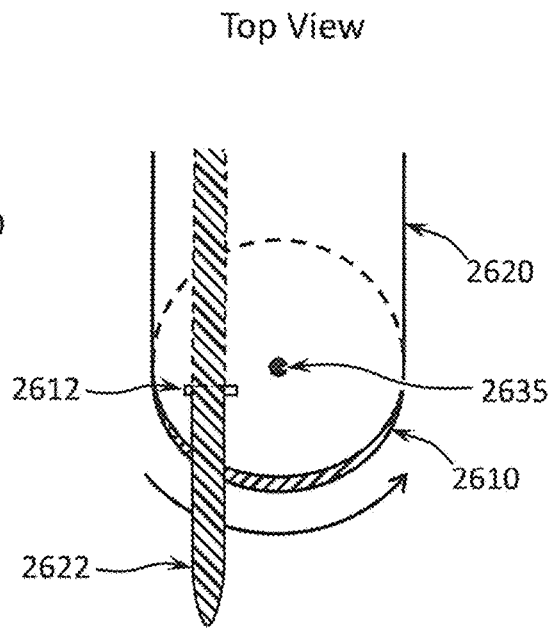

FIGS. 26A-1 and 26A-2 show a top and side view, respectively, of one embodiment of a Differential Dissecting Instrument 2600, similar to Differential Dissecting Instrument 2000, as shown in FIG. 20, but now also comprising a retractable scalpel blade that is covered during blunt dissection. FIG. 26A-1 and FIG. 26B-1 show side views while FIG. 26A-2 and FIG. 26B-2 show top views; FIG. 26A-1 and FIG. 26A-2 show the differential dissecting member with a retractable scalpel withdrawn. The retractable scalpel blade can be projected outward by a surgeon for sharp dissection and then retracted before proceeding with further blunt dissection. Differential Dissecting Instrument 2600 has an elongate member comprised of shroud 2620 to which DDM 2610 is rotatably mounted via rotational axle 2635. To one side of DDM 2610 is a slot 2612 under which lies retractable scalpel blade 2622 such that retractable scalpel blade 2622 is completely covered by shroud 2620. Retractable scalpel blade 2622 is actuated by a retraction mechanism (not illustrated) controlled by a surgeon. Actuation of the retractable scalpel blade 2622 can be controlled manually via a slider, by electrical actuation (such as a solenoid), or by any suitable mechanism controllable by an operator.

FIGS. 26B-1 and 26B-2 show Differential Dissecting Instrument 2600 with retractable scalpel blade 2622 extended for sharp dissection. FIG. 26B-1 and FIG. 26B-2 show the same differential dissecting member with the retractable scalpel extended. Retractable scalpel blade 2622 is one example of a sharp dissecting tool. In other embodiments, the Differential Dissecting Instrument 2600 could include other sharp dissection tools, such as an electrosurgery blade, ultrasonic cutter, or a disrupting hook. In other embodiments, the Differential Dissecting Instrument 2600 could include a tool for energetic disruption, for example an electrocautery blade or electrosurgery head. Additionally, instead of retraction, retractable scalpel blade 2622, or other suitable tool, could be selectively be exposed for use by one of several mechanisms, such as by pop-out, by unfolding, or other mechanism known in the art.

FIG. 27 shows a top and side view of another embodiment of a Differential Dissecting Instrument 2700, similar to Differential Dissecting Instrument 2600 shown in FIG. 26A and FIG. 26B, but now possessing a grasping member to allow the Differential Dissecting Instrument 2700 to also function as forceps. Differential Dissecting Instrument 2700 has a DDM 2710 rotatably attached to an instrument shaft 2720 and is rotated by a motorized mechanism (not shown). A push rod 2730 is inside instrument shaft 2720 and is activated by a mechanism residing in a handle (not shown) and activated manually by an operator. When DDM 2710 is active, it oscillates back-and-forth as indicated by arrow 2740. When the operator switches off the action of DDM 2710, the operator can then push with push rod 2730 on forceps jaw 2750 which has a control horn 2760 that causes forceps jaw 2750 to rotate around pivot point 2770 and thus to open. The opposing jaw for the forceps is the DDM 2710. The operator can then grasp and release objects between forceps jaw 2750 and DDM 2710 by pushing or pulling on push rod 2730.

Figure 28:
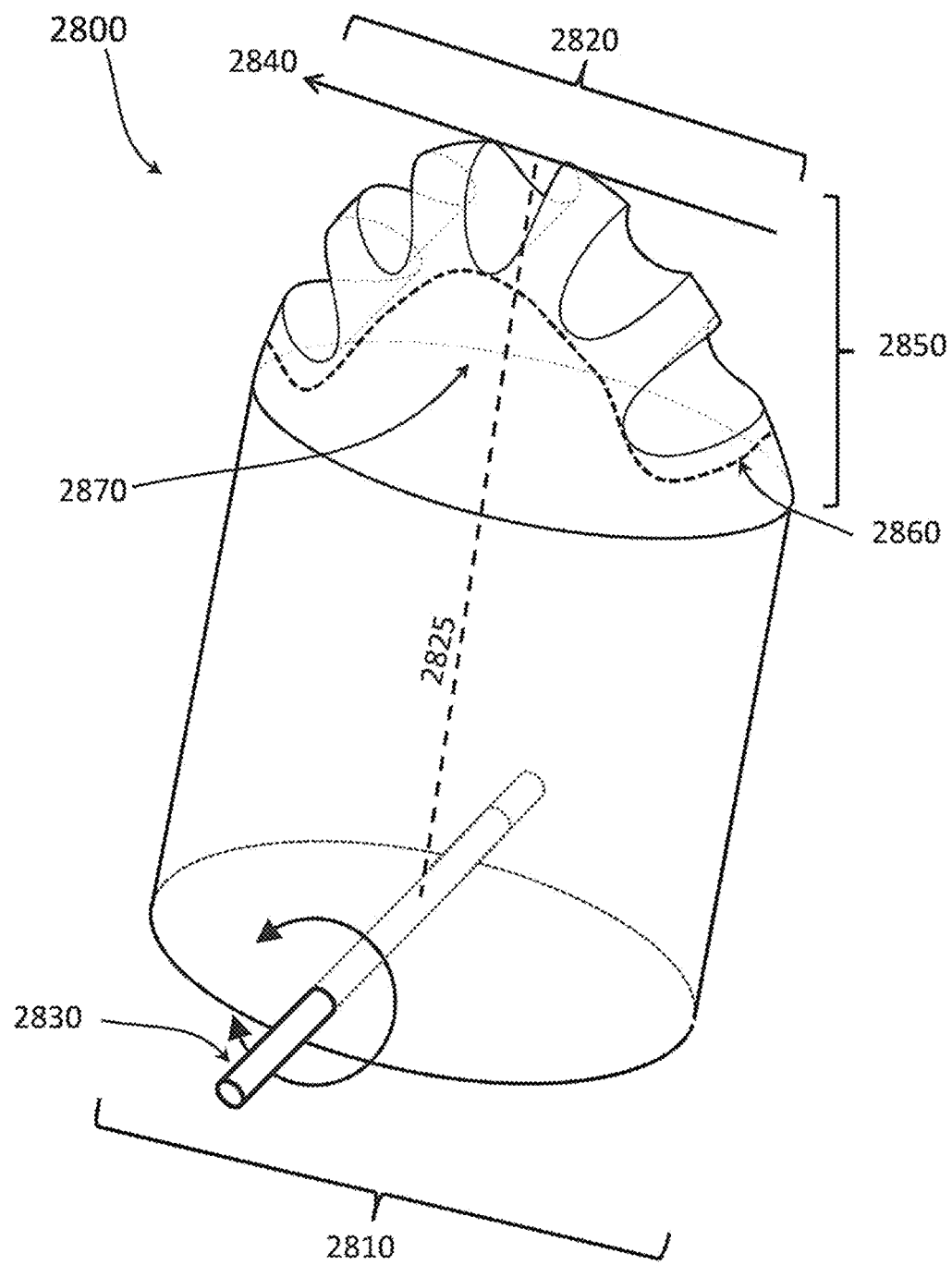
FIG. 28 shows an exemplary differential dissecting member having a tissue engaging surface and a lateral surface.

FIG. 28, and FIGS. 29A through 29D depict another embodiment of a DDM. In practice, this embodiment has provided great differential action and rapid dissection through complex tissues. For this embodiment of a DDM, the projections of the tissue engaging surface are formed by valleys cut into the surface of the DDM. Referring to FIG. 28, DDM 2800 has a first end 2810 and a second end 2820, with a central axis 2825 connecting the first end 2810 and second end 2820. First end 2810 is directed away from the complex tissue to be dissected (not shown) and is engaged with a drive mechanism (not shown) that moves DDM 2800 such that second end 2820 sweeps along a direction of motion. Here, the mechanism oscillates DDM 2800 about an axis of rotation 2830 that is perpendicular to the central axis 2825 such that the direction of motion 2840 is an arc of motion lying in a plane perpendicular to the axis of rotation 2830. The second end 2820 has a tissue-facing surface 2850 that is directed toward the complex tissue comprising at least one tissue engaging surface 2860 and at least one lateral surface 2870.

The motion of DDM 2800 in this example is a reciprocal (back-and-forth) oscillation, but other DDMs can have a continuous rotation or a rectilinear motion. The rotation is preferably between 2,000 and 25,000 cycles per minute, but can range from 60 cycles per minute up to 900,000 cycles per minute, all of which are well below ultrasonic. In certain embodiments, speeds of 300 to 25,000 cycles per minute have been found to be very effective.

Figure 29B:
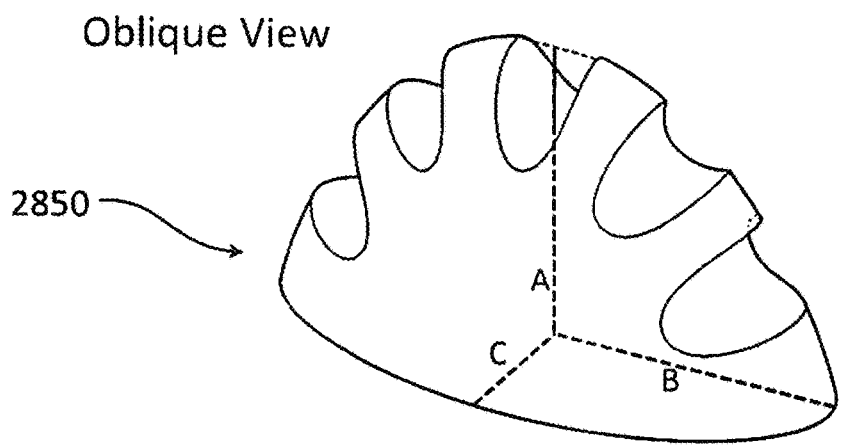
Figures 1, 29C:
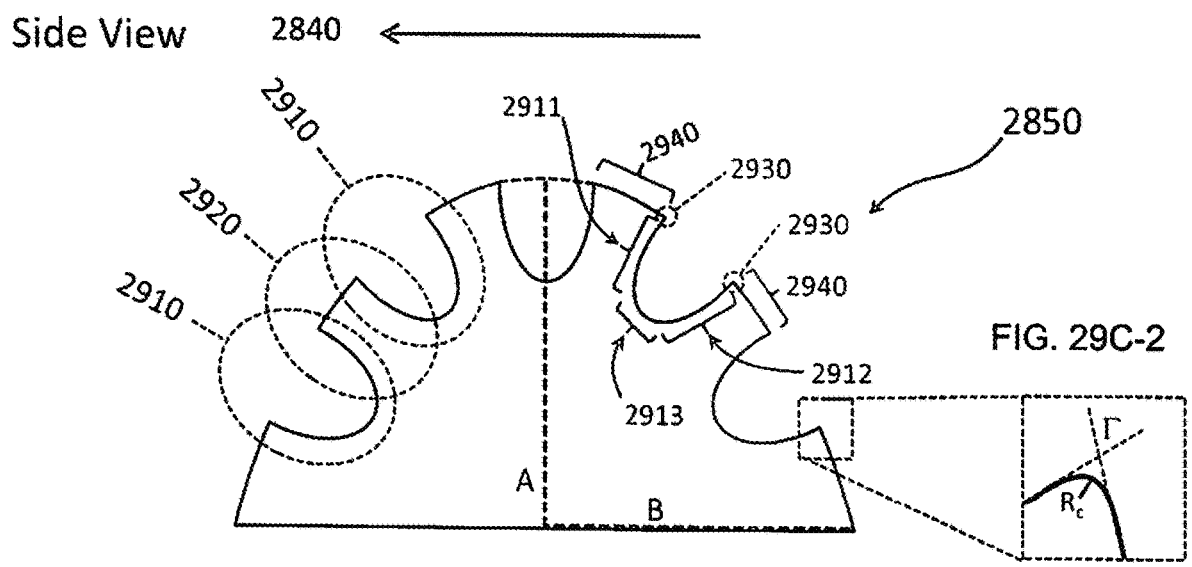
Figure 29D:
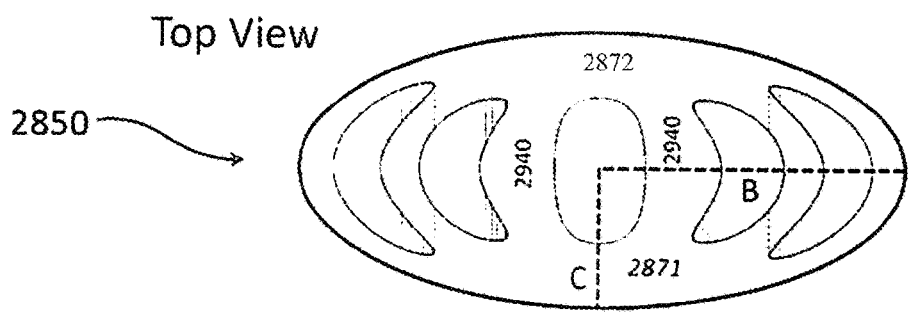
Figures 1, 29E:
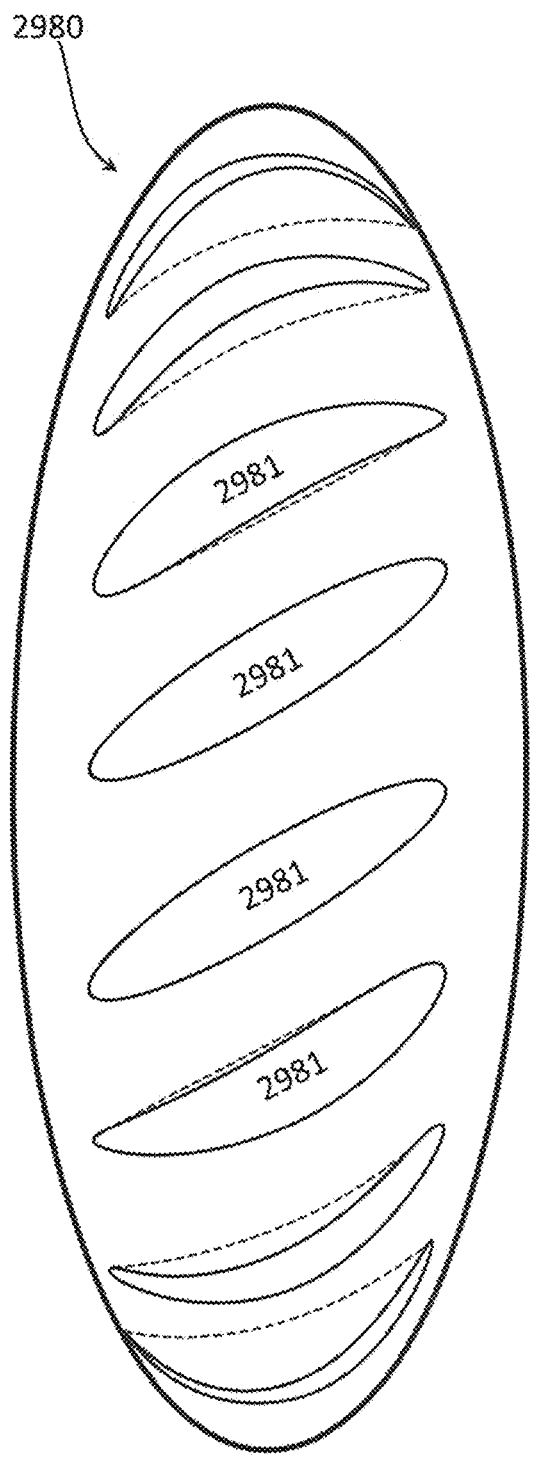
Figures 2, 29E:
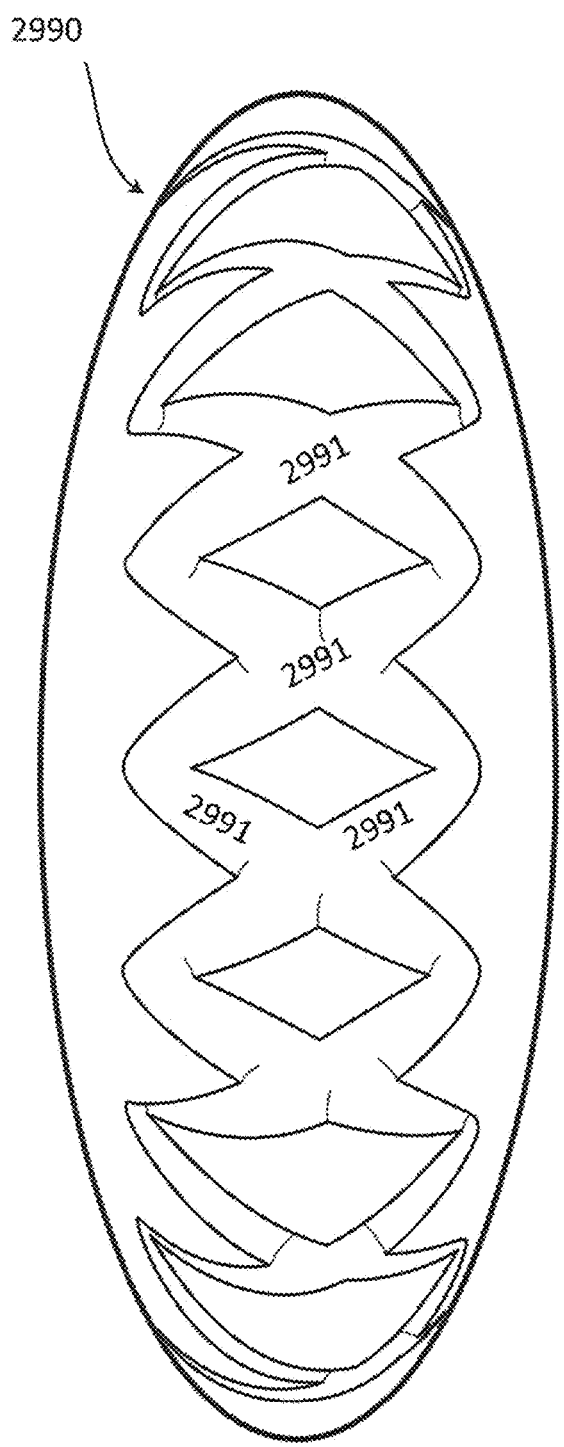

FIGS. 29A through 29E show magnified views of the tissue-facing surface 2850 of DDM 2800 from FIG. 28. FIG. 29A shows an oblique view of tissue-facing surface 2850 with components identified. FIGS. 29B-D show different views of tissue-facing surface 2850 with the geometry of the shape better described, especially with respect to components of tissue-facing surface 2850. FIG. 29C-2 depicts a close-up of the corner of a projection shown in FIG. 29C-1; FIG. 29E-1 and FIG. 29E-2 show two alternative versions of arrangements of valleys and projections forming the surface of a differential dissecting member. Finally, FIGS. 29E-1 and 29E-2 show different embodiments of some of these components. The tissue-facing surface 2850 has a tissue engaging surface 2860 and two lateral surfaces, a first lateral surface 2871 disposed lateral to and to one side of the tissue engaging surface 2860 and a second lateral surface 2872 disposed lateral to and to the opposing side of the tissue engaging surface. Referring to FIGS. 29A, 29C-1, and 29C-2, the tissue engaging surface 2860 is comprised of an alternating series of at least one valley 2910 and one projection 2920 arrayed along the direction of motion 2840 which is an arc of motion on the tissue-facing surface 2850 such that the intersection of the at least one valley 2910 and at least one projection 2920 define at least one valley edge 2930 oriented such that it has a component of direction perpendicular to the direction of motion 2840.

No valley edge 2930 should be sharp, e.g. it should not be capable of slicing into Complex Tissue, especially into Firm Tissue. For example, no point on a valley edge 2930 should have a radius of curvature $R_c$ smaller than approximately 0.025 mm (see FIG. 29C-1, expanded view). This radius of curvature $R_c$ is similar to the radius of curvature of the surface $R_s$ and of the edge $R_e$ as depicted in FIG. 15. We have shown through testing that edges with radius of curvature $R_e$ no smaller than approximately 0.050 mm can be effective, too. Additionally, the radius of curvature $R_c$ can vary along the length of valley edge 2930. In the embodiment shown in FIGS. 29A through 29D, the radius of curvature $R_c$ is smallest where the valley edge 2930 is furthest from the axis of rotation 2830 and increases closer to the first lateral surface 2871 and the second lateral surface 2872. Furthermore, the minimum radius of curvature $R_c$ for a valley edge 2930 can be different for different valley edges in the same DDM and even for the valley edges on opposing sides of the same valley.

Projections 2920 in DDM 2800 may be formed by subtractive manufacture in one embodiment. In effect, the valleys 2910 are cut out of the surface of a semi-ellipsoid, as shown in FIGS. 29B, 29C-1, and 29C-2, having a major semi-axis A aligned perpendicular to the rotational velocity 2830 and parallel to the central axis 2825 (see FIG. 28) (i.e. pointing toward the Complex Tissue), a first minor semi-axis B, and a second minor semi-axis C that is parallel to the rotational velocity 2830. The projections 2920 thus have projection tops 2940 that are the remaining semi-ellipsoidal surface and are continuous with the lateral surfaces 2971 and 2972. Tissue engaging surfaces 2860 are thus created by the lateral limits of the valleys 2910 in this embodiment and span the tissue-facing surface between the valleys 2910 that form the projection 2920. In other embodiments, projections can be formed by other means and can thus have more differently shaped projection tops, including projection tops that are not formed as the remainder of a surface. For example, in one embodiment, the projections can effectively be built up from a surface, enabling more complex projection tops.

Referring to FIG. 29A, FIGS. 29C, and 29C-2, each valley 2910 may have a first valley side 2911, a second valley side 2912, and a valley bottom 2913, whereby the first valley side 2911 and the second valley side 2912 lie on opposing sides of the valley 2910. The valley bottom 2913 is linear or curvilinear and can be two-dimensional or 3-dimensional. For example, the valley bottoms in DDM 2800 are straight lines aligned parallel to the rotational velocity 2830. The first valley side 2911 and the second valley side 2912 rise from the valley bottom 2913 to a valley edge 2930. The transition from valley bottom can be gradual and indeterminate, as in the valleys 2910 in DDM 2800, or the transition can be faceted. A valley 2910 may be curved in two dimensions, being straight in the direction parallel to the valley bottom 2913 (and thus also parallel to the axis of rotation 2830). Valley sides, however, can be any shape, including surfaces curved in three dimensions.

A valley edge is formed by the intersection of a valley wall with a projection top. Valley edges can thus have different shapes, depending on the shapes of the projection top and the valley edge. The valley edges 2930 on DDM 2800 trace three dimensional curves and thus have both curvature and torsion (as defined mathematically in geometry) that are non-zero and varying along the valley edge.

Valley edges can have smoothly varying curvature and torsion (as do valley edges 2930), or a valley edge can be bent.

FIG. 29C-1 presents an expanded view of a valley edge, in the plane perpendicular to the valley edge. The projection top 2920 and the valley side (2911 or 2912 here) form a face angle $\Gamma$ in this plane that is rounded at the intersection (i.e. it is "radiused" as a machinist would describe it) having the radius of curvature $R_c$ described above. The face angle $\Gamma$ can form an angle less than 90°, which appears sharp on first inspection, but sharpness is determined by the radius of curvature $R_c$ of the edge. The face angle $\Gamma$ can vary along the length of the valley edge, as it does for DDM 2800 where the face angle $\Gamma$ is smallest at the points on the valley edge furthest from the axis of rotation 2830. In one embodiment, face angles of about thirty degrees (30°) to about one hundred fifty degrees (150°) may be effective.

Valleys have a length, width, and depth where the valley length is the length of the valley bottom, the valley width is the distance separating the valley edges of one valley measured at their longest distance of separation, and the valley depth is the maximum vertical distance from a valley edge to the valley bottom (e.g. peak-to-trough height). Typical dimensions for a valley include valley lengths of 0.25 mm to 10 mm, valley widths of 0.1 mm to 10 mm, and valley depths of 0.1 mm to 10 mm. In one embodiment, a valley length of approximately three (3) mm, a valley depth of approximately three (3) mm, and a valley width of approximately two (2) mm has been found to be very effective.

When a DDM has multiple valleys, like DDM 2800, the valleys can be parallel, like valleys 2910 of DDM 2800, having valley bottoms 2913 that are all parallel, or they can be non-parallel with valley bottoms lying at non-zero angles with respect to each other or at variable angles with respect to each other.

The valleys 2910 of DDM 2800 have a single channel (the space bounded by the valley sides and valley bottom); however, valleys can have multiple, intersecting channels such that valley bottoms can fork or multiply branch or form networks on the tissue engaging surface. FIGS. 29E-1 and 29E-2 show top views of two DDMs, the left DDM 2980 having parallel valleys 2981 with valley bottoms that are not parallel to the rotational velocity while the right DDM 2990 has network 2991 of multiple intersecting valleys all at different angles with respect to the rotational velocity and to each other.

As described above, the tissue-facing surface 2850 of DDM 2800 has the surface of a semi-ellipsoid having a major semi-axis A aligned perpendicular to the axis of rotation 2830 and parallel to the central axis 2825, a first minor semi-axis B, and a second minor semi-axis C that is parallel to the axis of rotation 2830. Tissue-facing surface 2850 may have an ellipsoid shape in one embodiment, in which A>B>C. However, any relationship is possible between the lengths of the semi-axes. For example, in other embodiments, DDMs may be fabricated for which A=B=C (e.g., the tissue-facing surface is hemi-spherical).

The first lateral surface 2871 and the second lateral surface 2872 of DDM 2800 are continuations of the hemi-ellipsoidal shape. As such, they lie at an angle to one another, forming a wedge, as earlier depicted in FIG. 19D and FIG. 20, that aligns and strains fibrous components of a Complex Tissue allowing the projections to snag and break the fibrous components.

Figure 30A:
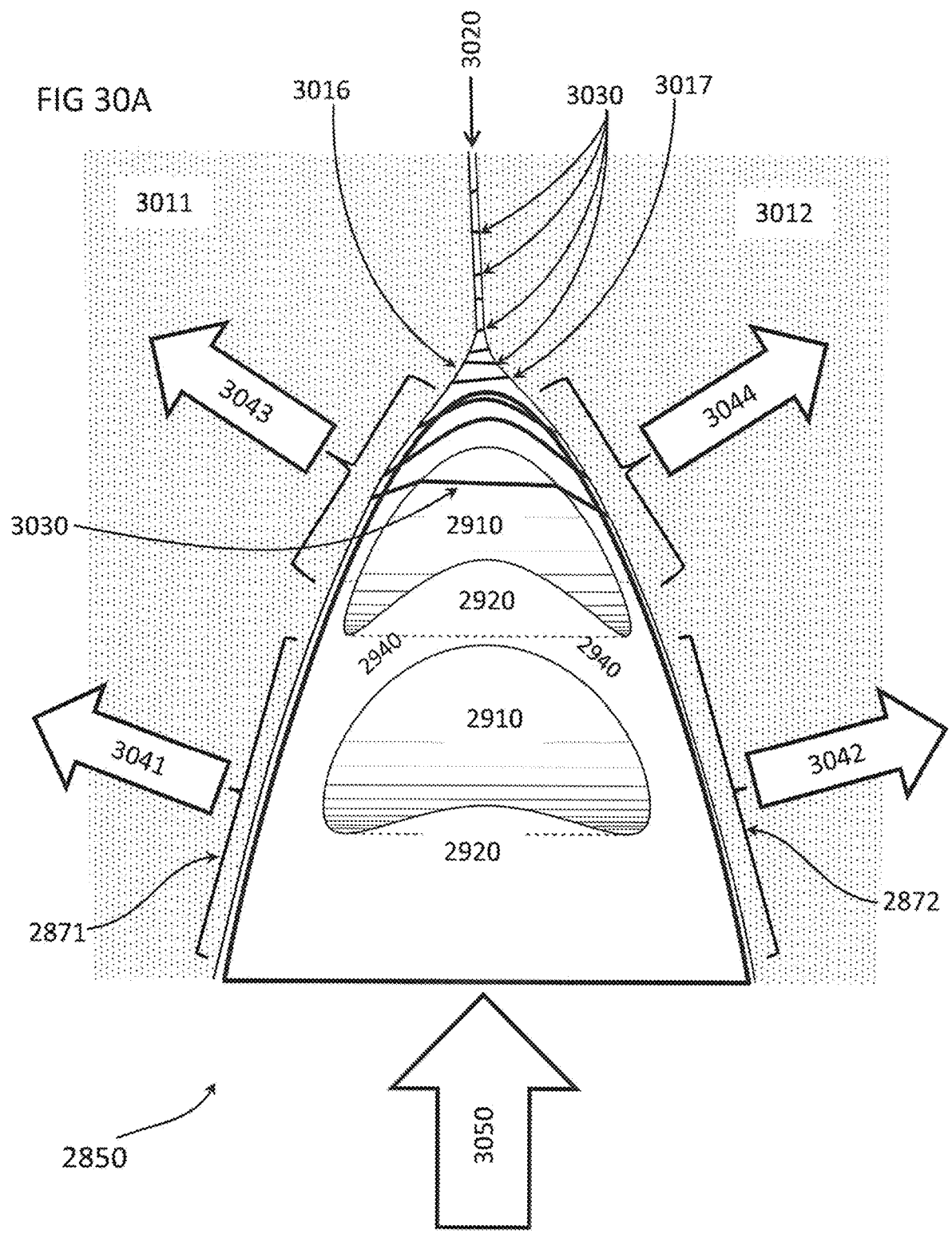
FIGS. 30A through 30D show how the lateral surface of the differential dissecting member in FIGS. 28 and 29A through 29C-2 align and strain tissues, including interstitial fibrous components and how straining of the interstitial fibrous components facilitates their alignment and entering a valley and then being torn by a projection.

FIG. 30A presents the situation of a first tissue region 3011 encased in first membrane 3016 and second tissue region 3012 encased in second membrane 3017. First membrane 3016 and second membrane 3017 abut at tissue plane 3020. First membrane 3016 and second membrane 3017 are formed of densely packed fibrous components and thus comprise a Firm Tissue. The interstitial materials spanning the tissue plane from first membrane 3016 to second membrane 3017 include fibrous components 3030. These fibrous components 3030 are less densely packed, so the interstitial materials comprise a Soft Tissue. As tissue-facing surface 2850 is pressed in the direction of arrow 3050 into the tissue plane 3020 to separate the two tissue regions 3011 and 3012, the first lateral surface 2871 and the second lateral surface 2872 exert a first spreading force 3041 and a second spreading force 3042 on tissue regions 3011 and 3012, respectively, that align and strain fibrous components 3030 at the projection tops 2940 (see FIGS. 29C-1 and 29C-2). This enables the fibrous components 3030 to enter the valleys 2910 and thus be snagged and then torn by a projection 2920 as the tissue-facing surface 2850 rotates about axis of rotation 2830 and so moves out of the plane of the page (toward the viewer). Additionally, as the projection tops 2940 are continuous with the lateral sides, the more lateral areas of the projection tops 2940 also exert additional spreading forces 3043 and 3044 that also wedge tissue regions 3011 and 3012 apart, further increasing the strain on fibrous components 3030.

Figure 30B:
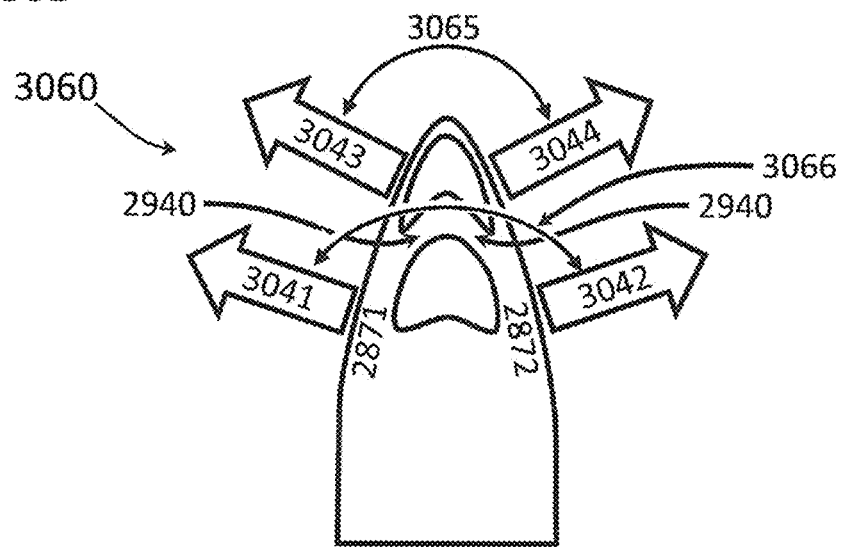
Figure 30C:
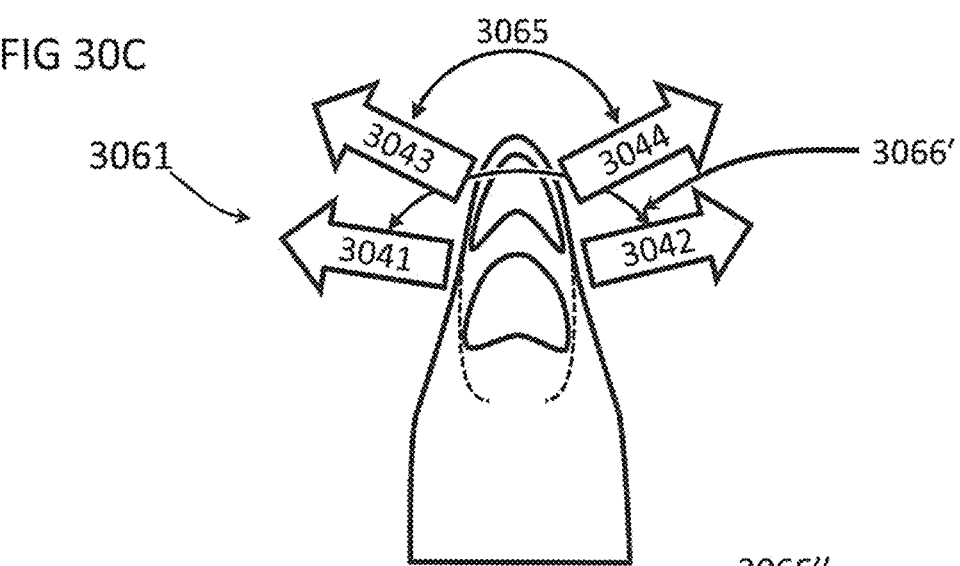
Figure 30D:
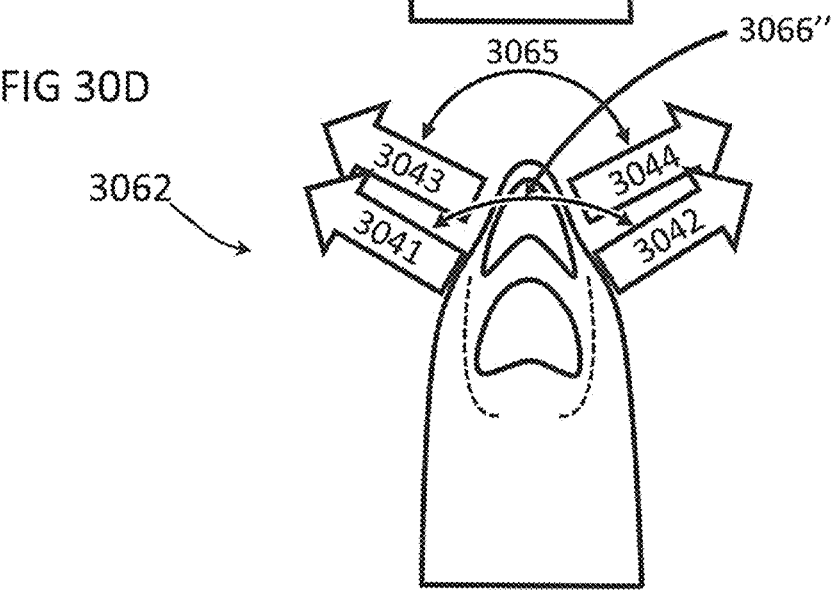

FIGS. 30B through 30D show how the curvature of first lateral surface 2871 and second lateral surface 2872 can be changed to make a DDM more or less aggressive. Consider first DDM 3060 in FIG. 30B. As explained in FIG. 30A, the more lateral areas of the projection tops 2940 exert spreading forces 3043 and 3044 that wedge adjacent tissue regions apart. Furthermore, the first lateral surface 2871 and the second lateral surface 2872 exert a first spreading force 3041 and a second spreading force 3042. As first angle 3065 formed by spreading forces 3043 and 3044 approaches 180° (as shown for DDM 3061 in FIG. 30C), the wedging action of the lateral areas of the projection tops 2940 decreases. (Note that angle 3065 is similar to the wedge angle ω described in FIGS. 21A through 21C.) If projections 2920 become also laterally (left-right in this figure) thinner, then the projections will more rapidly disrupt Soft Tissue but will also be more proned to abrade or disrupt Firm Tissue. As in FIG. 30A, first and second lateral surfaces 2871 and 2872 create spreading forces 3041 and 3042, respectively, forming a second angle 3066 (effectively, a second wedge angle ω). If second angle 3066 is similar to first angle 3065 (as shown for DDM 3060 in FIG. 30B), then these surfaces combine to create a single wedging surface. If, as in FIG. 30C, second angle 3066' is larger than first angle 3065 (i.e. lateral surfaces 2871 and 2872 are more nearly parallel), then second angle 3066' exerts little or no wedging action. Conversely, if, as in FIG. 30D, second angle 3066" is smaller than first angle 3065 (i.e. lateral surfaces 2871 and 2872 become more nearly perpendicular, then second angle 3066" exerts a greater wedging action. DDMs like 3061 have proven more effective in dissecting tissue planes possessing prominent collagen fibrils that span the tissue plane, crossing from one surface to the other.

Referring back to FIG. 30A, FIG. 30A also illustrates an important aspect of a DDM. A DDM will automatically follow a tissue plane. Because tissue planes tend to be bounded by Firm Tissues (e.g. membranes, ducts, etc.) and are spanned by Soft Tissues, a DDM will, by virtue of its differential action, not move into the Firm Tissue and will move into the Soft Tissue, thus following and separating a tissue plane will little or no guidance from an operator. This means that the operator need not have as detailed an understanding of the anatomy as is required by current practice or, conversely, a DDM allows a skilled surgeon to more confidently dissect an uncertain anatomy, e.g. when tissue planes are distorted by a tumor or when tissues are swollen or inflamed.

Figure 31:
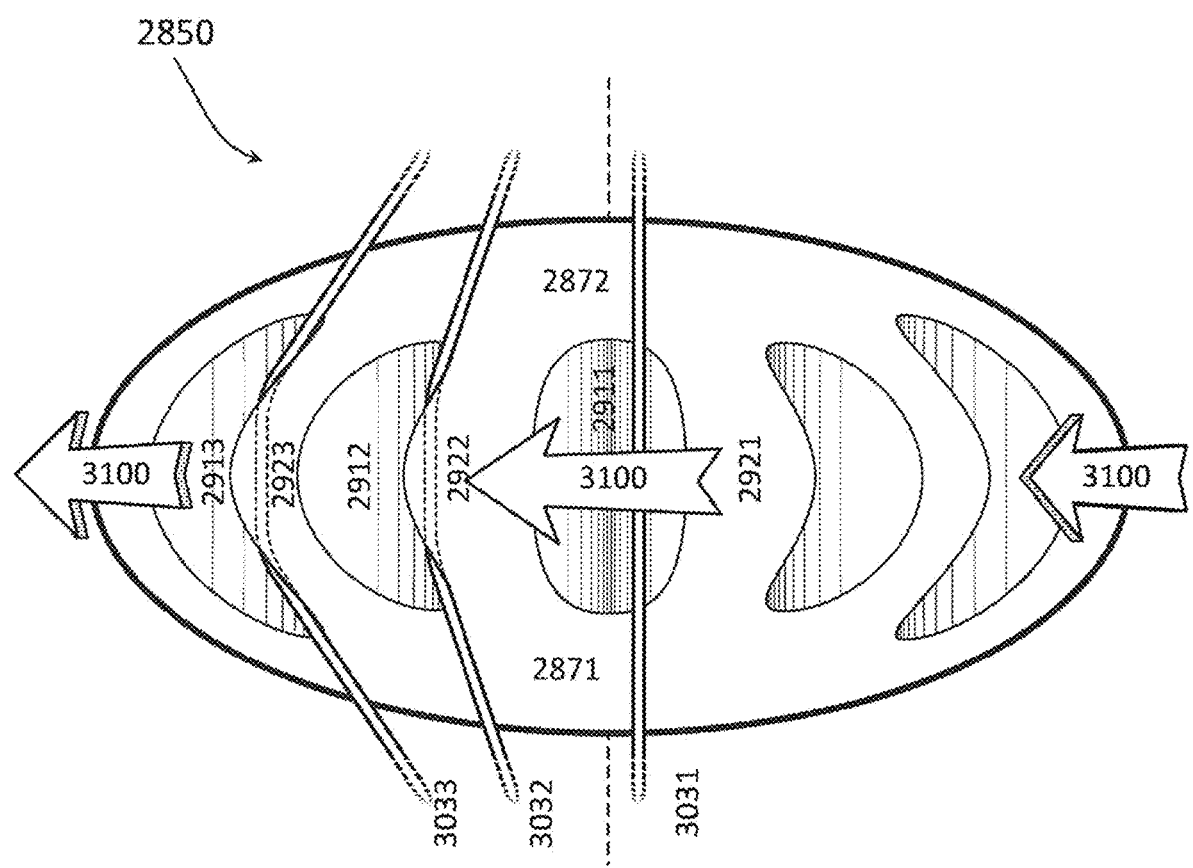
FIG. 31 further illustrates from a different view how fibrous components of a tissue enter a valley and are then strained and torn by a projection.

FIG. 31 shows an end-on view of the tissue-facing surface 2850 as it snags and then stretches to breaking the fibrous components 3030 shown in FIG. 30A. Three fibrous components (first fibrous component 3031, second fibrous component 3032, and third fibrous component 3033) have been snagged by three projections (first projection 2921, second projection 2922, and third projection 2923, respectively). Tissue facing surface 2850 rotates, generating a direction of motion 2840 which is an arc of motion as depicted by arrows 3100. First fibrous component 3031 has just entered the first valley 2911 and has not yet been snagged by first projection 2921. Second fibrous component 3032 entered the second valley 2912 at an earlier point in time and has been snagged and strained by second projection 2922. Third fibrous component 3033 entered the third valley 2913 at an even earlier point in time and has been snagged and strained even further by third projection 2923. Ultimately, all three fibrous components 3031, 3032, and 3033 will be strained to breaking.

FIG. 31 illustrates an important aspect of DDM 2800's design. Because the valleys span from one lateral surface 2871 to the opposing lateral surface 2872, each valley creates an open space spanning across the end of DDM 2800 into which strained fibrous components can enter, thus facilitating their being snagged by the projections.

It is important to note that DDM 2800 does not have arrays of small projections that give any part of its surface texture, as described earlier. Rather, all surfaces of DDM 2800 are smooth and, preferably, possess low friction surfaces. The shapes and configurations of the surface features of DDM 2800 are responsible for its ability to differentially dissect Complex Tissues. In fact, DDM 2800 works best when all of its surfaces that are in contact with tissue are well lubricated with, for example, a surgical lube.

Figure 32:
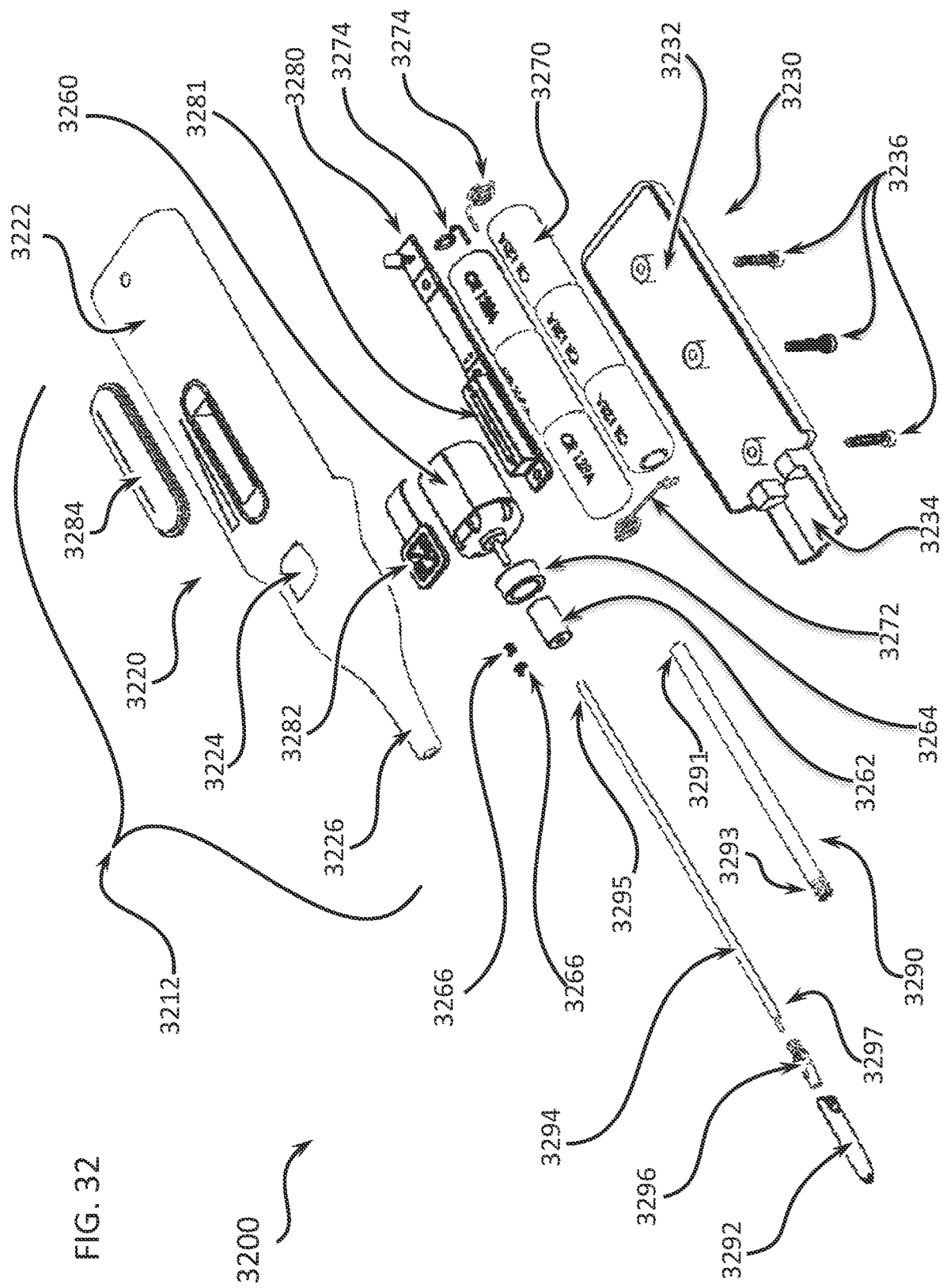
FIG. 32 shows an exploded view of a complete exemplary differential dissecting instrument.

FIG. 32 shows an exploded view of one embodiment of a complete differential dissecting instrument. The differential dissecting instrument 3200 is grossly comprised of an instrument handle 3212 from which projects an instrument insertion tube 3290 which has a first end 3291 attached to instrument handle 3212 and a second end 3293, to which is rotatably mounted a DDM 3292. The instrument handle 3212 is assembled from an upper housing 3220, which includes upper battery cover 3222, and a lower housing 3230, which are held together by instrument housing bolts 3236. Included in the upper housing 3220 and lower housing 3230 are a motor 3260 and a battery pack 3270. In the upper housing 3220 is a switch port 3224, through which can be accessed a switch 3282 (which may be a momentary switch or an on-off switch) for providing power to the motor 3260 from the battery pack 3270. A printed circuit board 3280 further containing a power level adjustment 3281 (which can be any convenient component, but is here shown as a linear potentiometer) is provided and can be accessed through a flexible switch cover 3284 mounted in surface of the upper housing 3220. Also included are forward spring battery connectors 3272 and aft spring battery connectors 3274, which route electric power from the battery pack 3270. The upper housing 3220 further contains an instrument insertion tube support 3226 to secure and orient the instrument insertion tube 3290 near and coaxial with the motor 3260.

The lower housing 3230 further provides access to and secures the battery pack 3270 with an integral lower battery cover 3232 and motor housing section 3234, further held to the upper housing 3220 using the three instrument housing bolts 3236. The motor housing section 3234 holds and secures the motor 3260 coaxial with the instrument insertion tube 3290, which passes through the instrument insertion tube support 3226. The motor 3260 is pressed forward by the motor housing section 3234 against the motor collar 3264, the inside diameter of which leaves room for the motor shaft coupler 3262. The motor shaft coupler 3262, with the help of the motor shaft coupler bolts 3266, mounts securely onto the end of the shaft of the motor 3260 and further grips a first end 3295 of a drive shaft 3294. The drive shaft 3294 is rotated by the motor 3260 inside of and concentrically with the instrument insertion tube 3290. The drive shaft 3294 also has a second end 3297 of drive shaft 3294, which is concentrically supported by a shaft bearing 3296 that is mounted onto a second end 3293 of instrument insertion tube 3290. The DDM 3292 is rotatably mounted onto shaft bearing 3296 such that drive shaft 3294 causes DDM 3292 to rotate. DDM 3292, shaft bearing 3296, drive shaft 3294, and instrument insertion tube 3290 collectively form the DDM assembly 3299, which is described next.

Figure 33A:
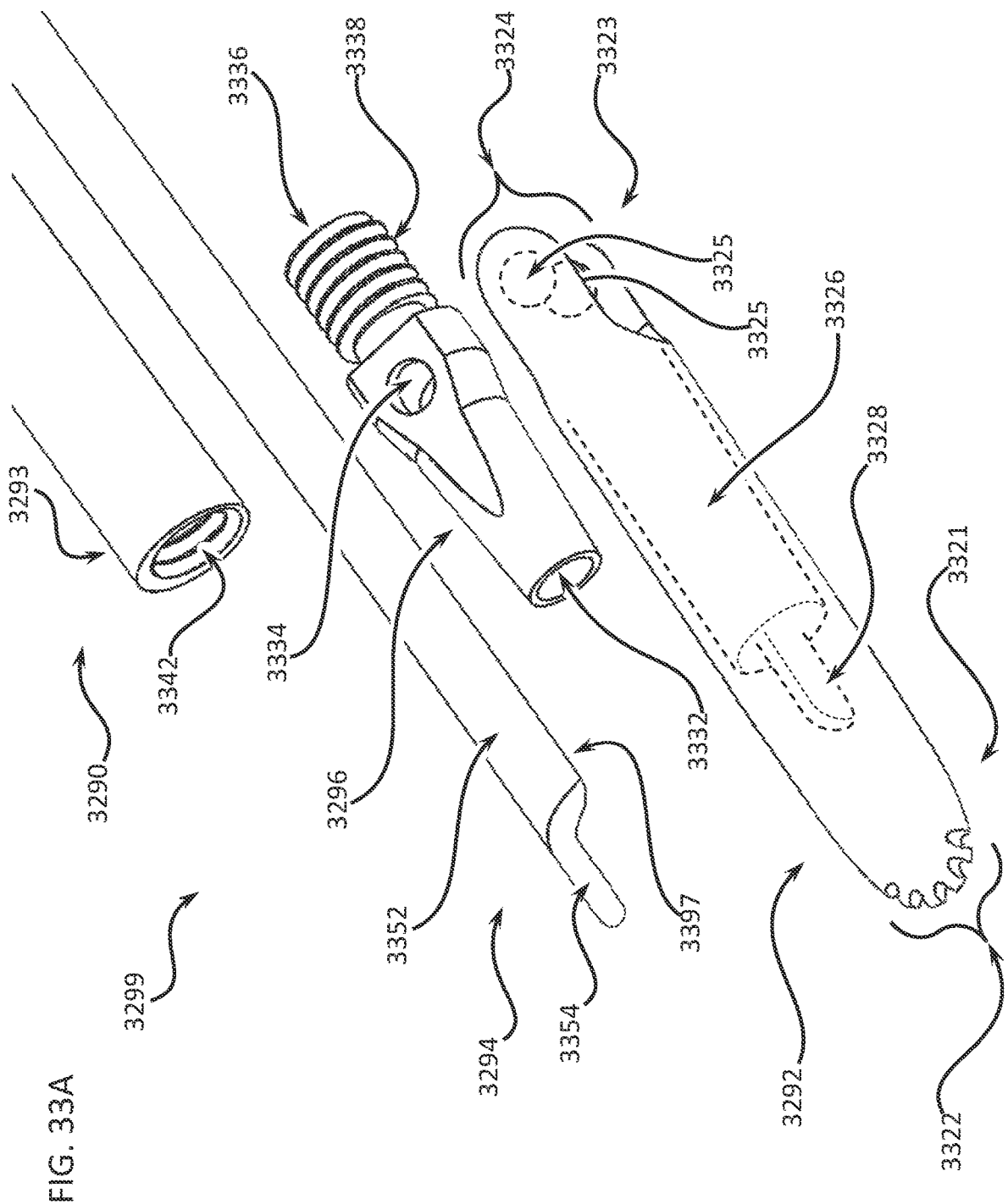
FIGS. 33A through 33C show an enlarged view of the differential dissecting member of the differential dissecting instrument in FIG. 32, with emphasis on how a scotch yoke mechanism permits a rotating shaft to drive the reciprocal oscillations of the differential dissecting member.
Figure 33B:
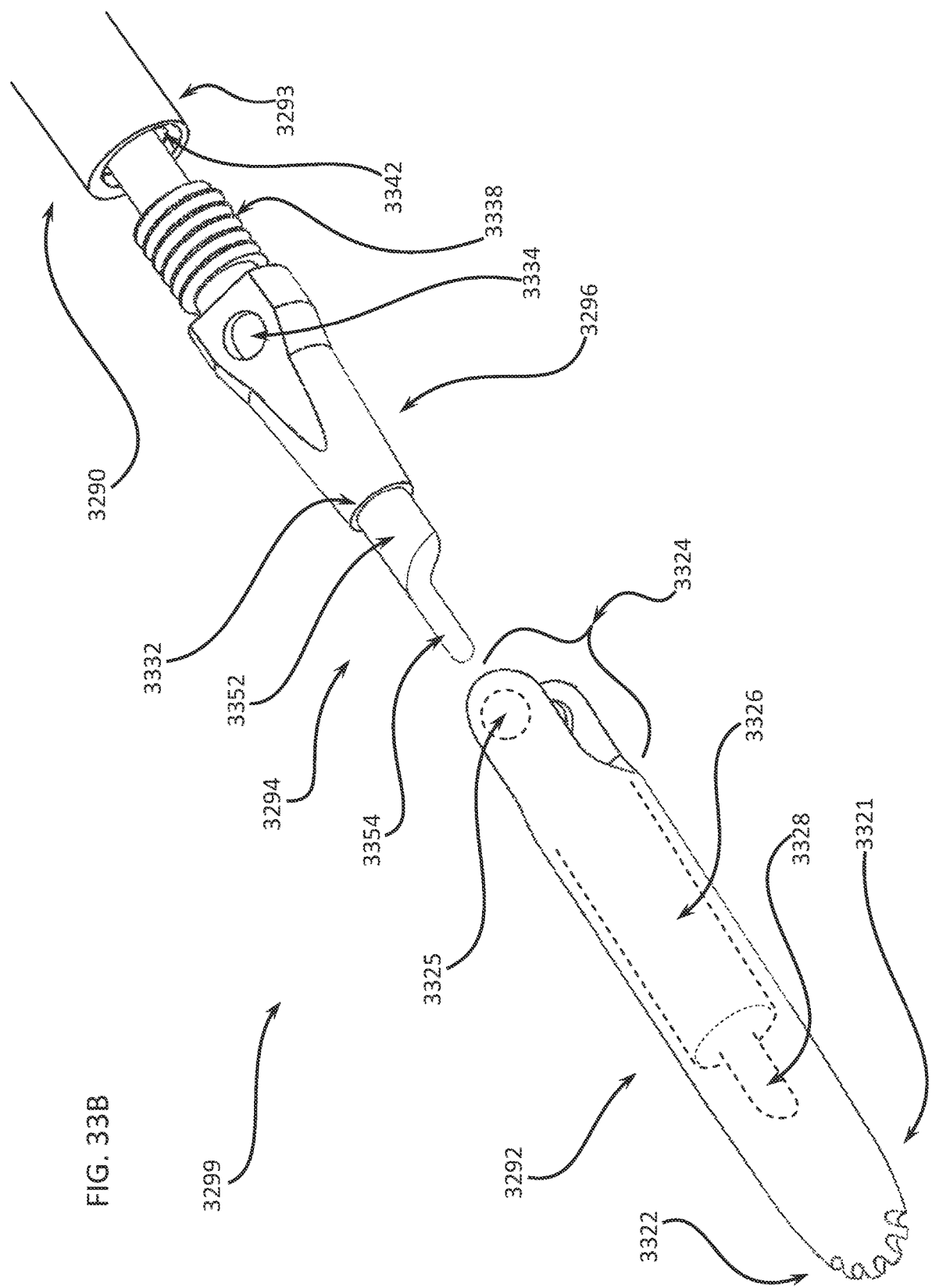
Figure 33C:
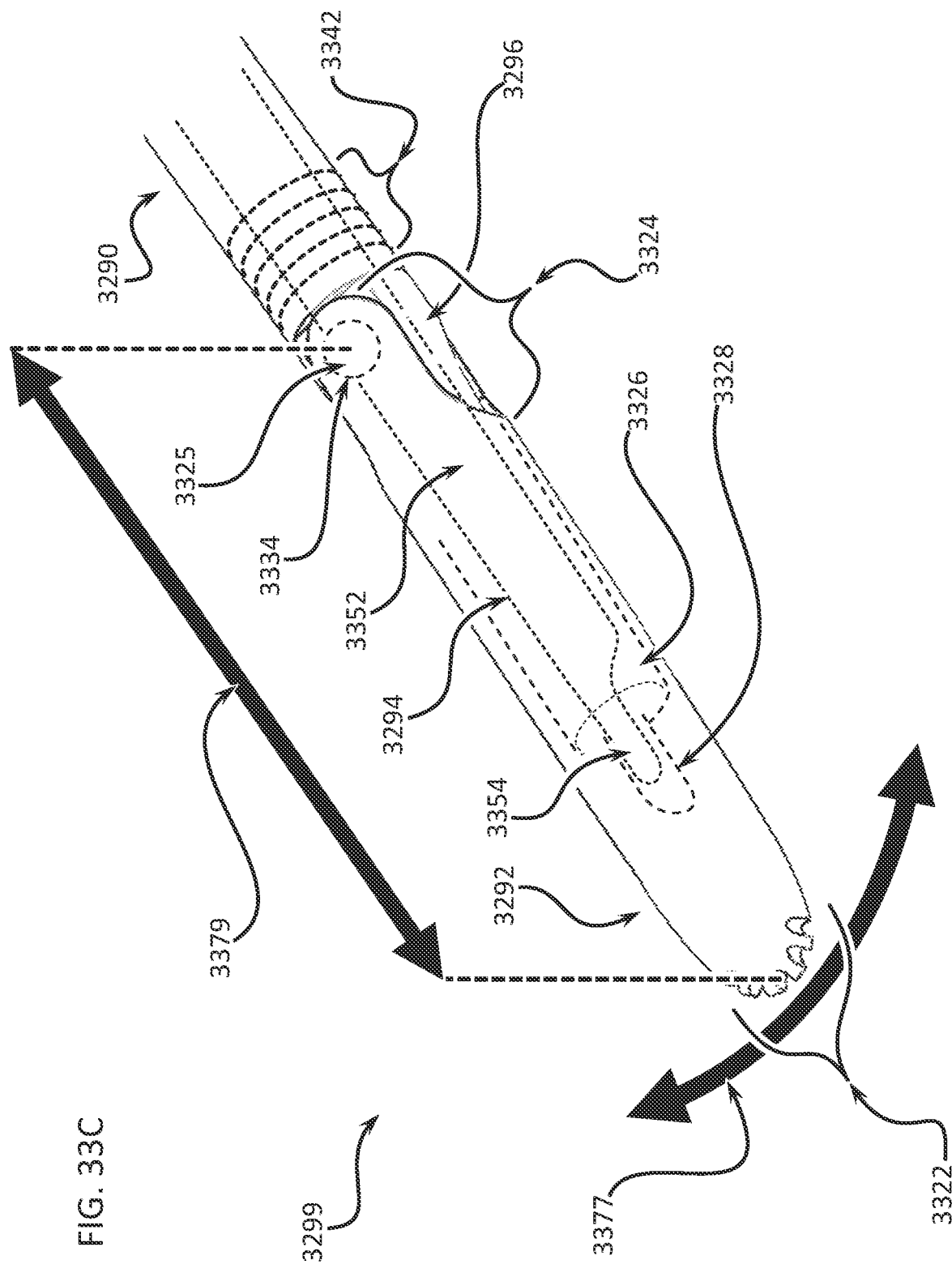

FIG. 33A, FIG. 33B, and FIG. 33C depict the details of the DDM assembly 3299, including how the DDM 3292 is assembled with other components such that the motor 3260 drives oscillation of DDM 3292.

Referring now to FIG. 33A, DDM 3292 in this embodiment comprises a tissue facing surface 3322 on a first end 3321 and a shaft bearing grip 3324 on a second end 3323. The shaft bearing grip 3324 is further fitted with two pivot pins 3325. The DDM 3292 may be partially hollow, possessing a shaft bearing cavity 3326 that permits the shaft bearing 3296 to fit inside. The shaft bearing cavity 3326 further sports a cam following cavity 3328. The shape of the cam following cavity 3328 may be oblong in that it is much narrower in one direction, forming a slot. Shaft bearing 3296 has a bore 3336, a shaft bearing tip 3332, a threaded bearing end 3338, and two pivot pin holes 3334. Threaded shaft bearing end 3338 screws into threaded shaft bearing mount 3342 on the second end 3293 of instrument insertion tube 3290. Bore 3336 can have a diameter greater than the diameter 3385 of drive shaft 3294 everywhere along its length, except at shaft bearing tip 3332, thereby decreasing the contact surface between shaft bearing 3296 and drive shaft 3294. The second end 3297 of drive shaft 3294 is modified to include a main shaft section 3352 and a cam shaft section 3354. The various sub-components of these components allow for their assembly and operation, as can be seen in FIG. 33B and FIG. 33C.

Referring now to FIG. 33B, drive shaft 3294 is shown as fitting coaxially within shaft bearing 3296 and instrument insertion tube 3290 of the DDM assembly 3299. This aligns threaded bearing end 3338 of shaft bearing 3296 for screwing into the threaded shaft bearing mount 3342 located at the second end 3293 of instrument insertion tube 3290. A shaft bearing tip 3332 accommodates drive shaft 3294, preventing misalignment with respect to the DDM 3292. The second end 3293 of drive shaft 3294 emits from shaft bearing tip 3332 such that cam shaft section 3354 is fully exposed. Once the instrument insertion tube 3290, shaft bearing 3296, and drive shaft 3294 are assembled, the DDM 3292 mounts onto shaft bearing 3296 such that (a) the pivot point pins 3325 insert into pivot pin holes 3334 and (b) cam shaft section 3354 inserts into cam following cavity 3328, as shown in FIG. 33C.

FIG. 33C depicts the assembled DDM assembly 3299. The DDM 3292 fits over the shaft bearing 3296, which is screwed into the threaded shaft bearing mount 3342 of the instrument insertion tube 3290, all of which coaxially encompass the drive shaft 3294. It is notable that the pivot pins 3325 on the shaft bearing grip 3324 fit into the pivot pin holes 3334 of the shaft bearing 3296. This arrangement, combined with the shaft bearing cavity 3326, allows the hollow DDM 3292 to rotate freely on the pivot pins 3325. Rotation of drive shaft 3294 causes cam shaft section 3354 to rotate inside cam following cavity 3328, driving DDM 3292 to oscillate about the pivot pin holes 3334 and sweeping tissue facing surface 3322 side-to-side as indicated by double sided arrow 3377.

In operation, referring to FIG. 32 and FIGS. 33A through 33C, a surgeon holds the differential dissecting instrument 3210 by the instrument handle 3212 and orients the distal tip sporting the DDM 3292 toward the complex tissue to be dissected. The surgeon selects the power level by sliding the power level adjustment 3281 to the desired position and then places his or her thumb upon the switch 3282 and presses it to close the switch. When switch 3282 closes, motor 3260 is turned on and rotates the motor shaft coupler 3262 and, in turn, the drive shaft 3294. The drive shaft 3294 is held coaxially and quite precisely in place by the shaft bearing 3296 and especially the shaft bearing tip 3332, so that the cam shaft section 3354 of the drive shaft 3294 oscillates rotationally inside the cam following cavity 3328 of the shaft bearing cavity 3326 of the DDM 3292. The cam following cavity 3328 is oblong, and in the embodiment shown in FIGS. 33A through 33C has its narrowest dimension occurring in the direction perpendicular to the axis of the rotational joint formed by the pivot pins 3325 and the pivot pin holes 3334. In this embodiment, the narrowest dimension of the cam following cavity 3328 just barely permits the passage of the cam shaft section 3354 of the now rotating drive shaft 3294. Accordingly, the rotational oscillation of the cam shaft section 3354 impinges on the long walls of the cam following cavity 3328, forcing the entire DDM 3292 to rotate through an oscillation arc 3377 lying in a plane perpendicular to the axis of the rotational joint formed by the pivot pins 3325 and the pivot pin holes 3334. In this embodiment, the amplitude of the oscillation arc 3377 through which the tissue facing surface 3322 of the differential dissecting member 3292 swings is a function of the diameter 3385 of the drive shaft 3294 out of which the cam shaft section 3354 is cut and the distance 3379 separating tissue facing surface 3322 and pivot pin holes 3334. The frequency of the oscillation matches the frequency of the oscillation of rotation of the motor 3260. The operator may control the oscillation frequency of the tissue facing surface 3322 by varying the position of the power level adjustment 3281. Note that this mechanism for converting rotation of motor 3260 and thus rotation of drive shaft 3294 into oscillation of the DDM 3292 is similar to the scotch yoke depicted in FIGS. 22 through 25C.

Differential Dissecting Instrument 3200 is one example of implementation of a DDM, and many variants are possible. For example, oscillation of a DDM can be driven by a crank and slider mechanism with the slider moving back-and-forth longitudinally inside an instrument insertion tube. Alternatively, a motor could be placed adjacent to the DDM, with the motor shaft directly driving the DDM and only electrical wires to power the motor running down the instrument insertion tube. Additionally, because a DDM adapts well to the end of a tube, greatly lengthening the instrument insertion tube allows differential dissecting instruments, such as Differential Dissecting Instrument 3200, for example, to be laparoscopic instruments. Differential Dissecting Instruments with instrument insertion tubes as long as thirty-six (36) cm may be used, although longer or shorter tubes are easily accommodated in the design. DDMs as disclosed herein can easily be adapted to the arm of a surgical robot, such as the Da Vinci Surgical Robot from Intuitive Surgical (Sunnyvale, Calif.). A DDM can be made very small; for example, effective Differential Dissecting Instruments in which the DDM and instrument insertion tube fit through a five (5) mm hole, such as a surgical port, can be built, enabling minimally invasive surgery. These smaller devices are easily built.

Further, Differential Dissecting Instruments can be used in which the drive shaft is replaced by a flexible drive shaft, and the instrument insertion tube is curved. This creates Differential Dissecting Instruments with curved instrument insertion tubes, like that shown in FIG. 6C. Articulation of the instrument insertion tube is also possible, using for example a drive shaft having a universal joint or other bendable coupler at the articulation.

As previously disclosed, additional functionality can be added to the end of a Differential Dissecting Instrument. For example,

- FIG. 11B and FIG. 13 show how the design of the DDM permits fluids to be delivered to a DDM for irrigation, or how suction can be applied to clear the surgical field, or how a light source can be placed on or near a DDM to illuminate the surgical field.
- FIG. 26A through FIG. 26D disclose a Differential Dissecting Instrument having an retractable cutting blade that can be made sharp for cutting or can be energized by a electrosurgical generator (unipolar or bipolar) for electrosurgery,
- FIG. 27 shows how the design of the DDM permits a DDM to be adapted to function as forceps.

Additional functionality can readily be added to a Differential Dissecting Instrument. For example, a patch of any size on the side of a DDM or a shroud holding a DDM can be energized such that the patch can be used for electrocautery. To simplify fabrication, the drive shaft can be used to conduct the electricity from the handle to the DDM. The design of the DDM permits the forceps shown in FIG. 27 to instead be used as scissors. Additional functionalities can include a video camera for imaging or ultrasonic surgery for sharp dissection. The improved design of the DDM permits many of these additional functionalities to be combined together in one Differential Dissecting Instrument. Advantages realized from combining functionalities with a DDM at the working end of a Differential Dissecting Instrument include: reducing the number of instruments a surgeon needs for a procedure; simplifying inventory for the hospital and logistics for support staff; and, most importantly, reducing instrument changes during surgery, which slow surgery and are a major source of surgical complications. This is especially true in laparoscopic and robotic surgeries, which require positioning instruments into the body through small incisions, frequently with airtight ports.

Figure 34:
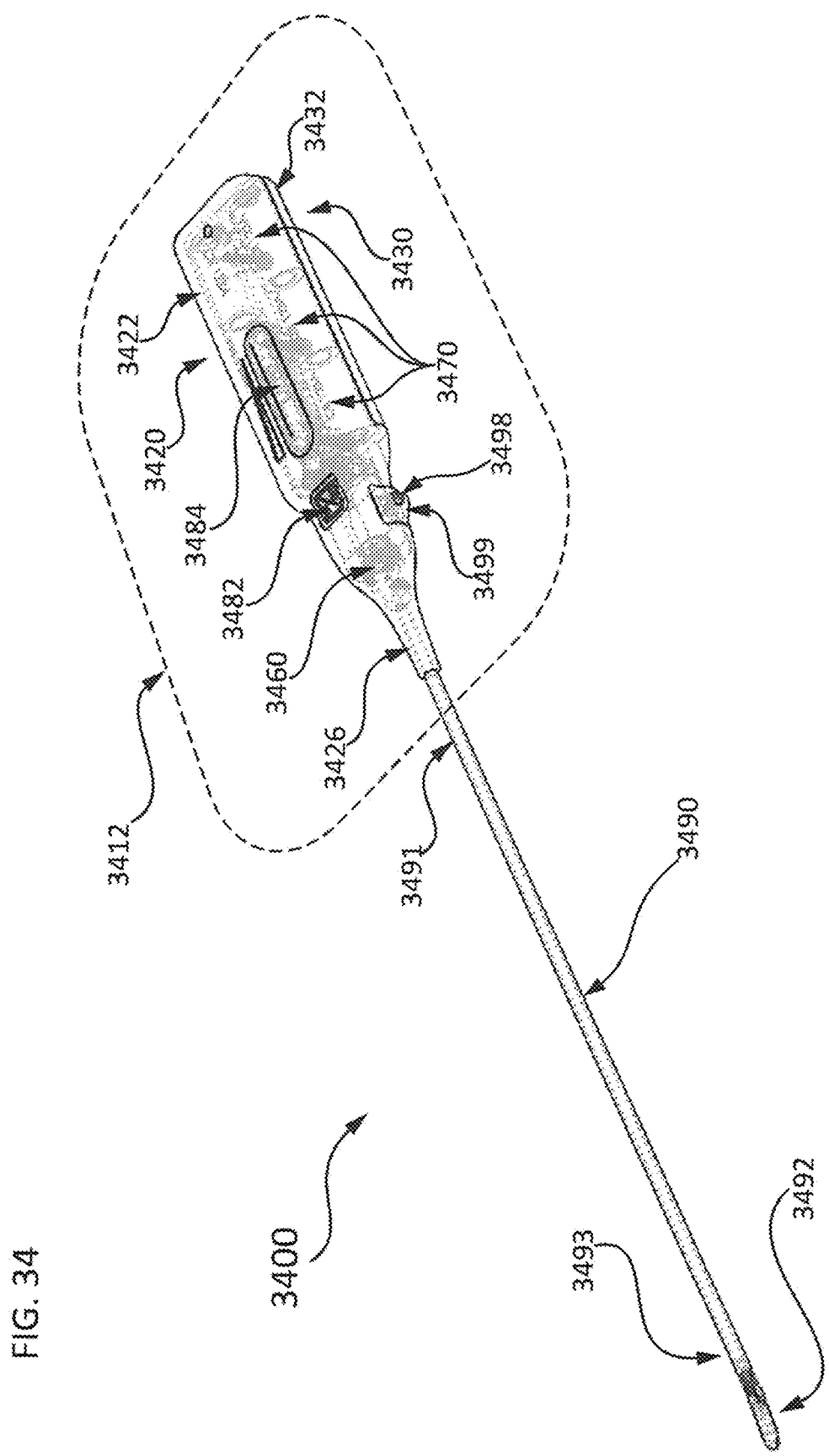
FIG. 34 shows an exploded view of another exemplary differential dissecting instrument having a retractable blade.

FIG. 34 shows an oblique view of one embodiment of an assembled Differential Dissecting Instrument. The Differential Dissecting Instrument 3400 is grossly comprised of an instrument handle 3412 from which projects an instrument insertion tube 3490 which has a first end 3491 attached to instrument handle 3412 and a second end 3493, to which is rotatably mounted a DDM 3492. The instrument handle 3412 is assembled from an upper housing 3420, which includes upper battery cover 3422, and a lower housing 3430, which includes lower battery cover 3432. Enclosed in the upper housing 3420 and lower housing 3430 are a motor 3460 and batteries 3470, which can, optionally, be assembled into a battery pack. In the upper housing 3420 is a switch 3482 (which may be a momentary switch or an on-off switch) for providing power to the motor 3460 from the battery pack 3470. A flexible switch cover 3484 mounted in the surface of the upper housing 3420 allows access to the power level adjustment 3581 (FIG. 35A) inside. The upper housing 3420 further comprises a retractable blade hook control button 3499 (secured by a control button bolt 3498), as well as an instrument insertion tube support 3426 to orient the instrument insertion tube 3490 near and coaxial with the motor 3460.

Figure 35A:
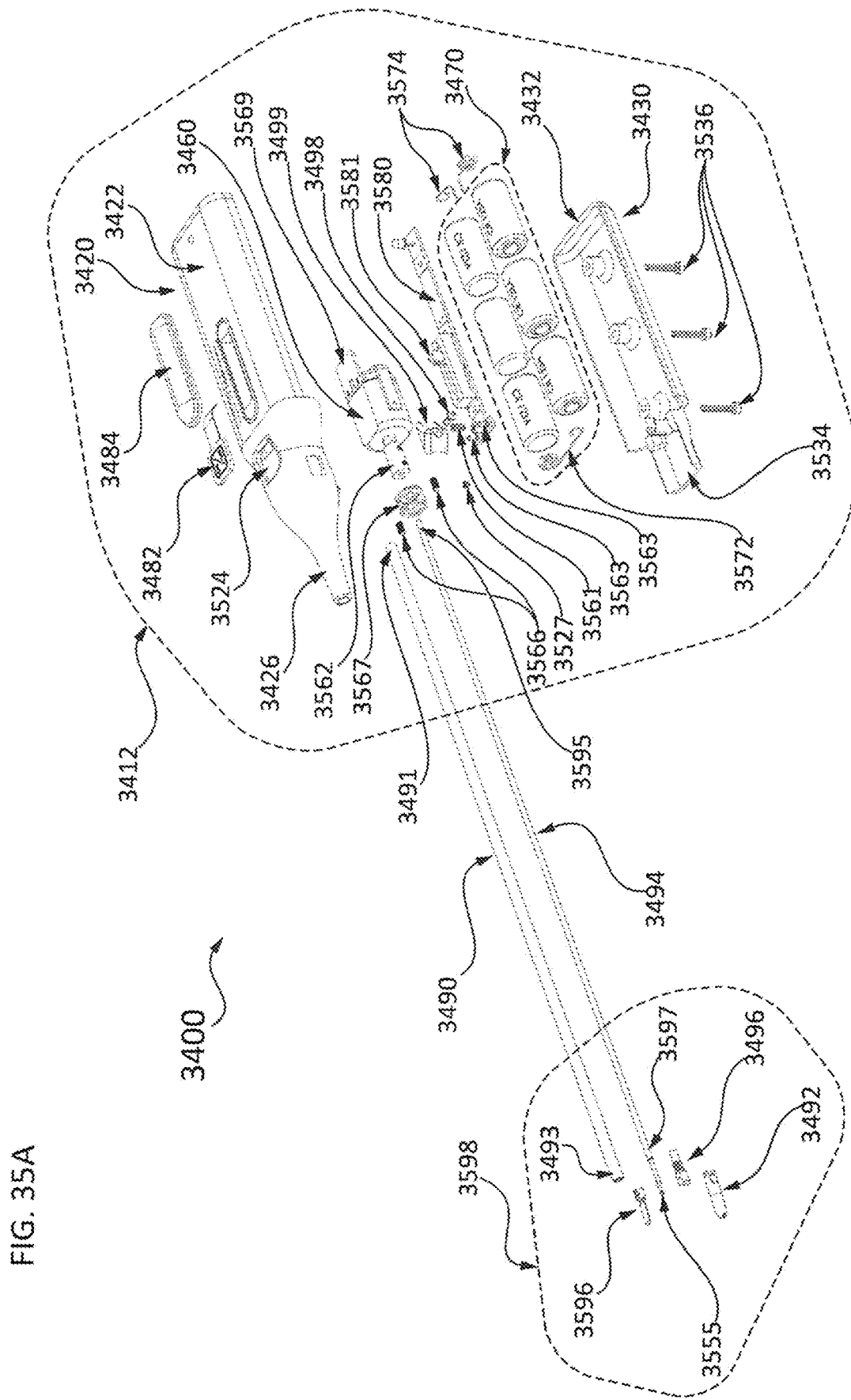

FIG. 35A shows an exploded view of Differential Dissecting Instrument 3400. The Differential Dissecting Instrument 3400 is grossly comprised of an instrument handle 3412 from which projects an instrument insertion tube 3490 which has a first end 3491 attached to instrument handle 3412 and a second end 3493, to which is rotatably mounted a DDM 3492. The instrument handle 3412 is assembled from an upper housing 3420, which includes upper battery cover 3422, and a lower housing 3430, which includes a lower battery cover 3432, which are held together by instrument housing bolts 3536. Included within the upper housing 3420 and lower housing 3430 are a motor 3460 and batteries 3470, here shown as battery type CR123A (3V each, 18V for all 6 batteries 3470) but other battery types and voltages can be used. We've used batteries totaling as low as 3V in some embodiments. In the upper housing 3420 is a switch port 3524, through which can be accessed switch 3482 (which may be a momentary switch or an on-off switch) for providing power to the motor 3460 from the battery pack 3470. A printed circuit board 3580 further containing a power level adjustment 3581 (which can be any convenient component, but is here shown as a linear potentiometer) is provided and can be accessed through a flexible switch cover 3484 mounted to the surface of the upper housing 3420. Also included are forward spring battery connectors 3572 and aft spring battery connectors 3574, which route electric power from the batteries 3470. The upper housing 3420 further contains an instrument insertion tube support 3426 to secure and orient the instrument insertion tube 3490 near and coaxial with the motor 3460. An instrument insertion tube retaining bolt 3527 holds the instrument insertion tube 3490 securely in the instrument insertion tube support 3426.

The lower housing 3430 further provides access to and secures the batteries 3470 with an integral lower battery cover 3432 and motor housing section 3534, further held to the upper housing 3420 using the three instrument housing bolts 3536. The motor housing section 3534 holds and secures the motor 3460 coaxial with the instrument insertion tube 3490, which passes through the instrument insertion tube support 3426. The motor 3460 is pressed forward by the motor housing section 3534 against the motor spring 3562, the inside diameter of which leaves room for the motor shaft coupler 3562. The motor shaft coupler 3562, with the help of the motor shaft coupler bolts 3566, mounts securely onto the end of the shaft of the motor 3460 and further grips a first end 3595 of a drive shaft 3494. The motor 3460 can slide longitudinally fore and aft within the motor housing section 3534 under the control of the retractable blade hook control button 3499. The motor 3460 further comprises a power contact plate 3569 which operably slides against sprung motor power contacts 3563 mounted on circuit board 3580. Also mounted on circuit board 3580 is an adjustable power contact pressure control bolt 3561. Normally, spring 3567 keeps motor 3460 aft. In that position, the sprung motor power contacts 3563 mounted on the printed circuit board 3580 are aligned with and press against the power contact plate 3569 on motor 3460, and so electric power from battery pack 3470 can drive motor rotation. Pressing the retractable blade hook control button 3499 forward causes motor 3460 to slide forward. The power contact plate 3569 is shorter than the full extent of travel of motor 3460 under the influence of retractable blade hook control button 3499, such that electric power from battery pack 3470 is automatically cut off when the motor 3460 is slid sufficiently far forward toward insertion tube second end 3493 to break contact with sprung motor power contacts 3563.

The drive shaft 3494 also has a second end 3597, which passes through and is concentrically supported by a shaft bearing 3496 that is mounted onto the second end 3493 of instrument insertion tube 3490. Referring also to FIG. 35 B, the second end 3597 of drive shaft 3494 further comprises (from the tip of second end of 3597 and working inward) a cam receiver retainer 3555, a cam receiver driver 3554, and a shaft bearing clearance section 3552. DDM 3492 is rotatably mounted onto shaft bearing 3496 such that drive shaft 3494 causes DDM 3492 to rotate with a reciprocal oscillation. DDM 3492, shaft bearing 3496, a cam receiver 3596, a cam receiver retainer 3555, drive shaft 3494, and instrument insertion tube 3490 collectively form the DDM assembly 3598, which is described next.

Figure 35B:
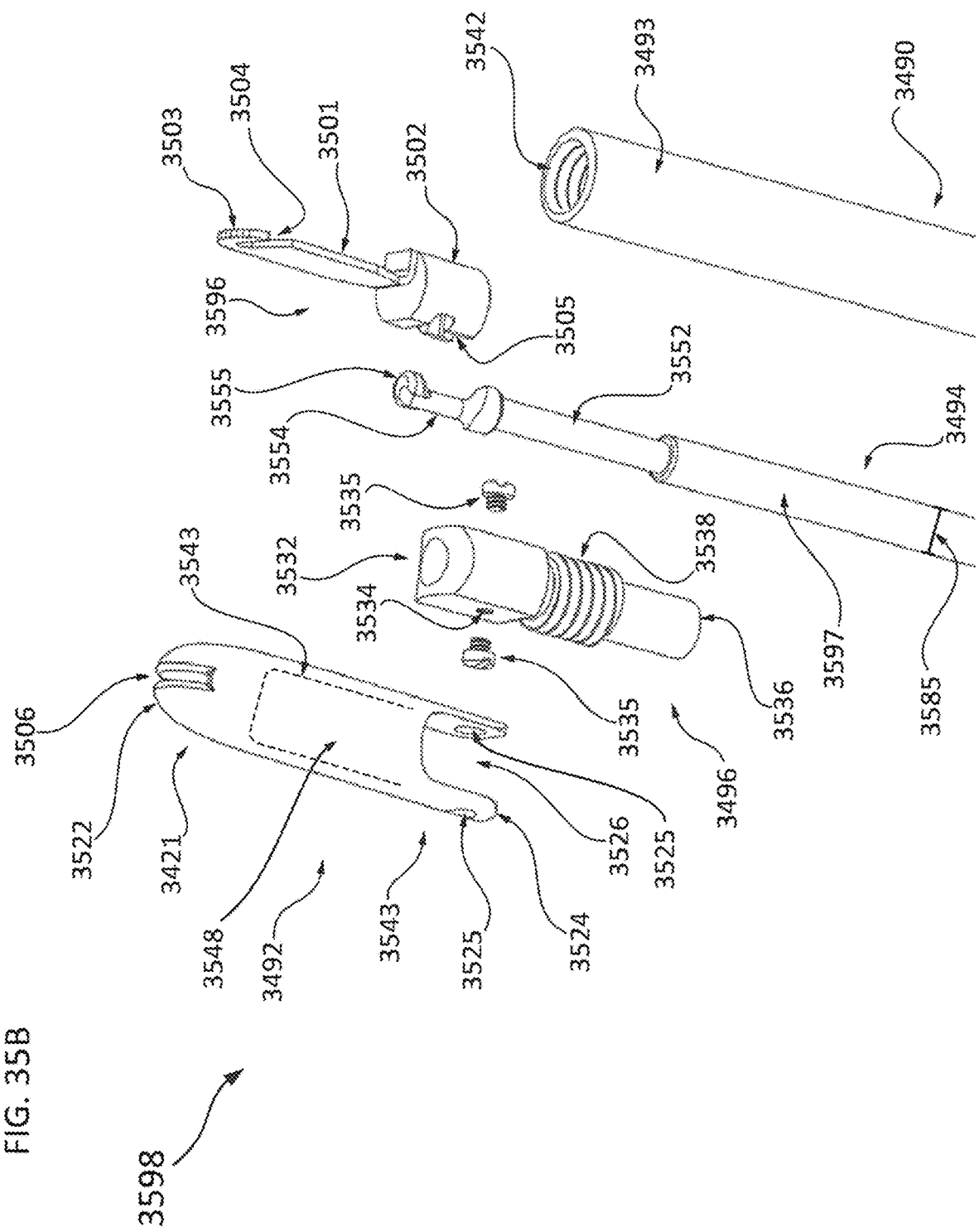

FIG. 35B depicts the details of DDM assembly 3598, including how DDM 3492 is assembled with other components such that the motor 3460 drives reciprocal oscillation of DDM 3492. DDM 3492 in this embodiment comprises a tissue facing surface 3522 on a first end 3521 and a shaft bearing grip 3524 on a second end 3543. The shaft bearing grip 3524 is further fitted with two pivot pin holes 3525. The DDM 3492 may be partially hollow, possessing a shaft bearing cavity 3526 that permits the shaft bearing 3496 to fit inside. The shaft bearing cavity 3526 further sports a cam receiver cavity 3548 shaped to permit cam receiver 3596 to easily slide therein. In this embodiment, tissue facing surface 3522 of DDM 3492 further comprises a retractable blade slot 3506. Shaft bearing 3496 has a bore 3536, a shaft bearing tip 3532, a threaded bearing end 3538, and two insertable pivot pins 3535 that fit into threaded holes 3534. The threaded shaft bearing end 3538 screws into threaded shaft bearing mount 3542 on the second end 3493 of instrument insertion tube 3490. Bore 3536 can have a diameter greater than the diameter 3585 of drive shaft 3494 everywhere along its length, except at shaft bearing tip 3532, thereby decreasing the contact surface between shaft bearing 3496 and drive shaft 3494. Second end 3497 of drive shaft 3494 is modified to include main shaft section 3552, cam shaft section 3554, and cam receiver retainer 3555. Cam receiver 3596 further comprises a cam receiver body 3502, a cam receiver chamber 3505, and a retractable blade 3501. Retractable blade 3501 can further comprise a hook 3504 and a tissue engaging surface 3503. Tissue engaging surface 3503 of retractable blade 3501 can be more or less aggressive than tissue engaging surface of DDM 3492. The various sub-components of these components allow for their assembly and operation, as is disclosed elsewhere in this document.

DDM 3492 fits over shaft bearing 3496, which is screwed into threaded shaft bearing mount 3542 of the instrument insertion tube 3490, all of which coaxially encompass drive shaft 3494. It is notable that pivot pin holes 3525 on shaft bearing grip 3524 fit onto pivot pins 3535 of shaft bearing 3496. This arrangement, combined with shaft bearing cavity 3526, allows DDM 3492 to rotate freely on the pivot pins 3535. Rotation of drive shaft 3494 causes cam shaft section 3554 to rotate inside cam receiver 3596, driving DDM 3492 to reciprocally oscillate about the pivot pin holes 3525 and sweeping tissue facing surface 3522 side-to-side. Tissue facing surface 3522 may possess a tissue-engaging surface (not depicted here) such that it performs as a DDM.

In operation, a surgeon holds the differential dissecting instrument 3400 by the instrument handle 3412 and orients the distal tip sporting the DDM 3492 toward the complex tissue to be dissected. The surgeon selects the power level by sliding the power level adjustment 3581 to the desired setting and then places his or her thumb upon the switch 3482 and presses it to close the switch. When switch 3482 closes, motor 3460 is turned on and rotates the motor shaft coupler 3562 and, in turn, the drive shaft 3494. The drive shaft 3494 is held coaxially and quite precisely in place by the shaft bearing 3496 and especially the shaft bearing tip 3532, so that the cam shaft section 3554 of the drive shaft 3494 oscillates rotationally inside the cam receiver chamber 3505 of cam receiver 3502 captured within the DDM 3492. The rotational oscillation of the cam shaft section 3554 impinges on the walls of the cam receiver chamber 3505 of cam receiver 3502 which is configured as a scotch yoke as described earlier, forcing the entire DDM 3492 to rotate through an oscillation arc lying in a plane perpendicular to the axis of the rotational joint formed by the pivot pins 3535 and the pivot pin holes 3525. The surgeon can extend retractable blade 3501 by pushing retractable blade hook control button 3499 forward. Forward motion of retractable blade hook control button 3499 causes motor 3460 and power contact plate 3569 to move forward, separating power contact plate 3569 from sprung motor power contacts 3563 and cutting power to the motor, as described earlier, and preventing oscillation of DDM 3492. Simultaneously, forward motion of motor 3460 pushes drive shaft 3494 forward, toward second end 3493 of instrument insertion tube 3490. Forward motion of drive shaft 3494 in turn pushes cam receiver retainer 3555 against the top of cam receiver chamber 3505 inside cam receiver body 3502, thereby pushing cam receiver body 3502 further up cam receiver cavity 3548 and extending retractable blade 3501 out of retractable blade slot 3506. Thus, forward motion of retractable blade hook control button 3499 causes the motor 3460 to stop and retractable blade 3501 to extend out of DDM 3492. When retractable blade hook control button 3499 is released, motor spring 3562 pushes motor 3460 aft, retracting retractable blade 3501 and restoring electrical contacts for the motor.

In this embodiment the amplitude of the oscillation through which the tissue facing surface 3522 of the differential dissecting member 3492 swings is a function of the diameter 3585 of the drive shaft 3494 out of which the cam shaft section 3554 is cut and the distance 3579 separating tissue facing surface 3522 and pivot pin holes 3525. The frequency of the reciprocal oscillation (cycles per minute) of the DDM 3492 against the complex tissue matches the frequency of rotation (rotations per minute) of the motor 3460. The operator may control the oscillation frequency of the tissue facing surface 3342 by varying the position of the power level adjustment 3581. Note that this mechanism for converting rotation of motor 3460 and thus rotation of drive shaft 3494 into oscillation of the DDM 3492 is similar to the scotch yoke depicted in FIGS. 22 through 25C.

FIGS. 35C-1 and 35C-2 illustrate that fore/aft motion of drive shaft 3494 and, thus of cam receiver body 3502, also alters the amplitude of reciprocal oscillation of DDM 3492. Drive shaft 3494 is depicted in the aft position (having moved in the direction of arrow 3595) in FIG. 35C-1 and in the fore position (having moved in the direction of arrow 3597) in FIG. 35C-2. Thus, as cam receiver body 3502 moves forward inside cam receiver cavity 3548, the distance D from cam receiver body 3548 and pivot pin holes 3525 increases to D' while the lateral displacement of the receiver 3599 remains constant (because it is determined by the diameter 3585 of drive shaft 3494, as described above). As D' increases, the larger angular amplitude of DDM 3596 in the left frame decreases to the smaller angular amplitude of DDM 3492 in the right frame. This effect can be used to decrease the amplitude of oscillation when a retractable blade is extended. It can also be used to alter the amplitude of oscillation during blunt dissection by the DDM, for example when a surgeon wants a narrower oscillation for more precise dissection.

Figures 1, 36B:
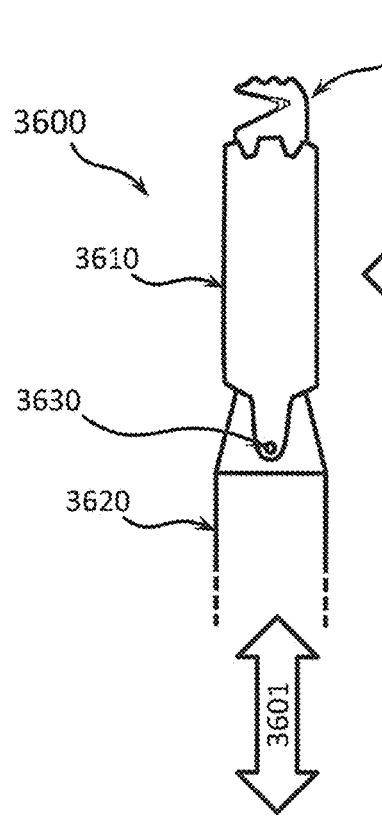
Figures 2, 36B:
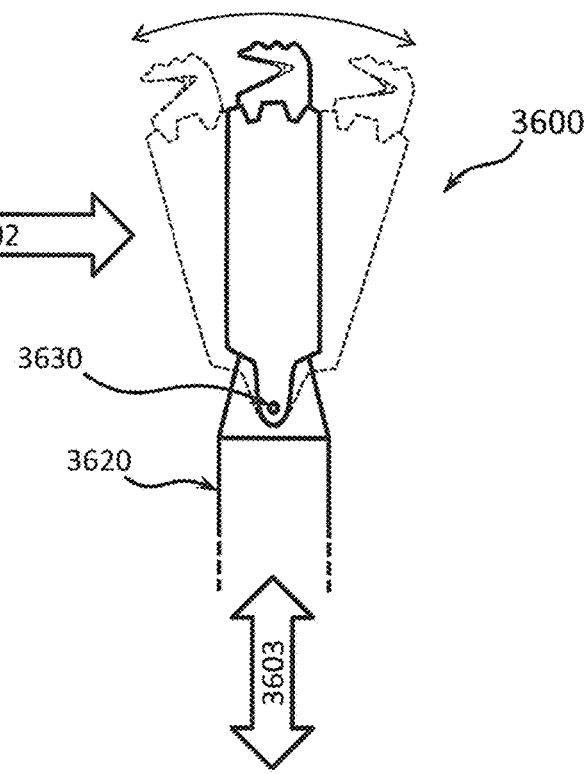
Figures 3, 36B:
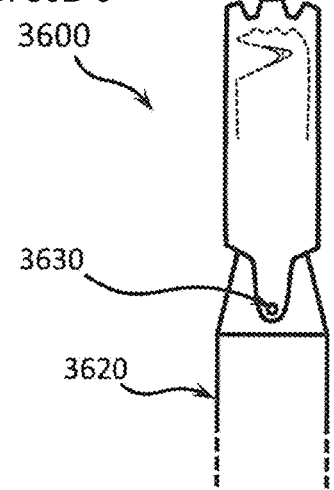
Figures 4, 36B:
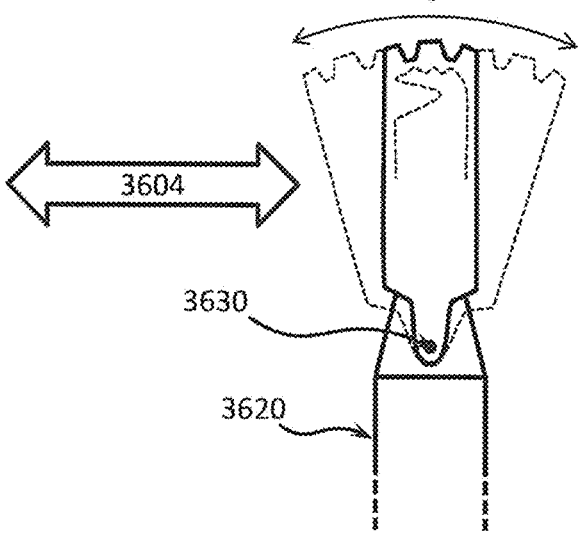

FIGS. 36A-1, 36A-2, 36B-1, 36B-2, 36B-3, and 36B-4 show the end of a Differential Dissecting Instrument 3600 having a DDM 3610 rotatably mounted to instrument insertion tube 3620 via rotational joint 3630. Differential Dissecting Instrument 3600 also has a retractable hook 3640 that can be extended or retracted by motion in the direction indicated by double headed arrow 3650. Retractable hook 3640 can be retracted or extended using, for example, the mechanism described in FIGS. 34, 35A, and 35B. FIG. 36A demonstrates how retractable hook 3640 can be placed into two configurations. CONFIGURATION 1 (FIG. 36A-1) shows retractable hook 3640 in the extended position, and CONFIGURATION 2 1 (FIG. 36A-2) shows retractable hook 3640 in the retracted position. Retractable hook 3640 can have a tip 3670 that can be pointed or rounded and a tissue engaging surface 3660 that can be more aggressive than tissue engaging surface 3690 of DDM 3610, or it can be less aggressive. Retractable hook 3640 possesses an elbow 3680 that can be sharpened to slice, as shown here, or it can be dull; furthermore, it can be serrated, and the sharpened region can be located anywhere within the elbow. In CONFIGURATION 2, retractable hook is hidden inside DDM 3610, and DDM 3610 alone interacts with the tissue. In CONFIGURATION 1, retractable hook 3640 is exposed and can be used to interact with the tissue such that tissue engaging surface 3690 interacts with the tissue (e.g. to disrupt softer tissues), or such that tip 3670 interacts with tissue (e.g. to pierce a tissue), or elbow 3680 interacts with tissue (e.g. to slice a tissue), depending on how an operator positions retractable hook 3640 with respect to the tissue. Additionally, retractable hook 3640 can be held at any intermediate position between CONFIGURATION 1 and CONFIGURATION 2, including being able to be variably extended by an operator.

FIGS. 36B-1 through 36B-4 show the end of a Differential Dissecting Instrument 3600 and illustrates that DDM 3610 can oscillate with retractable hook in the extended configuration (CONFIGURATION 1) 1 (FIG. 36B-1) or the retracted configuration (CONFIGURATION 2) 1 (FIG. 36B-2) and that retractable hook 3640 can be retracted or extended before activation of oscillation of DDM 3610 or during oscillation of DDM 3610. Arrow 3601 shows retractable hook moving between the retracted configuration (lower left frame) to the extended configuration (upper left frame—FIG. 36B-3) while DDM 3610 is not oscillating. Arrow 3602 shows that DDM 3610 can be switched from stationary (upper left frame) to oscillating (upper right frame—FIG. 36B-4) while retractable hook 3640 is in the extended configuration. Arrow 3603 shows that retractable hook 3640 can be moved from the extended configuration (upper right frame) to the retracted configuration (lower right frame) while DDM 3610 is oscillating. Arrow 3604 shows that DDM 3610 can change from stationary (lower left frame) to oscillating (lower right frame) while retractable hook 3640 is in the retracted configuration. Retractable hook 3640 can optionally be made of an electrically conductive material, like stainless steel, and electrically connected to an external surgical electrosurgical generator to allow retractable hook 3640 to act as an electrosurgical hook.

Figures 1, 37:
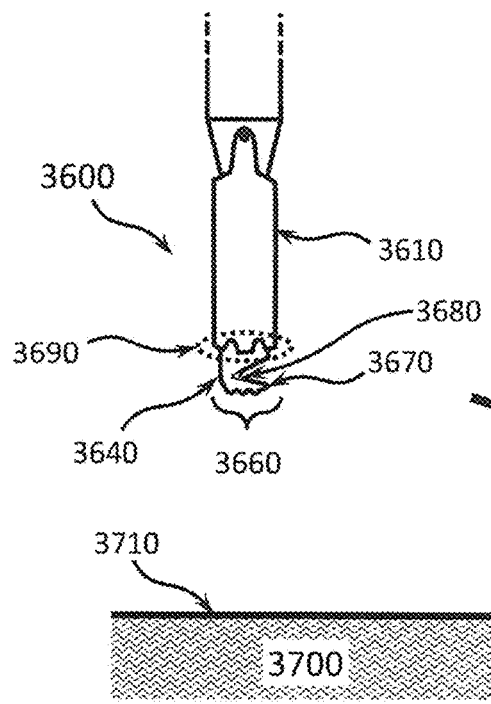
Figures 2, 37:
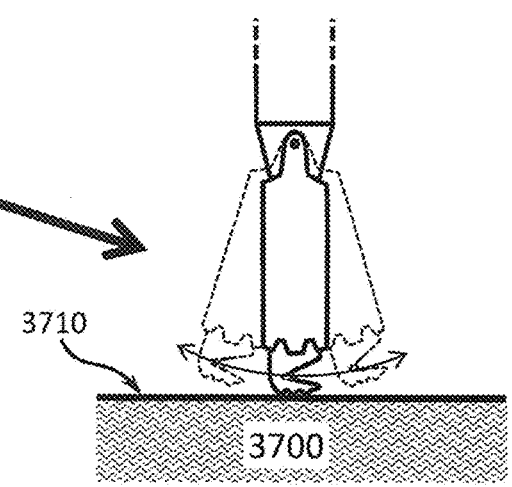
Figures 3, 37:
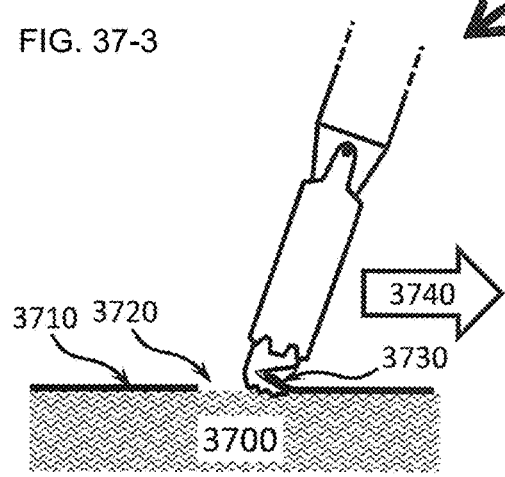
Figures 4, 37:
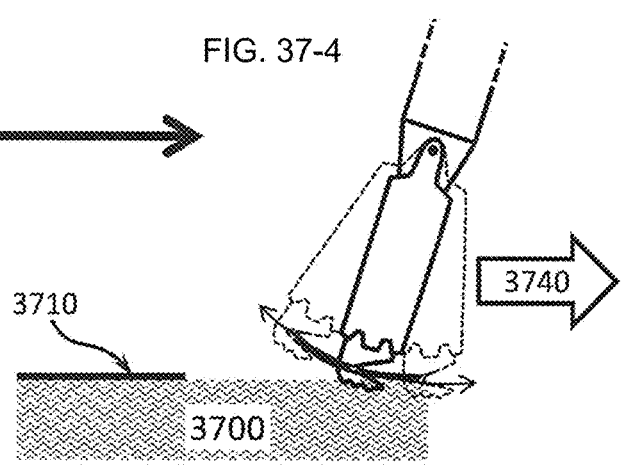

Many tissues to be dissected are wrapped in a membrane or capsule that a surgeon must divide to gain access to that tissue. Once that membrane or capsule has been divided, the surgeon proceeds with dissection through that tissue. FIGS. 37-1 through 37-4 illustrate in four panels a method by which a Differential Dissecting Instrument 3600 can be used to safely and quickly divide a membrane 3710 overlying a tissue 3700, such as the peritoneum overlying the gall bladder or the capsule surrounding a liver. In the upper left panel (FIG. 37-1), the Differential Dissecting Instrument is seen approaching membrane 3710 with the retractable hook 3640 in the extended configuration. In the upper right panel (FIG. 37-2), the tissue engaging surface 3660 of retractable hook 3640 is pressed by the surgeon against membrane 3710, and the DDM 3610 is oscillated such that tissue engaging surface 3660 abrades membrane 3710. (Alternatively, the retractable hook 3640 can be held in the retracted configuration, and the tissue engaging surface 3690 of DDM 3610 can be used to abrade membrane 3710. If the two tissue engaging surfaces 3660 and 3690 have different levels of aggressiveness, the surgeon then has the flexibility of choosing either the more aggressive or the less aggressive tissue engaging surface to abrade the membrane 3710.) The tissue is abraded until a small opening 3720 is made in membrane 3710. Next, as shown in the lower left panel (FIG. 37-3), the surgeon then pries the tip 3670 of retractable hook 3640 through opening 3720 and under membrane 3710, lifting or "tenting" a flap 3730 of membrane 3710 away from tissue 3700. The surgeon then moves DDM 3600 in the direction of arrow 3740, thereby forcing flap 3730 into the elbow 3680 of retractable hook 3640, the elbow 3680 being sharpened to slice tissue. Finally, as shown in the lower right panel (FIG. 37-4), the surgeon makes DDM 3610 oscillate, causing retractable hook 3640 to oscillate and, thus, the sharp edge of the elbow 3680 of retractable hook 3640 to quickly move into membrane 3710 as the surgeon continues moving DDM 3600 in the direction of arrow 3740. This has been demonstrated with fresh tissues to be an easy, quick, and safe way to divide a membrane, such as the peritoneum overlying the gall bladder and bile duct, without damaging underlying structures (e.g. the gall bladder, bile duct, or liver). The tip 3680 of retractable hook 3640 can be made sufficiently blunt that it does not easily penetrate the membrane 3710 or underlying structures; furthermore, the placement of the sharp edge only at elbow 3680 prevents critical structures from being exposed to the sharp edge 3680 and thus reducing the likelihood of such critical structures being cut. Examples of membranes or capsules overlying critical structures include the peritoneum overlying the liver, gall bladder, cystic duct, and cystic artery; and the pleura overlying the lung, pulmonary artery, pulmonary vein, and bronchus.

A retractable hook can be used in a method similar to that shown in FIGS. 37-1 through 37-4 to dissect tougher fibrous structures, like adhesions, fibrous tissues surrounding the renal artery or vein, and scar tissue. For example, a surgeon can use the tip of a retractable hook to grab all or a portion of a fibrous structure and then can push the tissue into the sharpened elbow of the hook. The surgeon can then oscillate the DDM and hook to use the sharp edge inside the hook to cut the tissue. An advantage of this approach is that it applies the stresses in the immediate location of the tissue to be divided. In current practice, surgeons divide such tissues by a variety of techniques, including simply grabbing the sides or ends of such tissues and pulling them until they break. This can at times put large stresses on the tissues being pulled, such as the wall of the intestine, leading to accidental tearing of critical tissues, such as the wall of the intestine (and thereby perforating the bowel). By applying the stresses more locally and directly to the tissue to be divided (specifically at the sharpened elbow of the hook), and not over larger expanses of tissues (e.g. between two pairs of forceps), a surgeon can have greater certainty that a more distant tissue, like the wall of the intestine, is unharmed.

It is important to note that these methods of dividing tissues by using a hook that is oscillated does not heat the tissues, in stark contrast to the extreme heat that arises from current practice using electrosurgery. The heat from electrosurgery is widely acknowledged as a major risk leading to accidental thermal damage of surrounding tissues. Competing technologies for sharp dissection, such as ultrasonic ablation (e.g. the "harmonic shears" from Ethicon Endosurgery), have been developed to reduce the heat and thereby decrease the risk of thermal damage to tissues. Nevertheless, local heating remains significant and the risk of thermal damage is still present. On the contrary, dividing a membrane or dissecting a fibrous structure as described here with an oscillating hook causes no heating of tissues, eliminating this major source of iatrogenic trauma.

Figure 38:
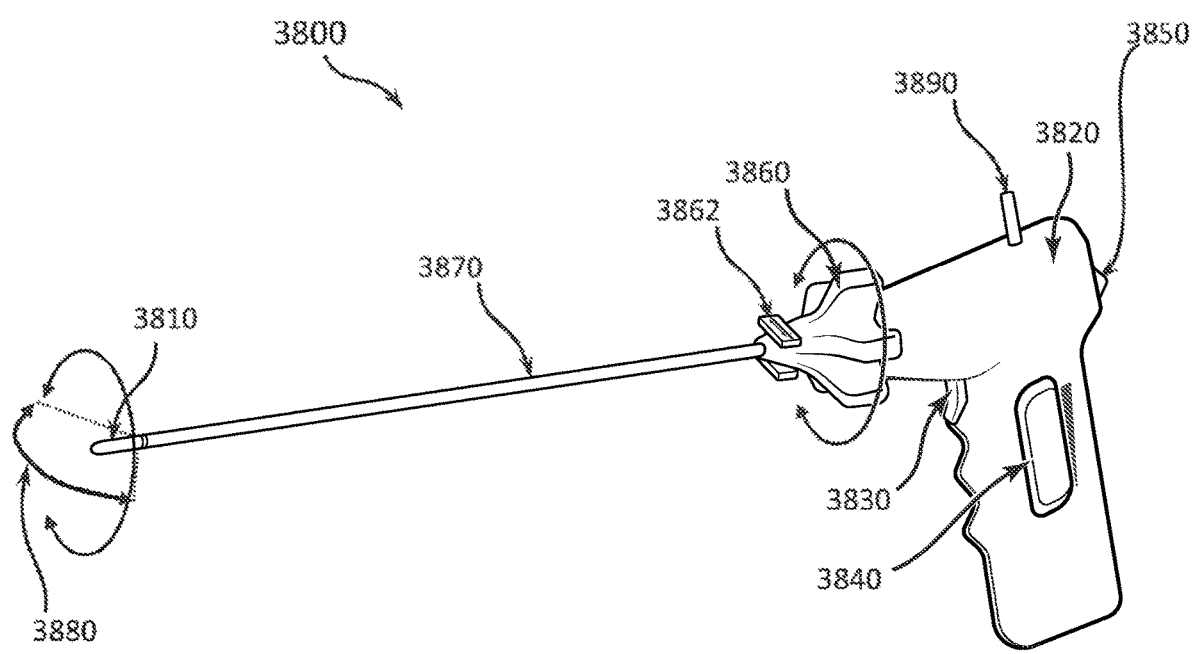
FIG. 38 shows a complete exemplary differential dissecting instrument having a pistol grip and the ability to rotate the instrument insertion tube and, thus, turn the plane of oscillation of the differential dissecting member.

FIG. 38 shows one embodiment of a Differential Dissecting Instrument 3800 for laparoscopic surgery. It uses the mechanism for oscillation of the DDM 3810 shown in FIGS. 34, 35A and 35B, including a retractable blade (not visible in this picture because it is in the retracted configuration). Differential Dissecting Instrument 3800 uses a pistol-style handle 3820 having a trigger 3830 to start/stop oscillation of the DDM 3810 and a speed control 3840 for controlling the speed of oscillation. A thumb-activated push-button 3850 is used to extend the retractable blade which is held in a normally retracted configuration by a spring mechanism inside handle 3820. A rotational wheel 3860 can be reached and turned with an index finger, and rotation of rotational wheel 3860 rotates instrument insertion tube 3870 and attached DDM 3810 such that the plane of oscillation 3880 of DDM 3810 can be easily turned through 360 degrees, thereby allowing a surgeon to orient the plane of oscillation 3880 with a tissue plane inside the body while maintaining good ergonomics for the handle 3820. An indicator 3862 on rotational wheel 3860 provides the surgeon with a visual cue outside the body as to the orientation of the plane of oscillation 3880, and, similarly, visual cues, such as embossed stripes, can be placed on the instrument insertion tube 3870 or on DDM 3810 thereby providing a visual cue on camera during laparoscopic viewing. An electrical plug 3890 allows optional attachment via cable to an external electrosurgical generator for electrosurgery and electrocautery (controlled by external foot pedals attached to the electrosurgical generator for control of the electrosurgical generator or, alternatively, push buttons (not shown) can be placed onto handle 3820 and used for control of the electrosurgical generator). Differential Dissecting Instrument 3800, therefore, allows a surgeon to perform blunt dissection (via differential dissection), sharp dissection (via retractable hook or electrosurgery), and coagulation (via electrocautery) with a single instrument, thereby reducing instrument changes which is complicated for laparoscopic surgery.

Figure 39:
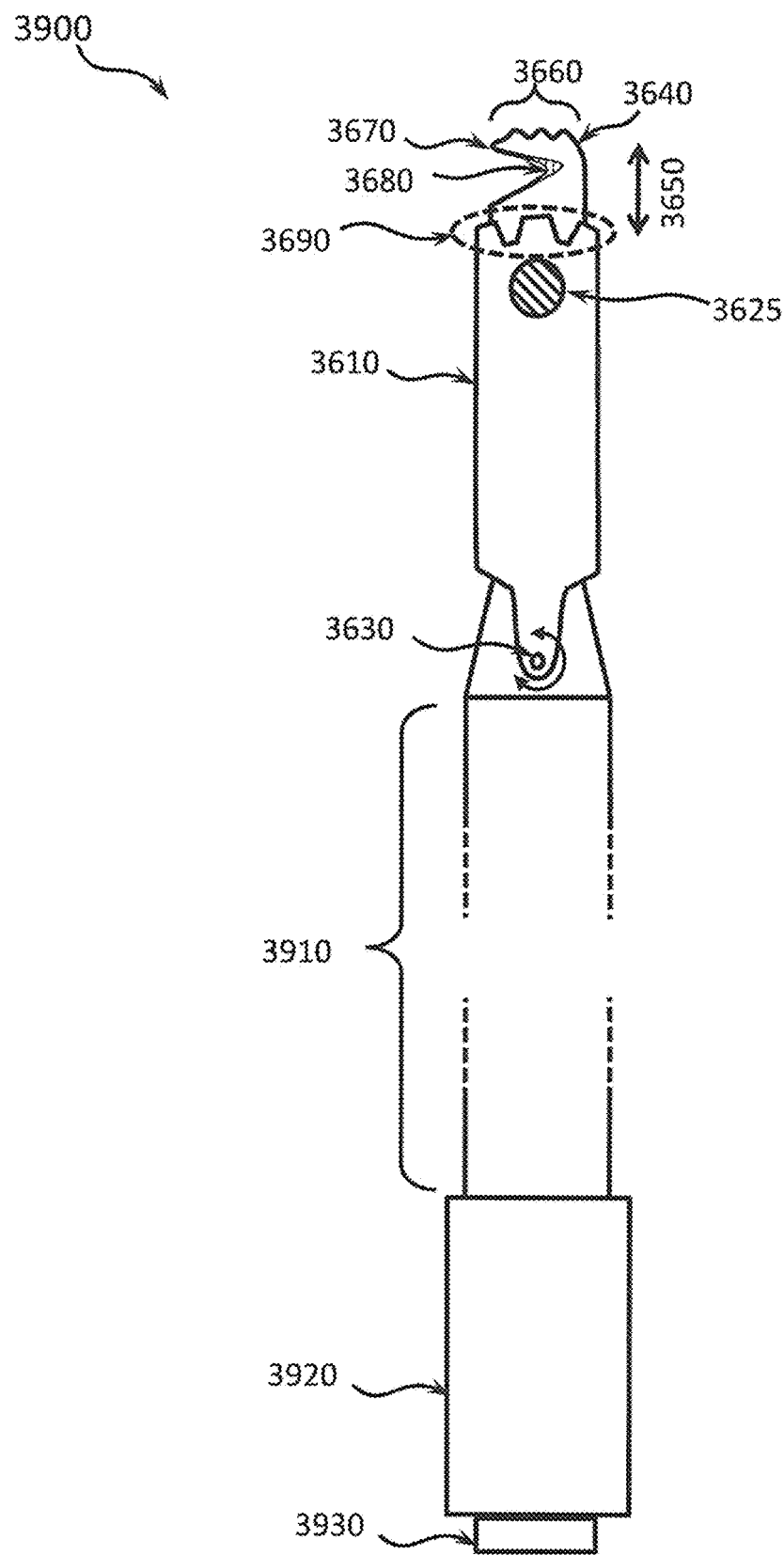
FIG. 39 shows how an exemplary differential dissecting instrument can be fitted to the arm of a surgical robot and can, optionally, be fitted with an electrically conducting patch for electrocautery.

FIG. 39 shows a Differential Dissecting Instrument 3900 configured as a tool to be attached to the arm of a surgical robot, such as the da Vinci Robot from Intuitive Surgical, Inc. DDM 3610 is rotatably attached to instrument insertion tube 3910 via rotational joint 3630. Retractable hook 3640 can move between retracted and extended configurations, as indicated by double headed arrow 3650. Retractable hook 3640 has a tissue engaging surface 3660, tip 3670, and elbow 3680 with a sharpened edge for sharp dissection. Retractable hook 3640 can, optionally, be electrically conductive and electrically connected to an external electrosurgical generator. Similarly, DDM 3610 or a small electrically conductive patch 3625 on DDM 3610 can be used for electrocautery. (Note that an electrically conductive patch can be placed anywhere on DDM 3610, including the tissue engaging surface 3690.) Instrument insertion tube 3910 attaches to housing 3920 which contains a motor to drive oscillation of DDM 3610 and retractable hook 3640 as described earlier. Housing 3920 is configured with socket 3930 having electrical and mechanical connections for connecting to the surgical robot's arm. Instrument insertion tube 3910 can be made long, such that housing 3920 is located outside the patient's body. Conversely, instrument insertion tube 3910 can be made short, such that housing 3920 is located inside the body, with articulations located in the robot arm and inside the patient's body to permit articulated motion of Differential Dissecting Instrument 3900 inside the patient's body.

Placement of a small motor in a housing closer to a DDM and inside the patient's body facilitates articulation of the instrument insertion tube of a Differential Dissecting Instrument because all connections from the housing to the handle or housing, and thus through the articulation, can be electrical, which can be much simpler than designs requiring the transmission of mechanical drives through an articulation. This is true for Differential Dissecting Instruments designed both for surgical robots and for laparoscopy.

Figure 40:
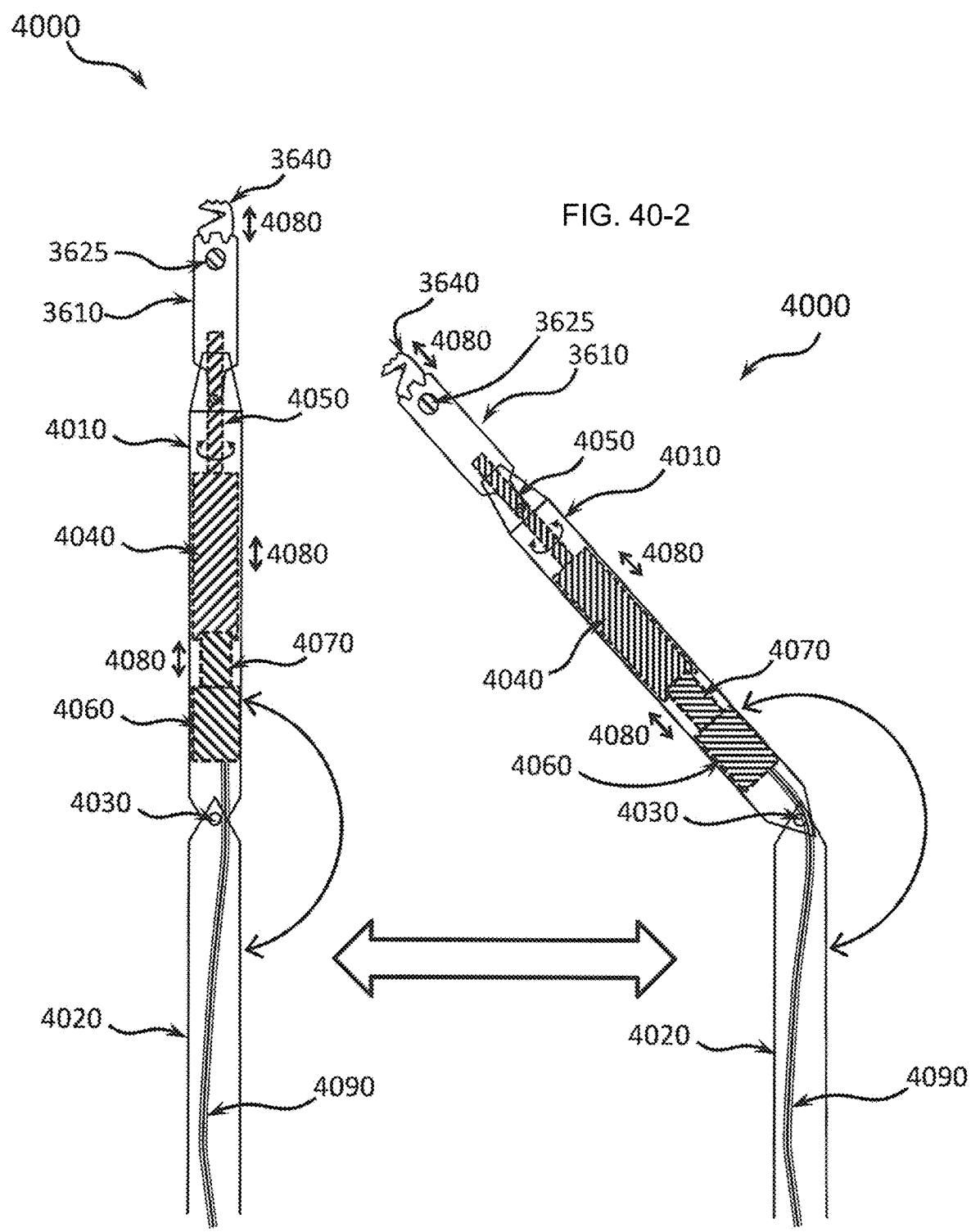

FIGS. 40-1 and 40-2 show one embodiment of such a device as the end of a laparoscopic Differential Dissecting Instrument 4000. FIGS. 40-1 and 40-2 show an exemplary laparoscopic version of a differential dissecting instrument having electromechanical actuators distal to an articulation, and in the straight and bent positions, respectively. A DDM 3610 is fitted with a retractable hook 3640 and electrically conducting patch 3625. DDM 3610 is rotatably attached to distal instrument insertion tube 4010 which is articulated at rotational joint 4030 to proximal instrument insertion tube 4020. Mounted inside distal instrument insertion tube 4010 are a motor 4040 with motor shaft 4050 and a solenoid 4060 with solenoid plunger 4070. Rotation of motor shaft 4050 by motor 4040 drives oscillation of DDM 4010 and, thus, retractable hook 3640, as described earlier. Solenoid 4060 is rigidly attached to distal instrument insertion tube 4010, and solenoid plunger 4070 is attached to motor 4040, which is free to slide inside distal insertion tube 4010. Thus, when solenoid 4060 is activated, solenoid plunger moves up/down (in the direction indicated by arrow 4080) thereby driving motor 4040, motor shaft 4050, and retractable hook 3640 up/down (as indicated by arrows 4080). Flexible conductor ribbon 4090 supplies the necessary electrical power and signals to drive motor 4040 and solenoid 4060. Articulation of laparoscopic Differential Dissecting Instrument 4000 at rotational joint 4030 allows distal instrument insertion tube 4010 to bend with respect to proximal instrument insertion tube 4020, as shown in the right hand panel. Motion of distal instrument insertion tube 4010 with respect to proximal instrument insertion tube 4020 can be driven by any of several mechanisms, such as a control horn driven by a push-pull rod actuated by a hand-powered mechanism in the handle of the laparoscopic Differential Dissecting Instrument 4000. This configuration of actuators (i.e. motor 4040 and solenoid 4060) and flexible conductor ribbon 4090 facilitates the transmission of complex actions past articulation at rotational joint 4030, transmission that would otherwise require complex mechanical parts that are expensive, add bulk, and are prone to failure.

Figure 41:
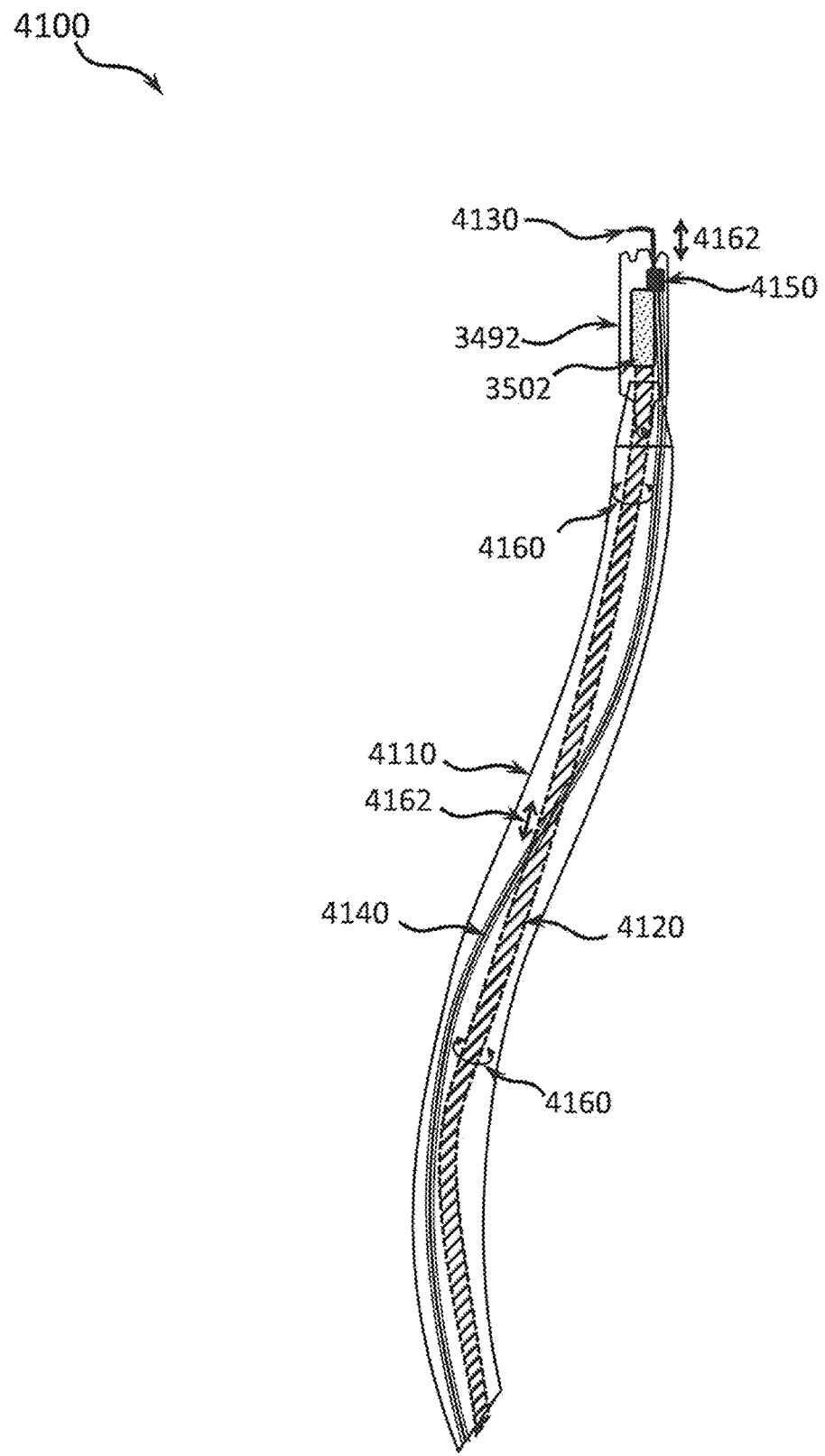
FIG. 41 shows one exemplary version of a differential dissecting instrument driven by a flexible drive shaft.

FIG. 41 shows a Differential Dissecting Instrument 4100 possessing a thin, flexible instrument insertion tube 4110 for use in surgical procedures like single-incision laparoscopic surgery (SILS) or natural orifice translumenal endoscopic surgery (NOTES). The actuation mechanisms are similar to the DDM 3492 and retractable hook 3596 in FIGS. 35A and 35B are identical to that shown in FIGS. 35A and 35B; however, the rigid instrument insertion tube 3490 and rigid drive shaft 3494 are replaced by flexible instrument insertion tube 4110 and flexible drive shaft 4120, and the retractable hook 3596 is replaced with an electrosurgical hook 4130. Flexible drive shaft 4120 can rotate (as shown by double-headed arrow 4160) to drive the oscillation of the DDM 3492 or it can push-pull (as shown by double-headed arrow 4162) to retract and extend the electrosurgical hook 4130. A multi-lumen flexible instrument insertion tube 4110 can be used to reduce wander of flexible drive shaft 4120 inside the flexible instrument insertion tube, thereby providing greater authority to the push-pull mechanism of the flexible drive shaft 4120 for extending and retracting a electrosurgical hook 4130. A flexible wire 4140 can also travel inside flexible insertion tube 4110 to allow conduction of electricity to electrosurgical hook 4130, with flexible wire 4140 and electrosurgical hook 4130 being connected via a solder weld 4150 or other appropriate mechanism to cam receiver body 3502. Thus, the Differential Dissecting Instrument 4100 is capable of blunt dissection, electrosurgical sharp dissection, and electrocautery with controls located on a handset outside the body or, for electrosurgery or electrocautery, via foot pedals.

FIGS. 42A through 42E show oblique and expanded views of one embodiment of a Differential Dissecting Instrument 4200 that has a slender, pencil grip handle that can be easily rotated in the hand, enabling 360° rotation of the plane of rotation of the DDM 4250 about the central, longitudinal axis 4299 of Differential Dissecting Instrument 4200.

Figure 42A:
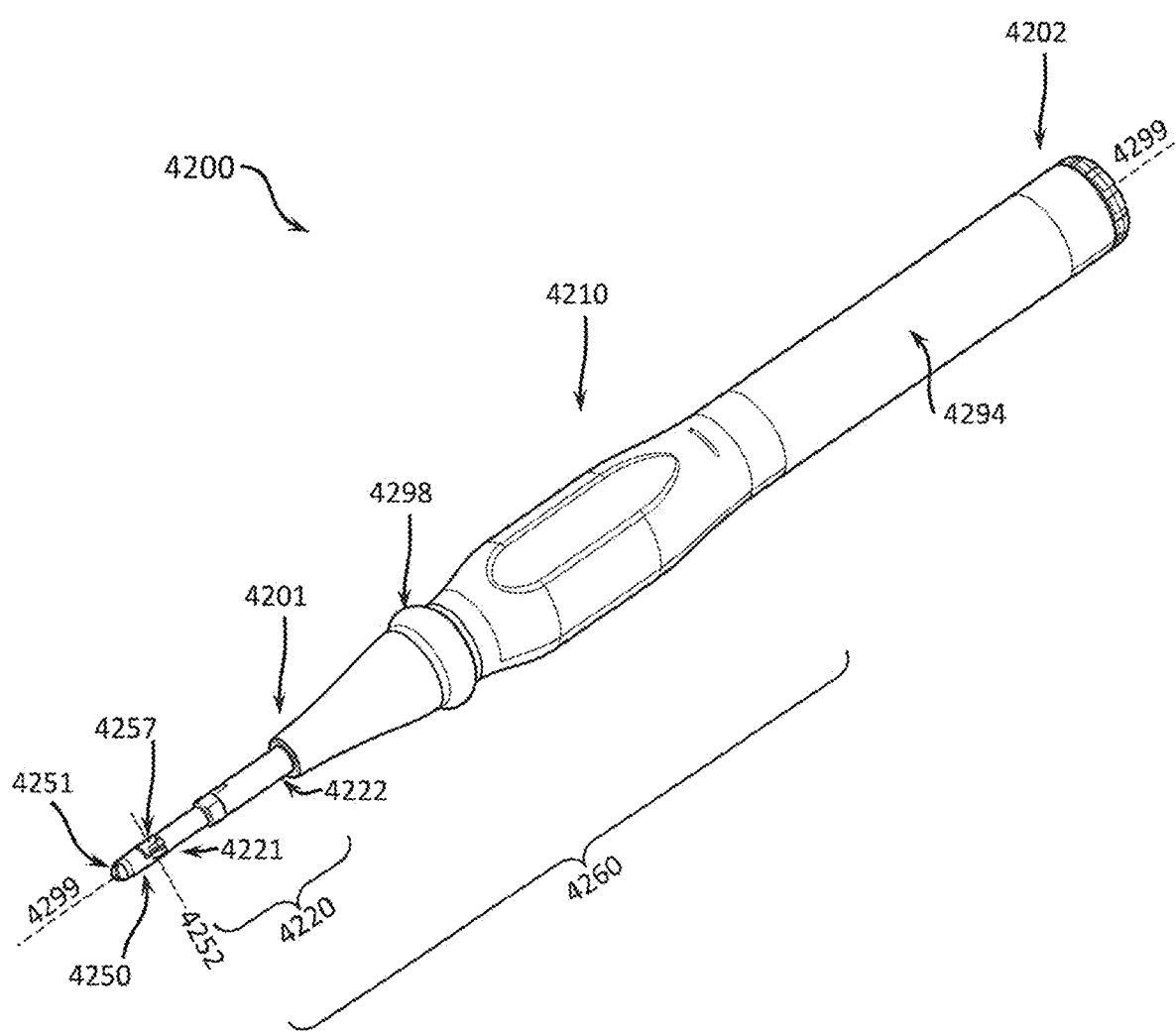
FIGS. 42A through 42E show an oblique view and expanded views of one embodiment of a differential dissecting instrument in slender pencil grip form designed especially for open surgery.
Figure 42B:
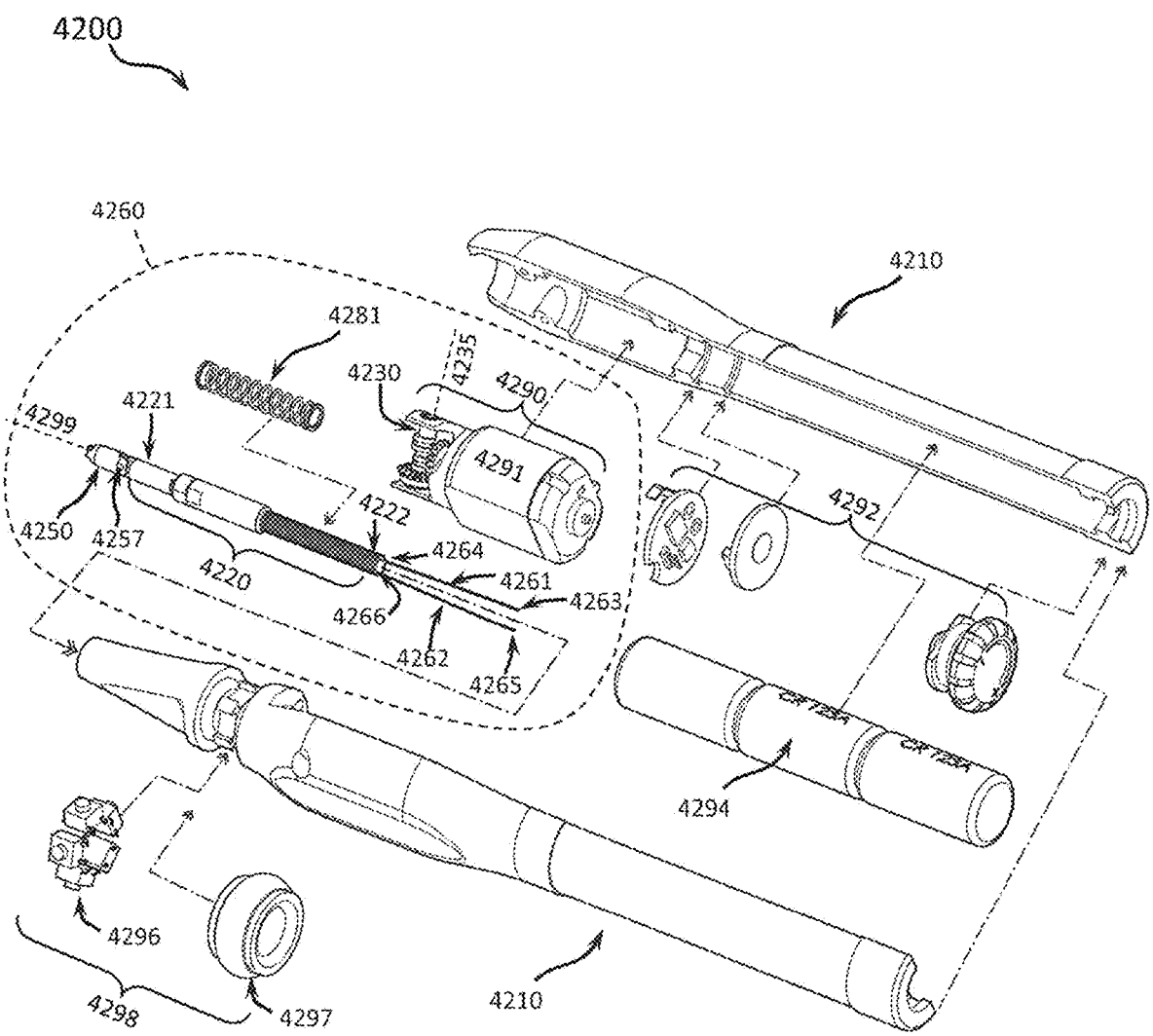

FIGS. 42A and 42B show Differential Dissecting Instrument 4200 in oblique view, assembled in FIG. 42A and expanded in FIG. 42B. Differential Dissecting Instrument 4200 has an approximately cylindrical handle 4210 possessing a longitudinal, central axis 4299. In use, a distal end 4201 of the handle 4210 is directed toward a tissue to be dissected, and a proximal end 4202 is pointed away from the complex tissue and toward the user. Attached to the distal end 4201 is an elongate member 4220 parallel to the longitudinal axis 4299, having a proximal end 4222 attached to the distal end 4201 of the handle 4210 and a distal end 4221 pointing toward the tissue to be dissected. DDM 4250 attaches to the distal end 4221 of the elongate member 4220. In this embodiment, cylindrical handle 4210 is hollow, with a clamshell construction, such that it houses a mechanism 4260 configured to mechanically rotate the DDM 4250, as described in the next paragraph.

Figure 42C:
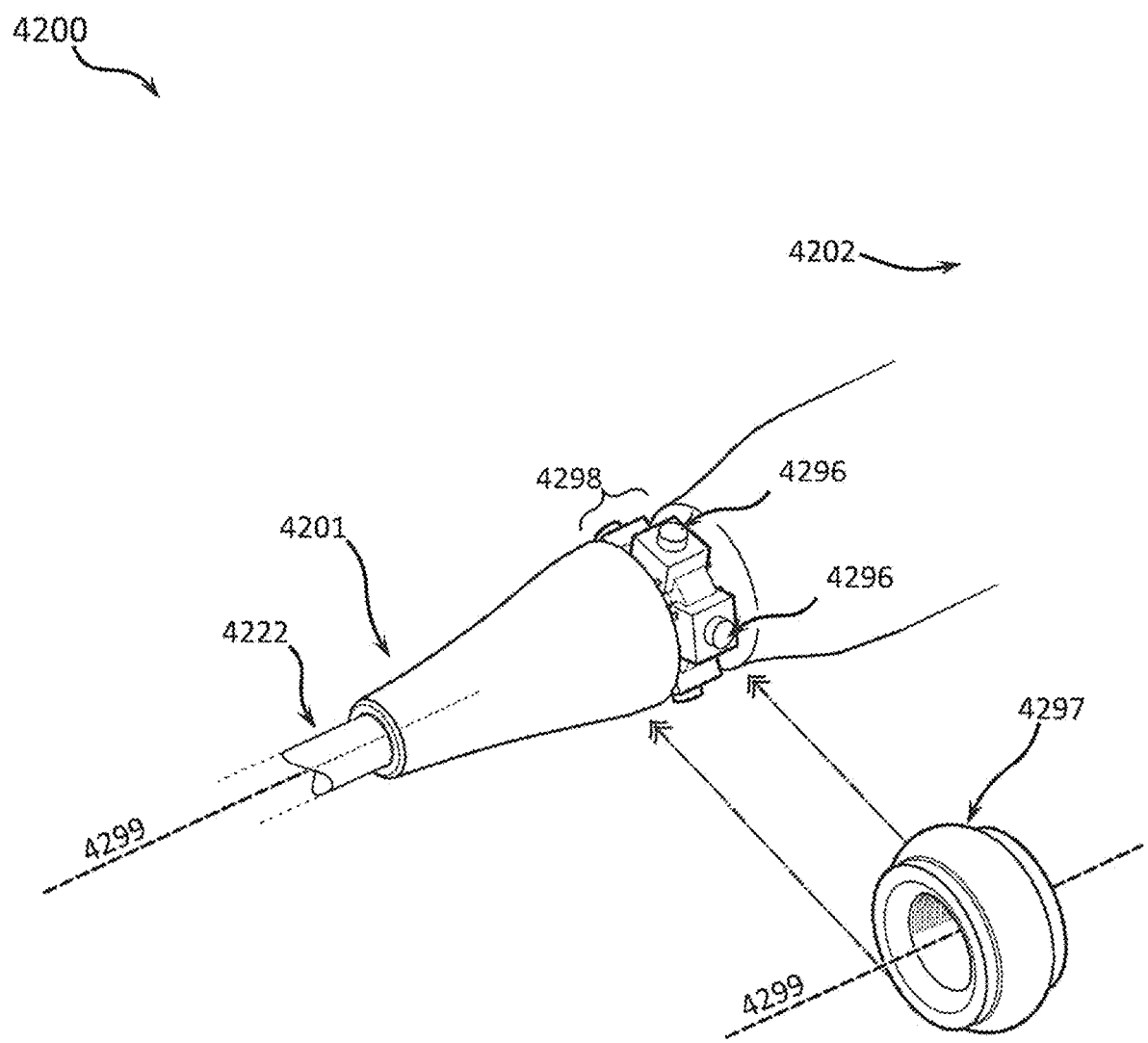
Figure 42D:
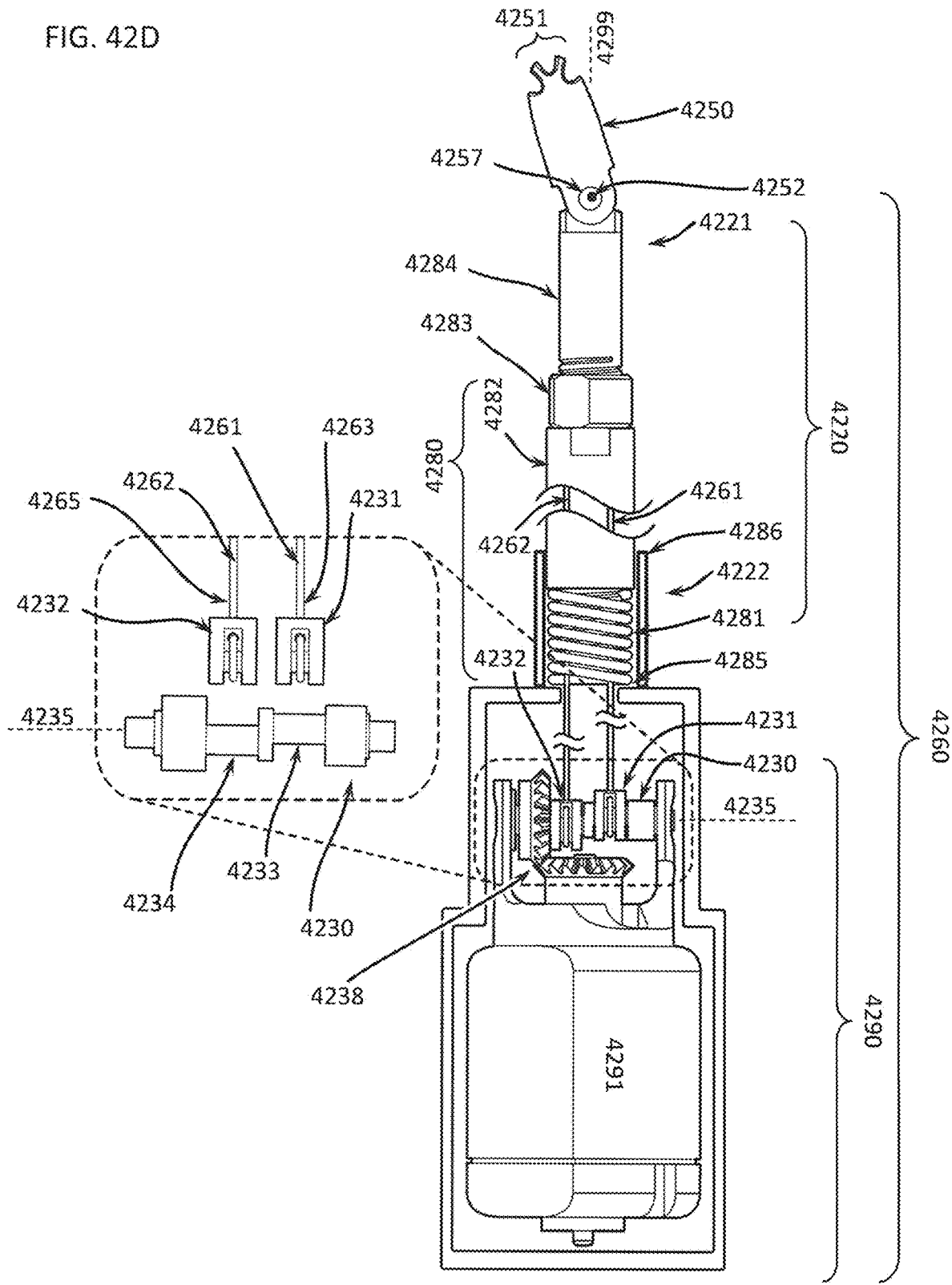
Figure 42E:
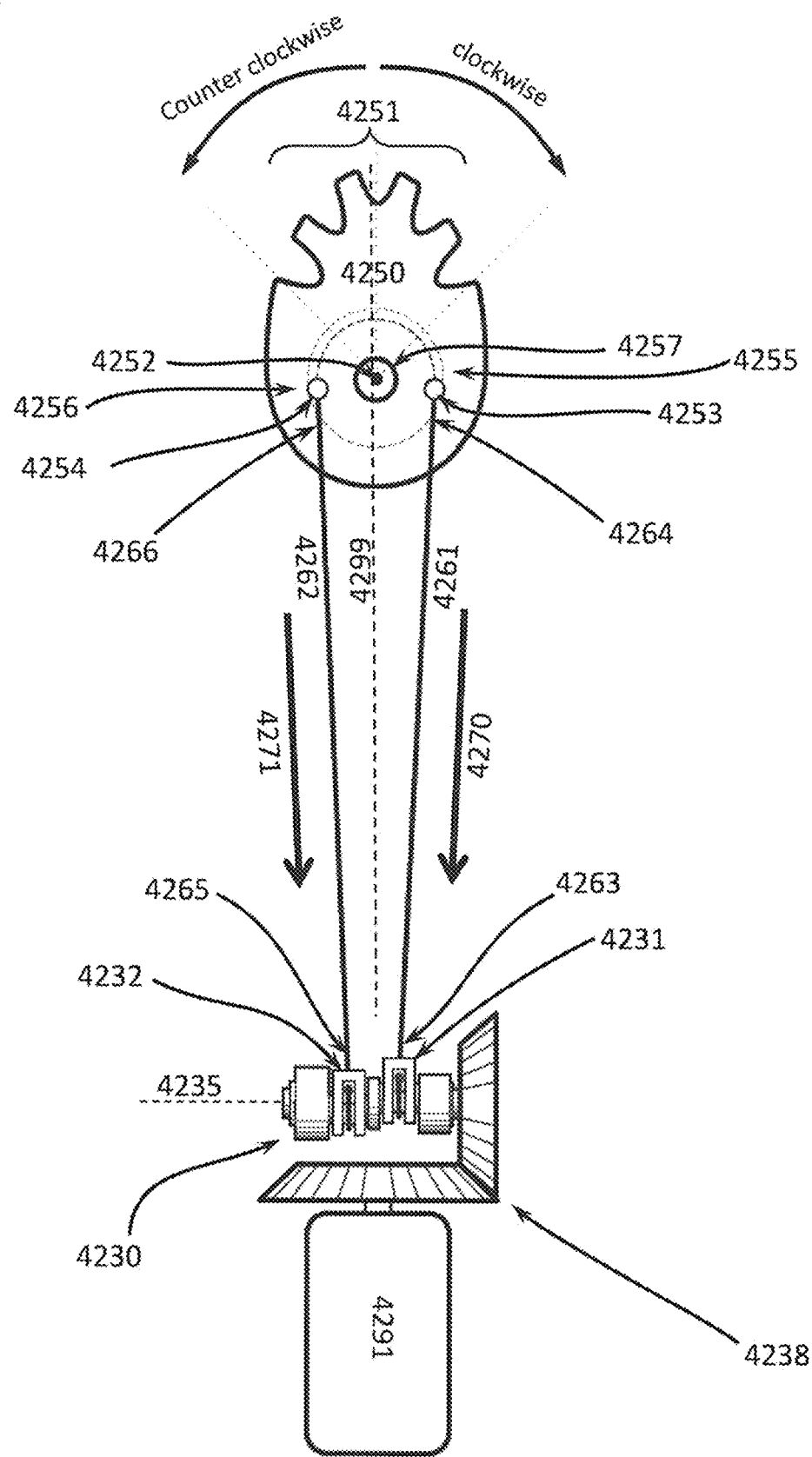

Referring now to FIGS. 42B, 42D, and 42E, FIG. 42B presents an expanded view of the Differential Dissecting Instrument 4200; FIG. 42D shows a closer view of the drive mechanism of the DDM 4250; and FIG. 42E shows a simplified view of the drive mechanism with emphasis on how the DDM 4250 is driven. DDM 4250 is rotatably attached to the distal end 4221 of the elongate member 4220 such that DDM 4250 rotates about an axis of rotation 4252. DDM 4250 possesses a first tissue engaging surface 4251 at the distal end 4221 of DDM 4250, such that it is directed toward the tissue to be dissected, and a first torque-point 4253 disposed to a first side 4255 of the axis of rotation 4252 of the DDM 4250 (see FIG. 42E). Application of a first force 4270 to first torque-point 4253 creates a moment on DDM 4250 about axis of rotation 4252 and thus drives clockwise rotation of DDM 4250 about axis of rotation 4252. In the embodiment presented here, there is a second torque-point 4254 disposed to a second side 4256 of the axis of rotation 4252, whereby application of a second force 4271 drives counterclockwise rotation of DDM 4250. Thus the moment created by application of first force 4270 at first torque-point 4253 creates a counter-torque to second force 4271 at second torque point 4254. Alternating application of first force 4270 and then second force 4271 thereby drives oscillation (clockwise then counterclockwise) of DDM 4250 about axis of rotation 4252. Note that first force transmitting member 4261 and second force transmitting member 4262 can be a flexible tension member, such as a cable, wire, string, rope, tape, belt, or chain, or a rigid member, such as a push rod or connecting rod. In the embodiment presented here, the first force transmitting member 4261 and the second for transmitting member 4264 are flexible tension members, such as cables.

Oscillation is driven by a motive source 4290 that is powered by a motor 4291. Thus, motive source 4290 drives at least one force-transmitting member 4261 axially, with respect to longitudinal axis 4299, proximally and distally, thereby driving first torque-point 4253 of DDM 4250 around axis of rotation 4252 and thereby making DDM 4250 oscillate around its axis of rotation 4252 such that the at least one tissue engaging surface 4251 is configured to selectively engage the tissue to be dissected and such that the at least one tissue engaging surface 4251 moves across the tissue to be dissected whereby the at least one tissue engaging surface 4251 disrupts at least one soft tissue in the tissue to be dissected, but does not disrupt firm tissue in the tissue to be dissected.

Referring now to FIGS. 42B, 42D, and 42E, mechanism 4260 drives the rotation of DDM 4250. Mechanism 4260 (see especially FIG. 42D) comprises at least one force-transmitting member 4261 that drives oscillation of DDM 4250, as described in the preceding paragraph. As seen in FIGS. 42B, 42D, and 42E first force-transmitting member 4261 and second force-transmitting member 4262 extend approximately parallel to longitudinal axis 4299 inside elongate member 4220, and distal end 4264 of first force-transmitting member 4261 attaches to first torque-point 4253 of DDM 4250, and distal end 4266 of second force-transmitting member 4262 attaches to second torque-point 4254 of DDM 4250. As seen in FIGS. 42B and 42D, proximal end 4263 of first force-transmitting member 4261 attaches to a first follower 4231 of a cam shaft 4230, and proximal end 4265 of second force-transmitting member 4262 attaches to a second follower 4232 of cam shaft 4230. First follower 4231 rides on a first eccentric cam 4233 (see inset) on cam shaft 4230, and second follower 4232 rides on a second eccentric cam 4234 (see inset) on cam shaft 4230. Cam shaft 4230 rotates about an axis of rotation 4235 that is perpendicular to longitudinal axis 4299, and first eccentric cam 4233 and second eccentric cam 4234 are positioned on opposite sides of axis of rotation 4235 such that first follower 4231 moves 180° out of phase with respect to second follower 4232 (see FIGS. 42D and 42E for more detail). Thus, rotation of cam shaft 4230 pulls alternately on first force-transmitting member 4261 and second force-transmitting member 4262, creating the alternating first and second forces 4270 and 4271, respectively, that drives oscillation of DDM 4250, as described above.

Rotation of cam shaft 4230 is driven by motor 4291 via a gear train. In the embodiment presented here, motor 4291 is a DC electric motor forming part of an electric circuit 4292 (see FIG. 42B) powered by at least one battery 4294, whereupon the device further includes at least one switch 4296 operatively associated with the motor 4291 and the at least one battery 4294 to at least start and stop the motor 4291. Further controls can be added to permit proportional speed control of motor 4291 or speed control via incremental steps. Motor 4291 can be one of several types of motors, including brushless DC motors, coreless DC motors, stepper motors, etc.

Spring mechanism 4280, compression spring 4281, compression nut 4282, lock nut 4283, inner sleeve 4284, outer sleeve 4286, and spring stop 4285 are described more completely after FIGS. 44A through 44C below.

In the embodiment shown in FIGS. 42A through 42C, switch 4296 is part of an omnidirectional control switch 4298 that makes the on-off switch for motor 4291 accessible from substantially any direction about the longitudinal axis 4299 of handle 4210 of Differential Dissecting Instrument 4200. In this embodiment, omnidirectional control switch 4298 is comprised of five (5) switches 4296 in a radial array distributed about the handle 4210, proximal to distal end 4201 of handle 4210, such that a switch 4296 can be easily activated with any finger regardless of the rotational orientation (about longitudinal axis 4299) of Differential Dissecting Instrument 4200 while in the user's hand. In this embodiment, the radial array of five switches 4296 is covered by a flexible boot 4297 made of a soft elastomer (e.g. silicone rubber) that prevents intrusion of fluids into switches 4296 but still permits easy actuation of switches 4296. The switches can be either momentary or latching. There may be any number of switches that form the radial array; they may lie in a single plane oriented transverse to the longitudinal axis 4299, or they may not, in which case the array of switches may further be distributed both around and along the longitudinal axis 4299 of the Differential Dissecting Instrument 4200. The array of switches may or may not be the same; each of the switches 4296 may vary in size, shape, type, function (momentary, latching on-off, normally on, normally off. single-pole single throw, single-pole double throw, double-pole double throw, double-pole single throw, or digital or analog proportional control), or distance from the longitudinal axis 4299, or any combination. Further, instead of an array of switches, the omnidirectional control switch 4298 may be substantially monolithic or of toroidal construction, and may be comprised of, for example, a first ring conductor held in abeyance from contact with second ring conductor, whereupon the surgeon may apply pressure to this version of the omnidirectional control switch 4298 from any direction, causing the first ring conductor to come into electric contact with the second ring conductor. Either the first ring conductor or the second ring conductor or both can be either rigid or flexible. For example, if the second ring conductor forms a small diameter rigid ring around the longitudinal axis 4299 of the Differential Dissecting Instrument 4200, the second ring conductor might be a large diameter ring elastically suspended out of contact and substantially coaxially with the first ring conductor. As one example, the surgeon's fingers might displace a rigid second ring conductor off-center until it contacts the first ring conductor, or, alternatively, the second ring conductor might flexibly deform until contact is established with the first ring conductor. The omnidirectional control switch 4298 might take the form of a power switch directly controlling the flow of electricity to a motor 4291, or, the omnidirectional control switch 4298 might transduce surgeon finger inputs into changes in resistance, capacitance, or other parameters in order to drive a logic circuit that then controls the motor 4291.

Figure 43A:
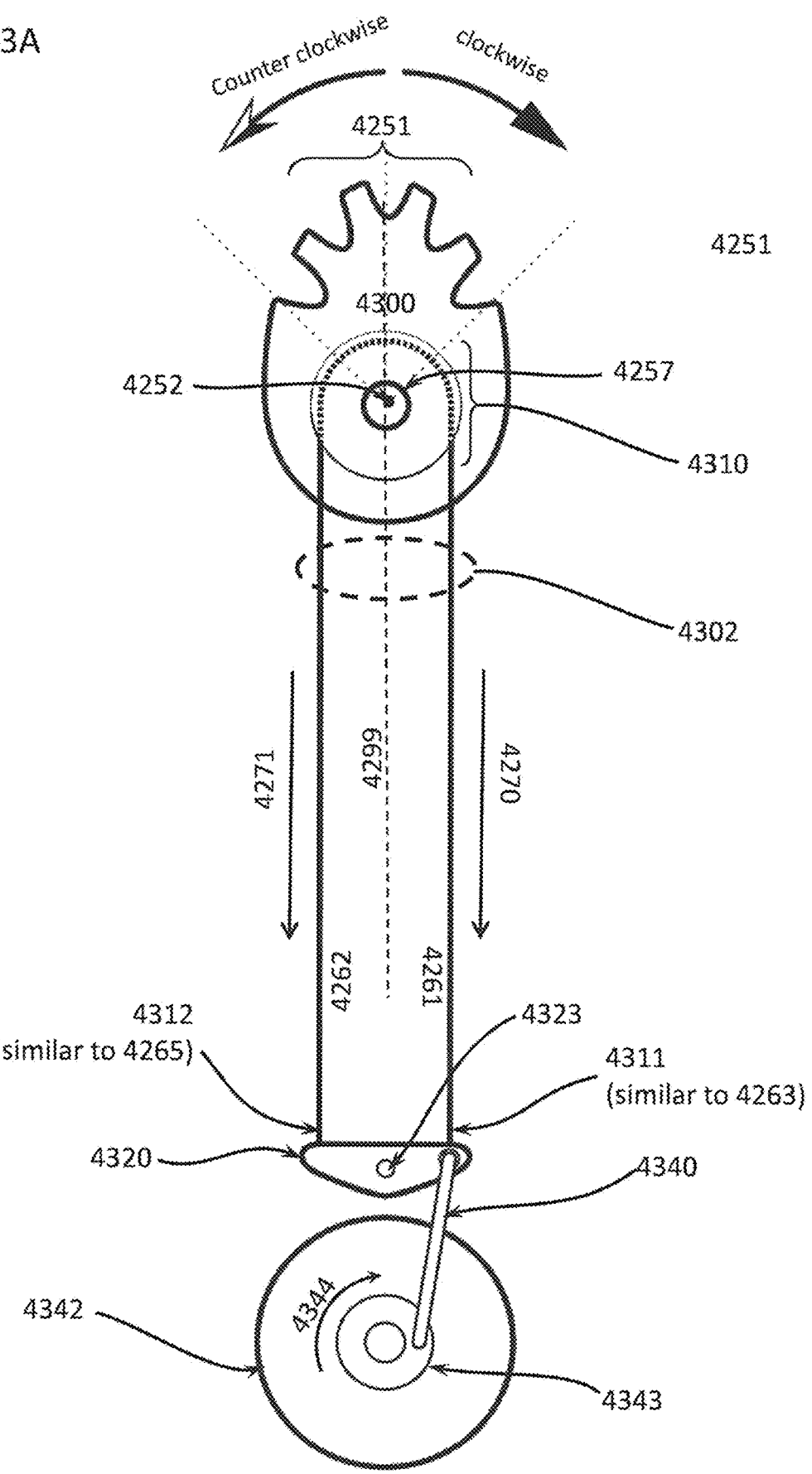
FIGS. 43A through 43C show different embodiments of some mechanisms that can drive the oscillation of a differential dissecting member.
Figure 43B:
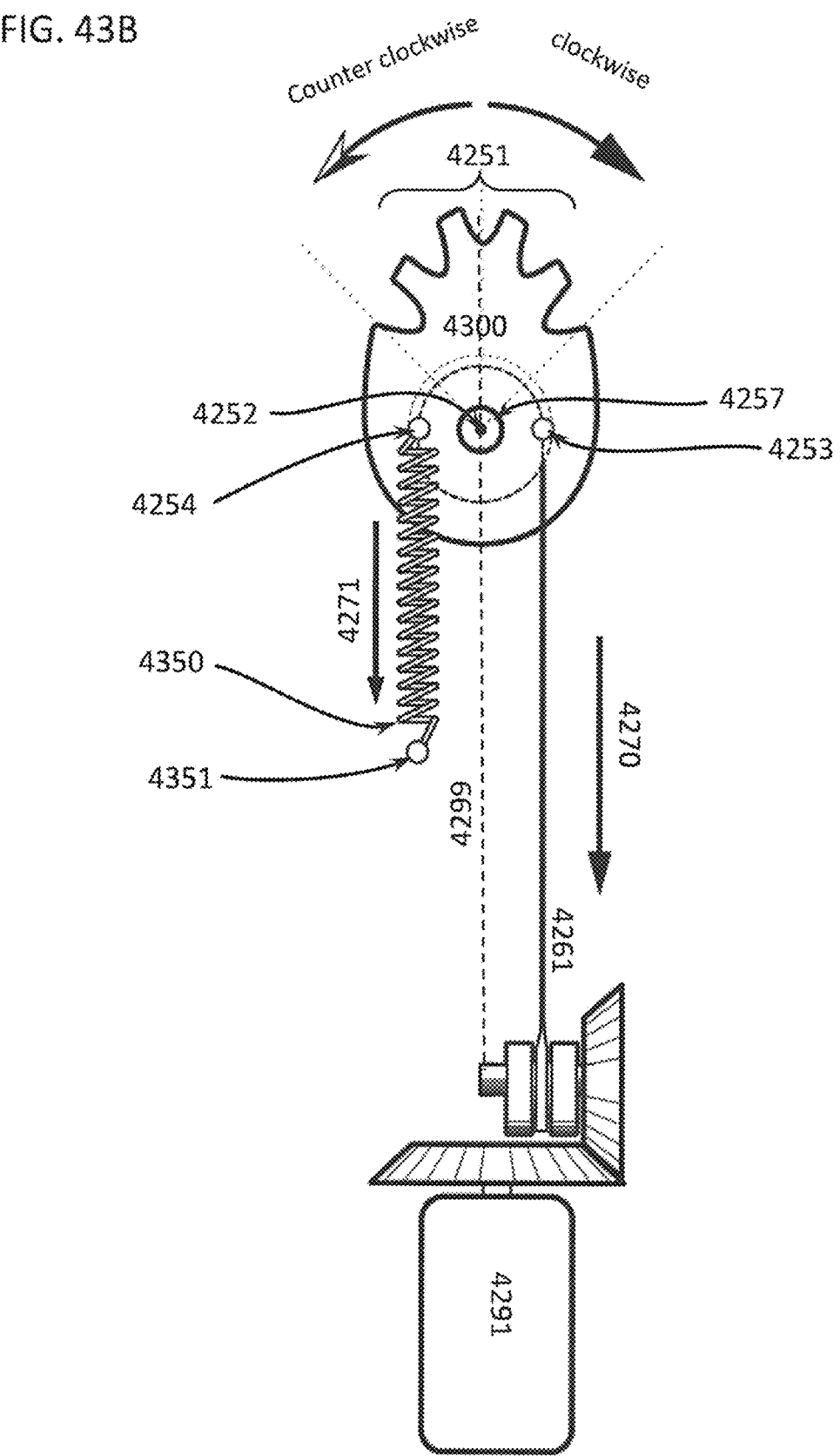
Figure 43C:
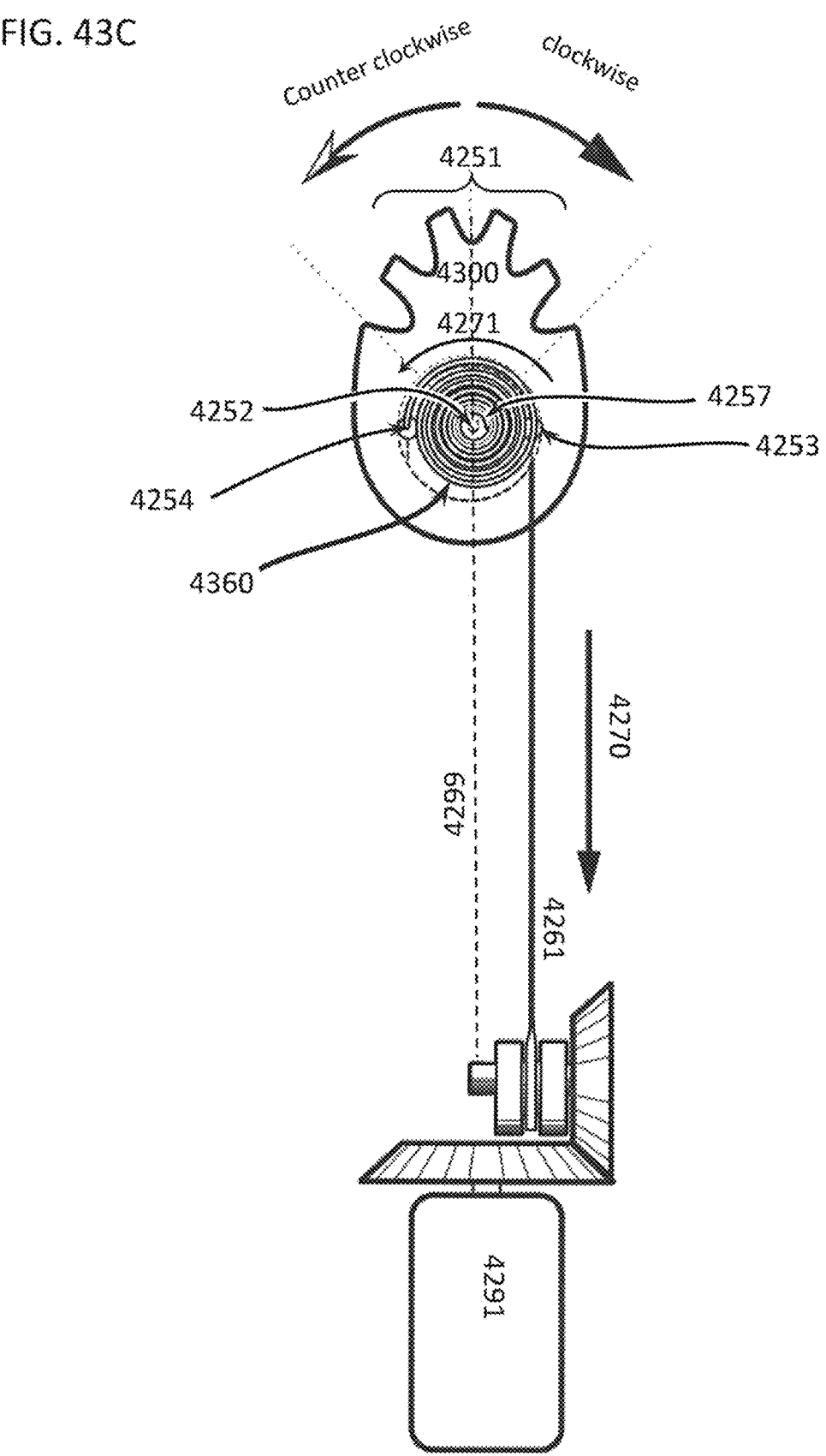

FIGS. 43A through 43C show different embodiments for imparting a torque and counter-torque on a DDM 4300. In FIG. 43A, first tension element 4261 and second tension element 4262 are two halves of a single cable 4302 wrapped around a drive cylinder 4310 attached to DDM 4300. Single cable 4302 drives rotation of drive cylinder 4310 either by friction or by being physically attached to drive cylinder 4310. Single cable 4302 has a first end 4311 and a second end 4312 with first end 4311 acting as the proximal end of the first force-transmitting member and the second end 4312 acting as the proximal end of the second force-transmitting member. First and second forces 4270 and 4271, respectively, are created by the motion of rocker arm 4320 that rocks about rocker pin 4323 when driven by linkage 4340 which is acentrically or eccentrically attached to drive pulley 4343 which rotates (as indicated by arrow 4344) due to motor 4342.

Another embodiment is shown in FIG. 43B where a linear spring 4350 attaches to second torque-point 4254 and a stationary anchor point 4351 such that application of first force 4270 rotates DDM 4300 and thereby stretches linear spring 4350 and the return force 4271 of linear spring 4350 generates the counter-torque when first force 4270 decreases. Similarly the counter-torque can be generated by a torsion spring 4360, as depicted in FIG. 43C.

Figure 44B:
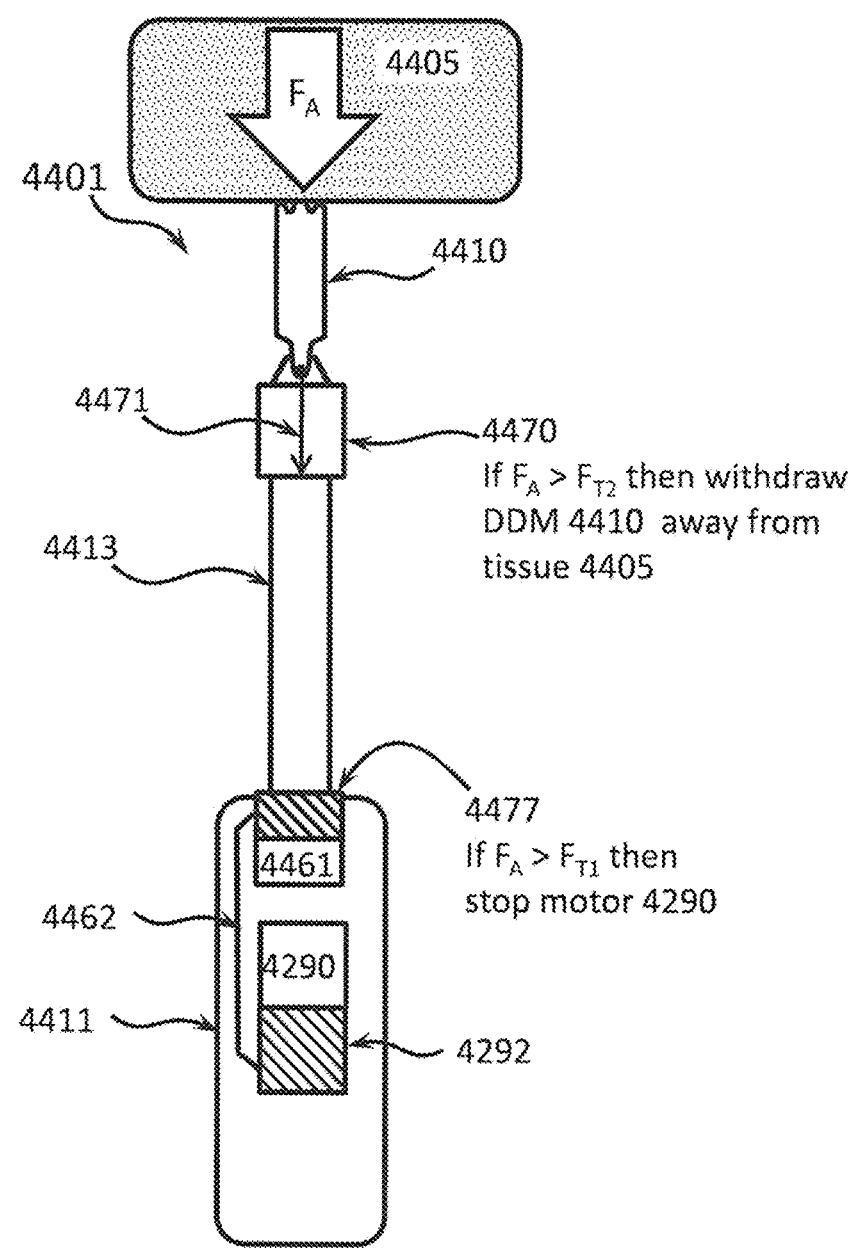

FIGS. 44A through 44C show different embodiments of mechanisms that protect a both a differential dissecting instrument and a tissue being dissected from excessive loading. FIG. 44A illustrates two difficulties for the construct and use of a Differential Dissecting Instrument 4400 that uses tension members as a force-transmitting member. DDM 4410 has a tissue engaging surface 4412 on its distal end and a rotational joint 4414 on its proximal end to rotatably connect to the distal end of an elongate member 4430. A first tension member 4421 connects to a first torque-point 4423, and a second tension member 4422 connects to a second torque-point 4424 such that first tension member 4421 and second tension member 4422 create a counter-torque around rotational joint 4414 to drive oscillation of DDM 4410. Difficulty #1: For first tension member 4421 and second tension member 4422 to effectively provide a counter-torque about rotational joint 4414, they must remain taut. However, poor fit of components, stretching of first tension member 4421 or second tension member 4422, wear, or other "play" in the Differential Dissecting Instrument 4400 will cause Differential Dissecting Instrument 4400 to perform poorly or to fail. Difficulty #2: During dissection of tissue 4405, application of an external force $F_A$ to the DDM 4410 can force the Differential Dissecting Instrument 4400 into an extreme position, creating excessive bending or wear of first tension member 4421 at point 4441 inside elongate member 4430 or of second tension member 4422 at point 4442 inside of elongate member 4430 (or at other points of contact between either first or second tension member 4421 or 4422 and another component). More broadly, excessive forces applied to the DDM of a Differential Dissecting Instrument can damage the Differential Dissecting Instrument or the tissue under dissection. Thus a means of preventing damage to either the instrument or the tissue would be helpful.

FIG. 44B illustrates an embodiment of a Differential Dissecting Instrument 4401 that addresses these difficulties including means for preventing damage due to an overload condition. Differential Dissecting Instrument 4401 possesses two overload mechanisms, a first overload mechanism 4477 that is responsive to a first threshold force $F_{T1}$ applied to DDM 4410 and a second overload mechanism 4470 that is responsive to a second threshold force $F_{T2}$ applied to DDM 4410. During dissection of tissue 4405, if force $F_A$ is applied to the DDM 4410 that exceeds a first threshold force $F_{T1}$, first overload mechanism 4477 stops rotation of DDM 4410 to reduce the risk of damage to either Differential Dissecting Instrument 4401 or to the tissue 4405 being dissected. For example, first overload mechanism 4477 can include a force sensor 4461 that measures the force $F_A$ applied to DDM 4410. Examples of force sensor 4461 include load cells, strain gauges, and spring-loaded electrical contacts. In this example, overload mechanism 4450 resides in the handle 4411 where elongate member 4413 attaches to handle 4411 but could be placed elsewhere, for example inside elongate member 4413. Force sensor 4461 is in communication via wire 4462 with electric circuit 4292, and when $F_{T1}$ exceeds $F_A$ a signal is sent via wire 4462 to electric circuit 4292 which responds by cutting power to motor 4290 thereby stopping oscillation of DDM 4410. Alternate means exist for stopping rotation of DDM 4410. For example, a clutch on motor 4290 could limit torque being applied by motor 4290 such that when external force $F_A$ is too large, the torque becomes too great and the clutch slips, or the motor 4290 could simply be sufficiently small that it stalls, etc.

If force $F_A$ is applied to DDM 4410 that exceeds a second threshold force $F_{T2}$, second overload mechanism 4470 withdraws DDM 4410 proximally away (in the direction of arrow 4471) from the tissue 4405 thereby reducing external force $F_A$. Note that first overload mechanism 4477 and second overload mechanism 4470 can be activated in response to any force, not just an axial force, as shown in FIG. 44B. Furthermore, first threshold force $F_{T1}$ can be equal to, greater than, or less than second threshold force $F_{T2}$, depending on the desired response. Also note that a Differential Dissecting Instrument can be fitted with only one of the two overload mechanisms 4470 and 4477.

FIG. 44C illustrates an embodiment of a Differential Dissecting Instrument 4402 with a single overload mechanism as described above for FIG. 44B. Differential Dissecting Instrument 4402 is similar to Differential Dissecting Instrument 4401, however, now elongate member 4430 is replaced by another exemplary overload mechanism 4450 which acts in the same way as second overload mechanism 4470 described above, by withdrawing DDM 4410 proximally away from tissue 4405. Overload mechanism 4450 comprises an outer sleeve 4451 with a first spring stop 4454, an inner sleeve 4452 with a second spring stop 4455, and a compression spring 4453. Outer sleeve 4451 and inner sleeve 4452 are aligned parallel to the longitudinal axis 4299 of the handle. DDM 4410 is attached to inner sleeve 4452 at rotational joint 4414. Inner sleeve 4452 is free to slide proximally inside outer sleeve 4451. As shown on the left-hand side (with no external force applied) compression spring 4453 causes inner sleeve 4452 to slide distally inside outer sleeve 4451 due to compression force 4460 being applied to first spring stop 4454 and second spring stop 4455. Sliding is limited by forces 4462 and 4463 exerted by first and second tension members 4421 and 4422, respectively, such that the combined force of force 4462 and force 4463 equals compression force 4460. Thus, overload mechanism 4450 fixes Difficulty #1 described above in that compression spring will adjust the position of inner sleeve 4452 relative to outer sleeve 4451 whenever any play accumulates, such as stretching of first and second tension members 4421 and 4422, respectively. The right-hand side of FIG. 44B shows how overload mechanism 4450 also alleviates the problems of Difficulty #2. When an external force $F_A$ is applied to DDM 4410, a moment is created about rotational joint 4414 forcing DDM 4410 into an extreme position and also applies a moment at torque-point 4424 that stretches second tension member 4422, creating a larger force 4463 on second tension member 4422. The increase in force 4463 thereby increases the compression force 4460 on compression spring 4453. In response, compression spring 4453 compresses allowing inner sleeve 4452 to slide proximally (arrow 4456) inside outer sleeve 4451 and thus shorten overload mechanism 4450. This withdraws DDM 4410 proximally away from the tissue being dissected thereby decreasing the magnitude of force 4463 on second tension member 4422 and reducing the risk of damage to Differential Dissecting Instrument 4402, and especially to second tension member 4422. Note that other embodiments for withdrawing a DDM in response to an overload are possible. Different configurations of springs, flexible or bendable elongate members, friction pads that slip on overload, etc. are all possible.

Figure 45A:
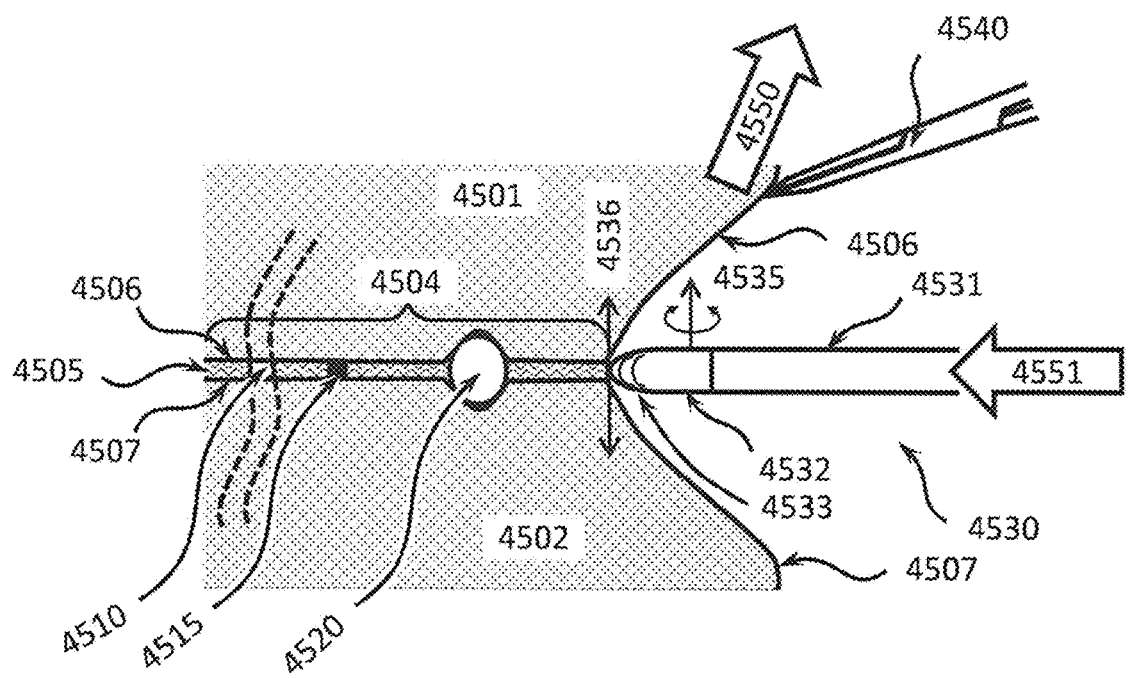
FIGS. 45A through 45G show a method for using a differential dissecting instrument for separating a tissue plane without damaging blood vessels and other anatomical structures in the tissue plane.

Returning now to FIG. 42D, spring mechanism 4280 comprises compression spring 4281, compression nut 4282, lock nut 4283, inner sleeve 4284, and spring stop 4285. Compression spring 4281 surrounds inner sleeve 4284 and is compressed between compression nut 4282 (which serves as the first spring stop 482) and spring stop 4285 (which serves as the second spring stop) such that it pulls on first tension element 4261 and second tension element 4262. The strength with which compression spring 4282 pulls is set by compression nut 4282 which is threaded onto inner sleeve 4284—advancing compression nut 4282 downward (with respect to the page) compresses compression spring 4281, increasing the strength with which compression spring 4281 pulls on first tension element 4261 and second tension element 4262. After an appropriate pull is established, compression nut 4283 can be locked with lock nut 4283. This means for varying the strength with which compression spring pulls on first tension element 4261 and second tension element 4262 effectively sets the threshold force at which the compression spring 4281 is overcome by an external force, as discussed in FIG. 44B. Furthermore, the distance of advance of compression nut 4283 along inner sleeve 4284 defines the distance over which compression spring can remove slack from the mechanism arising from, for example, stretch of first tension element 4261 and second tension element 4262. The travel of inner sleeve FIGS. 45A through 45G show a method for using a differential dissecting instrument for separating a tissue plane without damaging blood vessels and other anatomical structures in the tissue plane. FIGS. 45A through 46G depict a method for using a Differential Dissecting Instrument 4530 to dissect apart two tissues adjoining at a tissue plane. In FIG. 45A, first tissue 4501 and second tissue 4502 adhere at a common border 4504, with Soft Tissue 4505 acting as an adhesive between the first capsule 4506 of first tissue 4501 and a second capsule 4507 of second tissue 4502. In this example, one blood vessel 4520 (depicted in cross-section) lies in the plane of the common border 4504, in between the first capsule 4506 and the second capsule 4507; a second blood vessel is a "perforator" 4510 that crosses the common border 4504 going from tissue 4501 to tissue 4502; and one collagenous bundle 4515 also crosses the common border 4504 going from first tissue 4501 to second tissue 4502. Thus, if first tissue 4501 is to be separated from second tissue 4502 by blunt dissection, then soft tissue 4505 must be disrupted, preferably without disrupting the perforator 4510, collagenous bundle 4515, or blood vessel 4520. (Disruption of the blood vessels can lead to unnecessary bleeding.) Again, 4505 is a Soft Tissue, typically comprised of gelatinous materials, mesenteries, reticular fibers, and loosely organized collagen fibrils. Firm Tissues include first and second capsules 4506 and 4507, respectively, the walls of blood vessels 4510 and 4520, and collagenous bundle 4515.

Figure 45B:
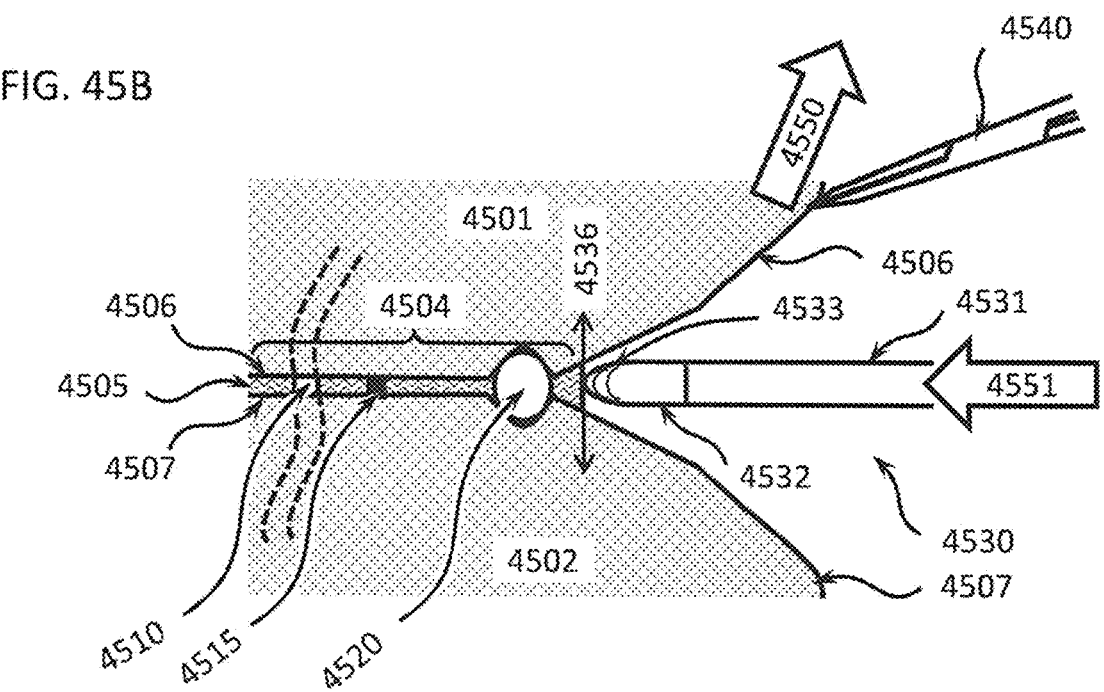

Blunt dissection is performed by first grasping first tissue 4501 with forceps 4540 and pulling in the direction of arrow 4550 to apply tension at the edge of common border 4504, as indicated by double-headed arrow 4536. Application of tension across common border 4504 is important throughout this dissection as such tension assists the differential action of the Differential Dissecting Instrument 4530, as discussed above. Differential Dissecting Instrument 4530 comprises a DDM 4532 with tissue engaging surface 4533, with DDM being rotatably mounted on instrument insertion tube 4531 such that it oscillates into and out of the plane of the page (as indicated by rotational axis 4535), causing tissue engaging surface 4533 to swipe against the edge of common border 4504. Force 4551 is applied by the operator to push tissue engaging surface 4533 into the edge of common border 4504, thereby causing ablation of Soft Tissue 4505 and ensuing separation of the first and second capsules 4506 and 4507 of the first and second tissues 4501 and 4502, respectively, as shown in FIG. 45B. If the tissue engaging surface 4533 wanders up or down due to inaccuracy of placement or misdirection of force 4551 by the operator, the tissue engaging surface 4533 will not disrupt and, therefore, will not cross either capsule 4506 or 4507. Thus, Differential Dissecting Instrument automatically follows the plane between the tissues, defined by common border 4504.

Figure 45C:
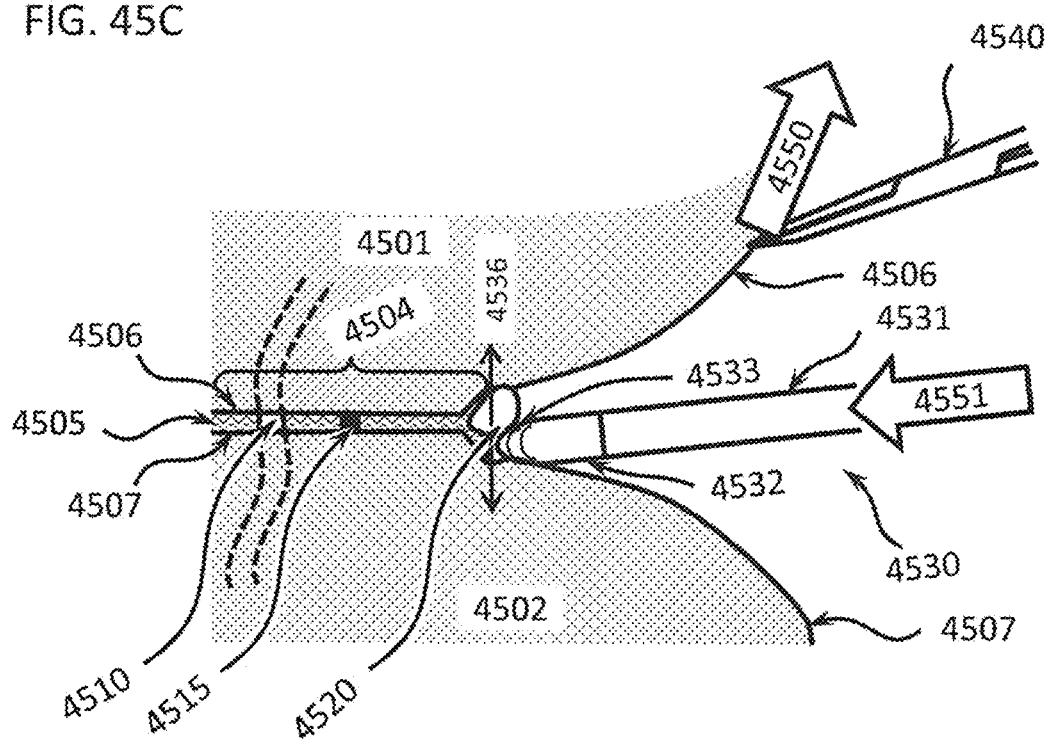

In FIG. 45C, tissue engaging surface 4533 continues along common border 4504 until it impinges on blood vessel 4520. Again, tissue engaging surface 4533 will not disrupt the Firm Tissue comprising the wall of blood vessel 4520. Instead, tissue engaging surface 4533 moves to one side or the other of blood vessel 4520 (here seen moving below blood vessel 4520), depending on whether Soft Tissue 4505 is more easily disrupted above or below blood vessel 4520 or if the operator pushes Differential Dissecting Instrument 4530 above or below the blood vessel 4520. The operator knows to push Differential Dissecting Instrument 4530 in a different direction because the operator can sense tissue engaging surface 4533 impinging on blood vessel 4520 as an increase in resistance to pushing Differential Dissecting Instrument 4530 into the common border 4504—progress of the Differential Dissecting Instrument 4530 practically stops because the tissue engaging surface 4533 will not disrupt and thus cross the Firm Tissue composing the wall of blood vessel 4520.

Figure 45D:
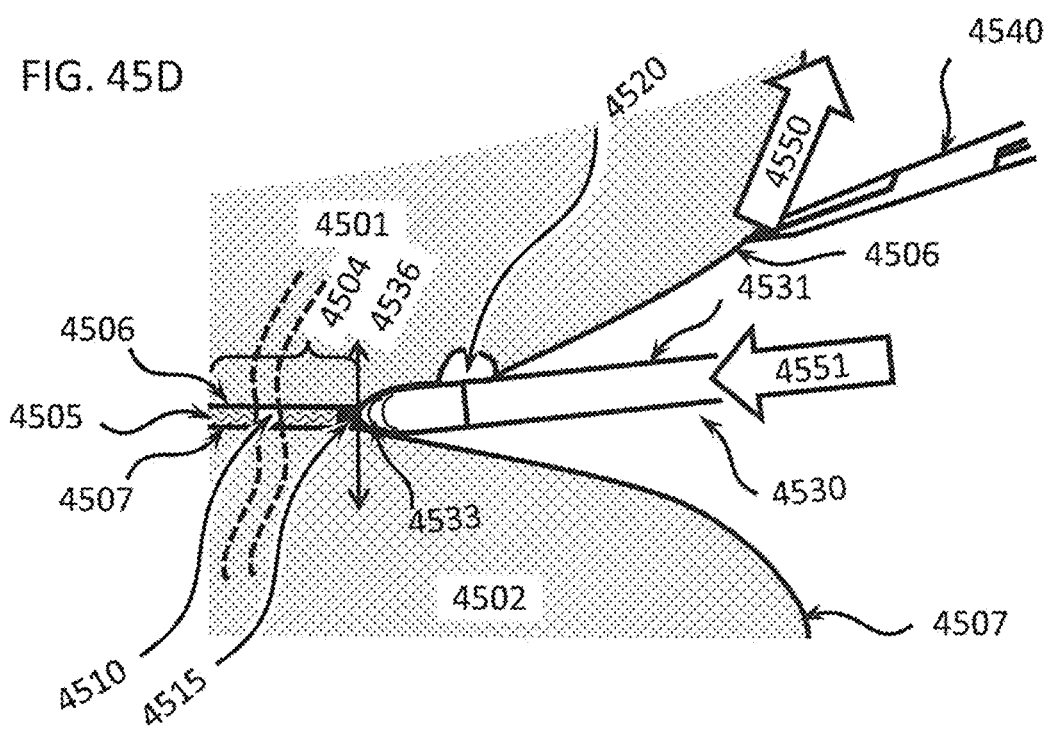
Figure 45E:
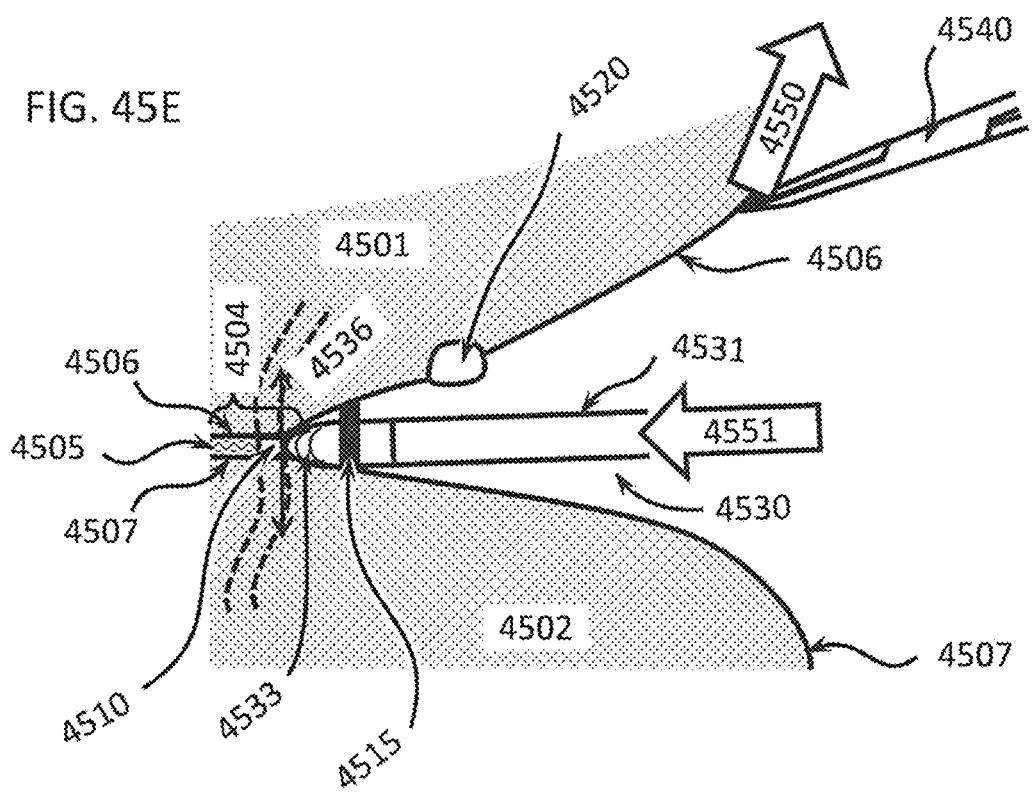
Figure 45F:
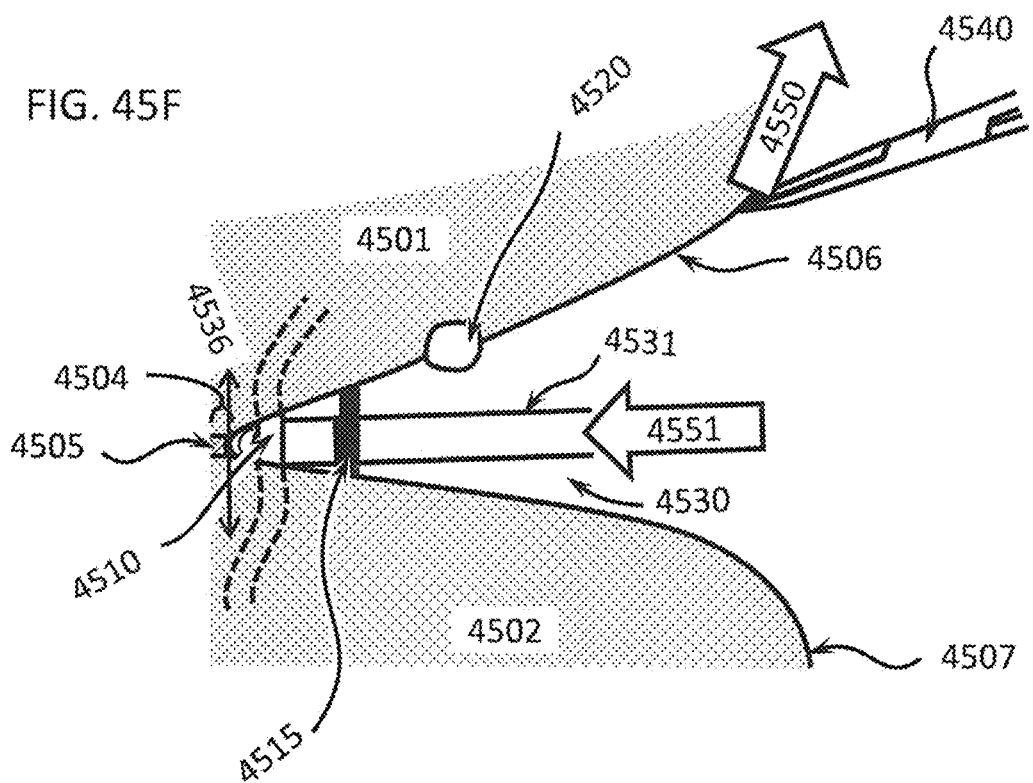

Blunt dissection continues in FIG. 45D along common border 4504 as the operator continues to apply tension 4536 across common border 4504 with forceps 4540 and to push Differential Dissecting Instrument 4530 into the common border 4504. Capsules 4506 and 4507 continue channeling the Differential Dissecting Instrument 4530 along common border 4504 by preventing the tissue engaging surface 4533 from crossing either first capsule 4506 or second capsule 4507 until tissue engaging surface 4503 impinges onto collagenous bundle 4515. Again, tissue engaging surface 4533 cannot disrupt collagenous bundle 4515, and, again, the operator senses that further progress of Differential Dissecting Instrument 4530 into the common border 4504 is blocked. The operator then works the Differential Dissecting Instrument to one side or the other, which as seen in FIG. 45E is to the rear of collagenous bundle 4515 for this example, and then continues dissecting along common border 4504 until tissue engaging surface 4533 impinges now on perforator 4510. Again, the operator senses an obstruction and moves the Differential Dissecting Instrument 4530 to one side or the other, which as seen in FIG. 45F is to the rear of perforator 4510 in this example.

Figure 45G:
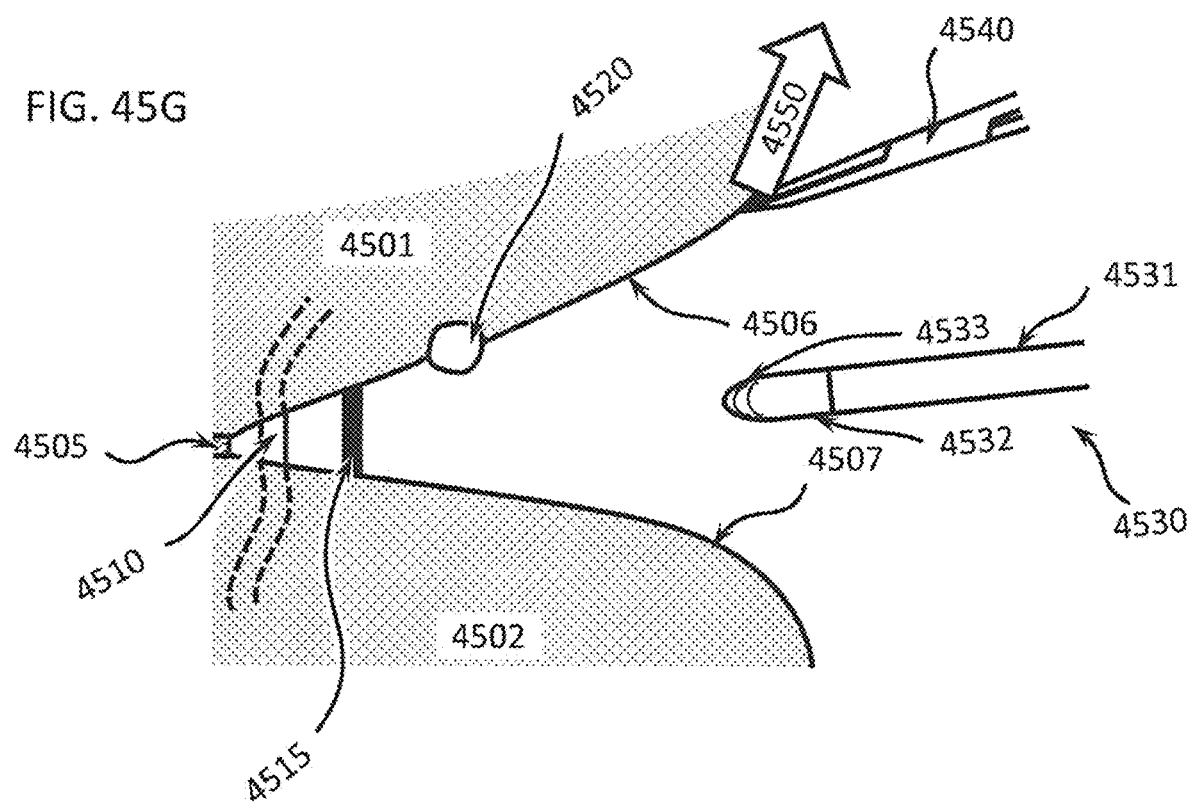

FIG. 45G shows the resulting dissection after Differential Dissecting Instrument 4530 has been removed. The common border 4504 has now been dissected such that the capsules 4506 and 4507 of tissues 4501 and 4502, respectively, are separated, providing a critical view for the surgeon. Importantly, blood vessel 4520 is unharmed; collagenous bundle 4515 is stretched in the gap between first capsule 4506 and second capsule 4507, and perforator 4510 is stretched across the gap between first capsule 4506 and second capsule 4507. Collagenous bundle 4515 and perforator 4520 are, thus, "skeletonized", they are seen now in open space where they can be cauterized and cut without touching either the capsules 4506 or 4507 or tissues 4501 or 4502. This is especially important if bleeding from perforator 4510 is to be controlled when tissues 4501 and 4502 are separated and, also, if contact with or thermal spread from the electrocautery surface might cause thermal damage to either tissue 4501 or 4502.

The dissection technique, such as that shown in FIGS. 45A through 45F, has been used by the inventors to perform several surgical dissections (in ex vivo animal tissues, live animal tissues (pig), and in human cadavers) such as, for example, to separate the gall bladder from the bed of the liver, to separate adjacent muscles, to separate a blood vessel from a bladder or from another blood vessel, to separate adjacent lobes of the lung, to isolate the pulmonary artery and the cystic duct and cystic artery, and many others. Strikingly, each of these dissections has been remarkably blood-free, owing to the Differential Dissector's ability to dissect without disrupting either blood vessels, even blood vessels as small as 0.5 mm outer diameter, or tissue capsules. Furthermore, the dissection has been remarkably safe. During these surgeries the surgeon deliberately attempted maneuvers that would have been catastrophic with another instrument. For example, the surgeon stabbed the liver repeatedly with the Differential Dissecting Instrument set on high speed, and bounced the Differential Dissecting Instrument on the pulmonary artery, and stabbed into the large bowel, urinary bladder, and lung—there was no damage to any organ. As described earlier, the absence of sharp edges in a DDM allows it to perform blunt dissection safely, unlike any other surgical instrument.

A dissection with a Differential Dissecting Instrument, such as that shown in FIGS. 45A through 45F can be used, for example, to dissect fascial planes during a tummy tuck procedure. In fact, it is possible to dissect these tissue planes without cauterizing or cutting perforators. Rather, by working around perforators to skeletonize them during dissection, using the Differential Dissecting Instruments shown herein, sufficient separation of tissue planes can be achieved to permit dissection to be advanced without having to cut perforators, which is usually done to avoid accidental tearing or to permit sufficient separation of the tissues to permit viewing the dissection as it advances. Preserving perforators, rather than cutting them, maintains normal blood flow to the superior layers which is otherwise compromised by disruption of perforators. This result is truly remarkable and of great clinical importance. Maintenance of normal blood flow lessens the chance of tissue necrosis (due to insufficient blood flow) and increases the chance for a rapid and complete recovery (due to sufficient blood flow). This is extremely important whenever skin has been lifted from underlying tissues (e.g. for cosmetic or reconstructive procedures) or whenever a flap of tissue is to be isolated but preserved.

A Differential Dissecting Instrument, such as any of those disclosed herein, can be used to dissect through fatty tissues; however, in such a dissection through fat there are no organ capsules or other Firm Tissues to guide the Differential Dissecting Instrument, and the dissection proceeds solely under guidance of the operator, rather than being guided by the bordering Firm Tissues. Such a dissection has been used to separate the skin from underlying tissues for a face lift in a human cadaver. Importantly, as described above, a sufficient gap was generated, without accidentally or intentionally disrupting perforating blood vessels, to advance the dissection through to completion. In a living patient, such a procedure would maintain normal blood flow to the tissues throughout the surgical procedure and, thus, into recovery. This is in stark contrast to the prior art which cauterizes perforation blood vessels, cutting off this circulation and badly comprising normal blood flow. As discussed above, preserving perforators, rather than cutting them, maintains normal blood flow to the skin which is otherwise compromised by disruption of perforators. Maintenance of normal blood flow lessens the chance of tissue necrosis (due to insufficient blood flow) and increases the chance for a rapid and complete recovery (due to sufficient blood flow). Both are strongly desired outcomes of all surgical procedures, but especially cosmetic surgical procedures.

A Differential Dissecting Instrument, such as any of those disclosed herein, can be used, in similar fashion, to tunnel into and through a portion of the body, allowing tissue capsules, blood vessel walls, nerve bundles, and other Firm Tissues to guide the tissue engaging surface along existing tissue planes. For tunneling, however, the operator does not move the Differential Dissecting Instrument from side to side to separate broad sections of tissue planes; rather, the operator pushes the Differential Dissecting Instrument into the tissue plane, with only limited motion to the side, to create a narrow tunnel. Such tunnels are used in many surgical procedures, such as tunneling to position pacing leads for pacemakers and other heart rhythm management devices, and are increasingly being used in minimally invasive surgical procedures, such as robotic, thoracoscopic, and laparoscopic surgery, to reduce the disruption of tissues, and thus trauma to tissues, during surgery. One problem that arises in tunneling is lack of visibility at the terminal end of the tunnel—surgeons do not like to work blind.

FIGS. 46A-1, 46A-2, 46B-1, 46B-2, 46C-1, and 46C-2 show an instrument for tunneling with a differential dissecting instrument coupled with an endoscope. FIGS. 46A through 46C depict a dissection system 4600 for tunneling with a Differential Dissecting Instrument and with visibility being provided by a television camera or other viewing device. As shown in FIGS. 46A-1 and 46A-2, dissection system 4600 is comprised of an instrument tube 4610 having two lumens, endoscope lumen 4620 and instrument lumen 4630. Additional lumens can be used to simultaneously introduce multiple instruments.

As seen in FIGS. 46B-1 and 46B-2, endoscope lumen 4620 houses an endoscope 4640 that is fitted with a television camera or other viewing device at the opposite end (not shown), thereby providing a view of the dissection to the operator. Endoscope 4640 can also include fiberoptics, separate from those used for the camera, to deliver light into the field of dissection. Instrument lumen 4630 is used to insert one of several different instruments into the field of view of the camera whereby they are used to dissect or otherwise manipulate tissue under view of the endoscope 4640. FIGS. 46B-1 and 46B-2 show instrument tube 4610 equipped with an endoscope 4640 inside endoscope lumen 4620 and a Differential Dissecting Instrument 4650 having a DDM 4655 inside instrument lumen 4630. Endoscope 4640 has a field of view 4645 that permits viewing of the DDM 4655 of Differential Dissecting Instrument 4650 and its interaction with tissue. Differential Dissecting Instrument 4650 can be rotated inside instrument lumen 4630 to permit the plane of oscillation of the DDM 4655 to be rotated to align with different tissue planes. (The plane of oscillation should be parallel to the tissue plane.)

Multiple instruments can be inserted, one at a time, into instrument lumen 4630, as needed. FIGS. 46C-1 and 46C-2 show an electrosurgical instrument (e.g. a hook) 4660 inserted into instrument lumen 4630. Electrosurgical hook 4660 can also be inserted into and rotated inside instrument lumen 4630 to allow the hook to point in any direction. In use, instrument tube 4610 is loaded with endoscope 4640 inside endoscope lumen 4620 and with Differential Dissecting Instrument 4650 loaded into instrument lumen 4630. The instrument tube is positioned by an operator at the correct point on a patient, as determined by viewing the display of endoscope 4640, who activates Differential Dissecting Instrument 4650 to initiate blunt dissection. Differential Dissecting Instrument 4650 can be rotated inside instrument lumen 4630, as indicated by curved double arrow 4657, to align the plane of oscillation with a tissue plane; furthermore, Differential Dissecting Instrument 4650 can be advanced into and out of instrument lumen 4630, as indicated by straight double arrow 4656, such that DDM 4655 projects further or less from the face 4605 of instrument tube 4610, as needed for dissection. As the tunnel is opened, dissection system 4600 is advanced into the tunnel, with endoscope 4640 providing a view for the operator as the tunnel is opened up. If sharp dissection or electrocautery is needed, then Differential Dissecting Instrument 4650 can be removed and electrosurgical hook 4660 can be introduced into instrument lumen 4630 to cut or to cauterize.

Conversely, a Differential Dissecting Instrument having an extendable electrosurgical hook, such as the Differential Dissecting Instrument shown in FIG. 41, can be used to avoid having to switch back and forth between Differential Dissecting Instrument 4650 and electrosurgical hook 4660. Other instruments, such as scissors, forceps, bipolar forceps, or ultrasonic cutters, can also be introduced via instrument lumen 4630 as needed for the dissection, or they can be part of a multi-function Differential Dissecting Instrument, as described earlier.

A dissection system such as dissection system 4600 can be used for many types of endoscopic tunneling, such as endoscopic saphenous vein harvesting, endoscopic tunneling for anterior access to the vertebral column, for tunneling into the neck, for tunneling into the lung for lobectomy, or for tunneling to the heart for minimally invasive valve replacement. A major advantage of dissection system 4600 over existing endoscopic saphenous vein harvesting systems is that addition of differential dissection decreases the chance of side branch evulsion or damage to the vessel wall. Normally, such trauma to the vessel requires surgical repair, such as suturing evulsions, and is thought to greatly impair the quality of the graft during coronary artery bypass grafting, degrading the long-term durability of the graft.

In one demonstration of the effectiveness of a Differential Dissecting Instrument, as disclosed herein, for safely dissecting a major vessel with side grafts, a surgeon inserted a Differential Dissecting Instrument into an incision over a vessel in a live pig (approximately 120 lbs) and then blindly advanced the Differential Dissecting Instrument along the path of least resistance, assuming this was the tissue plane overlying the vessel. At the conclusion of dissection along a 20 cm path, the surgeon dissected down, to the shaft of the Differential Dissecting Instrument, discovering that, yes, the Differential Dissecting Instrument had followed the vessel and that the vessel had been freed from surrounding tissue with no evulsions of side branches or bruising of the main vessel wall.

FIGS. 47A through 47D show another instrument for tunneling with a differential dissecting instrument coupled with an endoscope and including accessory components to enhance dissection and to improve the field of view for the endoscope. FIG. 47A through 47D depict a dissecting system 4700 like the dissecting system 4600 for tunneling into a tissue, such as along a blood vessel. However, the dissecting system 4700 includes:

an inflatable annular balloon 4710 located at the distal end of the instrument tube 4610 that, on inflation, both expands the diameter of the tunnel into the tissue 4701 and forms an airtight seal between the instrument tube 4610 and the surrounding tissue 4701 and an insufflation system 4720 (a system that injects air to expand a cavity inside the body) that permits both inflation/deflation of the balloon 4710 and injection of pressurized air into the end of the tunnel and thus into the tissue 4701 to expand the end of the tunnel, assisting blunt dissection, and providing a cavity 4702 distal to the face 4605 allowing the camera 4640 to view the tissue 4701 and the action of instruments inserted into the second instrument lumen 4630.

Figures 1, 47A:
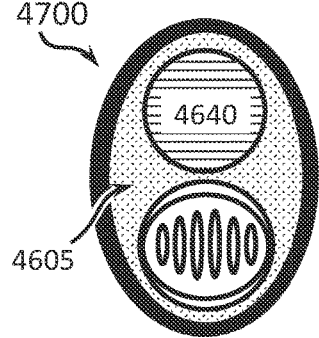
Figures 2, 47A:
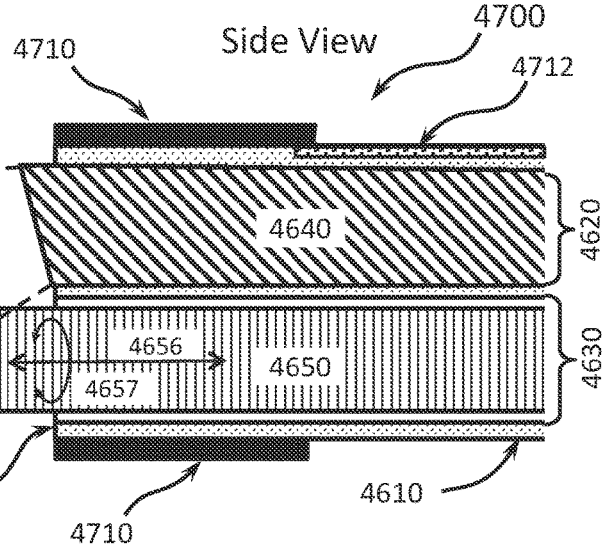

FIGS. 47A-1 and 47A-2 show front and side views, respectively, of the distal end of the dissecting system 4700. As with the dissecting system 4600, there is a multi-lumen instrument tube 4610 with an endoscope 4640 inserted into the first instrument lumen 4620 and a Differential Dissecting Instrument 4650 (or other instrument) inserted into the second instrument lumen 4630. The balloon 4710 wraps the end of the instrument tube 4610 and can be inflated by air flow 4714 through an inflation tube 4712. The balloon 4710 is shown deflated in FIGS. 47A-1 and 47A-2 whereby it lies closely apposed to the instrument tube 4610 to facilitate insertion of the instrument tube 4610 into the tissue 4701.

Figures 1, 47B:
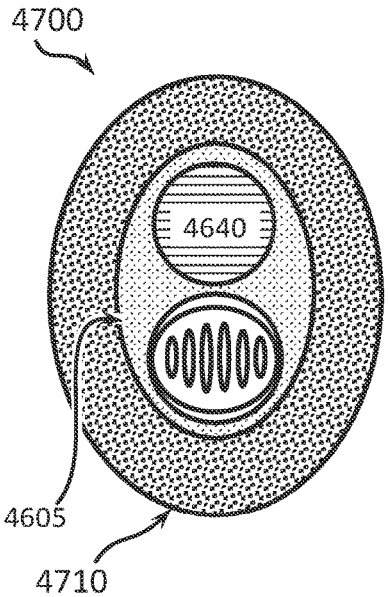
Figures 2, 47B:
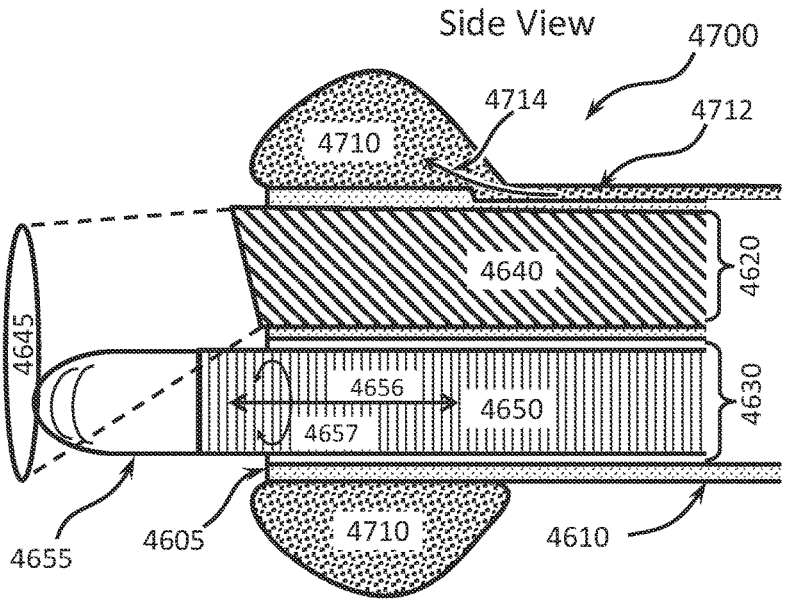
Figure 47C:
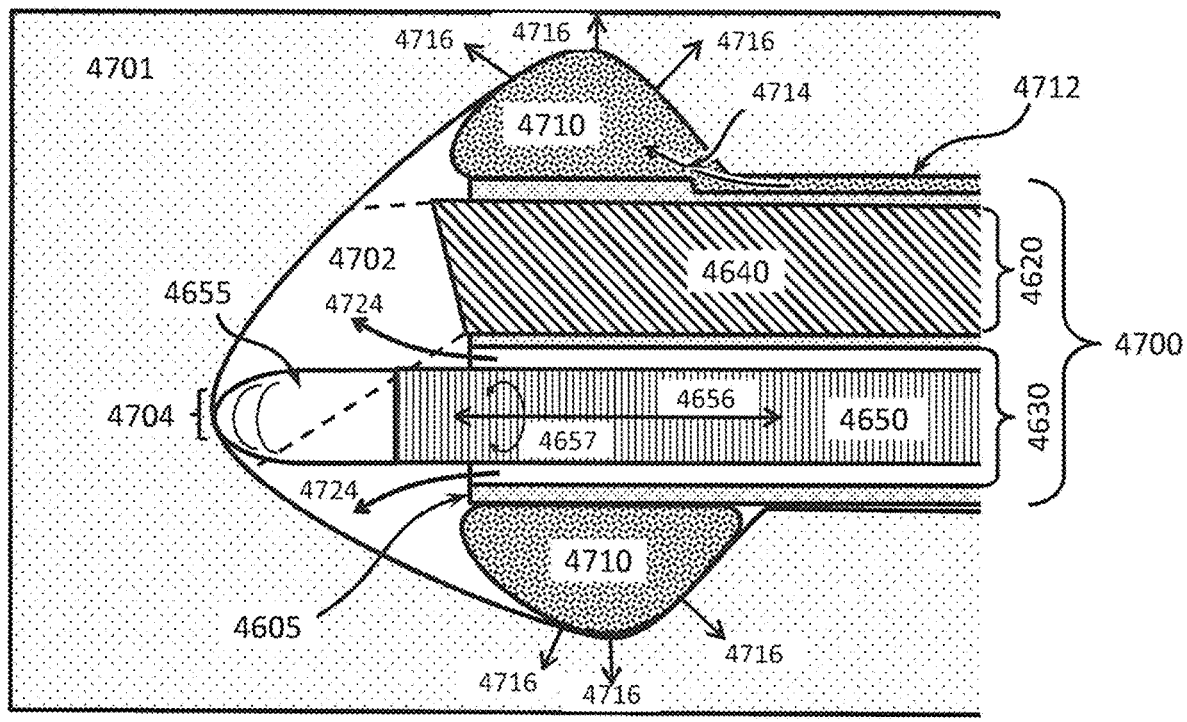
FIG. 47C shows a side view of the dissecting system of FIGS. 47A-1, 47A-2, 47B-1, and 47B-2, where inflation of the balloon pushes tissue radially away from the distal end of the dissecting system.
Figure 47D:
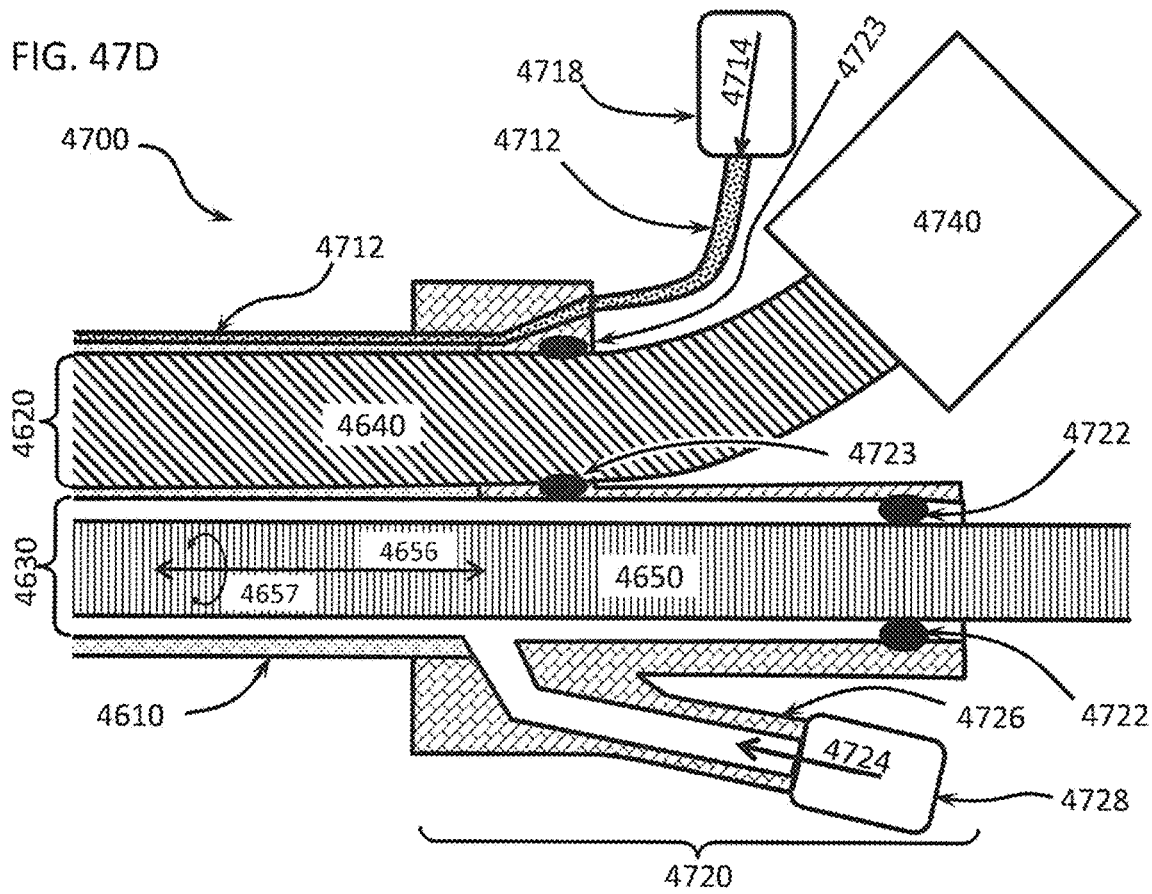

FIGS. 47B-1 and 47B-2 show front and side views, respectively, inflation of the balloon 4710 by an air flow 4714 which is provided by the balloon inflation tube 4712 and driven by air pumping device 4718 (shown in FIG. 47D). Air pumping device 4718 can be on of any number of devices for providing regulated air flows including syringes, air pumps, and such. Note that the airflow 4714 can be in the opposite direction as drawn, permitting deflation of the balloon 4710 when needed.

As shown in FIG. 47C, inflation of the balloon 4710 pushes the tissue 4701 radially away from the distal end of the instrument tube 4610, as indicated by the arrows 4716. Thus the instrument tube 4610 can be inserted into a tissue 4701 with the balloon 4710 deflated. After insertion, the balloon 4710 can be inflated to help create a cavity 4702 and thereby improve the view for the camera 4740 attached to the endoscope 4640.

An insufflation system 4720 can also be attached to the proximal end of the instrument tube 4610 (see FIG. 47D). The insufflation system 4720 comprises an insufflation tube 4726 that connects the second instrument lumen 4630 to an air pump 4728 that provides a regulated air flow. The regulated air flow is controllable by the operator such that air can be injected into or withdrawn from the second instrument lumen 4630 via insufflation tube 4726. Air pump 4728 can be one of any number of devices for providing regulated air flows, including syringes, air pumps, and such. Pressurized air flows into the insufflation tube 4726 (as shown by the arrow 4724), into and along the second instrument lumen 4630, and exits into the cavity 4702 at the distal end of the instrument tube 4610 as shown by arrow 4724 in FIG. 47C. Air is blocked from exiting the second instrument lumen 4630 by a seal 4722 between the Differential Dissecting Instrument 4650 (or any other instrument inserted into the second instrument lumen 4630) and second instrument lumen 4630. Air inside the cavity 4702 can thus be pressurized which further expands the cavity 4702 to improve visibility for the camera 4740 attached to the endoscope 4640 and maneuverability for the Differential Dissecting Instrument 4650. Pressurized air inside the cavity 4702 also tensions the tissues along the periphery of the cavity 4702 including the region of dissection 4704 for the DDM 4655. (As described earlier, tensioning of the tissue facilitates differential dissection; this can also be done by placing the differential dissecting member inside the balloon, working on and dissecting the tissues through the balloon membrane, and letting the balloon expansion apply the tension normally supplied by other instruments.) The seal 3022 can operate to block air flow both when an instrument, such as the Differential Dissecting Instrument 4650 or the electrosurgical hook 4660, is inserted into the second instrument lumen 4630. A second seal 4723 can optionally be placed between the endoscope 4640 and the first instrument lumen 4620 to stop airflow out any gaps.

The embodiments set forth herein are examples and are not intended to encompass the entirety of the invention. Many modifications and embodiments of the inventions set forth herein will come to mind to one skilled in the art to which these inventions pertain having the benefit of the teaching presented in the foregoing descriptions and the associated drawings. Therefore, it is to be understood that the inventions are not to be limited to the specific embodiments disclosed and that modifications and other embodiments are intended to be included within the scope of the appended claims. Although specific terms are used herein, they are used in a generic and descriptive sense only and not for the purposes of limitation.

We claim:

1. A differential dissecting instrument (DDI) for differentially dissecting complex tissue comprising:
a handle, having a central, longitudinal axis;
a distal end of the DDI configured to be pointed at a complex tissue, and a proximal end of the DDI configured to be pointed at a user;
a flexible elongate member having a distal end and a proximal end, the proximal end of the flexible elongate member connected to the handle; and
a differential dissecting member rotatably attached to the distal end of the flexible, elongate member, the differential dissecting member having a distal end, a proximal end, and an axis of rotational oscillation, the differential dissecting member comprising:
  at least one tissue-engaging surface; and
  a first torque-point, the first torque-point disposed proximal to the axis of rotational oscillation of the differential dissecting member; and
a mechanism, configured to mechanically oscillate the differential dissecting member around the axis of rotational oscillation thereby causing the at least one tissue-engaging surface to move back and forth against the complex tissue, the mechanism comprising:
  at least one force-transmitting member possessing a distal end and a proximal end, the distal end being mechanically coupled to the first torque-point of the differential dissecting member; and
  the proximal end of the at least one force-transmitting member attached to a motive source,
  wherein the at least one tissue-engaging surface is configured to selectively engage the complex tissue such that when the differential dissecting member is pressed into the complex tissue, the at least one tissue-engaging surface moves across the complex tissue and the at least one tissue-engaging surface disrupts at least one soft tissue in the complex tissue, but does not disrupt firm tissue in the complex tissue.

2. The DDI of claim 1, where the mechanical coupling of the at least one force-transmitting member to the first torque-point of the differential dissecting member comprises a scotch yoke.

3. The DDI as in claim 1, wherein the at least one force-transmitting member is a rod.

4. The DDI as in claim 1, wherein the at least one force-transmitting member is a drive shaft.

5. The DDI as in claim 1, wherein the proximal end of the at least one force-transmitting terminates on a motor.

6. The DDI as in claim 1, wherein the at least one force-transmitting member is a flexible drive shaft.

7. The DDI as in claim 1, wherein the at least one force-transmitting member is a single, continuous tension member.

8. The DDI as in claim 1, wherein the motive source is a motor.

9. The DDI as in claim 1, wherein the motive source is a rotary actuator.

10. The DDI as in claim 1, further comprising at least one first overload mechanism configured to, in response to at least a first threshold force, stop rotation of the differential dissecting member when a force exceeding the at least a first threshold force is applied to the differential dissecting member.

11. The DDI as in claim 10, wherein the at least one first overload mechanism is further configured to stop the motive source in response to the force that exceeds the at least a first threshold force.

12. The DDI as in claim 10, wherein at least at least one second overload mechanism is configured to respond to a force applied in a proximal direction onto the differential dissecting member such that when the force exceeds at least a second threshold force, the at least one second overload mechanism stops the oscillation of the differential dissecting member.

13. The DDI as in claim 12, further comprising a mechanism for adjusting the at least a first threshold force or the at least a second threshold force.

14. The DDI of claim 1, wherein the flexible elongate member comprises a flexible instrument insertion tube for use in surgical procedures such as laparoscopic surgery or endoscopic surgery.

15. The DDI of claim 14, wherein the flexible instrument insertion tube encloses a flexible draft shaft configured to rotate within and relative to the flexible instrument insertion tube.

16. The DDI of claim 1, wherein the DDI is part of a system including an endoscope, wherein the system comprises at least one instrument lumen, and wherein the DDI is configured to be placed inside the instrument lumen and rotated inside the instrument lumen to permit the differential dissecting member to be rotated to align with different tissue planes.

17. A differential dissecting instrument (DDI) for differentially dissecting complex tissue comprising:
  a handle;
  a flexible elongate member having a distal end and a proximal end, the proximal end connected to the handle;
  a differential dissecting member configured to be rotatably attached to the distal end, the differential dissecting member having an axis of rotational oscillation substantially transverse to the flexible elongate member and comprising:
    at least one tissue-engaging surface; and
    a first torque-point disposed on the proximal end of the differential dissecting member; and
  a mechanism configured to mechanically oscillate the differential dissecting member around the axis of rotational oscillation thereby causing the at least one tissue-engaging surface to move in a back-and-forth direction against the complex tissue, the mechanism comprising:
    at least one force-transmitting member having a distal end mechanically associated with the first torque-point of the differential dissecting member and a proximal end attached to an oscillator configured to drive the rotational oscillation of the differential dissecting member; and
    at least one overload mechanism configured to, in response to at least a first threshold force, stop rotation of the differential dissecting member when a force exceeding the at least a first threshold force is applied to the differential dissecting member,
    wherein the at least one tissue-engaging surface is configured to selectively engage the complex tissue such that when the differential dissecting member is pressed into the complex tissue, the at least one tissue-engaging surface moves back and forth across the complex tissue and the at least one tissue-engaging surface disrupts at least one soft tissue in the complex tissue, but does not disrupt firm tissue in the complex tissue.

18. A differential dissecting instrument (DDI) for differentially dissecting complex tissue comprising:
  a handle;
  a flexible elongate member having a distal end and a proximal end, the proximal end connected to the handle, and further possessing a central, longitudinal axis;
  a differential dissecting member configured to be rotatably attached to the distal end, the differential dissecting member having an axis of rotational oscillation substantially transverse to the central, longitudinal axis and comprising:
    at least one tissue-engaging surface; and a first torque-point disposed on the proximal end of the differential dissecting member, the first torque-point comprising a scotch yoke pin follower; and a mechanism configured to mechanically oscillate the differential dissecting member about the axis of rotational oscillation thereby causing the at least one tissue-engaging surface to move in a back-and-forth direction against the complex tissue, the mechanism comprising:

at least one flexible drive shaft having a distal end mechanically associated with the first torque-point of the differential dissecting member and a proximal end attached to a motor;

a scotch yoke associated with the distal end of the at least one flexible drive shaft, and configured with a scotch yoke pin to engage the scotch yoke pin follower on the proximal end of the differential dissecting member, the motor operatively associated with the at least one flexible drive shaft such that rotation of the motor turns the at least one flexible drive shaft;

a power source for the motor; and a control switch operatively associated with the motor and the power source, and wherein the control switch is configured to be accessible by a user, wherein the at least one tissue-engaging surface is configured to selectively engage the complex tissue such that when the differential dissecting member is pressed into the complex tissue, the at least one tissue-engaging surface moves back and forth across the complex tissue and the at least one tissue-engaging surface disrupts at least one soft tissue in the complex tissue, but does not disrupt firm tissue in the complex tissue.

19. A differential dissecting instrument (DDI) for differentially dissecting complex tissue comprising:

a handle, having a central, longitudinal axis;

a distal end of the DDI configured to be pointed at the complex tissue, and a proximal end of the DDI configured to be pointed at a user;

a flexible elongate member having a distal end and a proximal end, the proximal end of the flexible elongate member connected to the handle;

a differential dissecting member rotatably attached to the distal end of the flexible elongate member, the differential dissecting member having an axis of rotational oscillation substantially transverse to the central, longitudinal axis and comprising:

at least one tissue-engaging surface; and a first torque-point, the first torque-point disposed proximal to the axis of rotational oscillation of the differential dissecting member; and a mechanism, configured to mechanically oscillate the differential dissecting member about the axis of rotational oscillation, thereby causing the at least one tissue-engaging surface to move back and forth against the complex tissue, the mechanism comprising at least one force-transmitting member possessing a distal end and a proximal end, the distal end being mechanically associated with the first torque-point of the differential dissecting member, and the proximal end of the at least one force-transmitting member being attached to a motive source;

wherein the at least one tissue-engaging surface is configured to selectively engage the complex tissue such that when the differential dissecting member is pressed into the complex tissue, the at least one tissue-engaging surface moves back and forth across the complex tissue and the at least one tissue-engaging surface disrupts at least one soft tissue in the complex tissue, but does not disrupt firm tissue in the complex tissue.

20. The DDI as in claim 19, wherein the at least one force-transmitting member is a connecting rod.

21. The DDI as in claim 19, wherein the oscillation of the differential dissecting member imparted by the at least one force-transmitting member is counterbalanced by cyclic torque oscillation about the axis of rotational oscillation provided by a scotch yoke.

22. The DDI as in claim 21, where the at least one force-transmitting member is a flexible member.

23. The DDI as in claim 22, wherein a distal end of the flexible member terminates in a scotch yoke.

24. The DDI as in claim 22, wherein the flexible member is a flexible rotational drive shaft.

25. The DDI as in claim 24, wherein the flexible member comprises a helically wound drive shaft.

26. The DDI as in claim 24, wherein the flexible member has a first end and a second end, and wherein the first end of the flexible member forms the proximal end of the at least one force-transmitting member, and wherein the second end of the flexible member engages a proximal end of the differential dissecting member.

27. The DDI as in claim 26, wherein the motive source is a motor.

28. The DDI as in claim 26, wherein the drive shaft ends distally in a scotch yoke that with an eccentric pin that engages a cam follower on the proximal end of the differential dissecting member.

29. The DDI as in claim 26, wherein the motive source is a rotary actuator.

30. A differential dissecting instrument (DDI) for differentially dissecting complex tissue comprising:

a handle, having a central, longitudinal axis;

a distal end of the DDI configured to be pointed at the complex tissue, and a proximal end of the DDI configured to be pointed at a user;

a flexible elongate member having a distal end and a proximal end, the proximal end of the flexible elongate member connected to the handle;

a differential dissecting member rotatably attached to the distal end of the flexible elongate member, the differential dissecting member having an axis of rotational oscillation oriented substantially transverse to the central, longitudinal axis and comprising:

at least one tissue-engaging surface; and a first torque-point, the first torque-point disposed proximal to the axis of rotational oscillation of the differential dissecting member;

a mechanism, configured to mechanically oscillate the differential dissecting member back and forth around the axis of rotational oscillation, thereby causing the at least one tissue-engaging surface to move back and forth against the complex tissue, the mechanism comprising at least one force-transmitting member possessing a distal end and a proximal end, the distal end being mechanically associated with the first torque-point of the differential dissecting member and the proximal end of the at least one force-transmitting member being attached to a motive source; and at least one first overload mechanism configured to, in response to at least a first threshold force, stop rotation of the differential dissecting member when a force exceeding the at least a first threshold force is applied to the differential dissecting member, wherein the at least one tissue-engaging surface is configured to selectively engage the complex tissue such that when the differential dissecting member engages the complex tissue, the at least one tissue-engaging surface moves back and forth across the complex tissue and the at least one tissue-engaging surface disrupts at least one soft tissue in the complex tissue, but does not disrupt firm tissue in the complex tissue.

31. The DDI as in claim 30, wherein the at least one first overload mechanism is further configured to stop the motive source in response to the force that exceeds the at least a first threshold force.

\* \* \* \* \*